United States Patent
Xu et al.

(10) Patent No.: US 11,365,196 B2
(45) Date of Patent: Jun. 21, 2022

(54) FGFR INHIBITOR AND APPLICATION THEREOF

(71) Applicant: Betta Pharmaceuticals Co., Ltd., Hangzhou (CN)

(72) Inventors: Xiaofeng Xu, Beijing (CN); Jiabing Wang, Beijing (CN); Lieming Ding, Hangzhou (CN); Xiangyong Liu, Beijing (CN)

(73) Assignee: Betta Pharmaceuticals Co., Ltd., Hangzhou (CN)

( * ) Notice: Subject to any disclaimer, the term of this patent is extended or adjusted under 35 U.S.C. 154(b) by 232 days.

(21) Appl. No.: 16/488,899

(22) PCT Filed: Feb. 27, 2018

(86) PCT No.: PCT/CN2018/077314
§ 371 (c)(1),
(2) Date: Nov. 16, 2020

(87) PCT Pub. No.: WO2018/153373
PCT Pub. Date: Aug. 30, 2018

(65) Prior Publication Data
US 2021/0130353 A1 May 6, 2021

(30) Foreign Application Priority Data

Feb. 27, 2017 (WO) ................ PCT/CN2017/074967

(51) Int. Cl.
| | |
|---|---|
| *C07D 471/14* | (2006.01) |
| *A61K 31/519* | (2006.01) |
| *A61P 35/00* | (2006.01) |
| *C07D 519/00* | (2006.01) |

(52) U.S. Cl.
CPC ............ *C07D 471/14* (2013.01); *A61P 35/00* (2018.01); *C07D 519/00* (2013.01)

(58) Field of Classification Search
CPC C07D 471/14; A61K 31/519; A61K 31/4375; A61P 35/00
USPC .................... 544/251; 546/82; 514/257, 293
See application file for complete search history.

(56) References Cited

U.S. PATENT DOCUMENTS 4,666,812 A 5/1987 Wiedemann et al.

FOREIGN PATENT DOCUMENTS

| CN | 105481858 A | 4/2016 |
|---|---|---|
| DE | 2929414 A1 | 2/1981 |
| EP | 2543372 A1 | 1/2013 |
| EP | 3476846 A1 | 5/2019 |
| RU | 2014115478 A | 11/2015 |
| RU | 2015131148 A | 2/2017 |
| WO | WO 2003/082871 A1 | 10/2003 |
| WO | WO 2013/007708 A1 | 1/2013 |
| WO | WO 2013/048214 | 4/2013 |
| WO | WO 2014/105666 | 7/2014 |

OTHER PUBLICATIONS

Office Action and Search Report dated Apr. 16, 2020 in Russian Patent Application No. 2019129669/04(058403).
International Search Report issued in PCT/CN2018/077314, dated May 25, 2018.

*Primary Examiner* — Charanjit Aulakh
(74) *Attorney, Agent, or Firm* — Howson & Howson LLP

(57) ABSTRACT

An azatricyclic compound (as represented by Formula I) which acts as an inhibitor of fibroblast growth factor receptors (FGFR), as well as a pharmaceutical composition thereof, a preparation method, and a use therefor in the treatment of FGFR-mediated diseases are provided. The azatricyclic compound exerts an effect by means of participating in the regulation of a plurality of processes such as cell proliferation, apoptosis, migration, neovascularization, and the like.

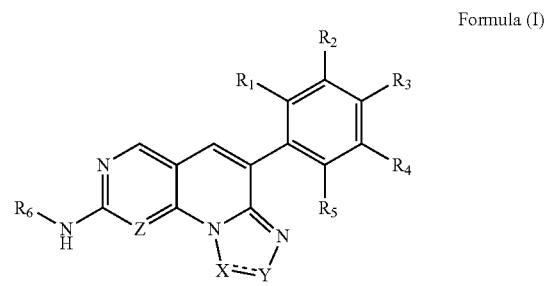

Formula (I)

33 Claims, 3 Drawing Sheets

FGFR INHIBITOR AND APPLICATION THEREOF

CROSS-REFERENCE TO RELATED APPLICATIONS

The present application is a National Stage Entry under 35 U.S.C. § 371 of International Patent Application No. PCT/CN2018/077314, filed Feb. 27, 2018, which claims priority to International Patent Application No. PCT/CN2017/074967, filed on Feb. 27, 2017, the entire disclosure of each of the aforesaid applications being incorporated by reference herein.

FIELD

The present disclosure relates to a series of azatricyclic compounds which act as inhibitors of fibroblast growth factor receptors (FGFR), as well as preparation method thereof, pharmaceutical composition. The present disclosure further relates to a use of the above azatricyclic compounds or pharmaceutical composition thereof in the treatment of FGFR-mediated disorders.

BACKGROUND

Protein kinases are enzymes that catalyze the phosphorylation of proteins, in most instances, the phosphorylation occurs on the serine (ser), threonine (thr) and tyrosine (tyr) residues of the protein. Many aspects of cell life processes (eg. cell growth, differentiation, proliferation, cell cycle and survival) are dependent on the activity of protein kinase. Furthermore, many diseases (eg. cancer and inflammation) are associated with the abnormal activity of protein kinase.

Protein Tyrosine Kinase (PTK) has been found to have more than 100 family members so far, which play an important role in regulating cell differentiation, growth and proliferation. According to the structure of PTK, it can be divided into two types: receptor type PTK and non-receptor type PTK. The former is also called transmembrane PTK, and the latter is also called intracellular PTK.

Fibroblast growth factor receptors (FGFR) belonging to a member of receptor tyrosine kinase (RTK) superfamily, has become one of the targets for global pharmaceutical companies developing novel anti-tumor drugs. FGFR involves in the modulation of cell proliferation, apoptosis, migration, neovascularization and other processes. Due to its wide range of uses, FGFR and other RTK are regulated strictly in normal circumstances. In the tumor, such as breast cancer, bladder cancer, prostate cancer (currently developed indications), etc. FGFR activation mutation or the overexpression of ligand/receptor leads to its continuous activation, which is not only closely related to tumor occurrence, development, poor prognosis, but also plays a vital role in tumor angiogenesis, tumor invasion and metastasis. Therefore, FGFR is recognized as an important candidate for targeted cancer therapies, and the development of FGFR small molecular inhibitors has received more and more attention gradually.

The FGFRs family mainly comprises FGFR1, FGFR2, FGFR3 and FGFR4, and is specifically divided into FGFR1b, FGFR1c, FGFR2b, FGFR2c, FGFR3b, FGFR3c and FGFR4 subtype. They possess common domain, including the extracellular immunoglobulin-like domain and the intracellular tyrosine kinase domain. (Peijuan Du, Chemistry & Bioengineering, Vol. 31, No. 12, 2014, 5-8). The FGFR1 gene encodes the FGFR1b and FGFR1c subtype at the 8p12 site of the human chromosome. Due to alternative splicing, they differ in the third immunoglobulin-like domain. The FGFR2 gene is located at 10q26 of the human chromosome, the FGFR3 gene is located at 4p16.3 of the human chromosome, and also encoded two types. In cancer cells, the activation of human proto-oncogenes by gene amplification, chromosomal translocations, and point mutations gives rises to FGFRs gene. FGFRs involves in tumorigenesis and angiogenesis in cancer cells and endothelial cells respectively, therefore, FGFRs-targeted drugs will produce direct or indirect anticancer effects.

The activation and transduction of fibroblast growth factor (FGFs): FGFs can initiate autophosphorylation of FGFRs on tyrosine residues of key activation loops in tyrosine kinase domain, resulting in the transition of the tyrosine kinase domain from an inactive state to an activated state. (Bae J H, Schlessinger J. Molecules and Cells, 2010, 29(5): 443-448). The activated tyrosine kinase domain in FGFRs will phosphorylate other tyrosine residues progressively along the FGFRs-binding adaptor molecule at the substrate binding site. Phosphorylation of tyrosine residues in the C-terminal region of FGFRs enables phosphatase Cγ (PLCγ) to be absorbed and activated, thereby catalyzing the conversion of phosphatidylinositol diphosphate (PIP2) to diglyceride (DAG) and triphosphate Alcohol (IP3). (Dailey L, Ambrostti D, Mansukhani A, et al. Cytokine & Growth Factor Reviews, 2005, 16(2), 233-247). Activated FGFR Phosphorylation Substrate 2 (FRS2) is capable of absorbing the Growth Factor Receptor Binding Protein 2 (GRB2) adaptor molecule.

FGFs signal can be transmitted to the Ras mitogen-activated protein kinase (Ras-MAPK) or PI3 kinase-protein kinase B (PI3K-AKT) signaling pathway via FRS2 and GRB2, and transmitted to protein kinase C (PKC) or protein kinase D (PKD) signaling pathway through PLCγ and DAG Kinase, and still transmitted to the calcium ion release cascade pathway through PLCγ and IP3. FGFs-induced Ras-MAPK activation involves in cell proliferation, whereas FGFs-induced PI3K-AKT activation involves in cell survival.

FGFs signal participates in various aspects of tumor biology, such as anti-apoptosis, angiogenesis, Epithelial to Mesenchymal Transition (EMT), and invasion, etc. Targeted therapy of FGFRs has become the topical issues in the field of clinical oncology, and small molecule compounds designed and developed to fit the ATP binding POCket in the tyrosine kinase domain have been used in cancer therapy.

The FGFR inhibitors currently developed comprise AZD4547, BGJ398 (Infigratinib), Debio-1347, JNJ42756493, FIIN-2, BLU-554, ARQ087 and PD173074, etc. Among them, AZD4547, BGJ398 and Debio-1347 are FGFR1/2/3 inhibitors, and AZD4547 is a multi-target inhibitor for FGFRs, colony-stimulating factor (CSF1R) and vascular endothelial growth factor receptor-2 (VEGFR-2); BLU-554 is a selective FGFR4 inhibitor; JNJ42756493 and FIIN-2 are pan-FGFR inhibitors; AZD4547, BGJ398 and Debio-1347 are reversible FGFR inhibitors, BLU-554 and FIIN-2 are irreversible FGFR inhibitors (Masaru Katoh, International Journal of Molecular Medicine, 2016, 38:3-15).

In human cancer cells with abnormal activation of FGFRs and anti-apoptotic potential, inhibition of FGFs signaling can reduce the load of cancer cells while inhibiting angiogenesis, and FGFR inhibitors can enhance cancer cells against conventional anticancer drugs (such as 5-fluorouracil, Sensitivity of irinotecan, paclitaxel, etc.). With the deepen understanding of FGFs signal networks and the intensive study of the mechanisms of action of FGFs and FGFRs, FGFR inhibitors with strong specificity and good therapeutic effects will be developed, and FGFR-targeted drugs may therefore used to treat tumors will have extremely broad prospects.

SUMMARY

The present disclosure relates to azatricyclic compounds which used as an inhibitor of fibroblast growth factor receptor (FGFR), as well as pharmaceutically acceptable salts, solvates, chelates, non-covalent complexes or prodrugs thereof. The compounds of the present disclosure have the general structures as Formula (I).

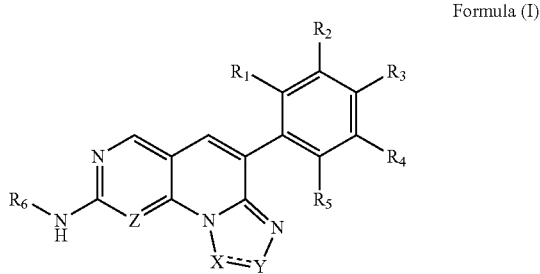

Formula (I)

wherein,

═ represents single bond or double bond;

X and Y are each independently selected from N, NH, C═O and $CR_{10}$;

Z is N or $CR_{10}$;

$R_1$, $R_2$, $R_3$, $R_4$ and $R_5$ are each independently selected from H, halogen, $C_{1-8}$ alkoxy, substituted $C_{1-8}$ alkoxy, $C_{1-8}$ alkyl, substituted $C_{1-8}$ alkyl, $C_{2-8}$ alkenyl, substituted $C_{2-8}$ alkenyl, $C_{2-8}$ alkynyl, substituted $C_{2-8}$ alkynyl, $C_{3-8}$ cycloalkyl, substituted $C_{3-8}$ cycloalkyl, $C_{6-10}$ aryl, substituted $C_{6-10}$ aryl, $C_{5-10}$ heteroaryl, substituted $C_{5-10}$ heteroaryl, $C_{3-10}$ heterocyclyl and substituted $C_{3-10}$ heterocyclyl; or $R_2$ and $R_3$ or $R_3$ and $R_4$ together with the carbon atom to which they are attached may form a 5-8 membered substituted or unsubstituted heterocyclic or heteroaryl ring, wherein the heterocyclic or heteroaryl ring comprises 1, 2 or 3 hetero atoms independently selected from N, O or S;

$R_6$ is $C_{1-8}$ alkyl, substituted $C_{1-8}$ alkyl, $C_{2-8}$ alkenyl, substituted $C_{2-8}$ alkenyl, $C_{2-8}$ alkynyl, substituted $C_{2-8}$ alkynyl, $C_{6-10}$ aryl, substituted $C_{6-10}$ aryl, $C_{3-8}$ cycloalkyl, substituted $C_{3-8}$ cycloalkyl, $C_{3-10}$ heterocyclyl, substituted $C_{3-10}$ heterocyclyl, $C_{5-10}$ heteroaryl or substituted $C_{5-10}$ heteroaryl;

$R_6$ may be optionally substituted by $R_7$;

$R_7$ is hydroxyl, halogen, $C_{1-8}$ alkyl, substituted $C_{1-8}$ alkyl, $C_{2-8}$ alkenyl, substituted $C_{2-8}$ alkenyl, $C_{2-8}$ alkynyl, substituted $C_{2-8}$ alkynyl, $C_{1-8}$ alkoxy, substituted $C_{1-8}$ alkoxy, $C_{6-10}$ aryl, substituted $C_{6-10}$ aryl, $C_{3-8}$ cycloalkyl, substituted $C_{3-8}$ cycloalkyl, $C_{3-10}$ heterocyclyl, substituted $C_{3-10}$ heterocyclyl, $C_{5-10}$ heteroaryl, substituted $C_{5-10}$ heteroaryl, heterocyclylalkyl, substituted heterocyclylalkyl, heterocyclic carbonyl, substituted heterocyclic carbonyl, —$NR_{11}R_{12}$, —$NR_{11}$—$C_{1-8}$ alkylene-$NR_{11}R_{12}$, or $R_7$ is substituted or unsubstituted $C_{5-8}$ heterocyclic ring which fused to $R_6$;

$R_{10}$ is H, halogen, amino, $C_{1-6}$ alkyl, substituted $C_{1-6}$ alkyl, $C_{2-8}$ alkenyl, substituted $C_{2-8}$ alkenyl, $C_{2-8}$ alkynyl, substituted $C_{2-8}$ alkynyl, $C_{3-8}$ cycloalkyl, substituted $C_{3-8}$ cycloalkyl, $C_{6-10}$ aryl, substituted $C_{6-10}$ aryl, $C_{5-10}$ heteroaryl, substituted $C_{5-10}$ heteroaryl, $C_{3-10}$ heterocyclyl or substituted $C_{3-10}$ heterocyclyl;

$R_{10}$ may be optionally substituted by $R_8$;

$R_8$ is hydroxyl, halogen, $C_{1-8}$ alkyl, substituted $C_{1-8}$ alkyl, $C_{2-8}$ alkenyl, substituted $C_{2-8}$ alkenyl, $C_{2-8}$ alkynyl, substituted $C_{2-8}$ alkynyl, $C_{3-10}$ heterocycloalkoxy, substituted $C_{3-10}$ heterocycloalkoxy, $C_{6-10}$ aryl, substituted $C_{6-10}$ aryl, $C_{3-8}$ cycloalkyl, substituted $C_{3-8}$ cycloalkyl, $C_{3-10}$ heterocyclyl, substituted $C_{3-10}$ heterocyclyl, —$S(O_2)C_{3-10}$ heterocyclyl, substituted —$S(O_2)C_{3-10}$ heterocyclyl, $C_{5-10}$ heteroaryl, substituted $C_{5-10}$ heteroaryl or —$NR_{11}R_{12}$;

$R_{11}$ and $R_{12}$ are each independently H, $C_{1-8}$ alkyl, substituted $C_{1-8}$ alkyl, $C_{2-8}$ alkenyl, substituted $C_{2-8}$ alkenyl, $C_{2-8}$ alkynyl, substituted $C_{2-8}$ alkynyl, $C_{3-8}$ cycloalkyl, substituted $C_{3-8}$ cycloalkyl, $C_{6-10}$ aryl, substituted $C_{6-10}$ aryl, $C_{5-10}$ heteroaryl, substituted $C_{5-10}$ heteroaryl, $C_{3-10}$ heterocyclyl or substituted $C_{3-10}$ heterocyclyl;

The present disclosure further provides some preferred technical solutions with regard to the compound of Formula I.

In some embodiments of Formula I, X is N or $CR_{10}$, $R_{10}$ is H, amino, $C_{1-6}$ alkyl, substituted $C_{1-6}$ alkyl, $C_{3-6}$ cycloalkyl or substituted $C_{3-6}$ cycloalkyl.

In some embodiments of Formula I, X is $CR_{10}$, $R_{10}$ is H.

In some embodiments of Formula I, X is $CR_{10}$, $R_{10}$ is $C_{1-6}$ alkyl, $C_{1-6}$ alkyl substituted with $C_{5-10}$ heterocyclyl, $C_{1-6}$ alkyl substituted with $C_{6-10}$ aryl, $C_{1-6}$ alkyl substituted with $C_{3-6}$ cycloalkyl, $C_{1-6}$ alkyl or $C_{3-6}$ cycloalkyl substituted with amino, wherein, the $C_{5-10}$ heterocyclyl, $C_{6-10}$ aryl, $C_{3-6}$ cycloalkyl or amino can be optionally substituted.

In some embodiments of Formula I, X is $CR_{10}$, $R_{10}$ is $C_{1-6}$ alkyl or $C_{3-6}$ cycloalkyl, $R_{10}$ can be substituted with $R_8$, $R_8$ is $(R_{11})$ ethylene-C(O)—N-phenyl, ethyl-C(O)—N-phenyl, morpholinyl, —$NR_{11}R_{12}$, cyclopropane, ethylene-C(O)-piperazinyl, ethylene-C(O)-azetidinoxy, ethylene-C(O)-piperidinyloxy, ethylene-C(O)-aza $C_{6-10}$ spirocyclic, ethylene-C(O)-aza $C_{6-10}$ bicyclic, ethylene-C(O)—N-piperidinyl, ethylene-C(O)-piperidinyl, ethylene-C(O)—$C_{1-8}$ alkyl piperazinyl, —$N(R_{11})$ ethylene-C(O)-piperidinyl, —$N(R_{11})$ ethylene-C(O)-aza $C_{6-10}$ bicyclic, ethylene-C(O)-piperidinyl-$S(O_2)$— or isopentenyl-C(O)-piperazinyl substituted with cyano.

In some embodiments of Formula I, Y is N or $CR_{10}$, $R_{10}$ is H, amino, $C_{1-6}$ alkyl, substituted $C_{1-6}$ alkyl, $C_{3-6}$ cycloalkyl or substituted $C_{3-6}$ cycloalkyl.

In some embodiments of Formula I, Y is N.

In some embodiments of Formula I, Y is $CR_{10}$, $R_{10}$ is $C_{1-6}$ alkyl, $C_{1-6}$ alkyl substituted with $C_{5-10}$ heterocyclyl, $C_{1-6}$ alkyl substituted with $C_{6-10}$ aryl, $C_{1-6}$ alkyl substituted with $C_{3-6}$ cycloalkyl, $C_{1-6}$ alkyl substituted with amino or $C_{3-6}$ cycloalkyl, wherein $C_{5-10}$ heterocyclyl, $C_{6-10}$ aryl, $C_{3-6}$ cycloalkyl or amino can be optionally substituted.

In some embodiments of Formula I, Y is $CR_{10}$, $R_{10}$ is $C_{1-6}$ alkyl or $C_{3-6}$ cycloalkyl, $R_{10}$ can be substituted with $R_8$, $R_8$ is $(R_{11})$ethylene-C(O)—N-phenyl, ethyl-C(O)—N-phenyl, morpholinyl, —$NR_{11}R_{12}$, cyclopropane, ethylene-C(O)-piperazinyl, ethylene-C(O)-azetidinoxy, ethylene-C(O)-piperidinyloxy, ethylene-C(O)-aza $C_{6-10}$ spirocyclic, ethylene-C(O)-aza $C_{6-10}$ bicyclyl, ethylene-C(O)—N-piperidinyl, ethylene-C(O)-piperidinyl, ethylene-C(O)—$C_{1-8}$ alkyl piperazinyl, —$N(R_{11})$ethylene-C(O)-piperidinyl, —$N(R_{11})$ethylene-C(O)-aza-$C_{6-10}$ bicyclyl, ethylene-C(O)-piperidinyl-$S(O_2)$— or isopenteny-C(O)-piperazinyl substituted with cyano.

In some embodiments of Formula I, X is C═O, Y is NH.

In some embodiments of Formula I, Z is N.

In some embodiments of Formula I, $R_1$, $R_3$ and $R_5$ are each independently H, F or Cl.

In some embodiments of Formula I, $R_1$ and $R_5$ are selected from the group below:
(i) both $R_1$ and $R_5$ are H;
(ii) both $R_1$ and $R_5$ are Cl;
(iii) $R_1$ is H, $R_5$ is Cl;
(iv) $R_1$ is Cl, $R_5$ is H;
(v) both $R_1$ and $R_5$ are F;
(vi) $R_1$ is H, $R_5$ is F; or
(vii) $R_1$ is F, $R_5$ is H.

In some embodiments of Formula I, $R_1$ is Cl, both $R_3$ and $R_5$ are H.

In some embodiments of Formula I, $R_3$ is H.

In some embodiments of Formula I, $R_2$ and $R_4$ are each independently selected from H and $C_{1-3}$ alkoxy.

In some embodiments of Formula I, both $R_2$ and $R_4$ are $CH_3O$—.

In some embodiments of Formula I, $R_2$ and $R_3$ or $R_3$ and $R_4$ together with the carbon atom to which they are attached form a substituted 5-membered heterocyclic ring comprising 1-2 hetero atoms independently selected from N, O or S, and the 5-membered heterocyclic ring is substituted with $C_{1-3}$ alkyl.

In some embodiments of Formula I, $R_2$ and $R_3$ or $R_3$ and $R_4$ together with the carbon atom to which they are attached form a substituted 5-membered heterocyclic ring comprising one or two nitrogen atoms; or one nitrogen atom and one sulfur atom; or one nitrogen and one oxygen atom, and the 5-membered heterocyclic ring is substituted with methyl.

In some embodiments of Formula I, $R_2$ and $R_3$ or $R_3$ and $R_4$ together with the carbon atom to which they are attached form a heterocyclic ring which is

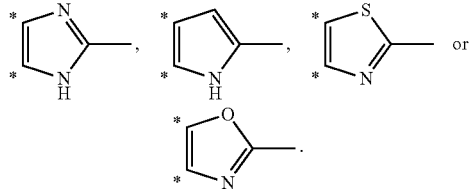

In some embodiments of Formula I, $R_6$ is $C_{1-6}$ alkyl, substituted $C_{1-6}$ alkyl, $C_{6-10}$ aryl, substituted $C_{6-10}$ aryl, $C_{3-6}$ cycloalkyl, substituted $C_{3-6}$ cycloalkyl, $C_{5-10}$ heterocyclyl, substituted $C_{5-10}$ heterocyclyl, $C_{6-10}$ heteroaryl or substituted $C_{6-10}$ heteroaryl.

In some embodiments of Formula I, $R_6$ is $C_{1-4}$ alkyl, cyclopentyl, phenyl, phenyl substituted with F, phenyl substituted with methoxy, phenyl substituted with Cl, phenyl substituted with methyl, pyridyl, tetrahydropyranyl, $R_6$ can be substituted with $R_7$, wherein $R_7$ is hydroxyl, F, Cl, piperazinyl substituted with ethyl, morpholinyl, piperazinyl substituted with isopropyl, piperazinyl substituted with oxetane, piperazinyl substituted with methyl, piperazinyl-$CH_2$— substituted with ethyl, piperazinyl substituted with ethyl and oxyl, piperazinyl substituted with trimethyl, trimethylethylenediamine, piperazinyl substituted with methyl piperidinyl, aza-$C_{6-10}$ bicyclyl substituted with methyl, aza-$C_{6-10}$ bicyclyl, —N(methyl)-$C_{1-6}$ methylene-morpholinyl, $C_{4-10}$ aza cycloalkyl substituted with $C_{2-6}$ alkoxy, piperidinyl substituted with morpholinyl, piperazinyl substituted with hydroxyethyl, $C_{2-6}$ alkoxy substituted with morpholinyl, piperidinyl substituted with ethyl, piperidinyl substituted with methyl, dimethylaminopiperidinyl, $C_{6-10}$ aza bicyclyl substituted with oxyl, nitroxoxa $C_{6-10}$ bicyclyl, morpholinyl-$CH_2$—, methyl piperazinyl-$CH_2$—, piperidinyl substituted with $C_{3-10}$ cycloalkyl, methylamino-piperidinyl, piperazinyl substituted with dimethyl, piperidinyl, piperazinyl-$CH_2$—, piperazinyl-C(O)-substituted with dimethyl, piperazinyl substituted with hydroxycyclobutane, trifluoromethyl-$CH_2$-piperazinyl, piperazinyl substituted with $C_{3-10}$ cycloalkyl, methyl-C(O)-piperazinyl, (dimethyl)-N—C(O)-piperazinyl, (dimethyl)-N—C(O)-aza-$C_{6-10}$ spirocyclic, (dimethyl)-N—C(O)-tetrahydropyrrole-NH—, $R_7$ is a nitrogen-containing 6-membered heterocyclic ring which fused to $R_6$, wherein the nitrogen-containing 6-membered heterocyclic ring is unsubstituted or substituted with ethyl.

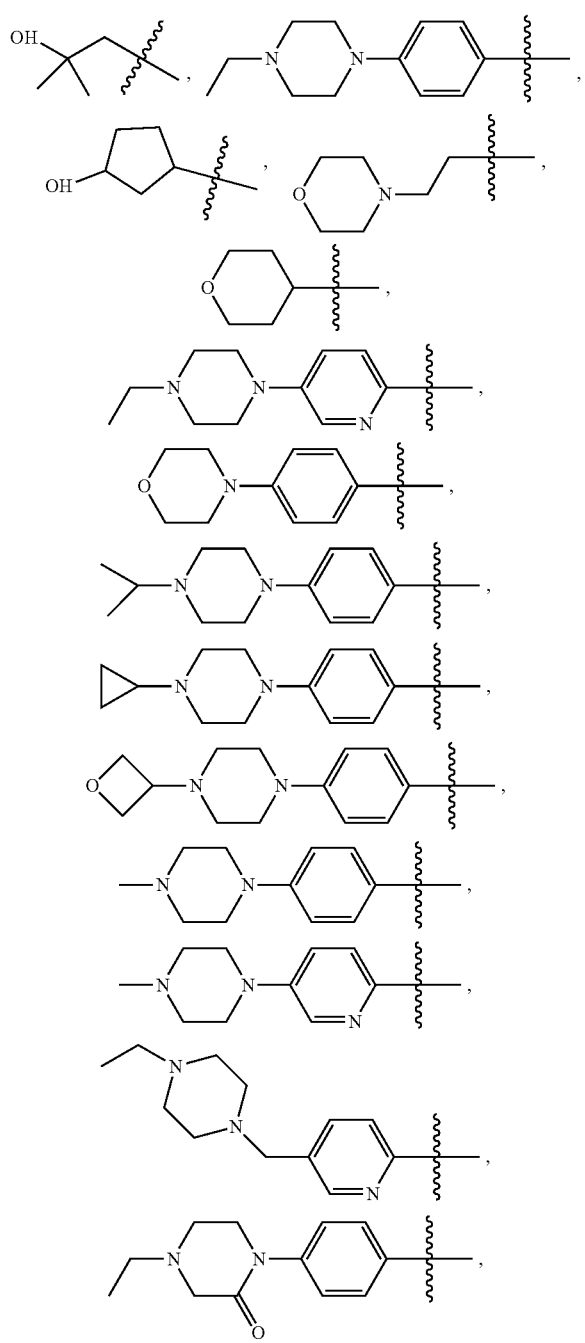

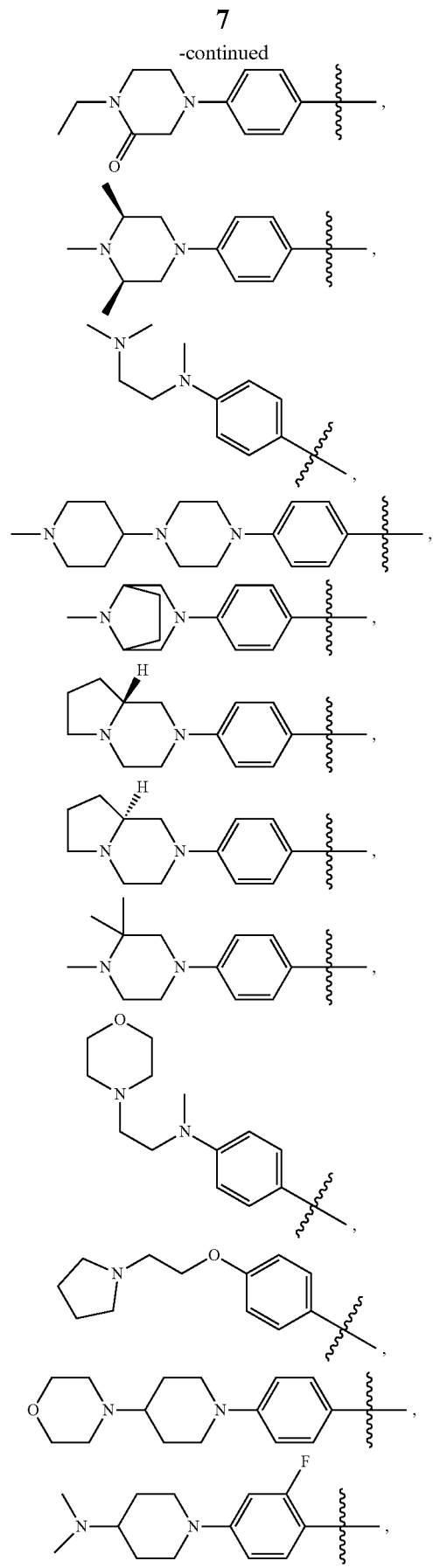
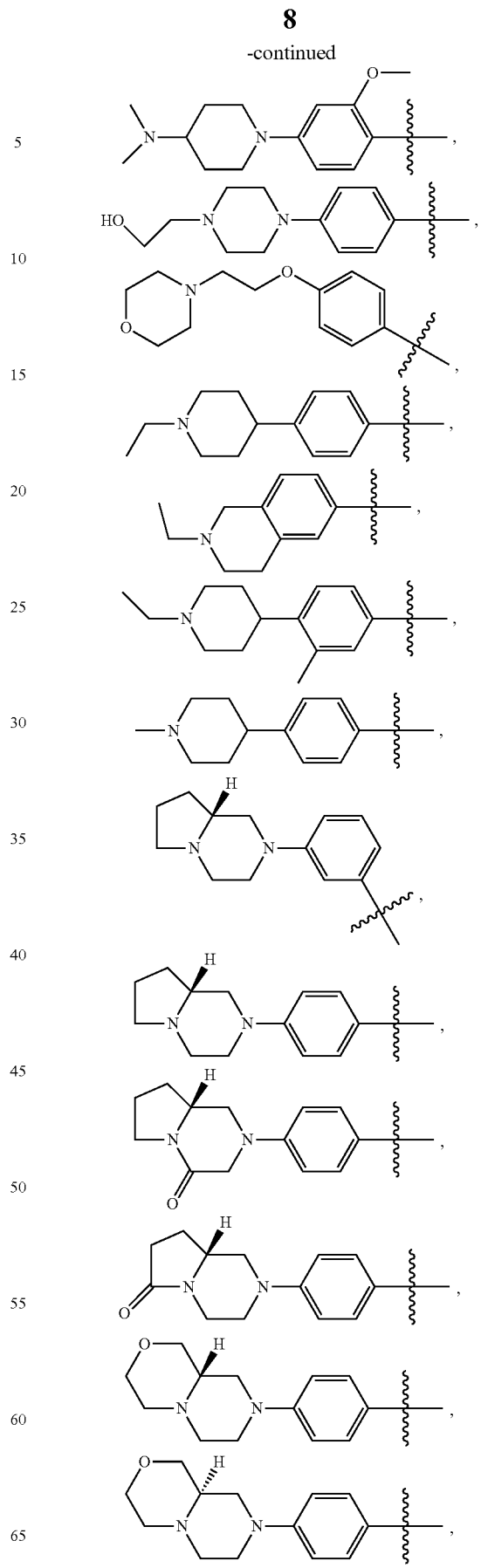

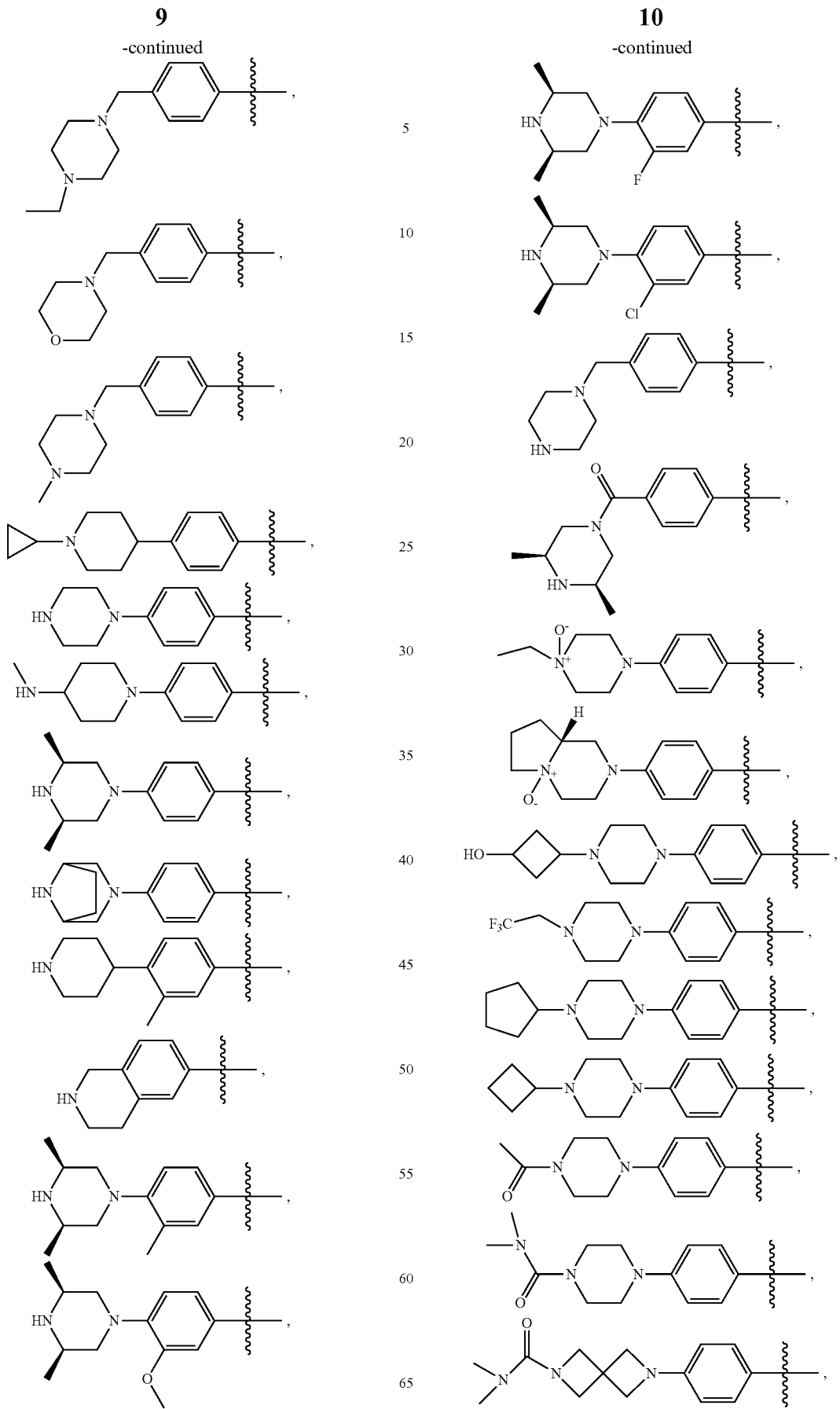

In some embodiments of Formula I, R₆ is methyl,

In some embodiments of Formula I, R₁₁ and R₁₂ are each independently selected from H, C₁₋₆ alkyl, substituted C₁₋₆ alkyl, C₃₋₆ cycloalkyl and substituted C₃₋₆ cycloalkyl.

In some embodiments of Formula I, R₁₁ and R₁₂ are each independently selected from H, methyl and ethyl.

In some embodiments of Formula I, R₁₀ is H, CH₃, amino,

-continued

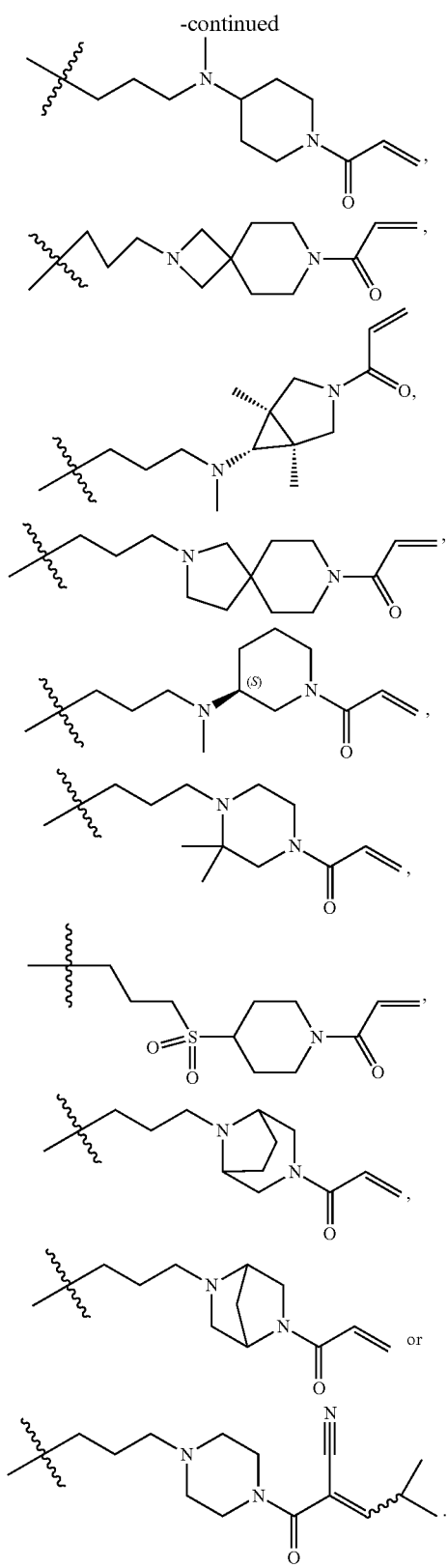

In some embodiments of Formula I, $R_{10}$ is H or —CH$_3$.

The present disclosure further provides some preferred technical solutions with regard to compounds of Formula I, the compounds is:

(1) 1-((6-(2-chloro-3,5-dimethoxyphenyl)-[1,2,4]triazolo[4',3':1,6]pyrido[2,3-d]pyrimidin-2-yl)amino)-2-methylpropan-2-ol;

(2) 4-(2-chloro-3,5-dimethoxyphenyl)-N-(4-(4-ethylpiperazin-1-yl)phenyl)-[1,2,4]triazolo[1',5':1,6]pyrido[2,3-d]pyrimidin-8-amine;

(3) 3-((6-(2-chloro-3,5-dimethoxyphenyl)-[1,2,4]triazolo[4',3':1,6]pyrido[2,3-d]pyrimidin-2-yl)amino)cyclopentan-1-ol;

(4) 6-(2-chloro-3,5-dimethoxyphenyl)-N-(4-(4-ethylpiperazin-1-yl)phenyl)-[1,2,4]triazolo[4',3':1,6]pyrido[2,3-d]pyrimidin-2-amine;

(5) 6-(2-chloro-3,5-dimethoxyphenyl)-N-(2-morpholinoethyl)-[1,2,4]triazolo[4',3':1,6]pyrido[2,3-d]pyrimidin-2-amine;

(6) 1-((4-(2-chloro-3,5-dimethoxyphenyl)-[1,2,4]triazolo[1',5':1,6]pyrido[2,3-d]pyrimidin-8-yl)amino)-2-methylpropan-2-ol;

(7) 6-(2-chloro-3,5-dimethoxyphenyl)-N-(tetrahydro-2H-pyran-4-yl)-[1,2,4]triazolo[4',3':1,6]pyrido[2,3-d]pyrimidin-2-amine;

(8) 6-(2-chloro-3,5-dimethoxyphenyl)-N-(5-(4-ethylpiperazin-1-yl)pyridin-2-yl)-[1,2,4]triazolo[4',3':1,6]pyrido[2,3-d]pyrimidin-2-amine;

(9) 6-(3,5-dimethoxyphenyl)-N-(4-(4-ethylpiperazin-1-yl)phenyl)-[1,2,4]triazolo[4',3':1,6]pyrido[2,3-d]pyrimidin-2-amine;

(10) 6-(2-chloro-3,5-dimethoxyphenyl)-N-(4-morpholinophenyl)-[1,2,4]triazolo[4',3':1,6]pyrido[2,3-d]pyrimidin-2-amine;

(11) 6-(2-chloro-3,5-dimethoxyphenyl)-N-(4-(4-isopropylpiperazin-1-yl)phenyl)-[1,2,4]triazolo[4',3':1,6]pyrido[2,3-d]pyrimidin-2-amine;

(12) 6-(2-chloro-3,5-dimethoxyphenyl)-N-(4-(4-cyclopropylpiperazin-1-yl)phenyl)-[1,2,4]triazolo[4',3':1,6]pyrido[2,3-d]pyrimidin-2-amine;

(13) 6-(2-chloro-3,5-dimethoxyphenyl)-N-(4-(4-(oxetan-3-yl)piperazin-1-yl)phenyl)-[1,2,4]triazolo[4',3':1,6]pyrido[2,3-d]pyrimidin-2-amine;

(14) 6-(2-chloro-3,5-dimethoxyphenyl)-N-(4-(4-(dimethylamino)piperidin-1-yl)phenyl)[1,2,4]triazolo[4',3':1,6]pyrido[2,3-d]pyrimidin-2-amine;

(15) 6-(2-chloro-3,5-dimethoxyphenyl)-N-(4-(4-methylpiperazin-1-yl)phenyl)-[1,2,4]triazolo[4',3':1,6]pyrido[2,3-d]pyrimidin-2-amine;

(16) 6-(2-chloro-3,5-dimethoxyphenyl)-N-(5-(4-methylpiperazin-1-yl)pyridin-2-yl)-[1,2,4]triazolo[4',3':1,6]pyrido[2,3-d]pyrimidin-2-amine;

(17) 6-(2-chloro-3,5-dimethoxyphenyl)-N-(5-((4-ethylpiperazin-1-yl)methyl)pyridin-2-yl)-[1,2,4]triazolo[4',3':1,6]pyrido[2,3-d]pyrimidin-2-amine;

(18) 6-(2-chloro-3,5-dimethoxyphenyl)-N-(4-(4-ethyl-2-oxopiperazin-1-yl)phenyl)-[1,2,4]triazolo[4',3':1,6]pyrido[2,3-d]pyrimidin-2-amine;

(19) 6-(2-chloro-3,5-dimethoxyphenyl)-N-(4-(4-ethyl-3-oxopiperazin-1-yl)phenyl)-[1,2,4]triazolo[4',3':1,6]pyrido[2,3-d]pyrimidin-2-amine;

(20) 6-(2-chloro-3,5-dimethoxyphenyl)-N-(4-((3S,5R)-3,4,5-trimethylpiperazin-1-yl)phenyl)-[1,2,4]triazolo[4',3':1,6]pyrido[2,3-d]pyrimidin-2-amine;

(21) 6-(2-chloro-3,5-dimethoxyphenyl)-N-(4-(N-(2-dimethylaminoethyl-N-methylamino)phenyl)-[1,2,4]triazolo[4',3':1,6]pyrido[2,3-d]pyridimin-2-amine;

(22) 6-(2-chloro-3,5-dimethoxyphenyl)-N-(4-(4-(1-methylpiperidin-4-yl) piperazin-1-yl)phenyl)-[1,2,4]triazolo[4',3':1,6]pyrido[2,3-d]pyrimidin-2-amine;

(23) 6-(2-chloro-3,5-dimethoxyphenyl)-N-(4-(8-methyl-3,8-diazabicyclo[3.2.1]octan-3-yl)phenyl)-[1,2,4]triazolo[4',3':1,6]pyrido[2,3-d]pyrimidin-2-amine;

(24) (R)-6-(2-chloro-3,5-dimethoxyphenyl)-N-(4-(hexahydropyrrolo[1,2-a]pyrazin-2(1H)-yl)phenyl)-[1,2,4]triazolo[4',3':1,6]pyrido[2,3-d]pyrimidin-2-amine;

(25) (S)-6-(2-chloro-3,5-dimethoxyphenyl)-N-(4-(hexahydropyrrolo[1,2-a]pyrazin-2(1H)-yl)phenyl)-[1,2,4]triazolo[4',3':1,6]pyrido[2,3-d]pyrimidin-2-amine;

(26) 6-(2-chloro-3,5-dimethoxyphenyl)-N-(4-(3,3,4-trimethylpiperazin-1-yl)phenyl)-[1,2,4]triazolo[4',3':1,6]pyrido[2,3-d]pyrimidin-2-amine;

(27) N1-(6-(2-chloro-3,5-dimethoxyphenyl)-[1,2,4]triazolo[4',3':1,6]pyrido[2,3-d]pyrimidin-2-yl)-N4-methyl-N4-(2-morpholinoethyl)benzene-1,4-diamine;

(28) 6-(2-chloro-3,5-dimethoxyphenyl)-N-(4-(2-(pyrrolidin-1-yl)ethoxy)phenyl)-[1,2,4]triazolo[4',3':1,6]pyrido[2,3-d]pyrimidin-2-amine;

(29) 6-(2-chloro-3,5-dimethoxyphenyl)-N-(4-(4-morpholinopiperidin-1-yl)phenyl)-[1,2,4]triazolo[4',3':1,6]pyrido[2,3-d]pyrimidin-2-amine;

(30) 6-(2-chloro-3,5-dimethoxyphenyl)-N-(4-(4-(dimethylamino)piperidin-1-yl)-2-fluorophenyl)-[1,2,4]triazolo[4',3':1,6]pyrido[2,3-d]pyrimidin-2-amine;

(31) 6-(2-chloro-3,5-dimethoxyphenyl)-N-(4-(4-(dimethylamino)piperidin-1-yl)-2-methoxyphenyl)-[1,2,4]triazolo[4',3':1,6]pyrido[2,3-d]pyrimidin-2-amine;

(32) 2-(4-(4-((6-(2-chloro-3,5-dimethoxyphenyl)-[1,2,4]triazolo[4',3':1,6]pyrido[2,3-d]pyrimidin-2-yl)amino)phenyl)piperazin-1-yl)ethan-1-ol;

(33) 6-(2-chloro-3,5-dimethoxyphenyl)-N-(4-(2-morpholinoethoxy)phenyl)-[1,2,4]triazolo[4',3':1,6]pyrido[2,3-d]pyrimidin-2-amine;

(34) 6-(2-chloro-3,5-dimethoxyphenyl)-N-(4-(1-ethylpiperidin-4-yl)phenyl)-[1,2,4]triazolo[4',3':1,6]pyrido[2,3-d]pyrimidin-2-amine;

(35) 6-(2-chloro-3,5-dimethoxyphenyl)-N-(2-ethyl-1,2,3,4-tetrahydroisoquinolin-6-yl)-[1,2,4]triazolo[4',3':1,6]pyrido[2,3-d]pyrimidin-2-amine;

(36) 6-(2-chloro-3,5-dimethoxyphenyl)-N-(4-(1-ethylpiperidin-4-yl)-3-methylphenyl)-[1,2,4]triazolo[4',3':1,6]pyrido[2,3-d]pyrimidin-2-amine;

(37) 6-(2-chloro-3,5-dimethoxyphenyl)-N-(4-(1-methylpiperidin-4-yl)phenyl)-[1,2,4]triazolo[4',3':1,6]pyrido[2,3-d]pyrimidin-2-amine;

(38) (R)-6-(2-chloro-3,5-dimethoxyphenyl)-N-(3-(hexahydropyrrolo[1,2-a]pyrazin-2(1H)-yl)phenyl)-[1,2,4]triazolo[4',3':1,6]pyrido[2,3-d]pyrimidin-2-amine;

(39) (R)-6-(3,5-dimethoxyphenyl)-N-(4-(hexahydropyrrolo[1,2-a]pyrazin-2(1H)-yl)phenyl)-[1,2,4]triazolo[4',3':1,6]pyrido[2,3-d]pyrimidin-2-amine;

(40) (R)-2-(4-((6-(2-chloro-3,5-dimethoxyphenyl)-[1,2,4]triazolo[4',3':1,6]pyrido[2,3-d]pyrimidin-2-yl)amino)phenyl)hexahydropyrrolo[1,2-a]pyrazin-4(1H)-one;

(41) (R)-2-(4-((6-(2-chloro-3,5-dimethoxyphenyl)-[1,2,4]triazolo[4',3':1,6]pyrido[2,3-d]pyrimidin-2-yl)amino)phenyl)hexahydropyrrolo[1,2-a]pyrazin-6(2H)-one;

(42) (S)-6-(2-chloro-3,5-dimethoxyphenyl)-N-(4-(hexahydropyrazino[2,1-c][1,4]oxazin-8(1H)-yl)phenyl)-[1,2,4]triazolo[4',3':1,6]pyrido[2,3-d]pyrimidin-2-amine

(43) (R)-6-(2-chloro-3,5-dimethoxyphenyl)-N-(4-(hexahydropyrazino[2,1-c][1,4]oxazin-8(1H)-yl)phenyl)-[1,2,4]triazolo[4',3':1,6]pyrido[2,3-d]pyrimidin-2-amine;

(44) 6-(2-chloro-3,5-dimethoxyphenyl)-N-(4-((4-ethylpiperazin-1-yl)methyl)phenyl)-[1,2,4]triazolo[4',3':1,6]pyrido[2,3-d]pyrimidin-2-amine;

(45) 6-(2-chloro-3,5-dimethoxyphenyl)-N-(4-(morpholinomethyl)phenyl)-[1,2,4]triazolo[4',3':1,6]pyrido[2,3-d]pyrimidin-2-amine;

(46) 6-(2-chloro-3,5-dimethoxyphenyl)-N-(4-((4-methylpiperazin-1-yl)methyl)phenyl)-[1,2,4]triazolo[4',3':1,6]pyrido[2,3-d]pyrimidin-2-amine;

(47) 6-(2-chloro-3,5-dimethoxyphenyl)-N-(4-(1-cyclopropylpiperidin-4-yl)phenyl)-[1,2,4]triazolo[4',3':1,6]pyrido[2,3-d]pyrimidin-2-amine;

(48) 6-(2-chloro-3,5-dimethoxyphenyl)-N-(4-(piperazin-1-yl)phenyl)-[1,2,4]triazolo[4',3':1,6]pyrido[2,3-d]pyrimidin-2-amine;

(49) 6-(2-chloro-3,5-dimethoxyphenyl)-N-(4-(4-(methylamino)piperidin-1-yl)phenyl)-[1,2,4]triazolo[4',3':1,6]pyrido[2,3-d]pyrimidin-2-amine;

(50) 6-(2-chloro-3,5-dimethoxyphenyl)-N-(4-((3S,5R)-3,5-dimethylpiperazin-1-yl)phenyl)-[1,2,4]triazolo[4',3':1,6]pyrido[2,3-d]pyrimidin-2-amine;

(51) N-(4-(3,8-diazabicyclo[3.2.1]octan-3-yl)phenyl)-6-(2-chloro-3,5-dimethoxyphenyl)[1,2,4]triazolo[4',3':1,6]pyrido[2,3-d]pyrimidin-2-amine;

(52) 6-(2-chloro-3,5-dimethoxyphenyl)-N-(3-methyl-4-(piperidin-4-yl)phenyl)-[1,2,4]triazolo[4',3':1,6]pyrido[2,3-d]pyrimidin-2-amine;

(53) 6-(2-chloro-3,5-dimethoxyphenyl)-N-(1,2,3,4-tetrahydroisoquinolin-6-yl)-[1,2,4]triazolo[4',3':1,6]pyrido[2,3-d]pyrimidin-2-amine;

(54) 6-(2-chloro-3,5-dimethoxyphenyl)-N-(4-((3 S,5R)-3,5-dimethylpiperazin-1-yl)-3-methylphenyl)-[1,2,4]triazolo[4',3':1,6]pyrido[2,3-d]pyrimidin-2-amine;

(55) 6-(2-chloro-3,5-dimethoxyphenyl)-N-(4-((3 S,5R)-3,5-dimethylpiperazin-1-yl)-3-methoxyphenyl)-[1,2,4]triazolo[4',3':1,6]pyrido[2,3-d]pyrimidin-2-amine;

(56) 6-(2-chloro-3,5-dimethoxyphenyl)-N-(4-((3S,5R)-3,5-dimethylpiperazin-1-yl)-3-fluorophenyl)-[1,2,4]triazolo[4',3':1,6]pyrido[2,3-d]pyrimidin-2-amine;

(57) 6-(2-chloro-3,5-dimethoxyphenyl)-N-(3-chloro-4-((3S,5R)-3,5-dimethylpiperazin-1-yl)phenyl)-[1,2,4]triazolo[4',3':1,6]pyrido[2,3-d]pyrimidin-2-amine;

(58) 6-(2-chloro-3,5-dimethoxyphenyl)-N-(4-(piperazin-1-ylmethyl)phenyl)-[1,2,4]triazolo[4',3':1,6]pyrido[2,3-d]pyrimidin-2-amine;

(59) (4-((6-(2-chloro-3,5-dimethoxyphenyl)-[1,2,4]triazolo[4',3':1,6]pyrido[2,3-d]pyrimidin-2-yl)amino)phenyl)((3 S,5R)-3,5-dimethylpiperazin-1-yl)methanone;

(60) (4-((6-(2,6-dichloro-3,5-dimethoxyphenyl)-[1,2,4]triazolo[4',3':1,6]pyrido[2,3-d]pyrimidin-2-yl)amino)phenyl)((3S,5R)-3,5-dimethylpiperazin-1-yl)methanone;

(61) 6-(2,6-dichloro-3,5-dimethoxyphenyl)-N-(4-(4-ethylpiperazin-1-yl)phenyl)-[1,2,4]triazolo[4',3':1,6]pyrido[2,3-d]pyrimidin-2-amine;

(62) 6-(2,6-dichloro-3,5-dimethoxyphenyl)-N-(2-morpholinoethyl)-[1,2,4]triazolo[4',3':1,6]pyrido[2,3-d]pyrimidin-2-amine;

(63) 4-(2,6-dichloro-3,5-dimethoxyphenyl)-N-(2-morpholinoethyl)-[1,2,4]triazolo[1',5':1,6]pyrido[2,3-d]pyrimidin-8-amine;

(64) (R)-6-(2,6-dichloro-3,5-dimethoxyphenyl)-N-(4-(hexahydropyrrolo[1,2-a]pyrazin-2(1H)-yl)phenyl)-[1,2,4]triazolo[4',3':1,6]pyrido[2,3-d]pyrimidin-2-amine;

(65) 6-(2,6-dichloro-3,5-dimethoxyphenyl)-N-(4-(4-morpholinopiperidin-1-yl)phenyl)-[1,2,4]triazolo[4',3':1,6]pyrido[2,3-d]pyrimidin-2-amine;

(66) 6-(2-chloro-3,5-dimethoxyphenyl)-N2-(4-(4-ethylpiperazin-1-yl)phenyl)-[1,2,4]triazolo[4',3':1,6]pyrido[2,3-d]pyrimidine-2,9-diamine;

(67) 6-(5-chloro-2-methyl-1H-benzo[d]imidazol-6-yl)-N-(4-(4-ethylpiperazin-1-yl)phenyl)-[1,2,4]triazolo[4',3':1,6]pyrido[2,3-d]pyrimidin-2-amine;

(68) N-(4-(4-ethylpiperazin-1-yl)phenyl)-6-(2-methyl-1H-benzo[d]imidazol-6-yl)-[1,2,4]triazolo[4',3':1,6]pyrido[2,3-d]pyrimidin-2-amine;

(69) 6-(4-chloro-2-methyl-1H-benzo[d]imidazol-5-yl)-N-(4-(4-ethylpiperazin-1-yl)phenyl)-[1,2,4]triazolo[4',3':1,6]pyrido[2,3-d]pyrimidin-2-amine;

(70) 6-(4,6-dichloro-2-methyl-1H-benzo[d]imidazol-5-yl)-N-(4-(4-ethylpiperazin-1-yl)phenyl)-[1,2,4]triazolo[4',3':1,6]pyrido[2,3-d]pyrimidin-2-amine;

(71) 6-(5-chloro-2-methyl-1H-indol-6-yl)-N-(4-(4-ethylpiperazin-1-yl)phenyl)-[1,2,4]triazolo[4',3':1,6]pyrido[2,3-d]pyrimidin-2-amine;

(72) 6-(6-chloro-2-methylbenzo[d]thiazol-5-yl)-N-(4-(4-ethylpiperazin-1-yl)phenyl)-[1,2,4]triazolo[4',3':1,6]pyrido[2,3-d]pyrimidin-2-amine;

(73) 6-(4-chloro-2-methylbenzo[d]thiazol-5-yl)-N-(4-(4-ethylpiperazin-1-yl)phenyl)-[1,2,4]triazolo[4',3':1,6]pyrido[2,3-d]pyrimidin-2-amine;

(74) 6-(6-chloro-2-methylbenzo[d]oxazol-5-yl)-N-(4-(4-ethylpiperazin-1-yl)phenyl) [1,2,4]triazolo[4',3':1,6]pyrido[2,3-d]pyrimidin-2-amine;

(75) 6-(4-chloro-2-methylbenzo[d]oxazol-5-yl)-N-(4-(4-ethylpiperazin-1-yl)phenyl) [1,2,4]triazolo[4',3':1,6]pyrido[2,3-d]pyrimidin-2-amine;

(76) 6-(5-chloro-2-methylbenzo[d]oxazol-6-yl)-N-(4-(4-ethylpiperazin-1-yl)phenyl) [1,2,4]triazolo[4',3':1,6]pyrido[2,3-d]pyrimidin-2-amine;

(77) 6-(7-chloro-2-methylbenzo[d]oxazol-6-yl)-N-(4-(4-ethylpiperazin-1-yl)phenyl) [1,2,4]triazolo[4',3':1,6]pyrido[2,3-d]pyrimidin-2-amine;

(78) 6-(5-chloro-2-methyl-1H-benzo[d]imidazol-6-yl)-N-(4-(4-(dimethylamino) piperidin-1-yl)phenyl)-[1,2,4]triazolo[4',3':1,6]pyrido[2,3-d]pyrimidin-2-amine;

(79) 6-(5-chloro-2-methyl-1H-benzo[d]imidazol-6-yl)-N-(4-(1-ethylpiperidin-4-yl)phenyl)-[1,2,4]triazolo[4',3':1,6]pyrido[2,3-d]pyrimidin-2-amine;

(80) 6-(5-chloro-2-methyl-1H-benzo[d]imidazol-6-yl)-N-(4-((3S,5R)-3,5-dimethylpiperazin-1-yl)phenyl)-[1,2,4]triazolo[4',3':1,6]pyrido[2,3-d]pyrimidin-2-amine;

(81) 6-(5-chloro-2-methyl-1H-benzo[d]imidazol-6-yl)-N-(4-morpholinophenyl)-[1,2,4]triazolo[4',3':1,6]pyrido[2,3-d]pyrimidin-2-amine;

(82) 6-(5,7-dichloro-2-methyl-1H-benzo[d]imidazol-6-yl)-N-(4-morpholinophenyl)-[1,2,4]triazolo[4',3':1,6]pyrido[2,3-d]pyrimidin-2-amine; tetrahydropyranyl

(83) 6-(7-chloro-2-methyl-1H-benzo[d]imidazol-6-yl)-N-(4-morpholinophenyl)-[1,2,4]triazolo[4',3':1,6]pyrido[2,3-d]pyrimidin-2-amine;

(84) N-(4-(hexahydropyrrolo[1,2-a]pyrazin-2(1H)-yl)phenyl)-[1,2,4]triazolo[4',3':1,6]pyrido[2,3-d]pyrimidin-2-amine;

(85) 6-(2-chloro-3,5-dimethoxyphenyl)-N-(4-(4-ethylpiperazin-1-yl)phenyl)-9-methyl-[1,2,4]triazolo[4',3':1,6]pyrido[2,3-d]pyrimidin-2-amine;

(86) N-(4-((6-(2-chloro-3,5-dimethoxyphenyl)-2-((2-morpholinoethyl)amino)-[1,2,4]triazolo[4',3':1,6]pyrido[2,3-d]pyrimidin-9-yl)methyl)phenyl)acrylamide;

(87) 4-(2-chloro-3,5-dimethoxyphenyl)-N-(4-(4-ethylpiperazin-1-yl)phenyl)-2-methyl-[1,2,4]triazolo[1',5':1,6]pyrido[2,3-d]pyrimidin-8-amine;

(88) N-(4-((4-(2-chloro-3,5-dimethoxyphenyl)-8-((4-(4-ethylpiperazin-1-yl)phenyl)amino)-[1,2,4]triazolo[1',5':1,6]pyrido[2,3-d]pyrimidin-2-yl)methyl)phenyl)acrylamide;

(89) 6-(2-chloro-3,5-dimethoxyphenyl)-N-(4-(4-ethylpiperazin-1-yl)phenyl)-9-(morpholinomethyl)-[1,2,4]triazolo[4',3':1,6]pyrido[2,3-d]pyrimidin-2-amine;

(90) N-(4-((6-(2-chloro-3,5-dimethoxyphenyl)-2-((4-(4-ethylpiperazin-1-yl)phenyl)amino)-[1,2,4]triazolo[4',3':1,6]pyrido[2,3-d]pyrimidin-9-yl)methyl)phenyl)acrylamide;

(91) N-(4-(2-(6-(2-chloro-3,5-dimethoxyphenyl)-2-((4-(4-ethylpiperazin-1-yl)phenyl)amino)-[1,2,4]triazolo[4',3':1,6]pyrido[2,3-d]pyrimidin-9-yl)ethyl)phenyl)acrylamide;

(92) 6-(2-chloro-3,5-dimethoxyphenyl)-9-((dimethylamino)methyl)-N-(4-(4-ethylpiperazin-1-yl)phenyl)-[1,2,4]triazolo[4',3':1,6]pyrido[2,3-d]pyrimidin-2-amine;

(93) 6-(2-chloro-3,5-dimethoxyphenyl)-9-(cyclopropylmethyl)-N-(4-(4-ethylpiperazin-1-yl)phenyl)-[1,2,4]triazolo[4',3':1,6]pyrido[2,3-d]pyrimidin-2-amine;

(94) 6-(2-chloro-3,5-dimethoxyphenyl)-9-cyclopropyl-N-(4-(4-ethylpiperazin-1-yl)phenyl)-[1,2,4]triazolo[4',3':1,6]pyrido[2,3-d]pyrimidin-2-amine;

(95) N-(4-((6-(2-chloro-3,5-dimethoxyphenyl)-2-(methylamino)-[1,2,4]triazolo[4',3':1,6]pyrido[2,3-d]pyrimidin-9-yl)methyl)phenyl)acrylamide;

(96) N-(4-((6-(2-chloro-3,5-dimethoxyphenyl)-2-((2-morpholinoethyl)amino)-[1,2,4]triazolo[4',3':1,6]pyrido[2,3-d]pyrimidin-9-yl)methyl)phenyl)propionamide;

(97) N-(4-(2-(6-(2-chloro-3,5-dimethoxyphenyl)-2-((2-morpholinoethyl)amino)-[1,2,4]triazolo[4',3':1,6]pyrido[2,3-d]pyrimidin-9-yl)ethyl)phenyl)acrylamide;

(98) 6-(2-chloro-3,5-dimethoxyphenyl)-2-((4-(4-ethylpiperazin-1-yl)phenyl)amino)-[1,2,4]triazolo[4',3':1,6]pyrido[2,3-d]pyrimidin-9(8H)-one;

(99) 4-(4-((6-(2-chloro-3,5-dimethoxyphenyl)-[1,2,4]triazolo[4',3':1,6]pyrido[2,3-d]pyrimidin-2-yl)amino)phenyl)-1-ethylpiperazine 1-oxide;

(100) (8aR)-2-(4-((6-(2-chloro-3,5-dimethoxyphenyl)-[1,2,4]triazolo[4',3':1,6]pyrido[2,3-d]pyrimidin-2-yl)amino)phenyl)octahydro-5H-pyrrolo[1,2-a]pyrazine 5-oxide;

(101) 3-(4-(4-((6-(2-chloro-3,5-dimethoxyphenyl)-[1,2,4]triazolo[4',3':1,6]pyrido[2,3-d]pyrimidin-2-yl)amino)phenyl)piperazin-1-yl)cyclobutan-1-ol;

(102) 6-(2-chloro-3,5-dimethoxyphenyl)-N-(4-(1-ethylpiperidin-4-yl)phenyl)-[1,2,4]triazolo[4',3':1,6]pyrido[2,3-d]pyrimidin-2-amine;

(103) 6-(2-chloro-3,5-dimethoxyphenyl)-N-(4-(4-(2,2,2-trifluoroethyl)piperazin-1-yl)phenyl)-[1,2,4]triazolo[4',3':1,6]pyrido[2,3-d]pyrimidin-2-amine;

(104) 6-(2-chloro-3,5-dimethoxyphenyl)-N-(4-(4-cyclopentylpiperazin-1-yl)phenyl)-[1,2,4]triazolo[4',3':1,6]pyrido[2,3-d]pyrimidin-2-amine;

(105) 6-(2-chloro-3,5-dimethoxyphenyl)-N-(4-(4-cyclobutylpiperazin-1-yl)phenyl)-[1,2,4]triazolo[4',3':1,6]pyrido[2,3-d]pyrimidin-2-amine;

(106) (6-(2-chloro-3,5-dimethoxyphenyl)-N-(4-(4-acetylpiperazine-1-yl)phenyl)-[1,2,4]triazolo[4',3':1,6]pyrido[2,3-d]pyrimidin-2-amine);

(107) 4-(4-((6-(2-chloro-3,5-dimethoxyphenyl)-[1,2,4]triazolo[4',3':1,6]pyrido[2,3-d]pyrimidin-2-yl)amino)phenyl)-N,N-dimethylpiperazine-1-carboxamide;

(108) 6-(4-((6-(2-chloro-3,5-dimethoxyphenyl)-[1,2,4]triazolo[4',3':1,6]pyrido[2,3-d]pyrimidin-2-yl)amino)phenyl)-N,N-dimethyl-2,6-diazaspiro[3.3]heptane-2-carboxamide;

(109) (S)-3-((4-((6-(2-chloro-3,5-dimethoxyphenyl)-[1,2,4]triazolo[4',3':1,6]pyrido[2,3-d]pyrimidin-2-yl)amino)phenyl)amino)-N,N-dimethylpyrrolidine-1-carboxamide;

(110) 6-(2-chloro-3,5-dimethoxyphenyl)-N-(6-(4-methylpiperazin-1-yl)pyridin-3-yl)-[1,2,4]triazolo[4',3':1,6]pyrido[2,3-d]pyrimidin-2-amine;

(111) 6-(2-chloro-3,5-dimethoxyphenyl)-N-(6-((4-ethylpiperazin-1-yl)methyl)pyridin-3-yl)-[1,2,4]triazolo[4',3':1,6]pyrido[2,3-d]pyrimidin-2-amine;

(112) N-(4-((4-(2-chloro-3,5-dimethoxyphenyl)-8-((2-morpholinoethyl)amino)-[1,2,4]triazolo[1',5':1,6]pyrido[2,3-d]pyrimidin-2-yl)methyl)phenyl)acrylamide;

(113) (1-(4-((6-(2-chloro-3,5-dimethoxyphenyl)-2-(methylamino)-[1,2,4]triazolo[4',3':1,6]pyrido[2,3-d]pyrimidin-9-yl)propyl)piperazin-1-yl)prop-2-en-1-one);

(114) 1-(4-(2-(6-(2-chloro-3,5-dimethoxyphenyl)-2-(methylamino)-[1,2,4]triazolo[4',3':1,6]pyrido[2,3-d]pyrimidin-9-yl)ethyl)piperazin-1-yl)prop-2-en-1-one;

(115) 1-(4-(3-(4-(2-chloro-3,5-dimethoxyphenyl)-8-(methylamino)-[1,2,4]triazolo[1',5':1,6]pyrido[2,3-d]pyrimidin-2-yl)propyl)piperazin-1-yl)prop-2-en-1-one;

(116) 1-(4-(2-(4-(2-chloro-3,5-dimethoxyphenyl)-8-(methylamino)-[1,2,4]triazolo[1',5':1,6]pyrido[2,3-d]pyrimidin-2-yl)ethyl)piperazin-1-yl)prop-2-en-1-one;

(117) 1-(4-((4-(2-chloro-3,5-dimethoxyphenyl)-8-(methylamino)-[1,2,4]triazolo[1',5':1,6]pyrido[2,3-d]pyrimidin-2-yl)methyl)piperazin-1-yl)prop-2-en-1-one;

(118) 1-(3-(2-(4-(2-chloro-3,5-dimethoxyphenyl)-8-(methylamino)-[1,2,4]triazolo[1',5':1,6]pyrido[2,3-d]pyrimidin-2-yl)ethoxy)azetidin-1-yl)prop-2-en-1-one;

(119) 1-(3-(2-(4-(2-chloro-3,5-dimethoxyphenyl)-8-(methylamino)-[1,2,4]triazolo[1',5':1,6]pyrido[2,3-d]pyrimidin-2-yl)ethoxy)piperidin-1-yl)prop-2-en-1-one;

(120) N-(4-(2-(4-(2,6-dichloro-3,5-dimethoxyphenyl)-8-(methylamino)-[1,2,4]triazolo[1',5':1,6]pyrido[2,3-d]pyrimidin-2-yl)ethyl)phenyl)acrylamide;

(121) N-(3-(2-(4-(2,6-dichloro-3,5-dimethoxyphenyl)-8-(methylamino)-[1,2,4]triazolo[1',5':1,6]pyrido[2,3-d]pyrimidin-2-yl)ethyl)phenyl)acrylamide;

(122) 1-(4-(3-(4-(2,6-dichloro-3,5-dimethoxyphenyl)-8-(methylamino)-[1,2,4]triazolo[1',5':1,6]pyrido[2,3-d]pyrimidin-2-yl)propyl)piperazin-1-yl)prop-2-en-1-one;

(123) 1-(4-(2-(4-(2,6-dichloro-3,5-dimethoxyphenyl)-8-(methylamino)-[1,2,4]triazolo[1',5':1,6]pyrido[2,3-d]pyrimidin-2-yl)methyl)piperazin-1-yl)prop-2-en-1-one;

(124) 1-(4-(2-(4-(2,6-dichloro-3,5-dimethoxyphenyl)-8-(methylamino)-[1,2,4]triazolo[1',5':1,6]pyrido[2,3-d]pyrimidin-2-yl)ethyl)piperazin-1-yl)prop-2-en-1-one;

(125) 1-(6-(3-(4-(2,6-dichloro-3,5-dimethoxyphenyl)-8-(methylamino)-[1,2,4]triazolo[1',5':1,6]pyrido[2,3-d]pyrimidin-2-yl)propyl)-2,6-diazaspiro[3.3]heptan-2-yl)prop-2-en-1-one;

(126) 1-(4-((2-(4-(2-chloro-3,5-dimethoxyphenyl)-8-(methylamino)-[1,2,4]triazolo[1',5':1,6]pyrido[2,3-d]pyrimidin-2-yl)cyclopropyl)methyl)piperazin-1-yl)prop-2-en-1-one;

(127) 1-(4-(2-(4-(2-chloro-3,5-dimethoxyphenyl)-8-(methylamino)-[1,2,4]triazolo[1',5':1,6]pyrido[2,3-d]pyrimidin-2-yl)ethoxy)piperidin-1-yl)prop-2-en-1-one;

(128) 1-((3aR,6aS)-5-(3-(4-(2,6-dichloro-3,5-dimethoxyphenyl)-8-(methylamino)-[1,2,4]triazolo[1',5':1,6]pyrido[2,3-d]pyrimidin-2-yl)propyl) hexahydropyrrolo[3,4-c]pyrrol-2(1H)-yl)prop-2-en-1-one;

(129) N-(1-(2-(4-(2,6-dichloro-3,5-dimethoxyphenyl)-8-(methylamino)-[1,2,4]triazolo[1',5':1,6]pyrido[2,3-d]pyrimidin-2-yl)propyl)piperidin-4-yl)acrylamide;

(130) 1-(4-(3-(4-(2,6-dichloro-3,5-dimethoxyphenyl)-8-(methylamino)-[1,2,4]triazolo[1',5':1,6]pyrido[2,3-d]pyrimidin-2-yl)propyl)piperidin-1-yl)prop-2-en-1-one;

(131) 1-((3S,5R)-4-(3-(4-(2,6-dichloro-3,5-dimethoxyphenyl)-8-(methylamino)-[1,2,4]triazolo[1',5':1,6]pyrido[2,3-d]pyrimidin-2-yl)propyl)-3,5-dimethylpiperazin-1-yl)prop-2-en-1-one;

(132) 1-(4-((1-((4-(2,6-dichloro-3,5-dimethoxyphenyl)-8-(methylamino)-[1,2,4]triazolo[1',5':1,6]pyrido[2,3-d]pyrimidin-2-yl)methyl)cyclopropyl)methyl)piperazin-1-yl)prop-2-en-1-one;

(133) 1-((2R,6S)-4-(3-(4-(2,6-dichloro-3,5-dimethoxyphenyl)-8-(methylamino)-[1,2,4]triazolo[1',5':1,6]pyrido[2,3-d]pyrimidin-2-yl)propyl)-2,6-dimethylpiperazin-1-yl)prop-2-en-1-one;

(134) 1-(4-((3-(4-(2,6-dichloro-3,5-dimethoxyphenyl)-8-(methylamino)-[1,2,4]triazolo[1',5':1,6]pyrido[2,3-d]pyrimidin-2-yl)propyl)(methyl)amino)piperidin-1-yl)prop-2-en-1-one;

(135) 1-((2R,6S)-4-(3-(8-((cyclopropylmethyl)amino)-4-(2,6-dichloro-3,5-dimethoxyphenyl)-[1,2,4]triazolo[1',5':1,6]pyrido[2,3-d]pyrimidin-2-yl)propyl)-2,6-dimethylpiperazin-1-yl)prop-2-en-1-one;

(136) 1-((2R,6S)-4-(3-(4-(2,6-dichloro-3,5-dimethoxyphenyl)-8-((2,2-difluoroethyl)amino)-[1,2,4]triazolo[1',5':1,6]pyrido[2,3-d]pyrimidin-2-yl)propyl)-2,6-dimethylpiperazin-1-yl)prop-2-en-1-one;

(137) 1-(4-(3-(4-(2,6-dichloro-3,5-dimethoxyphenyl)-8-((2,2,2-trifluoroethyl)amino)-[1,2,4]triazolo[1',5':1,6]pyrido[2,3-d]pyrimidin-2-yl)propyl)piperazin-1-yl)prop-2-en-1-one;

(138) 1-(2-(3-(4-(2,6-dichloro-3,5-dimethoxyphenyl)-8-(methylamino)-[1,2,4]triazolo[1',5':1,6]pyrido[2,3-d]pyrimidin-2-yl)propyl)-2,7-diazaspiro[3.5]nonan-7-yl)prop-2-en-1-one;

(139) 1-((1R,5S,6s)-6-((3-(4-(2,6-dichloro-3,5-dimethoxyphenyl)-8-(methylamino)-[1,2,4]triazolo[1',5':1,6]pyrido[2,3-d]pyrimidin-2-yl)propyl)(methyl)amino)-3-azabicyclo[3.1.0]hexan-3-yl)prop-2-en-1-one;

(140) 1-(2-(3-(4-(2,6-dichloro-3,5-dimethoxyphenyl)-8-(methylamino)-[1,2,4]triazolo[1',5':1,6]pyrido[2,3-d]pyrimidin-2-yl)propyl)-2,8-diazaspiro[4.5]decan-8-yl)prop-2-en-1-one;

(141) (S)-1-(3-((3-(4-(2,6-dichloro-3,5-dimethoxyphenyl)-8-(methylamino)-[1,2,4]triazolo[1',5':1,6]pyrido[2,3-d]pyrimidin-2-yl)propyl)(methyl)amino)piperidin-1-yl)prop-2-en-1-one;

(142) 1-(4-(3-(4-(2,6-dichloro-3,5-dimethoxyphenyl)-8-(methylamino)-[1,2,4]triazolo[1',5':1,6]pyrido[2,3-d]pyrimidin-2-yl)propyl)-3,3-dimethylpiperazin-1-yl)prop-2-en-1-one;

(143) 1-(4-((3-(4-(2,6-dichloro-3,5-dimethoxyphenyl)-8-(methylamino)-[1,2,4]triazolo[1',5':1,6]pyrido[2,3-d]pyrimidin-2-yl)propyl)sulfonyl)piperidin-1-yl)prop-2-en-1-one;

(144) 1-(8-(3-(4-(2,6-dichloro-3,5-dimethoxyphenyl)-8-(methylamino)-[1,2,4]triazolo[1',5':1,6]pyrido[2,3-d]pyrimidin-2-yl)propyl)-3,8-diazabicyclo[3.2.1]octan-3-yl)prop-2-en-1-one;

(145) 1-(5-(3-(4-(2,6-dichloro-3,5-dimethoxyphenyl)-8-(methylamino)-[1,2,4]triazolo[1',5':1,6]pyrido[2,3-d]pyrimidin-2-yl)propyl)-2,5-diazabicyclo[2.2.1]heptan-2-yl)prop-2-en-1-one;

(146) 1-(4-(3-(4-(5-chloro-2-methyl-1H-benzo[d]imidazol-6-yl)-8-(methylamino)-[1,2,4]triazolo[1',5':1,6]pyrido[2,3-d]pyrimidin-2-yl)propyl)piperazin-1-yl)prop-2-en-1-one;

(147) 2-(4-(3-(4-(2,6-dichloro-3,5-dimethoxyphenyl)-8-(methylamino)-[1,2,4]triazolo[1',5':1,6]pyrido[2,3-d]pyrimidin-2-yl)propyl)piperazine-1-carbonyl)-4-methylpent-2-enenitrile;

(148) 2-(4-(3-(4-(2,6-dichloro-3,5-dimethoxyphenyl)-8-(methylamino)-[1,2,4]triazolo[1',5':1,6]pyrido[2,3-d]pyrimidin-2-yl)propyl)piperazine-1-carbonyl)-4,4-dimethylpent-2-enenitrile.

The present disclosure also provides a pharmaceutical composition comprising a therapeutically effective amount of at least any one of the compounds of Formula (I) of the present disclosure and at least one pharmaceutically acceptable excipient.

The present disclosure further provides a pharmaceutical composition in which the weight ratio of the compound of the Formula (I) to the excipient can be 0.0001 to 10.

The present disclosure provides a use of the compound of the Formula (I) or pharmaceutical composition for the preparation of a medicament.

The present disclosure further provides a preferred technical solution for the use:

Preferably, a medicament thus prepared can be used for treating, protecting, delaying or preventing the onset or progression of cancer or cancer metastasis.

Preferably, the use is for the preparation of a medicament for the treatment of a disease mediated by FGFR. Preferably, the disease is cancer.

Preferably, the cancer is selected from the group consisting of breast cancer, multiple myeloma, bladder cancer, endometrial cancer, gastric cancer, cervical cancer, rhabdomyosarcoma, non-small cell lung cancer, small cell lung cancer, polymorphic lung cancer, ovarian cancer, esophagus cancer, melanoma, colorectal cancer, hepatocellular carcinoma, head and neck cancer, hepatobiliary cell carcinoma, myelodysplastic syndrome, malignant glioma, prostate cancer, thyroid cancer, Schwann cell tumor, lung squamous cell cancer, mossy keratosis, synovial sarcoma, skin cancer, pancreatic cancer, testicular cancer or liposarcoma.

Preferably, the medicament thus prepared can be used as an inhibitor of FGFR.

Preferably, in the above use, the FGFR comprises FGFR1, FGFR2, FGFR3 or FGFR4.

The present disclosure also provides a method of treating and/or preventing a disease mediated by FGFR by administering a therapeutically effective amount of at least any one of the compounds of Formula (I) or a pharmaceutical composition to a subject.

Preferably, in the above use, the FGFR comprises FGFR1, FGFR2, FGFR3 or FGFR4.

Preferably, in the above use, the disease mediated by FGFR is cancer.

Preferably, in the above use, the cancer is selected from the group consisting of breast cancer, multiple myeloma, bladder cancer, endometrial cancer, gastric cancer, cervical cancer, rhabdomyosarcoma, non-small cell lung cancer, small cell lung cancer, polymorphic lung cancer, ovarian cancer, esophagus cancer, melanoma, colorectal cancer, hepatocellular carcinoma, head and neck cancer, hepatobiliary cell carcinoma, myelodysplastic syndrome, malignant glioma, prostate cancer, thyroid cancer, Schwann cell tumor, lung squamous cell cancer, mossy keratosis, synovial sarcoma, skin cancer, pancreatic cancer, testicular cancer or liposarcoma.

The present disclosure also provides a method of treating cancer comprising administering to a subject a therapeutically effective amount of at least any one of the compounds of Formula (I) or a pharmaceutical composition, the cancer is selected from the group consisting of breast cancer, multiple myeloma, bladder cancer, endometrial cancer, gastric cancer, cervical cancer, rhabdomyosarcoma, non-small cell lung cancer, small cell lung cancer, polymorphic lung cancer, ovarian cancer, esophagus cancer, melanoma, colorectal cancer, hepatocellular carcinoma, head and neck cancer, hepatobiliary cell carcinoma, myelodysplastic syndrome, malignant glioma, prostate cancer, thyroid cancer, Schwann cell tumor, lung squamous cell cancer, mossy keratosis, synovial sarcoma, skin cancer, pancreatic cancer, testicular cancer or liposarcoma.

Preferably, in the above use, the subject to be treated is human.

The present disclosure relates to compounds used as FGFR inhibitor, and relates to the use of these compounds for the preparation of a medicament for the treatment or prevention of disease mediated by FGFR in vivo. The compound has the characteristics of simple structure, simple preparation method, and good therapeutic effect as an active ingredient. As a medicine to be marketed, the compound has the characteristics of low cost and convenience of taking, which is more conducive to the wide application of these drugs, and can more effectively help patients overcome the pain and improve the quality of life.

Unless otherwise stated, the terms used in the present disclosure have the following meanings:

The term "alkyl" includes saturated monovalent hydrocarbon radicals having straight, branched or cyclic moieties. For example, alkyl radicals include but not limited to methyl, ethyl, propyl, isopropyl, cyclopropyl, n-butyl, isobutyl, sec-butyl, t-butyl, cyclobutyl, n-pentyl, 3-(2-methyl)butyl, 2-pentyl, 2-methylbutyl, neopentyl, cyclopentyl, n-hexyl, 2-hexyl, 2-methylpentyl and cyclohexyl. Similarly, $C_{1-8}$, as in $C_{1-8}$ alkyl is defined to identify the group as having 1, 2, 3, 4, 5, 6, 7 or 8 carbon atoms in a linear, branched or cyclic arrangement.

Alkenyl and alkynyl groups include straight, branched chain or cyclic alkenes and alkynes. Likewise, "$C_{2-8}$ alkenyl" and "$C_{2-8}$ alkynyl" means an alkenyl or alkynyl radicals having 2, 3, 4, 5, 6, 7 or 8 carbon atoms in linear, branched or cyclic arrangement.

Alkoxy radicals are oxygen ethers formed from the previously described straight, branched chain or cyclic alkyl groups.

The term "aryl", as used herein, unless otherwise indicated, refers to an unsubstituted or substituted mono- or polycyclic ring system containing carbon ring atoms. The preferred aryls are mono cyclic or bicyclic 6-10 membered aromatic ring systems. Phenyl and naphthyl are preferred aryls. The most preferred aryl is phenyl.

The term "heteroaryl" refers to a monovalent heteroatom group formed by the removal of one hydrogen atom from a carbon atom of a parent heteroaromatic ring system. The heteroaryl group includes a 5- to 7-membered aromatic, monocyclic ring comprising at least one hetero atom selected from N, O or S, for example, 1 to 4 hetero atoms, or preferably 1 to 3 hetero atoms, and the other atom on the ring is carbon; the polyheteroaryl ring includes at least one hetero atom selected from N, O or S, for example, 1 to 4 hetero atoms, or preferably 1 to 3 hetero atoms, and other atoms on the ring is carbon and at least one of the heteroatoms is on the aromatic ring. Particularly preferred heteroaryl groups are $C_{3-10}$ heteroaryl groups including, but not limited to, pyrrolyl, furyl, thienyl, pyridyl, pyranyl, pyrazolyl, pyrimidinyl, pyridazinyl, pyrazinyl, imidazolyl, thiazolyl, oxazolyl, isoxazolyl, triazolyl, indolyl, benzofuranyl, benzothiazolyl, benzimidazolyl, benzopyrazolyl, benzotriazolyl, carbazolyl, quinolyl, isoquinolinyl, purinyl and the similar groups.

However, in any case, the heteroaryl group and the aryl group do not cross each other or contain each other. Thus, according to the above definition, if at least one all-carbon aromatic ring is fused to a heterocyclic group, a heteroaryl group is obtained instead of an aryl group.

"Cycloalkyl" means a saturated or unsaturated cyclic group without aromaticity. According to the particular level of saturation, the terms "cycloalkyl", "cycloalkenyl" or "cycloalkynyl" are employed, respectively. Representative cycloalkyl groups include, but are not limited to, cyclopropane, cyclobutane, cyclopentane, cyclohexane or cyclohexene, and the like. Specifically, the cycloalkyl group may be a $C_{3-10}$ cycloalkyl group such as a $C_{3-6}$ cycloalkyl group.

"Heterocycloalkyl" means a saturated or unsaturated cyclic group without aromaticity, and wherein one or more of the carbon atoms (and the attached hydrogen atoms) may be substituted with the same or different hetero atom and the corresponding hydrogen atom, respectively. Representative heteroatoms that substitute carbon atoms include, but are not limited to, N, P, O, S, and Si. The terms "heterocycloalkyl" or "heterocyclenyl" are used, respectively when it is necessary to describe the particular degree of saturation. Representative heterocycloalkyl groups include, but are not limited to, epoxy compounds, imidazolidines, morpholine, piperazine, piperidine, pyrazolidine, pyrrolidine, quinuclidine, tetrahydrofuran or tetrahydropyran, and the like. The substituted heterocycloalkyl group also includes a ring system substituted with at least one oxygen-containing (=O) or oxide (—O—) substituent, such as piperidine-nitrogen-oxide, morpholinyl-nitrogen-oxide, 1-oxo-1-thiomorpholinyl and 1-dioxy-1-thiomorpholinyl.

However, in any case, the heterocycloalkyl group and the cycloalkyl group do not cross each other or contain each other. Thus, according to the above definition, if at least one carbocyclic ring is fused to a heterocycloalkyl group to form a di-, poly- or spiro-ring, it will still be defined as a heterocycloalkyl group.

"Halogen" means fluorine (F), chlorine (Cl), bromine (Br) or iodine (I). Preferred halogen means fluorine, chlorine and bromine.

"Halo" means a fluoro, chloro, bromo or iodo group.

"Substituted" means that one or more hydrogen atoms in a group are each substituted with the same or different substituents. Representative substituents include, but are not limited to, halogen, amino, hydroxy, oxo, carbonyl, cyano, alkyl, alkoxy, aryl, cycloalkyl, heterocyclyl, heteroaryl, alkylpiperazine, morpholinyl. In some embodiments, the substituents include, but are not limited to, halogen, amino, hydroxy, cyano, cyclopropyl, phenyl, dimethylamino,

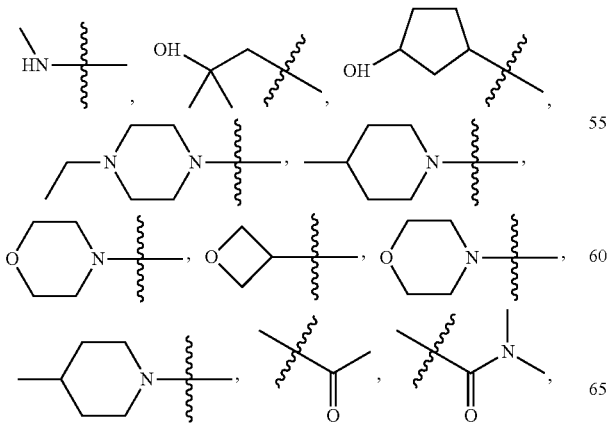

-continued

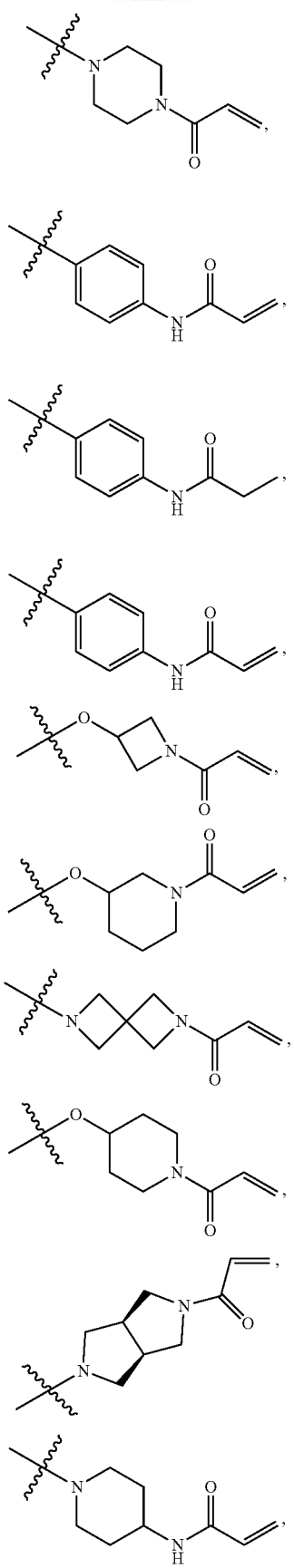

-continued

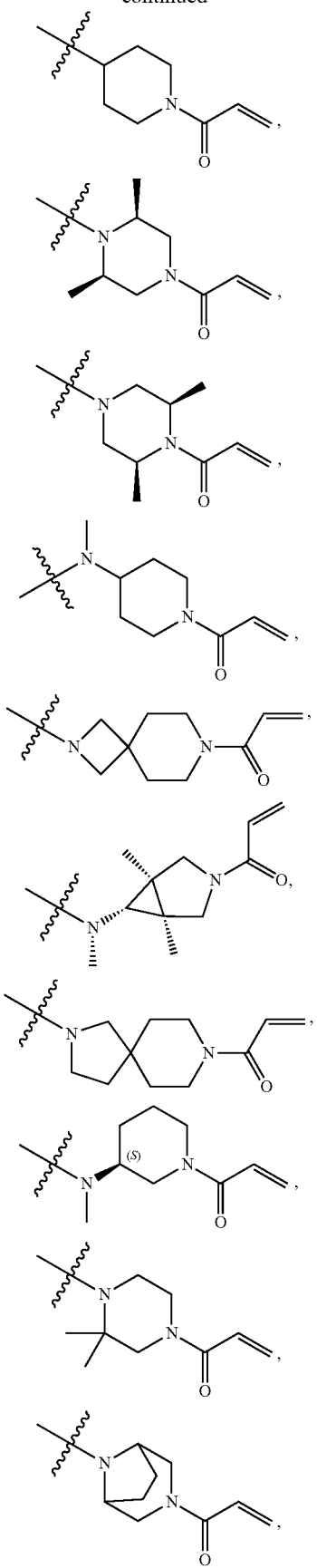

-continued

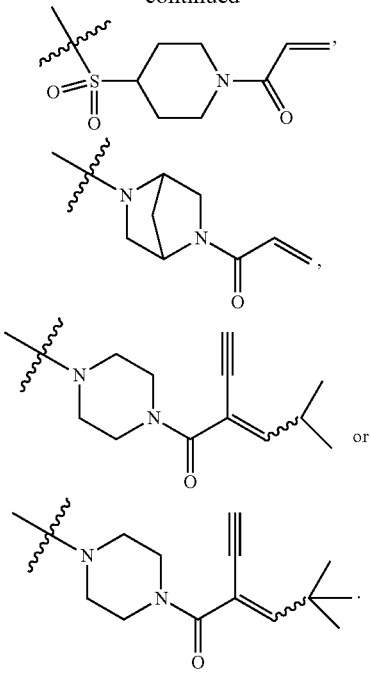

The "*" in the substituent of

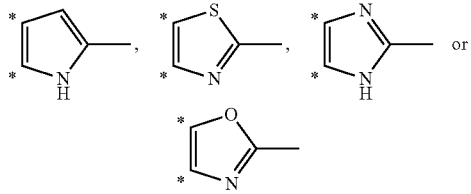

represents a site where the ring is attached to an adjacent ring.

Whenever, the term "alkyl" or "aryl" or its prefix root appears in the name of a substituent (such as an aralkyl group, or a dialkylamino group), the substituents should be defined according to the aforementioned "alkyl" and "aryl". The specified number of carbon atoms (e.g., $C_{1-6}$) will independently represent the number of carbon atoms in an alkyl moiety or an alkyl moiety in a larger substituent (wherein the alkyl group is the prefix root).

"Compound" as used herein includes a compound of Formula (I), and all pharmaceutically acceptable forms thereof. These pharmaceutically acceptable forms include salts, solvates, non-covalent complexes, chelates or prodrugs thereof, or any mixture of all of the above.

"Pharmaceutically acceptable" means well-known for use in animals, particularly for use in humans.

The term "composition" as used in the present disclosure includes products comprising a specific amount of a particular component, as well as any product derived directly or indirectly from a particular quantity of a particular component. Therefore, a pharmaceutical composition comprising the compound of the present disclosure as an active ingredient and a method of preparing the same are the contents of the present disclosure.

"Therapeutically effective amount" means that when a compound is administered to a subject to treat and prevent and/or inhibit at least one clinical condition of a disease, condition, symptom, indication, and/or discomfort, a dose sufficient to produce a certain effect on the treatment of disease, condition, symptom, indication, or discomfort. The specific "effective therapeutic amount" may vary depending on the compound, the route of administration, the age of the patient, the weight of the patient, the type of the disease or discomfort being treated, the symptoms and severity, and the like. Wherever possible, a suitable dosage will be apparent to those skilled in the art and may be determined by routine experimentation.

The compounds of the present disclosure may also be present in the form of pharmaceutically acceptable salts. For use in medicine, the salts of the compounds of the present disclosure refer to non-toxic "pharmaceutically acceptable salts". The pharmaceutically acceptable salt forms include pharmaceutically acceptable acidic/anionic or basic/cationic salts. The pharmaceutically acceptable acidic/anionic salt generally takes a form in which the basic nitrogen is protonated with an inorganic or organic acid. Representative organic or inorganic acids include hydrochloric, hydrobromic, hydriodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benzenesulfonic, oxalic, pamoic, 2-naphthalenesulfonic, p-toluenesulfonic, cyclohexanesulfamic, salicyclic, saccharinic or trifluoroacetic. Pharmaceutically acceptable basic/cationic salts include and are not limited to aluminum, calcium, chloroprocaine, choline, diethanolamine, ethylenediamine, lithium, magnesium, potassium, sodium and zinc.

The present disclosure includes within its scope the prodrugs of the compounds of the present disclosure. In general, such prodrugs will be functional derivatives of the compounds that are readily converted in vivo into the required compound. Thus, in the methods of treatment of the present disclosure, the term "administering" shall encompass the treatment of the various disorders described with the compound specifically disclosed or with a compound which may not be specifically disclosed, but which converts to the specified compound in vivo after administration to the subject. Conventional procedures for the selection and preparation of suitable prodrug derivatives are described, for example, in "Design of Prodrugs", ed. H. Bundgaard, Elsevier, 1985.

It is intended that the definition of any substituent or variable at a particular location in a molecule be independent of its definitions elsewhere in that molecule. It is understood that substituents and substitution patterns on the compounds of the present disclosure can be selected by one of ordinary skill in the art to provide compounds that are chemically stable and that can be readily synthesized by techniques know in the art as well as those methods set forth herein.

When the compound of Formula (I) and pharmaceutically acceptable salts thereof exist in the form of solvates or polymorphic forms, the present disclosure includes any possible solvates and polymorphic forms. A type of a solvent that forms the solvate is not particularly limited so long as the solvent is pharmacologically acceptable. For example, water, ethanol, propanol, acetone or the like can be used.

The term "pharmaceutically acceptable salts" refers to salts prepared from pharmaceutically acceptable non-toxic bases or acids. When the compound of the present disclosure is acidic, its corresponding salt can be conveniently prepared from pharmaceutically acceptable non-toxic bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Particularly preferred are the ammonium, calcium, magnesium, potassium, and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N',N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like.

When the compound of the present disclosure is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, formic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Preferred are citric, hydrobromic, formic, hydrochloric, maleic, phosohoric, sulfuric and tartaric acids. Particularly preferred are formic and hydrochloric acid. Since the compounds of Formula (I) are intended for pharmaceutical use they are preferably provided in substantially pure form, for example at least 60% pure, more suitably at least 75% pure, especially at least 98% pure (% are on a weight for weight basis).

The pharmaceutical compositions of the present disclosure comprise a compound represented by Formula I (or a pharmaceutically acceptable salt thereof) as an active ingredient, a pharmaceutically acceptable carrier and optionally other therapeutic ingredients or adjuvants. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administrated. The pharmaceutical compositions may be conveniently presented in unit dosage form and prepared by any of the methods well known in the art of pharmacy.

In practice, the compounds represented by Formula I, or a prodrug, or a metabolite, or pharmaceutically acceptable salts thereof, of the present disclosure can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). Thus, the pharmaceutical compositions of the present disclosure can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion, or as a water-in-oil liquid emulsion. In addition to the common dosage forms set out above, the compound represented by Formula I, or a pharmaceutically acceptable salt thereof, may also be administered by controlled release means and/or delivery devices. The compositions may be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical composition of the present disclosure may include a pharmaceutically acceptable carrier and a compound, or a pharmaceutically acceptable salt, of Formula I. The compounds of Formula I, or a pharmaceutically acceptable salt thereof, can also be included in pharmaceutical compositions in combination with one or more other therapeutically active compounds.

The pharmaceutical carrier employed can be, for example, a solid, liquid, or gas. Examples of solid carriers include lactose, gypsum powder, sucrose, talc, gelatin, agar, pectin, acacia, magnesium stearate, stearic acid, mannitol, sorbitol, microcrystalline cellulose, inorganic salts, starch, pregelatinized starch, powdered sugar and the like. Examples of liquid carriers are sugar syrup, peanut oil, olive oil, and water. Examples of gaseous carriers include carbon dioxide and nitrogen. In preparing the compositions for oral dosage form, any convenient pharmaceutical media may be employed. For example, water, glycols, oils, alcohols, flavoring agents, preservatives, coloring agents, and the like may be used to form oral liquid preparations such as suspensions, elixirs and solutions; while carriers such as starches, sugars, microcrystalline cellulose, diluents, granulating agents, lubricants, binders, disintegrating agents, and the like may be used to form oral solid preparations such as powders, capsules and tablets. Because of their ease of administration, tablets and capsules are the preferred oral dosage units whereby solid pharmaceutical carriers are employed. Optionally, tablets may be coated by standard aqueous or nonaqueous techniques.

A tablet containing the compounds or composition of the present disclosure may be prepared by compression or molding, optionally with one or more accessory ingredients or adjuvants. Compressed tablets may be prepared by compressing, in a suitable machine, the active ingredient in a free-flowing form such as powder or granules, optionally mixed with a lubricant, inert diluent, surface active or dispersing agent. Molded tablets may be made by molding in a suitable machine, a mixture of the powdered compound or composition moistened with an inert liquid diluent. Each tablet preferably contains from about 0.01 mg to about 5 g of the active ingredient and each cachet or capsule preferably containing from about 0.1 mg to about 0.5 g of the active ingredient. For example, a formulation intended for the oral administration to humans may contain from about 0.1 mg to about 0.5 g of active agent, compounded with an appropriate and convenient amount of carrier material which may vary from about 5 to about 99.99 percent of the total composition. Unit dosage forms will generally contain between from about 0.1 mg to about 0.5 g of the active ingredient, typically 0.1 mg, 0.2 mg, 0.5 mg, 1 mg, 2 mg, 2.5 mg, 5 mg, 10 mg, 25 mg, 50 mg, 100 mg, 200 mg, 300 mg, 400 mg or 500 mg.

Pharmaceutical compositions of the present disclosure suitable for parenteral administration may be prepared as solutions or suspensions of the active compounds in water. A suitable surfactant can be included such as sodium lauryl sulfate, polysorbate-80 (Tween-80), polyoxyethylene hydrogenated castor oil, poloxamer. Dispersions can also be prepared in glycerol, liquid polyethylene glycols, and mixtures thereof in oils. Further, a preservative can be included to prevent the detrimental growth of microorganisms.

Pharmaceutical compositions of the present disclosure suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacterial and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present disclosure can be in a form suitable for topical use such as, for example, an aerosol, cream, ointment, lotion, dusting powder, or the like. Further, the compositions can be in a form suitable for use in transdermal devices. These formulations may be prepared, utilizing a compound represented by Formula I of the present disclosure, or a pharmaceutically acceptable salt thereof, via conventional processing methods. As an example, a cream or ointment is prepared by admixing hydrophilic material and water, together with about 5 wt % to about 50 wt % of the compound, to produce a cream or ointment having a desired consistency.

Pharmaceutical compositions of the present disclosure can be in a form suitable for rectal administration wherein the carrier is a solid. It is preferable that the mixture forms unit dose suppositories. Suitable carriers include cocoa butter and other materials commonly used in the art. The suppositories may be conveniently formed by first admixing the composition with the softened or melted carriers followed by chilling and shaping in molds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including antioxidants) and the like. Furthermore, other adjuvants can be included to render the formulation isotonic with the blood of the intended recipient. Compositions containing a compound described by Formula I, or a pharmaceutically acceptable salts thereof, may also be prepared in powder or liquid concentrate form.

DETAILED DESCRIPTION

Figure 1:
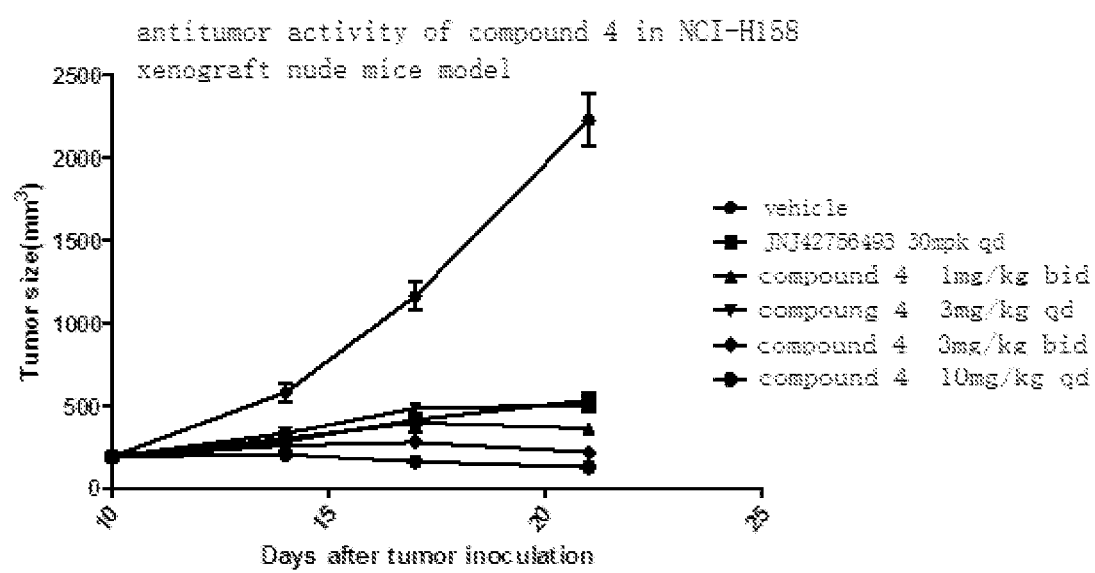
FIG. 1: Inhibition curve of compound 4 in human NCI-H1581 cell line xenograft nude mice; abscissa represents the number of days after inoculation of NCI-H1581 cells, and ordinate represents tumor volume.

The present disclosure is further exemplified, but not limited, by the following examples that illustrate the present disclosure. In the examples of the present disclosure, the techniques or methods, unless expressly stated otherwise, are conventional techniques or methods in the art.

Unless otherwise indicated, all parts and percentages of the present disclosure are by weight, the temperature are measured in degrees Celsius (CC).

The following abbreviations have been used in the examples:

BuN₄F-THF: Tetrabutylammonium fluoride-tetrahydrofuran solution;
2-BuOH: Secondary butanol;
CH₃CN: Acetonitrile;
DCM: Dichloromethane;
DIEA: N,N-diisopropylethylamine;
DMF: N,N-dimethylformamide;
DMF-DMA: N,N-dimethylformamide dimethyl acetal;
DMSO: Dimethyl sulfoxide;
EA: Ethyl acrylate;
EtOH: Ethanol;
h, hr or hrs: hour;
HATU: 2-(7-oxobenzotriazole)-N,N,N',N'-tetramethyluron hexafluorophosphate;
hex or Hex: Hexane;
HOAc: acetic acid;
i-PrOH: Isopropanol;
KOAc: Potassium acetate;
LiAlH4: Lithium tetrahydrogen aluminum;
m-CPBA: M-chloroperoxybenzoic acid;
MeOH: Methanol;
MeONa: Sodium methoxide;
min or mins: minutes;
NCS: N-chlorosuccinimide;
NMP: N-methylpyrrolidone;
Pd(dppf)Cl₂: [1,1'-bis(diphenylphosphino)ferrocene]palladium dichloride;
rt or RT: room temperature;
SEMCl: 2-(trimethylsilyl)ethoxymethyl chloride;
TBAI: Tetrabutylammonium iodide;
t-BuOK: Potassium tert-butoxide;
TEA: Triethylamine;
TFA: Trifluoroacetate;
TFAA: Trifluoroacetic anhydride;
THF: Tetrahydrofuran;
TMSCl: Trimethylchlorosilane;
TMSCN: Trimethylcyanosilane;
xantPhos: 4,5-bis-diphenylphosphino-9,9-dimethyloxazepine.

Preparation of Intermediate M1

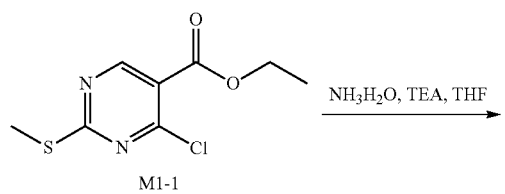

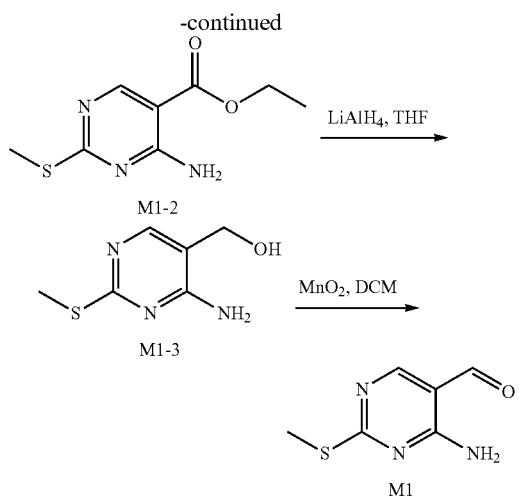

Step 1: Preparation of Compound M1-2

500 g of compound M1-1, 651 g of TEA and 782 ml of aqueous ammonia (25%) were dissolved in 2.4 L of THF and stirred at RT for 12 hrs. The reaction mixture was diluted with water, extracted with EA, washed with water, and then dried with anhydrous Na₂SO₄. The precipitate was collected by vacuum concentration to obtain M1-2 (yield: 98.3%), it was used for the next step directly without purification.
LC-MS [M+H⁺]214.

Step 2: Preparation of Compound M1-3

Under nitrogen at −20° C., 250 g of compound M1-2 was dissolved in 2 L of THF and to which 570 ml of LiAlH₄ (2.5N, suspended in THF) was added with stirring. The reaction mixture was stirred at −10° C. for 3 hrs, 50 ml of water was added to the reaction solution to terminate the reaction, below 15° C., 50 ml of 15% NaOH solution was added with stirring, 150 ml of water was added then. Filtration was to collect solid, the solid was washed with EA, the filtrate was collected and concentrated under reduced pressure to yield 180 g of compound M1-3 (yield: 89.7%). It was used for the next step directly without purification.
LC-MS [M+H⁺] 172.1.

Step 3: Preparation of Compound M1

A mixture of 320 g of M1-3, 1465 g of MnO₂ and 3 L of DCM was stirred for 12 hrs at RT, filtration was to collect solid, the solid was washed with DCM, the filtrate was collected and concentrated under reduced pressure to yield 261 g of compound M1 (yield: 82.5%). It was used for the next step directly without purification.
LC-MS [M+H⁺] 170.0.

Preparation of Intermediate M2

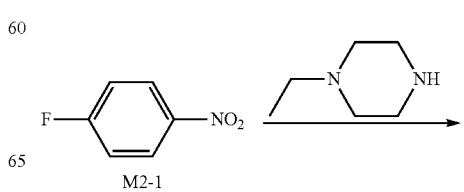

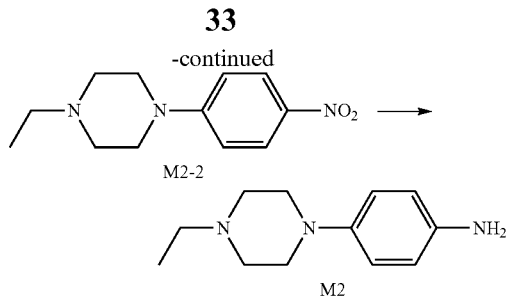

Step 1: Preparation of Compound M2-2

A mixture of 20 g of M2-1, 19 g of 1-ethylpiperazine, 39 g of $K_2CO_3$ and 100 mL of DMF was stirred for 12 hrs at RT. The reaction mixture was added in 250 ml of water, the reaction was continued for 1 h and then filtered. The solid was washed with water and evaporated to dryness to give 30 g of M2-2 (yield: 90.0%). It was used for the next step directly without purification.

LC-MS [M+H$^+$] 236.1.

Step 2: Preparation of Compound M2

30 g of M2-2, 500 ml of methanol and 4.0 g of palladium carbon (5% Pd) was reacted for 12 hrs under the circumstance of hydrogen. Filtration was to collect solid, the solid was washed with methanol, and the filtrate was collected and concentrated under reduced pressure to yield 28.9 g of crude product M2, which is brown solid. It was used for the next step directly without purification.

LC-MS [M+H$^+$] 206.2.

Preparation of Intermediate M3

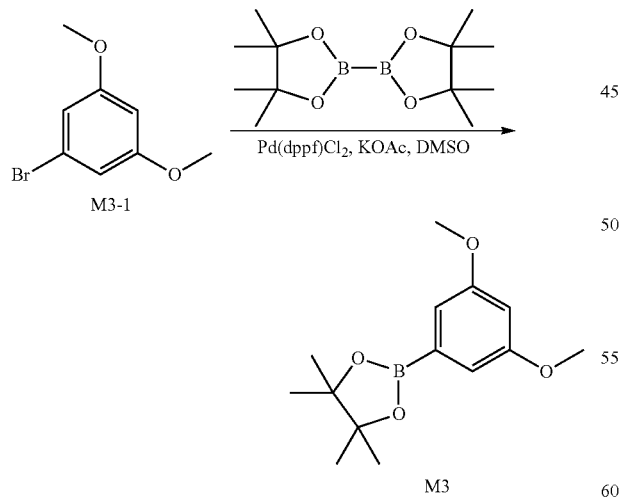

1 g of M3-1, 1.4 g of benzoic acid pinacol ester, 337 mg of Pd(dppf)Cl$_2$, 903 mg of CH$_3$COOK and 20 ml of DMSO was reacted for 2 hrs under nitrogen at 100° C. The reaction mixture was diluted with water, extracted with hexane, washed with water, dried over anhydrous Na$_2$SO$_4$ and concentrated under reduced pressure to give 1.4 g of crude product M3, which is white solid. It was used for the next step directly without purification.

LC-MS [M+H$^+$] 265.2.

Preparation of Intermediate M4

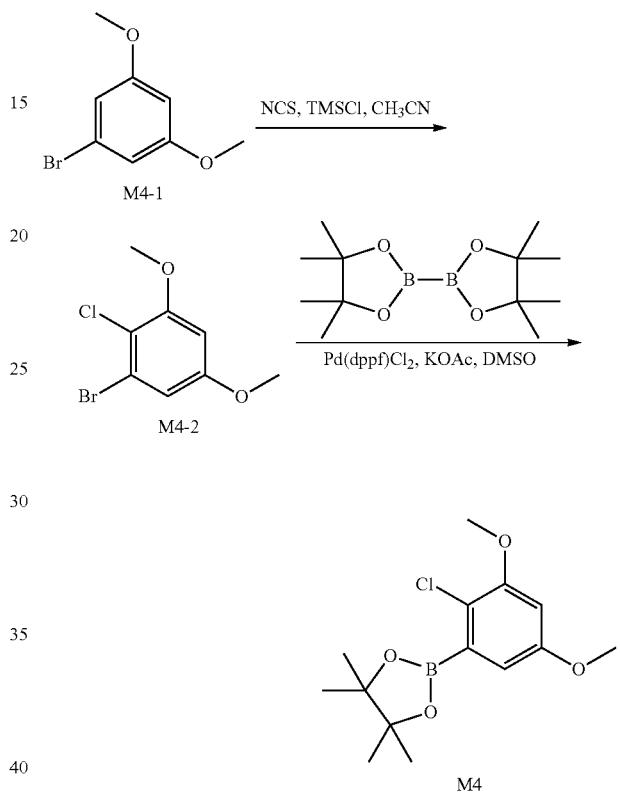

Step 1: Preparation of Compound M4-2

A mixture of 5.01 g of M4-1, 3.38 g of N-chlorosuccinimide, 50 ml of CH$_3$CN, 0.25 g of trimethylchlorosilane was stirred for 1 h at RT. The reaction was terminated with water, extracted with EA, washed with water, dried over anhydrous Na$_2$SO$_4$ and concentrated under reduced pressure to give 6.21 g of crude product M4-2, which is white solid. It was used for the next step directly without purification.

Step 2: Preparation of Compound M4

A mixture of 2.01 g of M4-2, 3.03 g of benzoic acid pinacol ester, 580 mg of Pd(dppf)Cl$_2$, 1.56 g of CH$_3$COOK and 20 ml of 1,4-dioxane was stirred for 12 hrs under nitrogen at 80° C. The reaction mixture was diluted with water, extracted with Hexane, washed with water, dried over anhydrous Na$_2$SO$_4$ and concentrated under reduced pressure to give 2.5 g of crude product M4, which is white solid. It was used for the next step directly without purification.

LC-MS [M+H$^+$] 299.1.

Preparation of Intermediate M5

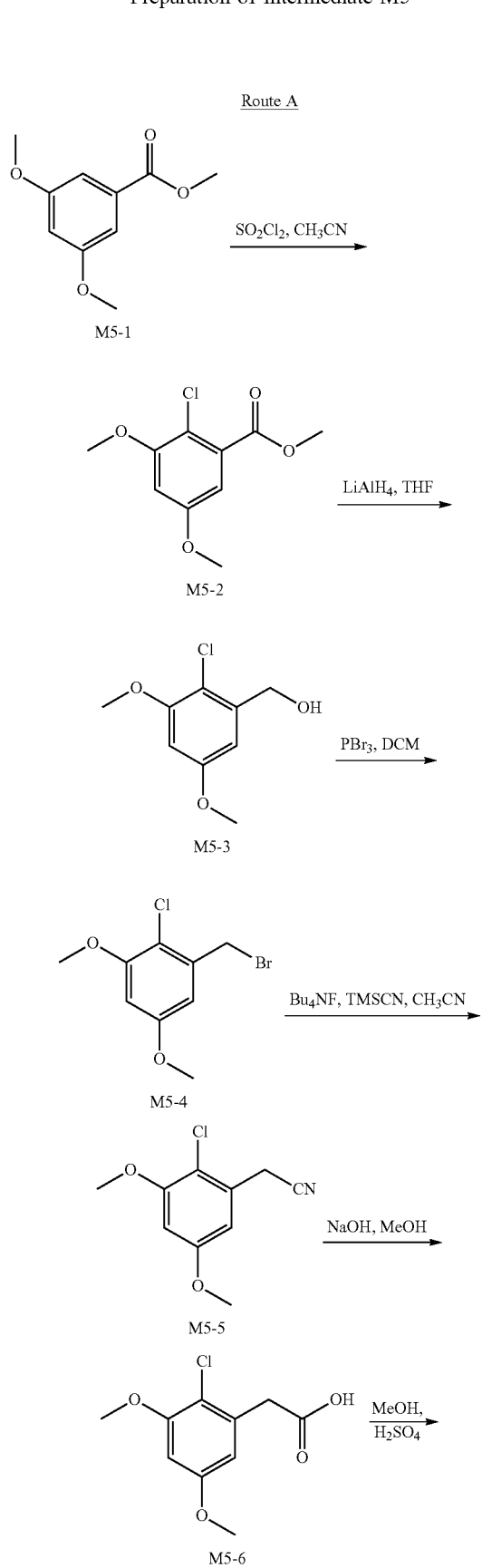

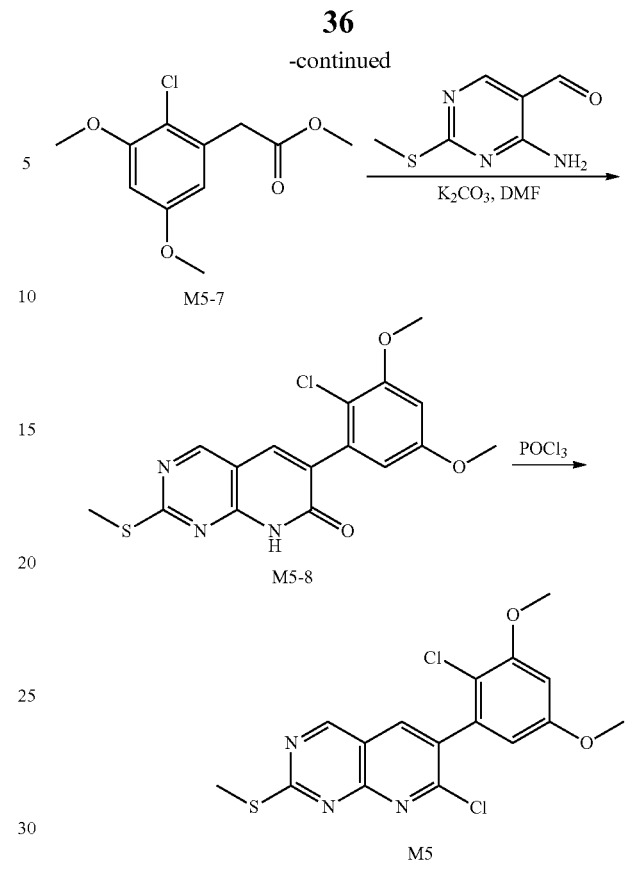

Step 1: Preparation of Compound M5-2

Under the circumstance of nitrogen at −10° C., 86 g of $SO_2Cl_2$ was slowly added to a solution of 100 g of M5-1 dissolved in 1000 ml of $CH_3CN$. The reaction was maintained below 0° C. and stirred for 90 mins. The reaction was terminated with water at 0° C. and adjusted the pH to 7-8 with 10% NaOH solution. The reaction mixture was extracted with EA, washed with water, dried over anhydrous $Na_2SO_4$ and concentrated under reduced pressure to give 129.5 g of crude product M5-2, which is white solid. It was used for the next step directly without purification.

LC-MS [M+H$^+$] 231.0.

Step 2: Preparation of Compound M5-3

Under the circumstance of nitrogen at −0° C., 24 ml of LiAlH4 (2.5N, suspended in THF) was slowly added to a solution of 129.5 g of M5-2 dissolved in 1.2 L of THF with stirring. The reaction was maintained for 90 mins at 0° C., EtOAc was added to the reaction mixture, and was stirred for 30 mins at 0° C., then to which dropwise added saturated $Na_2SO_4$. The reaction mixture was filtered, and the filtrate was washed with EA, combined the filtrate, then washed with saturated saline solution, dried over anhydrous $Na_2SO_4$ and concentrated under reduced pressure to give 168 g of crude product M5-3, which is white solid. It was used for the next step directly without purification.

Step 3: Preparation of Compound M5-4

Under the circumstance of nitrogen at −10° C., 94.7 ml of phosphorus tribromide was added to a solution of 168 g of M5-3 dissolved in 1.1 L of dichloromethane with stirring.

The reaction was maintained for 1.2 hrs at 0° C., then the reaction mixture was added to ice water and adjusted the pH to 7-8 with 10% NaOH solution. The reaction mixture was extracted with dichloromethane, washed with water, dried over anhydrous Na₂SO₄ and concentrated under reduced pressure. The residue was purified through silica column chromatography (hexane/dichloromethane=10:1) to yield 91 g of white solid of M5-4.

Step 4: Preparation of Compound M5-5

15.23 g of M5-4 and 11.38 g of trimethylcyanosilane were dissolved in 150 ml of CH₃CN, then to which dropwise added 114.7 ml 1.0N of BuN₄F-THF under 20° C. The reaction was maintained for 30 mins at 70° C. The reaction mixture was warmed to room temperature and quenched with water. Filtration was to collect solid, the solid was washed with water and evaporated to dryness to give 11.22 g white solid of M5-25 (yield: 92.4%).

Step 5: Preparation of Compound M5-6

A mixture of 11.22 g of M5-5, 10.60 g of NaOH, 100 ml of methanol and 150 ml of water was refluxed for 3 hrs. The reaction solution was concentrated under reduced pressure, and the residue was dissolved in water, then extracted with EA, combined the water phase, adjusted the pH to 2-3 with 1N hydrochloric acid. Filtration was to collect solid, the solid was washed with water, dried under reduced pressure to yield 8.06 g of compound M5-6, which is white solid. It was used for the next step directly without purification.
LC-MS [M+H⁺] 231.0.

Step 6: Preparation of Compound M5-7

A mixture of 8.06 g of M5-6, 80 ml of methanol and 8.0 ml of concentrated sulfuric acid was refluxed for 3 hrs. The reaction mixture was warmed to room temperature and added into ice water. The reaction mixture was extracted with EA, washed with water, dried over anhydrous Na₂SO₄ and concentrated under reduced pressure to yield 4.02 g of M5-7, which is white solid. It was used for the next step directly without purification.
LC-MS [M+H⁺] 245.1.

Step 7: Preparation of Compound M5-8

A mixture of 9.42 g of M5-7, 5.20 g of M1, 5.85 g of K₂CO₃ and 180 ml of DMF was stirred for 8 hrs at 110° C. The reaction mixture was diluted with water, extracted with EA, washed with saturated sodium chloride, dried over anhydrous Na₂SO₄ and concentrated under reduced pressure. The residue was purified through silica column chromatography (hexane/ethyl acetate=3:1) to yield 2.30 g of white solid of M5-8.
LC-MS [M+H⁺] 364.0.

Step 8: Preparation of Compound M5

A mixture of 2.71 g of M5-8 and 50 ml of phosphorus oxychloride was stirred for 3 hrs at 100° C. The reaction solution was concentrated, and most of the phosphorus oxychloride was removed. The residue was quenched with ice water and adjusted the pH to 8 with saturated NaHCO₃. The reaction mixture was extracted with EA, washed with saturated sodium chloride, dried over anhydrous Na₂SO₄ and concentrated under reduced pressure to yield 3.01 g of M5, which is white solid. It was used for the next step directly without purification.
LC-MS [M+H⁺] 382.0.

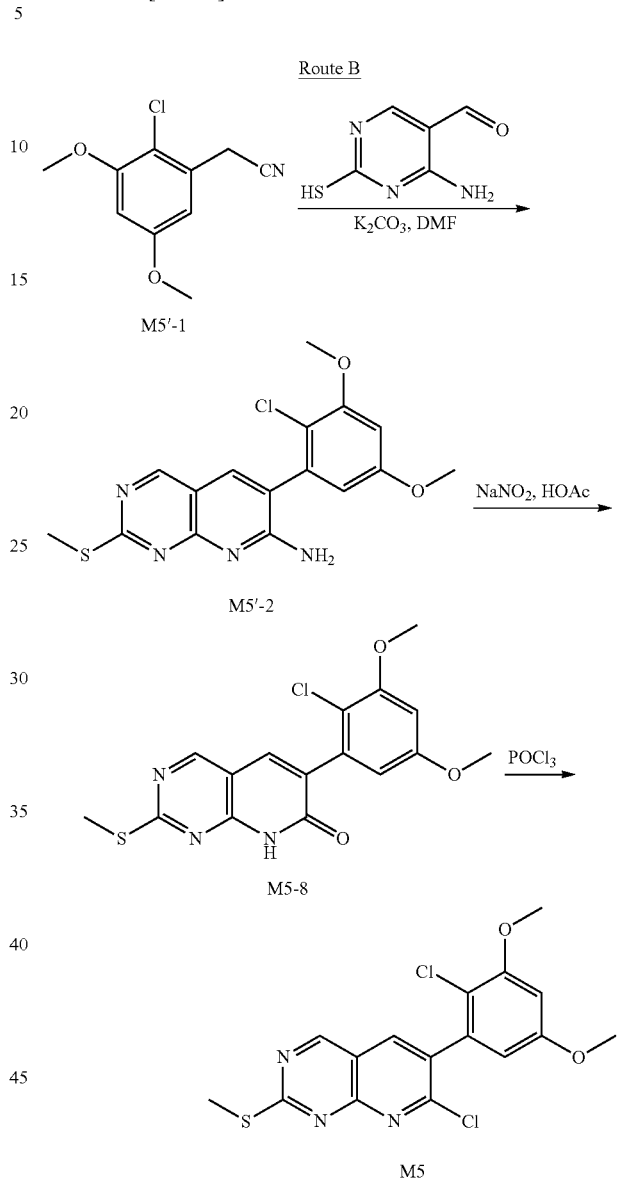

Step 1: Preparation of Compound M5'-2

A mixture of 16.77 g of M5'-1, 11.17 g of M1, 27.33 g of K₂CO₃ and 150 ml of DMF was stirred for 12 hrs at 110° C. The reaction mixture was warmed to room temperature and added into ice water. Filtration was to collect solid, the solid was washed with water, dried under reduced pressure to yield 17.21 g of compound M5'-2, which is yellow solid. It was used for the next step directly without purification.
LC-MS [M+H⁺] 363.1.

Step 2: Preparation of Compound M5-8

16.75 g of M5'-2 was dissolved into 50 ml of acetic acid, and the mixture was stirred at RT, to which 15.97 g of NaNO₂ was added in several times. The reaction mixture was stirred for 3 hrs at 70° C., cooled down to RT, and added into ice water. Filtration was to collect solid, the solid was washed with water, dried under reduced pressure to yield 15.21 g of compound M5-8, which is light yellow solid.

LC-MS [M+H$^+$] 364.0.

Step 3: Preparation of Compound M5

The preparation is similar to step 8 of route A in M5.

Preparation of Intermediate M6

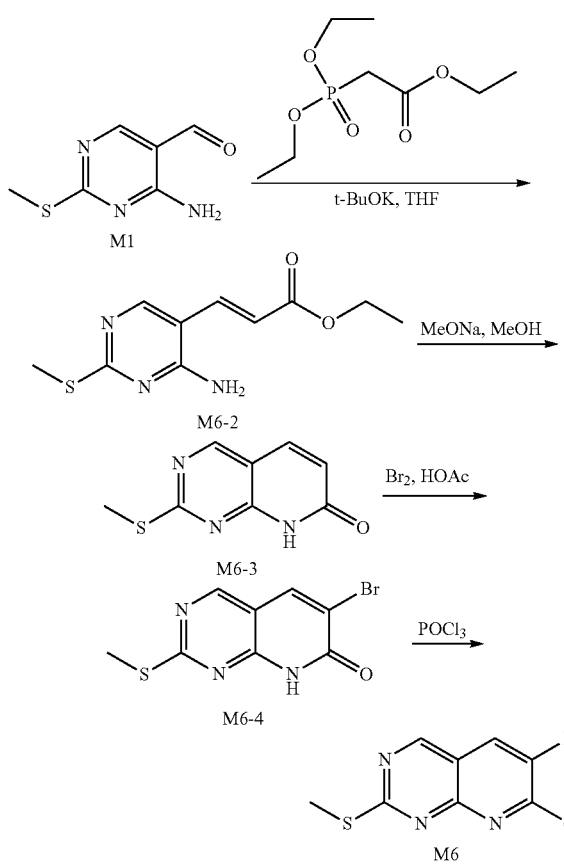

Step 1: Preparation of Compound M6-2

Under the circumstance of nitrogen at 0° C., 16 g of triethyl phosphonoacetate was added to a solution of 8.6 g of t-BuOK dissolved in 300 mL of THF with stirring. The reaction was maintained for 1 hr at this temperature. 10 g of M1 was added into the reaction solution in several times at 0° C. and was stirred for 12 hrs at RT. The reaction was quenched with water, extracted with EA, washed with water, dried over anhydrous Na$_2$SO$_4$ and concentrated under reduced pressure to yield 14 g of crude product M6-2, which is white solid. It was used for the next step directly without purification.

LC-MS [M+H$^+$] 240.1.

Step 2: Preparation of Compound M6-3

14 g of M6-2, 200 ml of methanol and 6.3 g of sodium methoxide was dissolved into 21 ml of methanol, the mixture was refluxed for 4 hrs. The solvent was removed by reduce pressure, the residue was suspended in 200 ml of water, and adjusted the pH to 8 with 2N hydrochloric acid solution. Filtration was to collect solid, the solid was washed with water, dried under reduced pressure to yield 9 g of crude product M6-3, which is white solid. It was used for the next step directly without purification.

LC-MS [M+H$^+$] 194.0.

Step 3: Preparation of Compound M6-4

A mixture of 9 g of M6-3, 300 ml of acetic acid and 4.8 ml of liquid bromine was stirred for 12 hrs at 50° C. The reaction solution was diluted with dichloromethane, filtration was to collect solid, and the solid was washed with methanol, dried under reduced pressure to yield 12.9 g of crude product M6-4, which is grayish white solid.

LC-MS [M+H$^+$] 271.9.

Step 4: Preparation of Compound M6

A mixture of 12.9 g of M6-4 and 300 ml of POCl$_3$ was stirred for 12 hrs at 110° C., most of POCl$_3$ was removed by reduced pressure, and the residue was quenched with ice water. Filtration was to collect solid, the solid was washed with water and dried under reduced pressure to yield 13 g of crude product M6, which is white solid.

LC-MS [M+H$^+$] 289.9.

Preparation of Intermediate M7

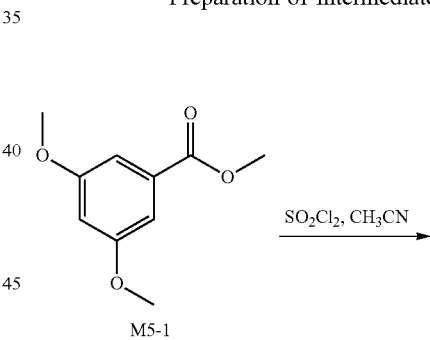

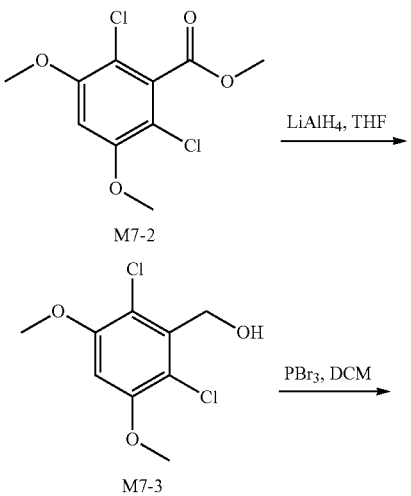

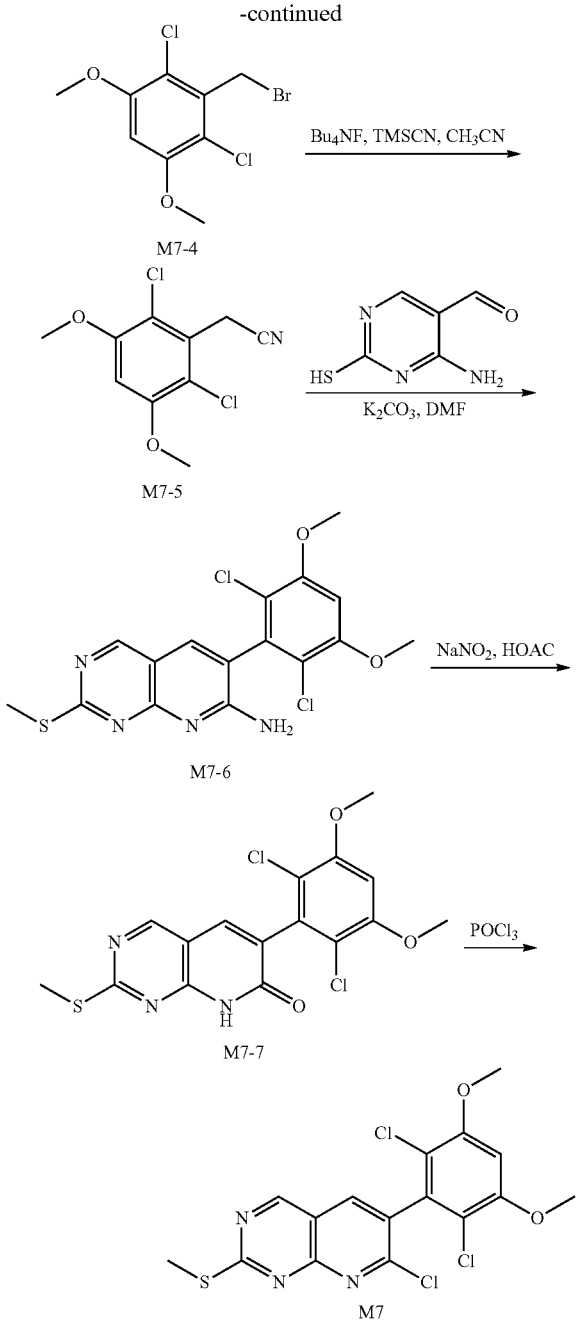

Step 1: Preparation of Compound M7-2

100 g of M5-1 was dissolved into 1000 ml of CH$_3$CN, under the circumstance of nitrogen at −10° C., to which was added 172 g of SO$_2$Cl$_2$ slowly with stirring. The reaction was maintained for 90 mins below 0° C. The reaction was quenched with water below 0° C. and adjusted the pH to 7-8 with 10% NaOH. The reaction mixture was extracted with EA, washed with water, dried over anhydrous Na$_2$SO$_4$ and concentrated under reduced pressure to yield 148.8 g of M7-2, which is white solid. It was used for the next step directly without purification.

LC-MS [M+H$^+$] 265.0.

Step 2: Preparation of Compound M7-3

149 g of M7-2 was dissolved into 1.2 L of THF, under the circumstance of nitrogen at 0° C., to which was added 224 ml 2.5N of LiAlH4-THF solution with stirring. The reaction was maintained for 90 mins at 0° C., EA was added into the reaction solution, and the reaction was maintained for 30 mins at 0° C., then to which was added saturated Na$_2$SO$_4$ solution. Filtration was to collect filtrate, the filtrate was washed with EA, and the filtrate was collected, washed with saturated sodium chloride, dried over anhydrous Na$_2$SO$_4$ and concentrated under reduced pressure to yield 196 g of crude product M7-3, which is white solid. It was used for the next step directly without purification.

Step 3: Preparation of Compound M7-4

196 g of M7-3 was dissolved into 1.1 L of dichloromethane, under the circumstance of nitrogen at −10° C., to which was added 94.7 ml of phosphorus tribromide with stirring. The mixture was stirred for 1.2 hrs at 0° C., then added into ice water, and adjusted the pH to 7-8 with 10% NaOH. The reaction mixture was extracted with dichloromethane, washed with water, dried over anhydrous Na$_2$SO$_4$ and concentrated under reduced pressure. The residue was purified through silica column chromatography (hexane/dichloromethane=10:1) to yield 100 g of white solid of M7-4.

Step 4: Preparation of Compound M7-5

17.19 g of M7-4, 11.38 g of trimethylcyanosilane and 150 ml of CH$_3$CN was formed to mixture, to which was added 114.7 ml of 1.0N BuN$_4$F-THF solution with stirring below 20° C. The reaction solution was stirred for 30 mins at 70° C., cooled down to RT and quenched with water. Filtration was to collect solid, the solid was washed with water, and dried under reduced pressure to yield 14.34 g of M7-5 (yield: 90.0%), which is white solid.

Step 5: Preparation of Compound M7-6

A mixture of 29.25 g of M7-5, 14.35 g of 4-amino-2-methylpyrimidin-5-formaldehyde, 49.20 g of K$_2$CO$_3$ and 400 ml of DMF was stirred for 12 hrs at 110° C. The reaction solution was diluted with water, filtrated, the solid was washed with water, and dried under reduced pressure to yield 31.02 g of M7-6, which is light yellow solid.

LC-MS [M+H$^+$] 397.0.

Step 6: Preparation of Compound M7-7

22.06 g of NaNO$_2$ was added to a solution of 25.41 g of M7-6 dissolved in 100 mL of acetic acid in several times with stirring at RT. The reaction solution was stirred for 3 hrs at 70° C., cooled down to RT, added to ice water, and filtrated. The solid was washed with water and dried under reduced pressure to yield 23.42 g of M7-7, which is yellow solid.

LC-MS [M+H$^+$] 398.0.

Step 7: Preparation of Compound M7

A mixture of 18.40 g of M7-7 and 100 ml of phosphorus oxychloride was stirred for 3 hrs at 100° C., the reaction solution was concentrated and most of the phosphorus oxychloride was removed. The residue was quenched with ice water and adjusted the pH to 8 with saturated NaHCO$_3$ solution. The reaction mixture was extracted with EA, washed with saturated sodium chloride, dried over anhydrous Na₂SO₄ and concentrated under reduced pressure to yield 15.01 g of M7, which is white solid, it was used for the next step directly without purification.

LC-MS [M+H⁺] 416.0.

Example 1: Preparation of 1-((6-(2-chloro-3,5-dimethoxyphenyl)-[1,2,4]triazolo[4',3':1,6]pyrido[2,3-d]pyrimidin-2-yl)amino)-2-methylpropan-2-ol

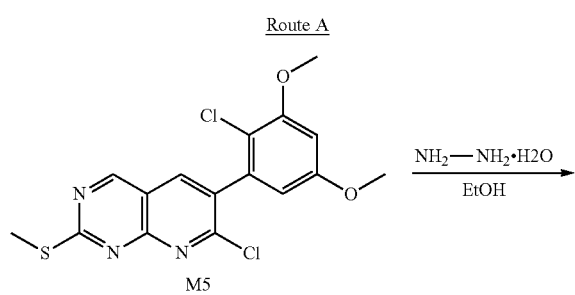

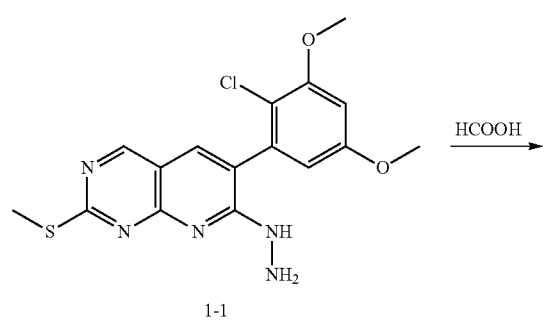

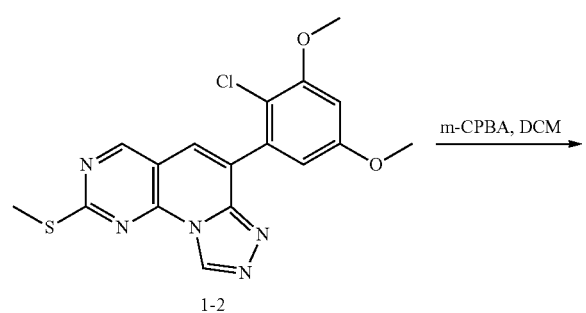

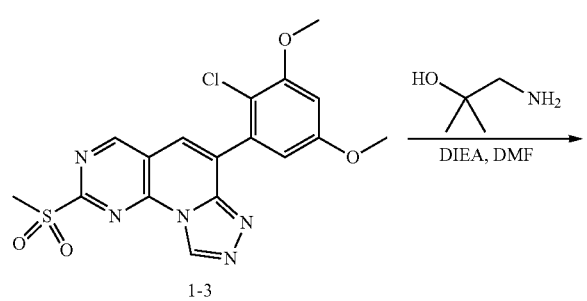

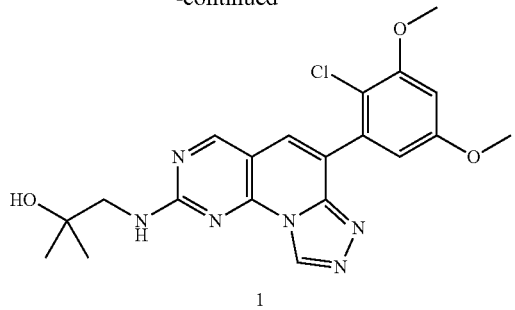

Step 1: Preparation of Compound 1-1

A mixture of 500 mg of M5, 818 mg of hydrazine (80%) and 25 ml of ethanol was refluxed for 2 hrs, and concentrated under reduced pressure to yield 520 mg of crude product 1-1, which is yellow solid, it was used for the next step directly without purification.

LC-MS [M+H⁺] 378.1.

Step 2: Preparation of Compound 1-2

A mixture of 520 mg of compound 1-1 and 25 ml of formic acid was refluxed for 1 hr. The reaction solution was diluted with water, and filtrated. The solid was washed with water to yield 310 mg of compound 1-2 (yield: 58%), which is light yellow solid.

LC-MS [M+H⁺] 388.1.

Step 3: Preparation of Compound 1-3

378 mg of m-chloroperoxybenzoic acid was added to solution of 340 mg of compound 1-2 dissolved into 40 ml of dichloromethane in several times with stirring at 0° C. The reaction solution was stirred for 2 hrs at RT, and quenched with saturated NaHCO₃ solution. The reaction mixture was extracted with dichloromethane, washed with 5% sodium thiosulfate and brine successively, dried over anhydrous Na₂SO₄ and concentrated under reduced pressure to yield 340 mg of crude product 1-3, which is light yellow solid, it was used for the next step directly without purification.

LC-MS [M+H⁺] 420.1.

Step 4: Preparation of Compound 1

A mixture of 100 mg of compound 1-3, 60 mg of 1-amino-2-methyl-2-propanol, 93 mg of DIEA and 10 ml of DMF was stirred for 2 hrs at 80° C. The reaction solution was cooled down to RT, diluted with water, then extracted with EA, washed with saturated sodium chloride, dried over anhydrous Na₂SO₄ and concentrated by reduced pressure. The residue was purified through silica column chromatography (dichloromethane/methanol=10:1) to yield 80 mg of yellow solid of compound 1 (yield: 78.3%).

LC-MS[M+H⁺] 429.1.

¹H NMR (DMSO-d6, 400 MHz) δ 9.74 (s, 1H), 9.02 (s, 1H), 7.61 (s, 1H), 6.83 (s, 1H), 6.73 (s, 1H), 3.91 (s, 3H), 3.80 (s, 3H), 3.52-3.50 (m, 2H), 3.37 (m, 2H), 1.14 (s, 6H).

Route B

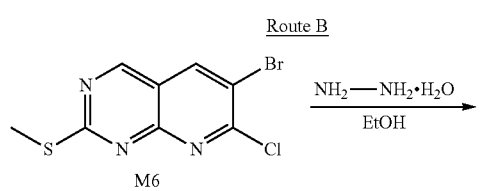

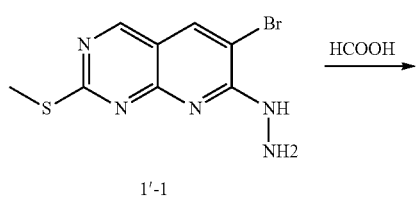

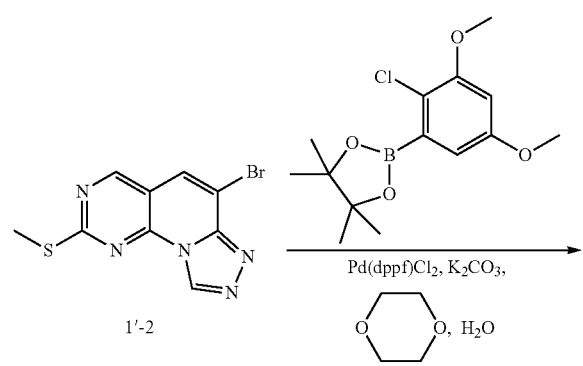

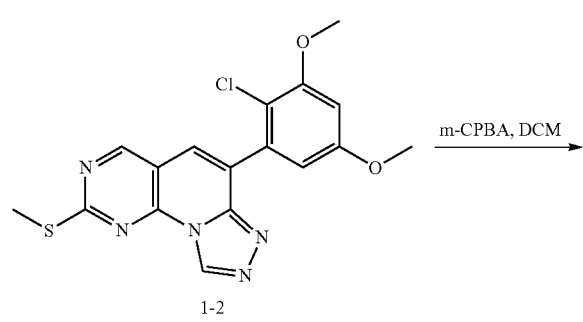

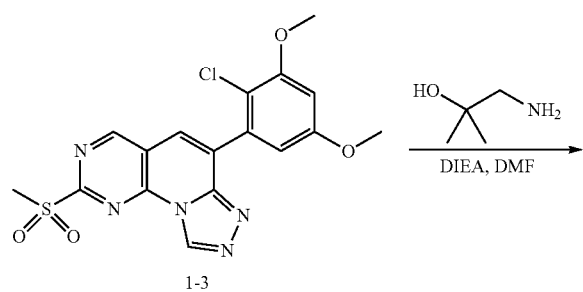

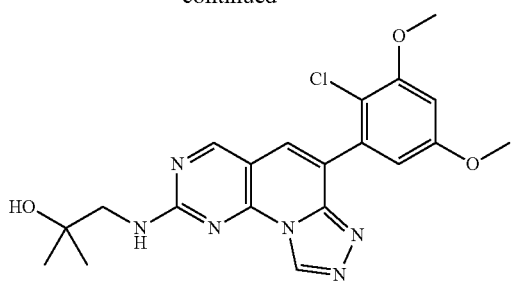

Step 1: Preparation of Compound 1'-1

A mixture of 12.5 g of M6, 200 ml of EtOH and 50 ml of hydrazine (80%) was refluxed for 2 hrs, the reaction mixture was cooled down to RT, and filtrated. The solid was washed with EtOH, and dried under reduced pressure to yield 11 g of compound 1'-1, which is grayish white solid, it was used for the next step directly without purification.

LC-MS [M+H$^+$] 286.0.

Step 2: Preparation of Compound 1'-2

A mixture of 11 g of compound 1'-1 and 100 ml of formic acid was refluxed for 3 hrs. The reaction mixture was cooled down to RT and filtrated. The solid was washed with water and dried under reduce pressure to yield 5 g of compound 1'-2, which is white solid, it was used for the next step directly without purification.

LC-MS [M+H$^+$] 296.0.

Step 3: Preparation of Compound 1-2

Under nitrogen, a mixture of 16.2 g of compound 1'-2, 24.5 g of M4, 4.0 g of Pd(dppf)Cl$_2$, 22.6 g of K$_2$CO$_3$, 320 ml of 1,4-dioxane and 32 ml of water was stirred for 12 hrs at 100° C. The reaction was concentrated under reduced pressure, and the residue was purified through silica column chromatography (DCM/EA=10:1) to yield 12 g of compound 1-2, which is grayish white solid.

LC-MS [M+H$^+$] 388.1.

Step 4: Preparation of Compound 1-3

The method was similar with the preparation of compound 1-3 of step 3 in route A for example 1.

Step 5: Preparation of Compound 1

The method was similar with the preparation of compound 1 of step 4 in route A for example 1.

Example 2 Preparation of 4-(2-chloro-3,5-dimethoxyphenyl)-N-(4-(4-ethylpiperazin-1-yl)phenyl)-[1,2,4]triazolo[1',5':1,6]pyrido[2,3-d]pyrimidin-8-amine Step 2: Preparation of Compound 2-2

A mixture of 520 mg of compound 2-1, 25 ml of isopropanol and 342 mg of DMF-DMA was refluxed for 12 hrs.

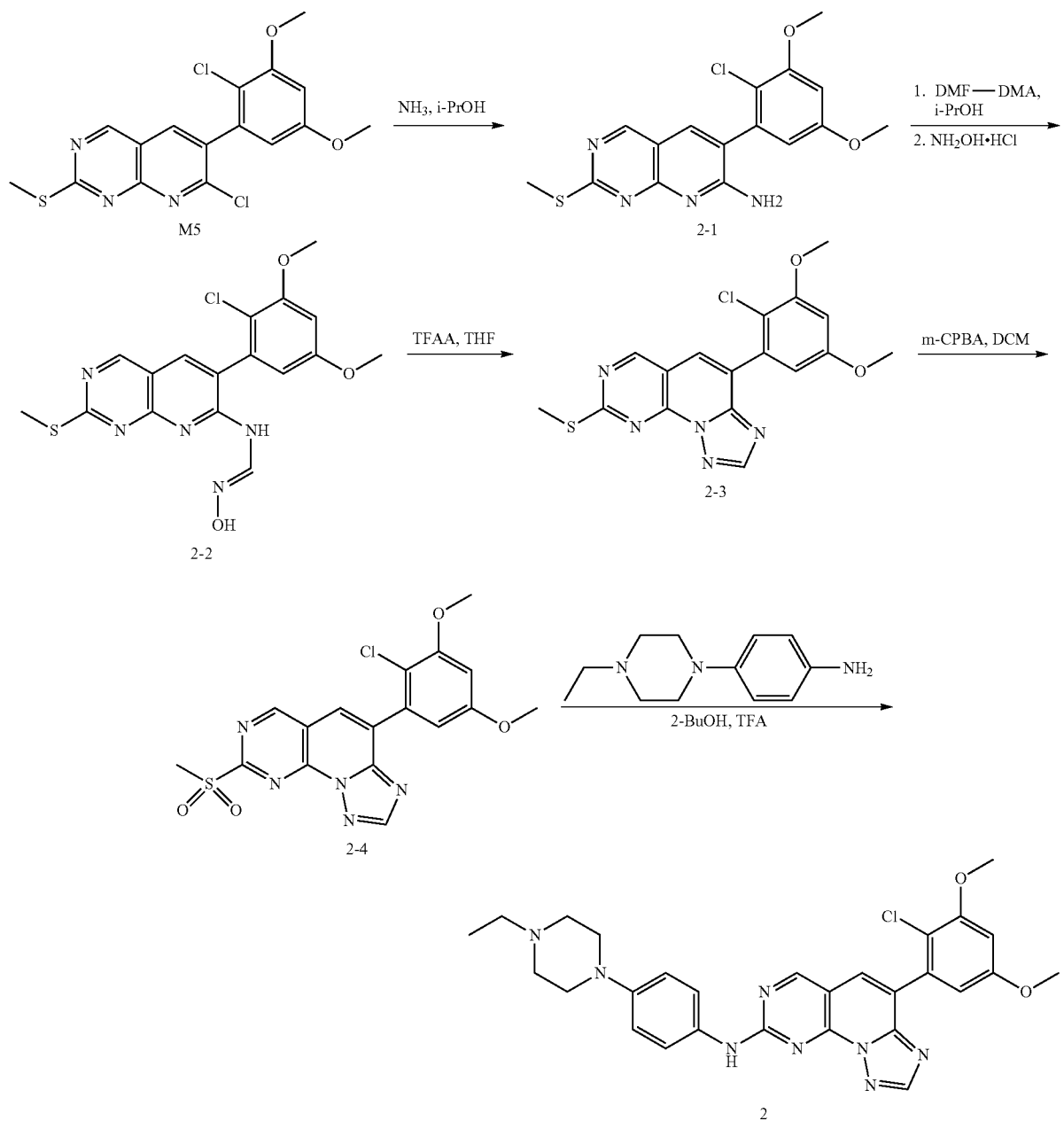

Step 1: Preparation of Compound 2-1

A mixture of 100 mg of M5, 0.37 ml of ammonia-methanol and 5 ml isopropanol was stirred for 24 hrs at 70° C. The reaction solution was concentrated under reduced pressure to yield 90 mg of crude product 2-1, which is light yellow solid, it was used for the next step directly without purification.

LC-MS [M+H$^+$] 363.1.

The reaction mixture was warmed to 50° C., then to which was added to 199 mg of hydroxylamine hydrochloride. The reaction was stirred for 12 hrs at 50° C., and cooled down to RT. Filtration was to collect solid, the solid was washed with isopropanol, and dried under reduced pressure to yield 450 mg of compound 2-2, which is yellow solid. It was used for the next step directly without purification.

LC-MS [M+H$^+$] 406.1.

Step 3: Preparation of Compound 2-3

Under the circumstance of nitrogen at 0° C., 349 mg of TFAA was added to a solution of 450 mg of compound 2-2 dissolved into 120 ml of THF. The reaction solution was stirred for 12 hrs at RT, and quenched with saturated NaHCO₃, then extracted with EA, washed with water, dried over anhydrous Na₂SO₄ and concentrated under reduced pressure. The residue was purified through silica column chromatography (hexane/ethyl acetate=10:1) to yield 450 mg of yellow solid of compound 2-3.

LC-MS [M+H⁺] 388.1.

Step 4: Preparation of Compound 2-4

A mixture of 420 mg of compound 2-3, 16 ml of dichloromethane and 281 mg of m-CPBA was stirred for 2 hrs at RT. The reaction solution was quenched with saturated NaHCO₃, then extracted with dichloromethane, washed with sodium thiosulfate and saline solution, dried over anhydrous Na₂SO₄ and concentrated under reduced pressure to yield 300 mg of compound 2-4, which is yellow solid, it was used for the next step directly without purification.

LC-MS [M+H⁺] 420.1.

Step 5: Preparation of Compound 2

A mixture of 300 mg of compound 2-4, 176 mg of M2, 5 ml of secondary butanol and 0.5 ml TFA was placed in a sealing tube and was stirred for 12 hrs at 120° C. The reaction solution was concentrated by reduce pressure, and the residue was dissolved into dichloromethane, and washed with saturated Na₂CO₃ solution and saline solution successively, dried over anhydrous Na₂SO₄ and concentrated under reduced pressure. The residue was purified through silica column chromatography (dichloromethane/methanol=50:1) to yield 290 mg of yellow solid of compound 2-3. The yield is 74.5%.

LC-MS[M+H⁺] 545.2.

¹H NMR (DMSO-d6, 400 MHz) δ 9.28 (s, 1H), 8.61 (s, 1H), 7.97 (s, 1H), 7.92-7.67 (m, 2H), 6.99 (d, J=8 Hz, 2H), 6.84 (s, 1H), 6.76 (s, 1H), 6.68-6.47 (m, 1H), 3.92 (s, 3H), 3.81 (s, 3H), 3.13 (brs, 4H), 2.53 (brs, 4H), 2.41-2.39 (m, 2H), 1.04 (t, J=6 Hz, 3H).

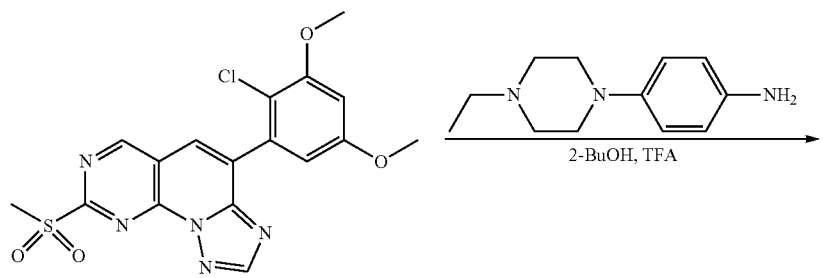

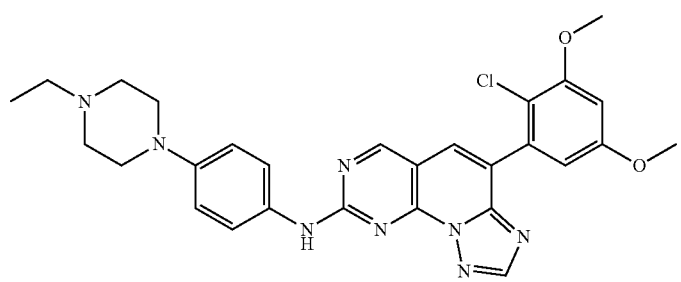

Route B

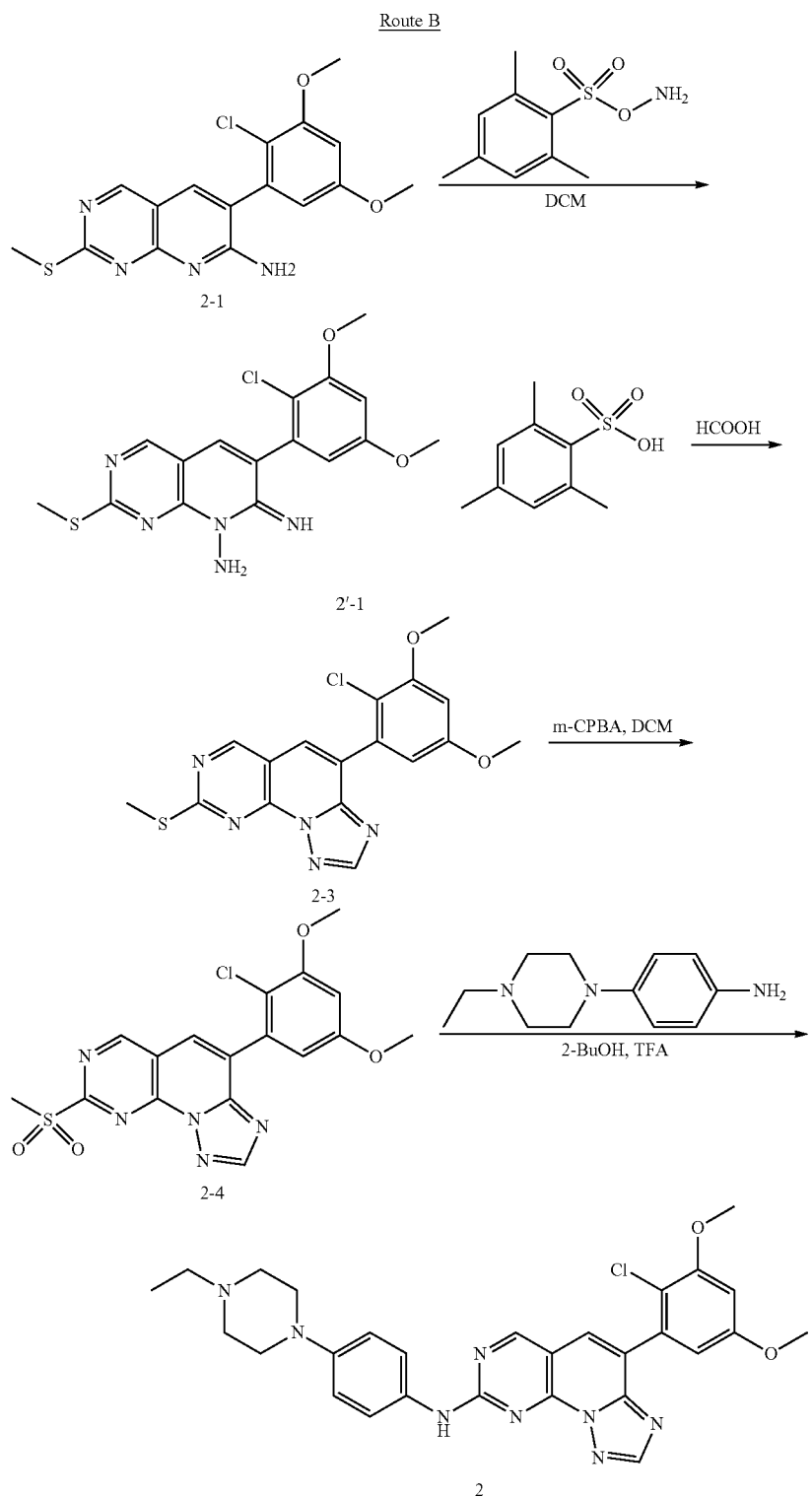

Step 1: Preparation of Compound 2'-1

3.56 g of 2-[(aminooxy)sulfonyl]-1,3,5-trimethylbenzene was dispersed in 60 mL of dichloromethane, and cooled to 0° C., to which was added 3.0 g of compound 2-1 with stirring, and naturally warmed to room temperature. The reaction was maintained overnight, when completed, the reaction system is concentrated to about 20 ml. Filtration was to collect solid, the solid was washed with little DCM twice, then dried to yield 3.5 g of compound 2'-1, which is light yellow solid, the yield is 73.2%.

LC-MS [M+H$^+$] 378.1.

Step 2: Preparation of Compound 2-3

A mixture of 600 mg of compound 2'-1 and 25 mL of formic acid was refluxed for 1 h. After completed, cooled to room temperature, and added into water with stirring, then a large number of light yellow solid was precipitated. Filtration was to collect solid, the solid was rinsed three times with water to neutral and dried under vacuum at 50° C. overnight to yield 300 mg of compound 2-3, which is light yellow solid, the yield is 74.5%.

LC-MS [M+H$^+$] 388.1.

Step 3: Preparation of Compound 2-4

The compound of 2-4 was synthesized in the same manner as in step 4 of route A using compound 2-3 as material.

LC-MS [M+H$^+$] 420.1.

Step 4: Preparation of Compound 2

The compound of 2 was synthesized in the same manner as in step 5 of route A using compound 2-4 as material.

LC-MS [M+H$^+$] 545.2.

The compounds of table 1 were prepared in a similar manner to Examples 1 and 2 via different reaction starting materials and suitable reagents.

TABLE 1

| Examples | Chemical structure | Chemical name | LC-MS [M + H$^+$] |
|---|---|---|---|
| 3 | 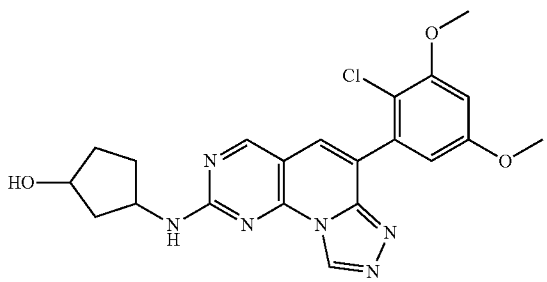 [SMILES: COc1cc(OC)c(Cl)c(-c2cc3cnc(NC4CCC(O)C4)nc3n3cnnc23)c1] | 3-((6-(2-chloro-3,5-dimethoxyphenyl)-[1,2,4]triazolo[4',3':1,6]pyrido[2,3-d]pyrimidin-2-yl)amino)cyclopentan-1-ol | 441.1 |
| 4 | 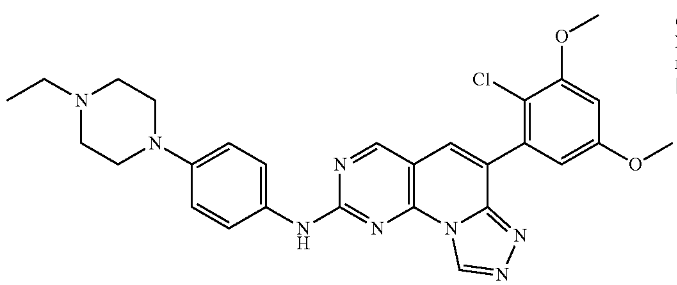 | 6-(2-chloro-3,5-dimethoxyphenyl)-N-(4-(4-ethylpiperazin-1-yl)phenyl)-[1,2,4]triazolo[4',3':1,6]pyrido[2,3-d]pyrimidin-2-amine | 545.2 |
| 5 | 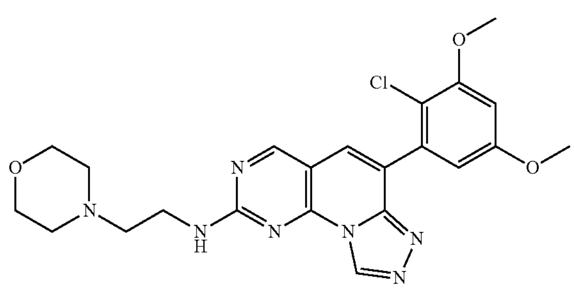 [SMILES: COc1cc(OC)c(Cl)c(-c2cc3cnc(NCCN4CCOCC4)nc3n3cnnc23)c1] | 6-(2-chloro-3,5-dimethoxyphenyl)-N-(2-morpholinoethyl)-[1,2,4]triazolo[4',3':1,6]pyrido[2,3-d]pyrimidin-2-amine | 470.2 |
| 6 | 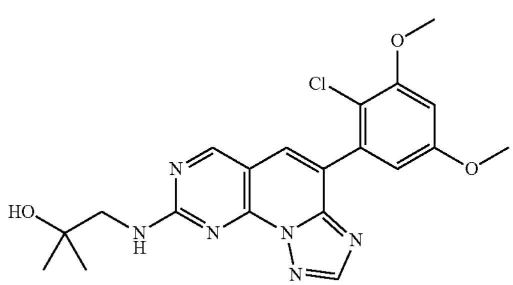 [SMILES: COc1cc(OC)c(Cl)c(-c2cc3cnc(NCC(C)(C)O)nc3n3ncnc23)c1] | 1-((4-(2-chloro-3,5-dimethoxyphenyl)-[1,2,4]triazolo[1',5':1,6]pyrido[2,3-d]pyrimidin-8-yl)amino)-2-methylpropan-2-ol | 429.1 |

TABLE 1-continued

| Examples | Chemical structure | Chemical name | LC-MS [M + H+] |
|---|---|---|---|
| 7 | 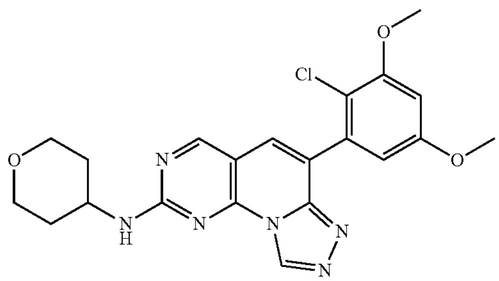 [SMILES: COc1cc(OC)c(Cl)c(-c2cc3cnc(NC4CCOCC4)nc3n3cnnc23)c1] | 6-(2-chloro-3,5-dimethoxyphenyl)-N-(tetrahydro-2H-pyran-4-yl)-[1,2,4]triazolo[4',3':1,6]pyrido[2,3-d]pyrimidin-2-amine | 441.1 |
| 8 | 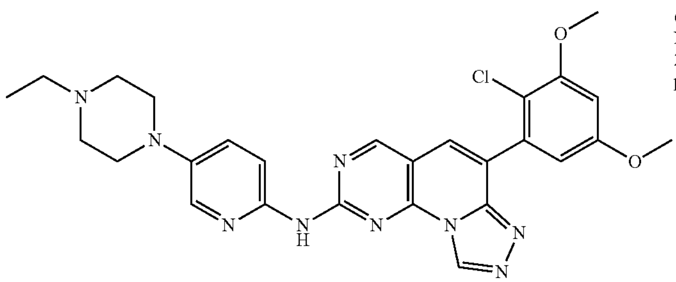 | 6-(2-chloro-3,5-dimethoxyphenyl)-N-(5-(4-ethylpiperazin-1-yl)pyridin-2-yl)-[1,2,4]triazolo[4',3':1,6]pyrido[2,3-d]pyrimidin-2-amine | 546.2 |
| 9 | 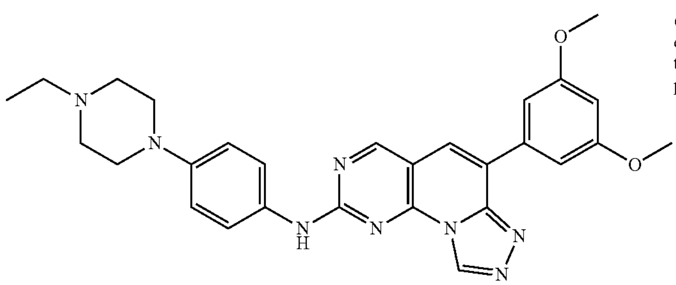 | 6-(3,5-dimethoxyphenyl)-N-(4-(4-ethylpiperazin-1-yl)phenyl)-[1,2,4]triazolo[4',3':1,6]pyrido[2,3-d]pyrimidin-2-amine | 511.3 |
| 10 | 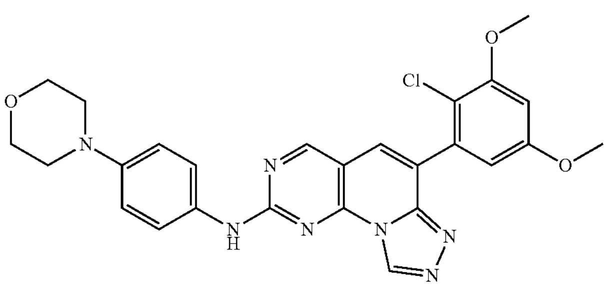 [SMILES: COc1cc(OC)c(Cl)c(-c2cc3cnc(Nc4ccc(N5CCOCC5)cc4)nc3n3cnnc23)c1] | 6-(2-chloro-3,5-dimethoxyphenyl)-N-(4-morpholinophenyl)-[1,2,4]triazolo[4',3':1,6]pyrido[2,3-d]pyrimidin-2-amine | 518.0 |
| 11 | 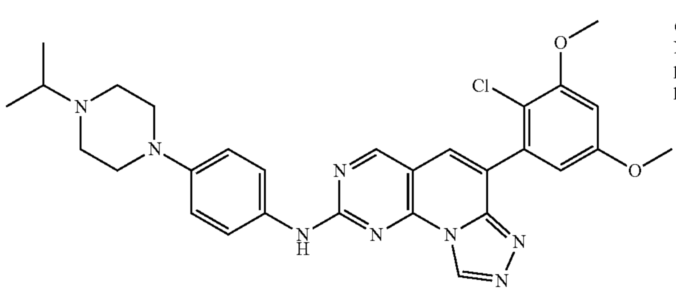 | 6-(2-chloro-3,5-dimethoxyphenyl)-N-(4-(4-isopropylpiperazin-1-yl)phenyl)-[1,2,4]triazolo[4',3':1,6]pyrido[2,3-d]pyridimin-2-amine | 559.1 |

TABLE 1-continued

| Examples | Chemical structure | Chemical name | LC-MS [M + H⁺] |
|---|---|---|---|
| 12 | 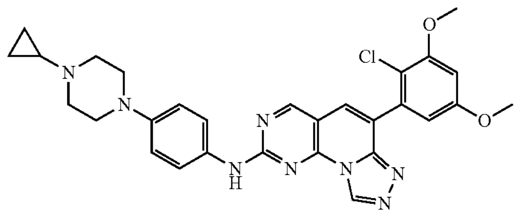 [SMILES: COc1cc(OC)c(Cl)c(-c2cc3cnc(Nc4ccc(N5CCN(C6CC6)CC5)cc4)nc3n3cnnc23)c1] | 6-(2-chloro-3,5-dimethoxyphenyl)-N-(4-(4-cyclopropylpiperazin-1-yl)phenyl)-[1,2,4]triazolo[4',3':1,6]pyrido[2,3-d]pyrimidin-2-amine | 557.1 |
| 13 | 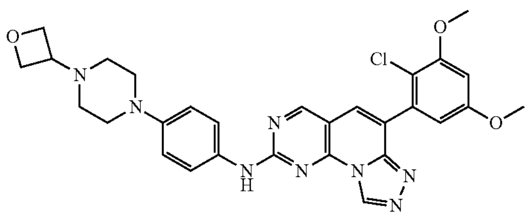 [SMILES: COc1cc(OC)c(Cl)c(-c2cc3cnc(Nc4ccc(N5CCN(C6COC6)CC5)cc4)nc3n3cnnc23)c1] | 6-(2-chloro-3,5-dimethoxyphenyl)-N-(4-(4-(oxetan-3-yl)piperazin-1-yl)phenyl)-[1,2,4]triazolo[4',3':1,6]pyrido[2,3-d]pyrimidin-2-amine | 573.1 |
| 14 | 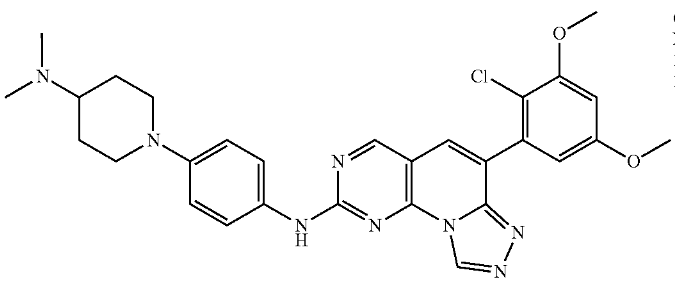 | 6-(2-chloro-3,5-dimethoxyphenyl)-N-(4-(4-(dimethylamino)piperidin-1-yl)phenyl)-[1,2,4]triazolo[4',3':1,6]pyrido[2,3-d]pyrimidin-2-amino | 559.2 |
| 15 | 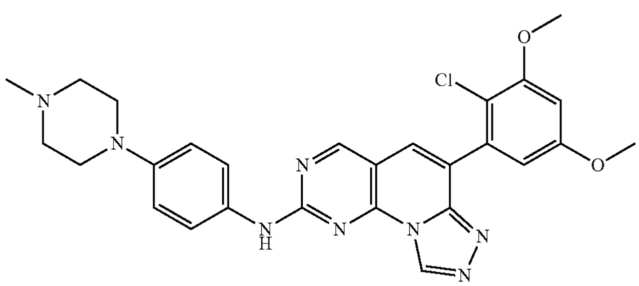 | 6-(2-chloro-3,5-dimethoxyphenyl)-N-(4-(4-methylpiperazin-1-yl)phenyl)-[1,2,4]triazolo[4',3':1,6]pyrido[2,3-d]pyridimin-2-amine | 531.0 |
| 16 | 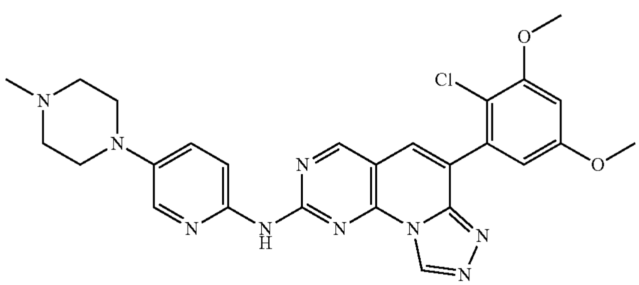 | 6-(2-chloro-3,5-dimethoxyphenyl)-N-(5-(4-methylpiperazin-1-yl)pyridin-2-yl)-[1,2,4]triazolo[4',3':1,6]pyrido[2,3-d]pyrimidin-2-amine | 532.0 |
| 17 | 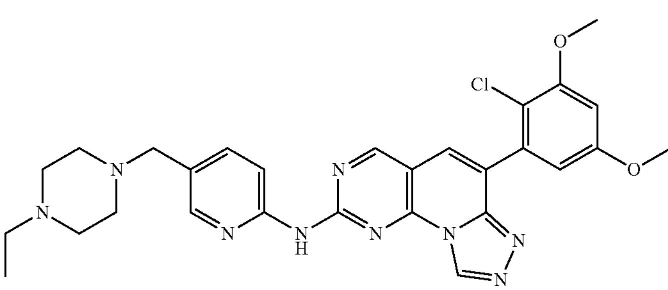 [SMILES: CCN1CCN(Cc2ccc(Nc3ncc4cc(-c5cc(OC)cc(OC)c5Cl)c5nncn5c4n3)nc2)CC1] | 6-(2-chloro-3,5-dimethoxyphenyl)-N-(5-((4-ethylpiperazin-1-yl)methyl)pyridin-2-yl)-[1,2,4]triazolo[4',3':1,6]pyrido[2,3-d]pyrimidin-2-amine | 560.2 |

TABLE 1-continued

| Examples | Chemical structure | Chemical name | LC-MS [M + H+] |
|---|---|---|---|
| 18 | 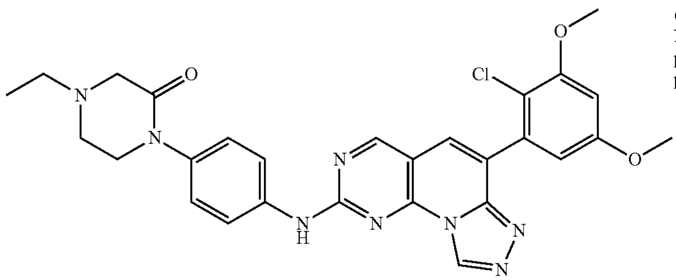 [SMILES: CCN1CCN(c2ccc(Nc3ncc4cc(-c5cc(OC)cc(OC)c5Cl)c5nncn5c4n3)cc2)C(=O)C1] | 6-(2-chloro-3,5-dimethoxyphenyl)-N-(4-(4-ethyl-2-oxopiperazin-1-yl)phenyl)-[1,2,4]triazolo[4',3':1,6]pyrido[2,3-d]pyrimidin-2-amine | 559.0 |
| 19 | 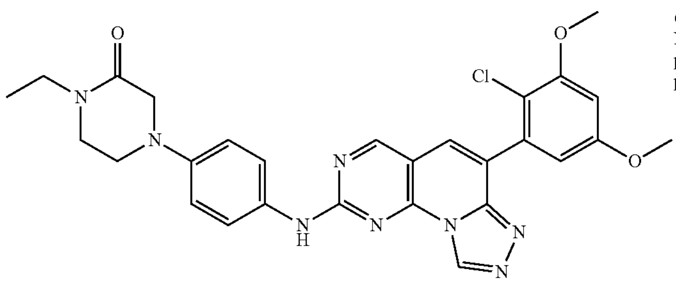 [SMILES: CCN1CCN(c2ccc(Nc3ncc4cc(-c5cc(OC)cc(OC)c5Cl)c5nncn5c4n3)cc2)CC1=O] | 6-(2-chloro-3,5-dimethoxyphenyl)-N-(4-(4-ethyl-3-oxopiperazin-1-yl)phenyl)-[1,2,4]triazolo[4',3':1,6]pyrido[2,3-d]pyrimidin-2-amine | 559.0 |
| 20 | 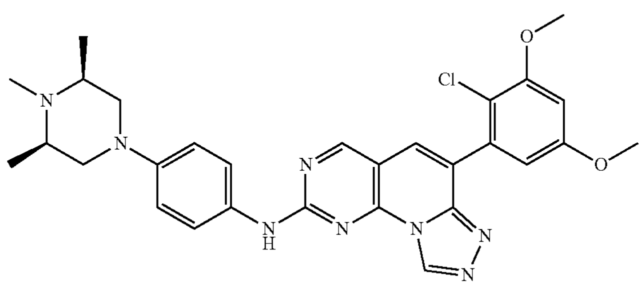 | 6-(2-chloro-3,5-dimethoxyphenyl)-N-(4-((3S,5R)-3,4,5-trimethylpiperazin-1-yl)phenyl)-[1,2,4]triazolo[4',3':1,6]pyrido[2,3-d]pyrimidin-2-amine | 559.1 |
| 21 | 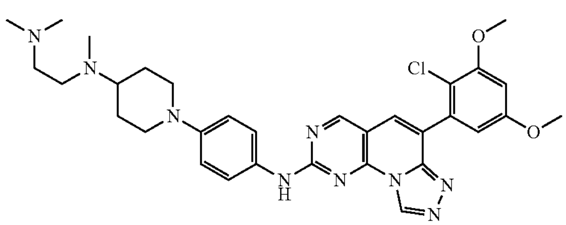 | 6-(2-chloro-3,5-dimethoxyphenyl)-N-(4-(N-(2-dimethylaminoethyl-N-methylamino)phenyl)-[1,2,4]triazolo[4',3':1,6]pyrido[2,3-d]pyridimin-2-amine | 533.0 |
| 22 | 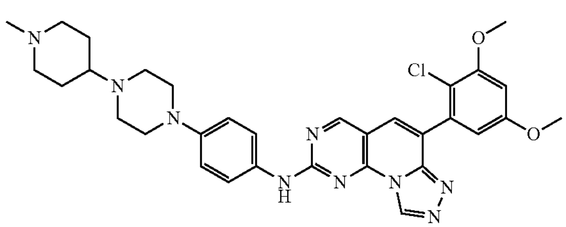 | 6-(2-chloro-3,5-dimethoxyphenyl)-N-(4-(4-(1-methylpiperidin-4-yl)piperazin-1-yl)phenyl)-[1,2,4]triazolo[4',3':1,6]pyrido[2,3-d]pyrimidin-2-amine | 614.2 |

TABLE 1-continued

| Examples | Chemical structure | Chemical name | LC-MS [M + H⁺] |
|---|---|---|---|
| 23 | 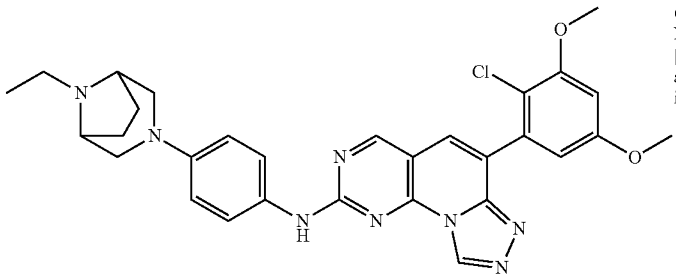 [SMILES: CCN1C2CCC1CN(c1ccc(Nc3ncc4cc(-c5cc(OC)cc(OC)c5Cl)c5nncn5c4n3)cc1)C2] | 6-(2-chloro-3,5-dimethoxyphenyl)-N-(4-(8-methyl-3,8-diazabicyclo[3.2.1]octan-3-yl)phenyl)-[1,2,4]triazolo[4',3':1,6]pyrido[2,3-d]pyrimidin-2-amine | 557.1 |
| 24 | 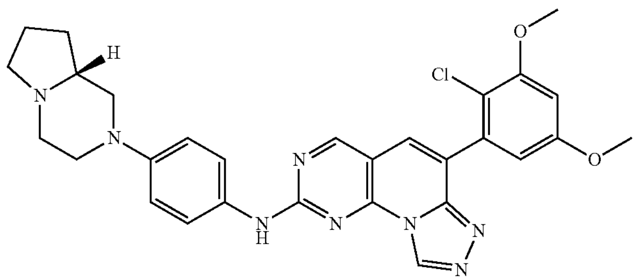 [SMILES: COc1cc(OC)c(Cl)c(-c2cc3cnc(Nc4ccc(N5CCN6CCC[C@@H]6C5)cc4)nc3n3cnnc23)c1] | (R)-6-(2-chloro-3,5-dimethoxyphenyl)-N-(4-(hexahydropyrrolo[1,2-a]pyrazin-2(1H)-yl)phenyl)-[1,2,4]triazolo[4',3':1,6]pyrido[2,3-d]pyrimidin-2-amine | 557.1 |
| 25 | 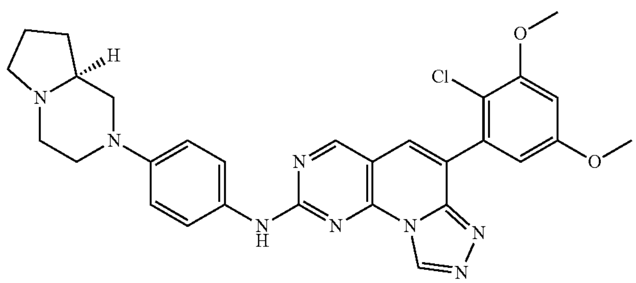 [SMILES: COc1cc(OC)c(Cl)c(-c2cc3cnc(Nc4ccc(N5CCN6CCC[C@H]6C5)cc4)nc3n3cnnc23)c1] | (S)-6-(2-chloro-3,5-dimethoxyphenyl)-N-(4-(hexahydropyrrolo[1,2-a]pyrazin-2(1H)-yl)phenyl)-[1,2,4]triazolo[4',3':1,6]pyrido[2,3-d]pyrimidin-2-amine | 557.1 |
| 26 | 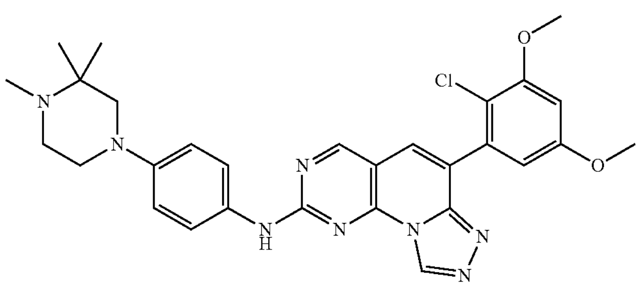 | 6-(2-chloro-3,5-dimethoxyphenyl)-N-(4-(3,3,4-trimethylpiperazin-1-yl)phenyl)-[1,2,4]triazolo[4',3':1,6]pyrido[2,3-d]pyridimin-2-amine | 559.1 |
| 27 | 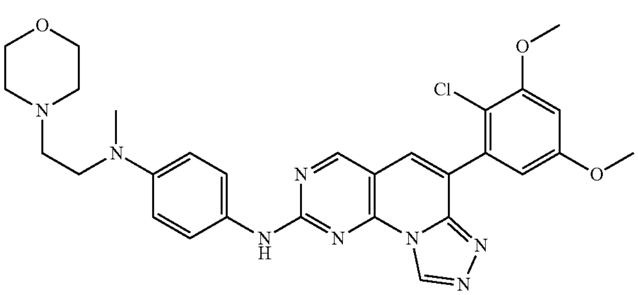 [SMILES: COc1cc(OC)c(Cl)c(-c2cc3cnc(Nc4ccc(N(C)CCN5CCOCC5)cc4)nc3n3cnnc23)c1] | N¹-(6-(2-chloro-3,5-dimethoxyphenyl)-[1,2,4]triazolo[4',3':1,6]pyrido[2,3-d]pyridimin-2-yl)-N⁴-methyl-N⁴-(2-morpholinoethyl)benzene-1,4-diamine | 575.1 |

TABLE 1-continued

| Examples | Chemical structure | Chemical name | LC-MS [M + H+] |
|---|---|---|---|
| 28 | 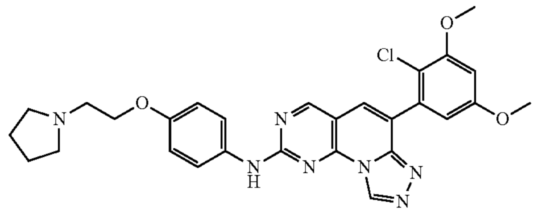 [SMILES: COc1cc(OC)c(Cl)c(-c2cc3cnc(Nc4ccc(OCCN5CCCC5)cc4)nc3n3cnnc23)c1] | 6-(2-chloro-3,5-dimethoxyphenyl)-N-(4-(2-(pyrrolidin-1-yl)ethoxy)phenyl)-[1,2,4]triazolo[4',3':1,6]pyrido[2,3-d]pyrimidin-2-amine | 546.0 |
| 29 | 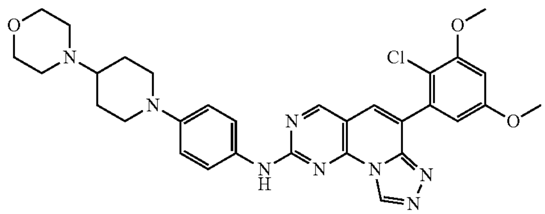 [SMILES: COc1cc(OC)c(Cl)c(-c2cc3cnc(Nc4ccc(N5CCC(N6CCOCC6)CC5)cc4)nc3n3cnnc23)c1] | 6-(2-chloro-3,5-dimethoxyphenyl)-N-(4-(4-morpholinopiperidin-1-yl)phenyl)-[1,2,4]triazolo[4',3':1,6]pyrido[2,3-d]pyrimidin-2-amine | 601.1 |
| 30 | 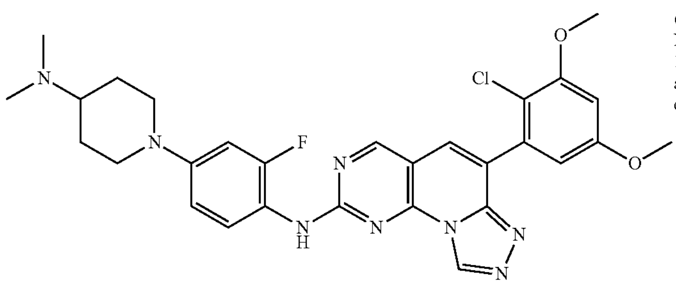 | 6-(2-chloro-3,5-dimethoxyphenyl)-N-(4-(4-(dimethylamino)piperidin-1-yl)-2-fluorophenyl)-[1,2,4]triazolo[4',3':1,6]pyrido[2,3-d]pyrimidin-2-amine | 577.1 |
| 31 | 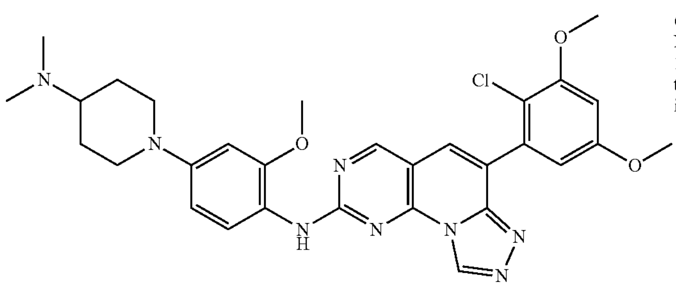 | 6-(2-chloro-3,5-dimethoxyphenyl)-N-(4-(4-(dimethylamino)piperidin-1-yl)-2-methoxyphenyl)-[1,2,4]triazolo[4',3':1,6]pyrido[2,3-d]pyrimidin-2-amine | 589.1 |
| 32 | 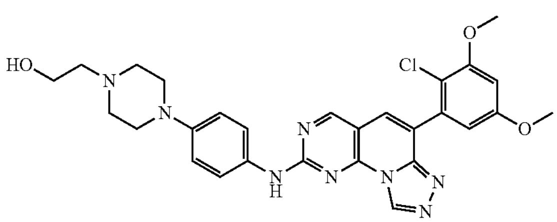 [SMILES: COc1cc(OC)c(Cl)c(-c2cc3cnc(Nc4ccc(N5CCN(CCO)CC5)cc4)nc3n3cnnc23)c1] | 2-(4-(4-((6-(2-chloro-3,5-dimethoxyphenyl)-[1,2,4]triazolo[4',3':1,6]pyrido[2,3-d]pyrimidin-2-yl)amino)phenyl)piperazin-1-yl)ethan-1-ol | 561.0 |
| 33 | 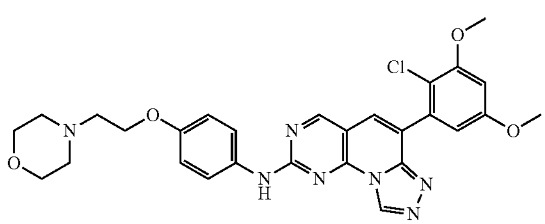 [SMILES: COc1cc(OC)c(Cl)c(-c2cc3cnc(Nc4ccc(OCCN5CCOCC5)cc4)nc3n3cnnc23)c1] | 6-(2-chloro-3,5-dimethoxyphenyl)-N-(4-(2-morpholinoethoxy)phenyl)-[1,2,4]triazolo[4',3':1,6]pyrido[2,3-d]pyrimidin-2-amine | 562.0 |

TABLE 1-continued

| Examples | Chemical structure | Chemical name | LC-MS [M + H⁺] |
|---|---|---|---|
| 34 | 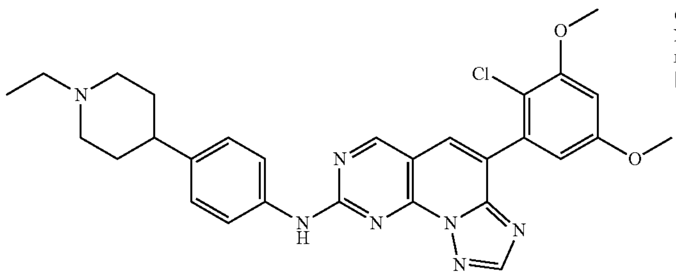 | 6-(2-chloro-3,5-dimethoxyphenyl)-N-(4-(1-ethylpiperidin-4-yl)phenyl)-[1,2,4]triazolo[4',3':1,6]pyrido[2,3-d]pyrimidin-2-amine | 544.1 |
| 35 | 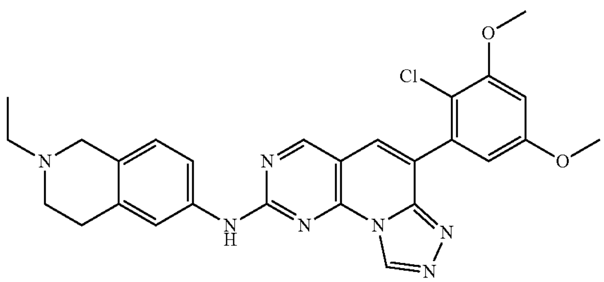 [SMILES: CCN1CCc2cc(Nc3ncc4cc(-c5cc(OC)cc(OC)c5Cl)c5nncn5c4n3)ccc2C1] | 6-(2-chloro-3,5-dimethoxyphenyl)-N-(2-ethyl-1,2,3,4-tetrahydroisoquinolin-6-yl)-[1,2,4]triazolo[4',3':1,6]pyrido[2,3-d]pyrimidin-2-amine | 516.0 |
| 36 | 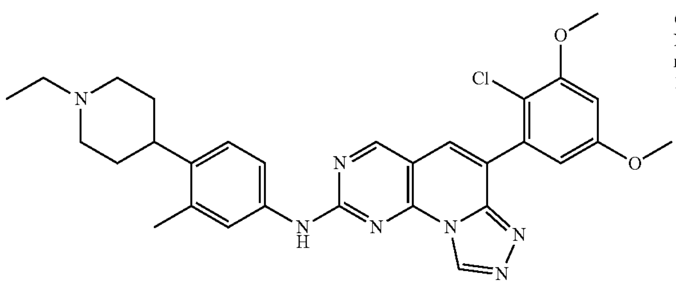 | 6-(2-chloro-3,5-dimethoxyphenyl)-N-(4-(1-ethylpiperidin-4-yl)-3-methylphenyl)-[1,2,4]triazolo[4',3':1,6]pyrido[2,3-d]pyrimidin-2-amine | 558.1 |
| 37 | 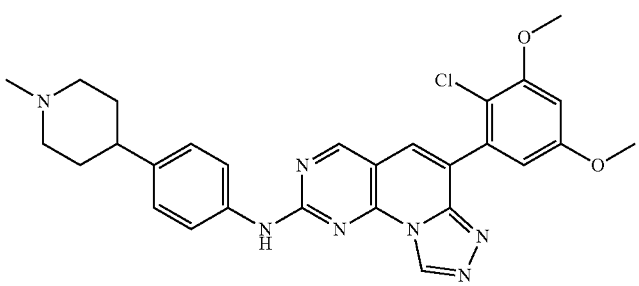 | 6-(2-chloro-3,5-dimethoxyphenyl)-N-(4-(1-methylpiperidin-4-yl)phenyl)-[1,2,4]triazolo[4',3':1,6]pyrido[2,3-d]pyrimidin-2-amine | 530.0 |
| 38 | 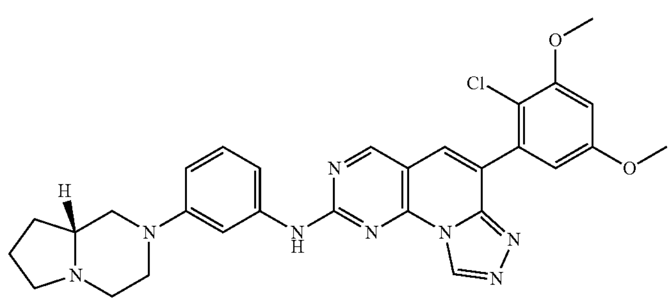 [SMILES: COc1cc(OC)c(Cl)c(-c2cc3cnc(Nc4cccc(N5CCN6CCC[C@@H]6C5)c4)nc3n3cnnc23)c1] | (R)-6-(2-chloro-3,5-dimethoxyphenyl)-N-(3-(hexahydropyrrolo[1,2-a]pyrazin-2(1H)-yl)phenyl)-[1,2,4]triazolo[4',3':1,6]pyrido[2,3-d]pyrimidin-2-amine | 557.1 |

TABLE 1-continued

| Examples | Chemical structure | Chemical name | LC-MS [M + H+] |
|---|---|---|---|
| 39 | 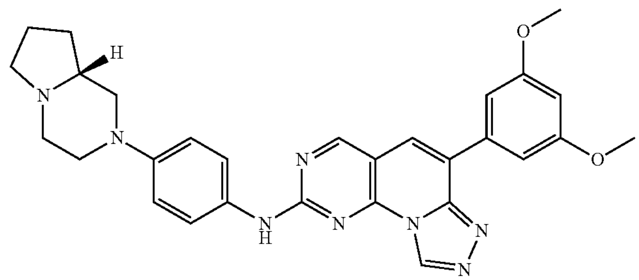 [SMILES: COc1cc(OC)cc(-c2cc3cnc(Nc4ccc(N5CCN6CCC[C@@H]6C5)cc4)nc3n3cnnc23)c1] | (R)-6-(3,5-dimethoxyphenyl)-N-(4-(hexahydropyrrolo[1,2-a]pyrazin-2(1H)-yl)phenyl)-[1,2,4]triazolo[4',3':1,6]pyrido[2,3-d]pyrimidin-2-amine | 522.6 |
| 40 | 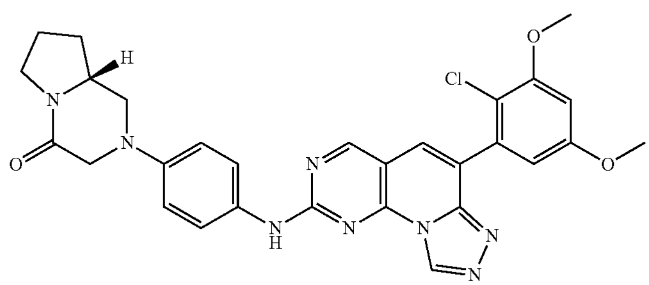 [SMILES: COc1cc(OC)c(Cl)c(-c2cc3cnc(Nc4ccc(N5CC(=O)N6CCC[C@@H]6C5)cc4)nc3n3cnnc23)c1] | (R)-2-(4-((6-(2-chloro-3,5-dimethoxyphenyl)-[1,2,4]triazolo[4',3':1,6]pyrido[2,3-d]pyrimidin-2-yl)amino)phenyl)hexahydropyrrolo[1,2-a]pyrazin-4(1H)-one | 571.2 |
| 41 | 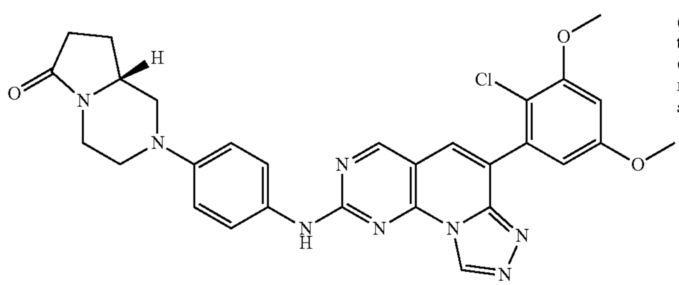 [SMILES: COc1cc(OC)c(Cl)c(-c2cc3cnc(Nc4ccc(N5CCN6C(=O)CC[C@@H]6C5)cc4)nc3n3cnnc23)c1] | (R)-2-(4-((6-(2-chloro-3,5-dimethoxyphenyl)-[1,2,4]triazolo[4',3':1,6]pyrido[2,3-d]pyrimidin-2-yl)amino)phenyl)hexahydropyrrolo[1,2-a]pyrazin-6(2H)-one | 571.2 |
| 42 | 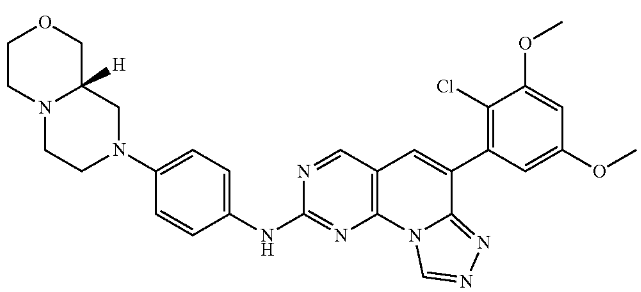 [SMILES: COc1cc(OC)c(Cl)c(-c2cc3cnc(Nc4ccc(N5CCN6CCOC[C@@H]6C5)cc4)nc3n3cnnc23)c1] | (S)-6-(2-chloro-3,5-dimethoxyphenyl)-N-(4-(hexahydropyrazino[2,1-c][1,4]oxazin-8(1H)-yl)phenyl)-[1,2,4]triazolo[4',3':1,6]pyrido[2,3-d]pyrimidin-2-amine | 573.2 |
| 43 | 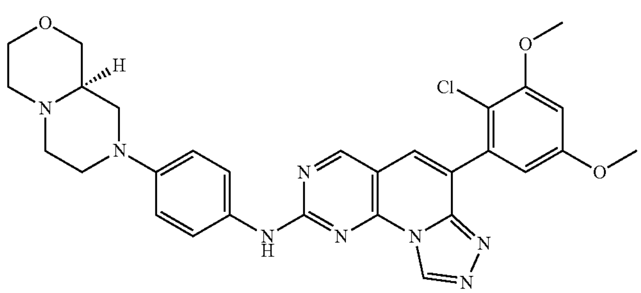 [SMILES: COc1cc(OC)c(Cl)c(-c2cc3cnc(Nc4ccc(N5CCN6CCOC[C@H]6C5)cc4)nc3n3cnnc23)c1] | (R)-6-(2-chloro-3,5-dimethoxyphenyl)-N-(4-(hexahydropyrazino[2,1-c][1,4]oxazin-8(1H)-yl)phenyl)-[1,2,4]triazolo[4',3':1,6]pyrido[2,3-d]pyrimidin-2-amine | 573.2 |

| Examples | Chemical structure | Chemical name | LC-MS [M + H+] |
|---|---|---|---|
| 44 | 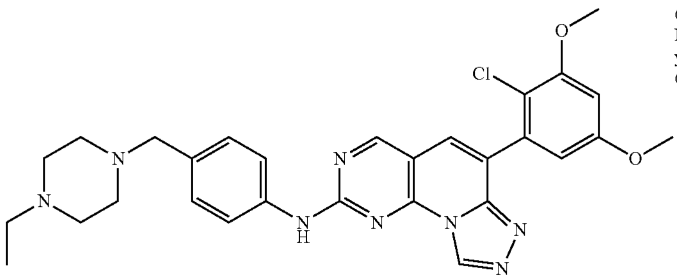 | 6-(2-chloro-3,5-dimethoxyphenyl)-N-(4-((4-ethylpiperazin-1-yl)methyl)phenyl)-[1,2,4]triazolo[4',3':1,6]pyrido[2,3-d]pyrimidin-2-amine | 559.2 |
| 45 | 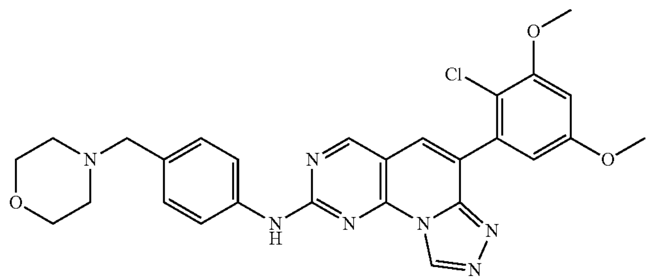 [SMILES: COc1cc(OC)c(Cl)c(-c2cc3cnc(Nc4ccc(CN5CCOCC5)cc4)nc3n3cnnc23)c1] | 6-(2-chloro-3,5-dimethoxyphenyl)-N-(4-(morpholinomethyl)phenyl)-[1,2,4]triazolo[4',3':1,6]pyrido[2,3-d]pyrimidin-2-amine | 532.0 |
| 46 | 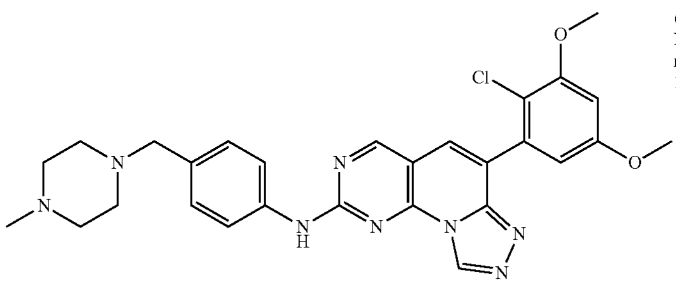 | 6-(2-chloro-3,5-dimethoxyphenyl)-N-(4-((4-methylpiperazin-1-yl)methyl)phenyl)-[1,2,4]triazolo[4',3':1,6]pyrido[2,3-d]pyrimidin-2-amine | 545.0 |
| 47 | 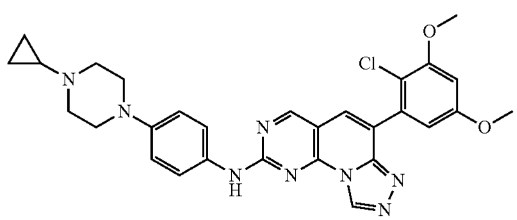 [SMILES: COc1cc(OC)c(Cl)c(-c2cc3cnc(Nc4ccc(N5CCN(C6CC6)CC5)cc4)nc3n3cnnc23)c1] | 6-(2-chloro-3,5-dimethoxyphenyl)-N-(4-(1-cyclopropylpiperidin-4-yl)phenyl)-[1,2,4]triazolo[4',3':1,6]pyrido[2,3-d]pyrimidin-2-amine | 556.1 |

Nuclear magnetic data of compound 3, 4, 5, 22, 23, 24, 25, 26, 28, 29, 31, 32, 33, 34, 37, 42, 45, 46 and 52 are shown as below:

$^1$H NMR (DMSO-d6, 400 MHz) δ 9.70 (s, 1H), 9.01 (s, 1H), 7.63 (s, 1H), 6.83 (s, 1H), 6.73 (s, 1H), 4.47-4.29 (m, 1H), 4.13 (m, 1H), 3.91 (s, 3H), 3.80 (s, 3H), 3.38 (m, 2H), 2.36-2.11 (m, 1H), 2.11-1.84 (m, 1H), 1.77-1.53 (m, 4H) (compound 3);

$^1$H NMR (DMSO-d6, 400 MHz) δ 9.67 (s, 1H), 9.16 (s, 1H), 7.78 (brs, 2H), 7.68 (s, 1H), 7.02 (d, J=8 Hz, 2H), 6.85 (s, 1H), 6.76 (s, 1H), 3.93 (s, 3H), 3.81 (s, 3H), 3.16 (brs, 4H), 2.75-2.59 (m, 4H), 2.44-2.33 (m, 2H), 1.09 (t, J=6 Hz, 3H) (compound 4);

$^1$H NMR (DMSO-d6, 400 MHz) δ 9.68-9.47 (m, 1H), 9.01-9.01 (m, 1H), 7.61 (s, 1H), 6.83 (s, 1H), 6.74 (s, 1H), 3.92 (s, 3H), 3.90 (s, 3H), 3.63-3.56 (m, 8H), 2.60-2.56 (m, 2H), 2.43 (m, 2H) (compound 5);

$^1$H NMR (DMSO-d6, 400 MHz) δ 10.35 (s, 1H), 9.66 (s, 1H), 9.17 (s, 1H), 7.77 (br, 2H), 7.69 (s, 1H), 7.01 (d, J=8 Hz, 2H), 6.84 (s, 1H), 6.75 (s, 1H), 3.95 (s, 3H), 3.81 (s, 3H), 3.18-2.92 (m, 13H), 2.44 (s, 3H), 2.01-1.65 (m, 4H) (compound 22);

$^1$H NMR (DMSO-d6, 400 MHz) δ 10.31 (s, 1H), 9.64 (s, 1H), 9.15 (s, 1H), 7.74 (br, 2H), 7.67 (s, 1H), 6.90 (d, J=8 Hz, 2H), 6.84 (s, 1H), 6.75 (s, 1H), 3.91 (s, 3H), 3.80 (s, 3H), 3.44-3.39 (m, 2H), 3.09-3.09 (m, 2H), 2.50 (br, 2H), 2.45 (s, 3H), 2.07-2.05 (m, 2H), 1.80-1.78 (m, 2H) (compound 23);

$^1$H NMR (DMSO-d6, 400 MHz) δ 10.31 (s, 1H), 9.65 (s, 1H), 9.14 (s, 1H), 7.75 (br, 2H), 7.67 (s, 1H), 7.00 (d, J=8 Hz, 2H), 6.84 (s, 1H), 6.75 (s, 1H), 3.92 (s, 3H), 3.81 (s, 3H), 3.75-3.58 (m, 2H), 3.04-2.72 (m, 3H), 2.44-2.08 (m, 4H), 1.87-1.34 (m, 4H) (compound 24);

$^1$H NMR (DMSO-d6, 400 MHz) δ 10.34 (s, 1H), 9.66 (s, 1H), 9.16 (s, 1H), 7.77 (br, 2H), 7.68 (s, 1H), 7.03 (d, J=8 Hz, 2H), 6.85 (s, 1H), 6.75 (s, 1H), 3.92 (s, 3H), 3.81 (s, 3H), 3.76-3.58 (m, 2H), 3.11-2.72 (m, 3H), 2.44-2.08 (m, 4H), 1.91-1.40 (m, 4H) (compound 25);

$^1$H NMR (DMSO-d6, 400 MHz) δ 10.31 (s, 1H), 9.65 (s, 1H), 9.14 (s, 1H), 7.75 (br, 2H), 7.67 (s, 1H), 7.00 (d, J=8

Hz, 2H), 6.84 (s, 1H), 6.75 (s, 1H), 3.92 (s, 3H), 3.81 (s, 3H), 3.75-3.58 (m, 2H), 3.04-2.72 (m, 3H), 2.44-2.08 (m, 4H), 1.87-1.34 (m, 4H) (compound 26);

¹H NMR (DMSO-d6, 400 MHz) δ 10.42 (s, 1H), 9.68 (s, 1H), 9.18 (s, 1H), 7.82 (br, 2H), 7.69 (s, 1H), 7.04 (d, J=8 Hz, 2H), 6.85 (s, 1H), 6.76 (s, 1H), 4.22 (t, J=6 Hz, 2H), 3.93 (s, 3H), 3.81 (s, 3H), 3.29 (t, J=4 Hz, 2H), 3.05 (br, 4H), 1.88-1.85 (m, 4H) (compound 28);

¹H NMR (DMSO-d6, 400 MHz) δ 10.31 (s, 1H), 9.65 (s, 1H), 9.15 (s, 1H), 7.76 (s, 2H), 7.68 (s, 1H), 7.00 (d, J=8 Hz, 2H), 6.86 (s, 1H), 6.76 (s, 1H), 3.93 (s, 3H), 3.81 (s, 3H), 3.72-3.57 (m, 6H), 2.67-2.51 (m, 5H), 2.46-2.16 (m, 2H), 1.93-1.86 (m, 2H), 1.58-1.51 (m, 2H) (compound 29);

¹H NMR (DMSO-d6, 400 MHz) δ 9.53 (s, 1H), 9.10 (s, 1H), 9.15 (s, 1H), 7.76 (br, 1H), 7.66 (s, 1H), 6.85 (s, 1H), 6.75 (s, 1H), 6.71-6.70 (m, 1H), 6.62-6.60 (m, 1H), 3.92 (s, 3H), 3.83 (s, 3H), 3.80 (s, 3H), 3.53-3.23 (m, 5H), 2.71 (s, 6H), 2.15-2.07 (m, 2H), 1.83-1.71 (m, 2H) (compound 31);

¹H NMR (DMSO-d6, 400 MHz) δ 10.35 (s, 1H), 9.66 (s, 1H), 9.16 (s, 1H), 7.76 (br, 2H), 7.68 (s, 1H), 6.99 (d, J=8 Hz, 2H), 6.84 (s, 1H), 6.75 (s, 1H), 4.62 (br, 1H), 3.92 (s, 3H), 3.80 (s, 3H), 3.57 (t, J=6 Hz, 2H), 3.16-3.14 (m, 4H), 2.68-2.64 (m, 4H), 2.55-2.51 (m, 2H) (compound 32);

¹H NMR (DMSO-d6, 400 MHz) δ 10.41 (s, 1H), 9.67 (s, 1H), 9.18 (s, 1H), 7.86-7.81 (m, 2H), 7.69 (s, 1H), 6.99 (d, J=8 Hz, 2H), 6.85 (s, 1H), 6.75 (s, 1H), 4.08 (t, J=6 Hz, 2H), 3.92 (s, 3H), 3.80 (s, 3H), 3.58 (t, J=4 Hz, 4H), 2.69 (t, J=6 Hz, 2H), 2.48 (t, J=6 Hz, 4H) (compound 33);

¹H NMR (DMSO-d6, 400 MHz) δ 10.60 (s, 1H), 9.35 (s, 1H), 8.64 (s, 1H), 8.02 (s, 2H), 7.74 (d, J=8 Hz, 1H), 7.28 (d, J=8 Hz, 2H), 6.85 (s, 1H), 6.76 (s, 1H), 3.92 (s, 3H), 3.80 (s, 3H), 3.29-3.24 (m, 1H), 3.12-3.05 (m, 2H), 3.01-2.96 (m, 4H), 2.17-1.93 (m, 4H), 1.27 (t, J=6 Hz, 3H) (compound 34);

¹H NMR (DMSO-d6, 400 MHz) δ 10.49 (s, 1H), 9.73 (s, 1H), 9.21 (s, 1H), 7.87 (d, J=8 Hz, 2H), 7.71 (s, 1H), 7.29 (d, J=8 Hz, 2H), 6.86 (d, J=4 Hz, 1H), 6.77 (d J=4 Hz, 1H), 3.93 (s, 3H), 3.82 (s, 3H), 3.34 (s, 3H), 3.20-3.17 (m, 2H), 2.64-2.55 (m, 3H), 1.87-1.74 (m, 4H) (compound 37);

¹H NMR (DMSO-d6, 400 MHz) δ 10.35 (s, 1H), 9.64 (s, 1H), 9.13 (s, 1H), 7.78 (br, 2H), 7.65 (s, 1H), 7.02 (d, J=8 Hz, 2H), 6.78 (s, 1H), 6.68 (s, 1H), 3.97-3.92 (m, 2H), 3.90 (s, 3H), 3.78 (s, 3H), 3.75-3.65 (m, 2H), 3.46-3.25 (m, 4H), 3.06-2.82 (m, 4H), 2.69-2.54 (m, 1H) (compound 42);

¹H NMR (DMSO-d6, 400 MHz) δ 10.55 (s, 1H), 9.75 (s, 1H), 9.35 (s, 1H), 7.91 (d, J=8 Hz, 2H), 7.72 (s, 1H), 7.38 (d, J=8 Hz, 2H), 6.86 (s, 1H), 6.76 (s, 1H), 3.92 (s, 3H), 3.81 (s, 3H), 3.63 (br, 6H), 2.51-2.49 (m, 4H) (compound 45);

¹H NMR (DMSO-d6, 400 MHz) δ 10.54 (s, 1H), 9.73 (s, 1H), 9.21 (s, 1H), 7.89 (d, J=8 Hz, 2H), 7.71 (s, 1H), 7.34 (d, J=8 Hz, 2H), 6.84 (s, 1H), 6.75 (s, 1H), 3.91 (s, 3H), 3.81 (s, 3H), 3.54 (s, 2H), 2.84 (br, 4H), 2.59 (br, 4H), 2.50 (s, 3H) (compound 46).

Example 48: Preparation of Compound 48 6-(2-chloro-3,5-dimethoxyphenyl)-N-(4-(piperazin-1-yl)phenyl)-[1,2,4]triazolo[4',3%1,6]pyrido[2,3-d]pyrimidin-2-amine)

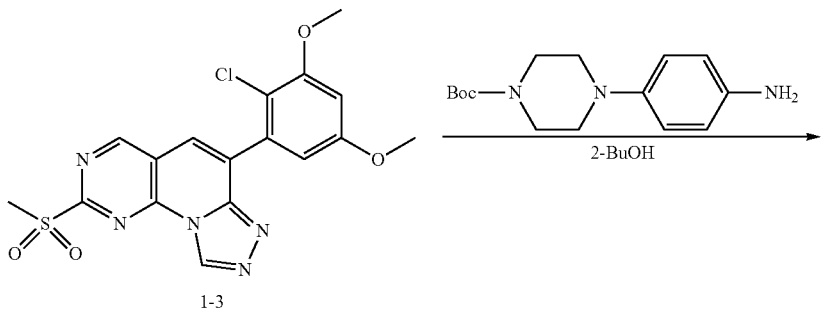

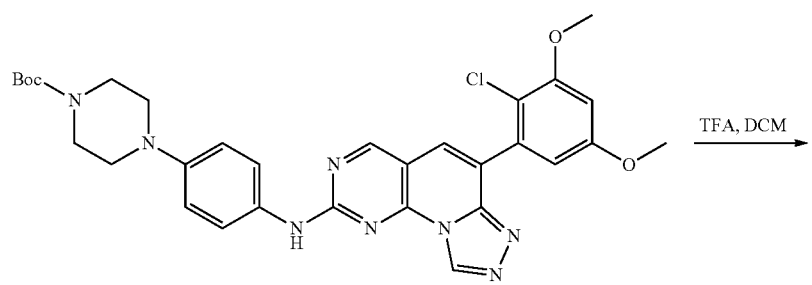

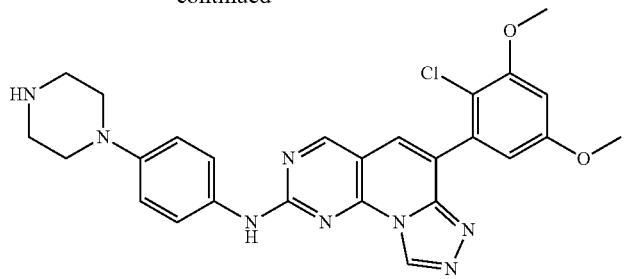

48

Step 1: Preparation of Compound 48-1

A mixture of 1.0 g of compound 1-3, 1.03 g of 1-Boc-4-(4-aminophenyl) piperazine and 20 mL of sec-butyl alcohol was heated to reflux for 2.5 hrs. The mixture was cooled to room temperature. Filtration, the filter cake was washed three times with sec-butyl alcohol, washed three times with methyl-butyl ether and dried over anhydrous sodium sulfate to give 1.16 g of compound 48-1, which is a yellow solid. LC-MS [M+H$^+$] 617.2.

Step 2: Preparation of Compound 48

A mixture of 1.12 g of compound 48-1, 60 mL of dichloromethane and 12 mL of TFA was stirred at room temperature overnight. The mixture was concentrated under reduced pressure, the resulting was dissolved with 50 mL of DCM/MeOH=10/1. The mixture was washed with saturated sodium bicarbonate and saturated saline, and dried over anhydrous sodium. Filtrated, and concentrated under reduced pressure. The obtained solid was beaten with 5 ml of EA/DCM=10/1, filtered, and the filter cake was rinsed with EA/DCM=10/1 and dried to give 1.02 g of compound 48, which is a yellow solid.

LC-MS [M+H$^+$] 517.2.

$^1$H NMR (DMSO-d6, 400 MHz) δ 10.33 (s, 1H), 9.65 (s, 1H), 9.15 (s, 1H), 7.77 (br, 2H), 7.67 (s, 1H), 7.00 (d, J=8 Hz, 2H), 6.85 (d, J=4 Hz, 1H), 6.76 (d J=4 Hz, 1H), 3.92 (s, 3H), 3.81 (s, 3H), 3.72 (br, 1H), 3.12 (t, J=6 Hz, 4H), 2.97 (t, J=6 Hz, 4H).

TABLE 2

| Examples | Chemical structure | Chemical name | LC-MS [M + H$^+$] |
|---|---|---|---|
| 49 | 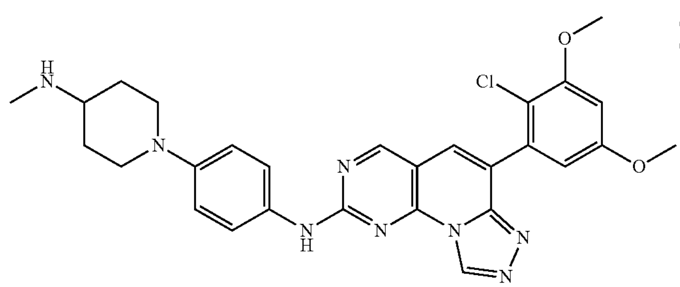 | 6-(2-chloro-3,5-dimethoxyphenyl)-N-(4-(4-methylaminopiperidin-1-yl)phenyl)-[1,2,4]triazolo[4',3':1,6]pyrido[2,3-d]pyrimidin-2-amine | 545.0 |
| 50 | 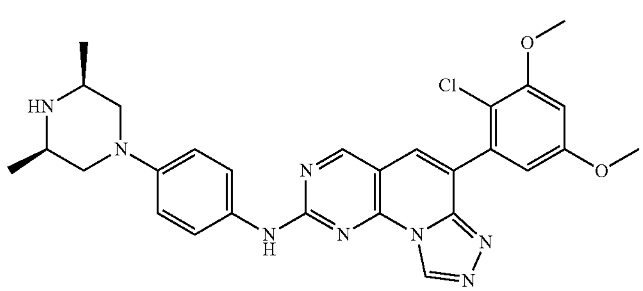 | 6-(2-chloro-3,5-dimethoxyphenyl)-N-(4-((3S,5R)-3,5-dimethylpiperazin-1-yl)phenyl)-[1,2,4]triazolo[4',3':1,6]pyrido[2,3-d]pyrimidin-2-amine | 545.0 |

TABLE 2-continued

| Examples | Chemical structure | Chemical name | LC-MS [M + H+] |
|---|---|---|---|
| 51 | 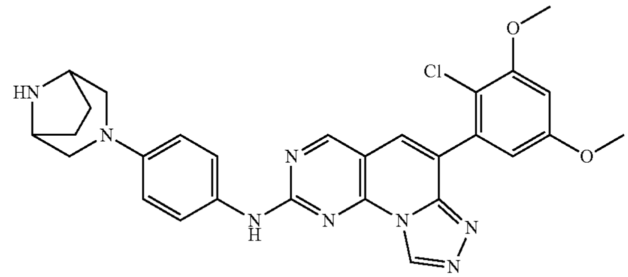 [SMILES: COc1cc(OC)c(Cl)c(-c2cc3cnc(Nc4ccc(N5CC6CCC(C5)N6)cc4)nc3n3cnnc23)c1] | N-(4-(3,8-diazabicyclo[3.2.1]octan-3-yl)phenyl)-6-(2-chloro-3,5-dimethoxyphenyl)-[1,2,4]triazolo[4',3':1,6]pyrido[2,3-d]pyrimidin-2-amine | 543.0 |
| 52 | 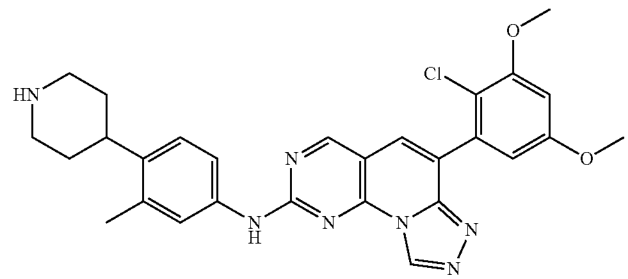 [SMILES: COc1cc(OC)c(Cl)c(-c2cc3cnc(Nc4ccc(C5CCNCC5)c(C)c4)nc3n3cnnc23)c1] | 6-(2-chloro-3,5-dimethoxyphenyl)-N-(3-methyl-4-(piperidin-4-yl)phenyl)-[1,2,4]triazolo[4',3':1,6]pyrido[2,3-d]pyrimidin-2-amine | 530.0 |
| 53 | 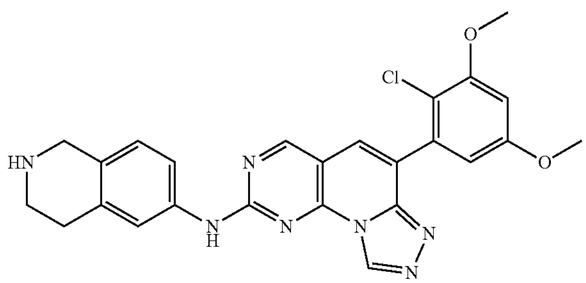 [SMILES: COc1cc(OC)c(Cl)c(-c2cc3cnc(Nc4ccc5c(c4)CCNC5)nc3n3cnnc23)c1] | 6-(2-chloro-3,5-dimethoxyphenyl)-N-(1,2,3,4-tetrahydroisoquinolin-6-yl)-[1,2,4]triazolo[4',3':1,6]pyrido[2,3-d]pyrimidin-2-amine | 488.0 |
| 54 | 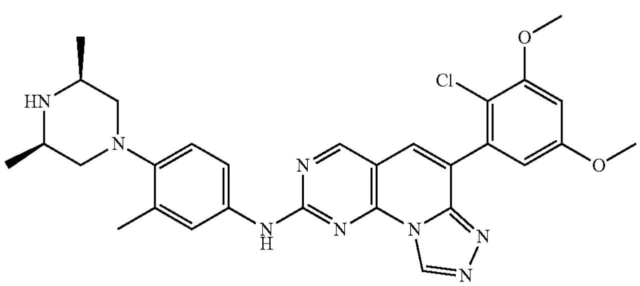 | 6-(2-chloro-3,5-dimethoxyphenyl)-N-(4-((3S,5R)-3,-5-dimethylpiperazin-1-yl)-3-methylphenyl)-[1,2,4]triazolo[4',3':1,6]pyrido[2,3-d]pyrimidin-2-amine | 589.1 |
| 55 | 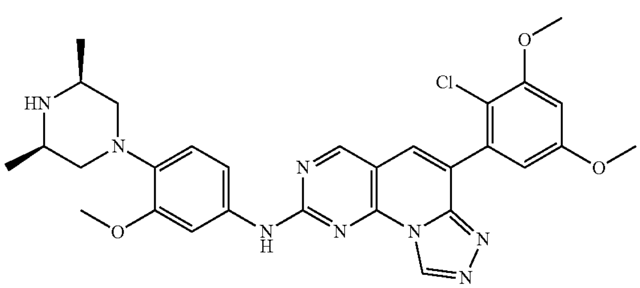 | 6-(2-chloro-3,5-dimethoxyphenyl)-N-(4-((3S,5R)-3,-5-dimethylpiperazin-1-yl)-3-methoxyphenyl)-[1,2,4]triazolo[4',3':1,6]pyrido[2,3-d]pyrimidin-2-amine | 575.1 |

TABLE 2-continued

| Examples | Chemical structure | Chemical name | LC-MS [M + H+] |
|---|---|---|---|
| 56 | 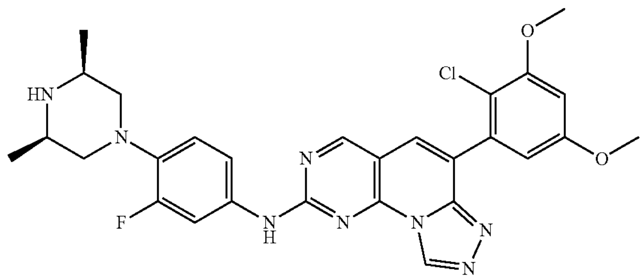 | 6-(2-chloro-3,5-dimethoxyphenyl)-N-(4-((3S,5R)-3,-5-dimethylpiperazin-1-yl)-3-fluorophenyl)-[1,2,4]triazolo[4',3':1,6]pyrido[2,3-d]pyrimidin-2-amine | 563.0 |
| 57 | 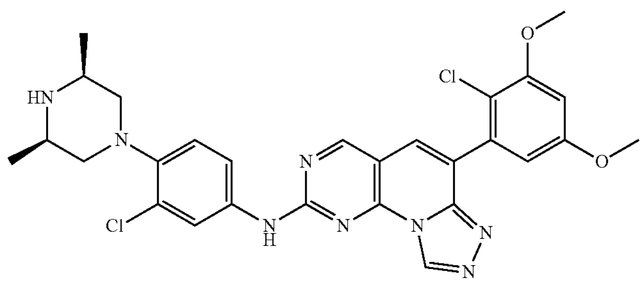 | 6-(2-chloro-3,5-dimethoxyphenyl)-N-(4-((3S,5R)-3,-5-dimethylpiperazin-1-yl)-3-chlorophenyl)-[1,2,4]triazolo[4',3':1,6]pyrido[2,3-d]pyrimidin-2-amine | 579.5 |
| 58 | 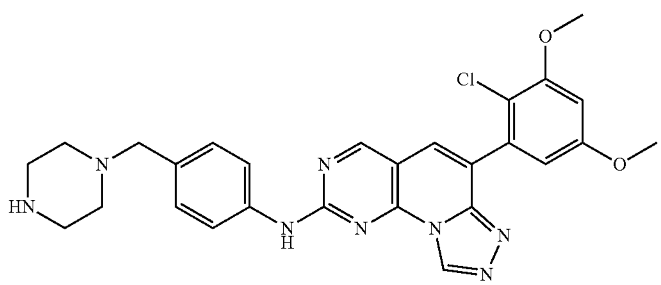 [SMILES: COc1cc(OC)c(Cl)c(-c2cc3cnc(Nc4ccc(CN5CCNCC5)cc4)nc3n3cnnc23)c1] | 6-(2-chloro-3,5-dimethoxyphenyl)-N-(4-(piperazin-1-ylmethyl)phenyl)-[1,2,4]triazolo[4',3':1,6]pyrido[2,3-d]pyrimidin-2-amine | 531.2 |
| 59 | 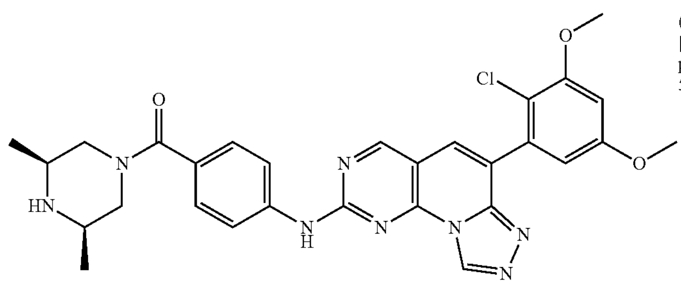 | (4-((6-(2-chloro-3,5-dimethoxyphenyl)-[1,2,4]triazolo[4',3':1,6]pyrido[2,3-d]pyrimidin-2-yl)amino)phenyl)((3S,5R)-3,5-dimethylpiperazin-1-yl)methanone | 573.0 |
| 60 | 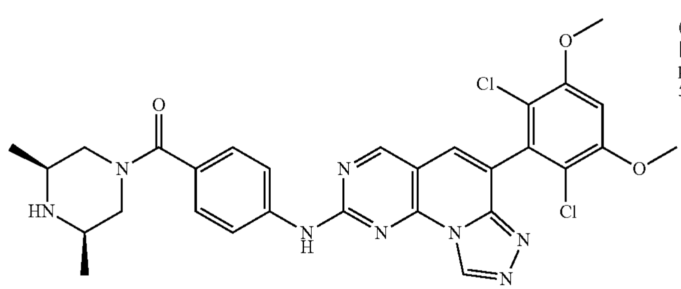 | (4-((6-(2-chloro-3,5-dimethoxyphenyl)-[1,2,4]triazolo[4',3':1,6]pyrido[2,3-d]pyrimidin-2-yl)amino)phenyl)((3S,5R)-3,5-dimethylpiperazin-1-yl)methanone | 607.5 |

Nuclear magnetic data of compound 50, 52, 53, 56 and 59 are as shown below:

$^1$H NMR (DMSO-d6, 400 MHz) δ 10.30 (s, 1H), 9.65 (s, 1H), 9.13 (s, 1H), 7.75 (br, 2H), 7.66 (s, 1H), 6.98 (d, J=8 Hz, 2H), 6.84 (s, 1H), 6.75 (s, 1H), 3.92 (s, 3H), 3.91 (s, 3H), 3.51 (d, J=8 Hz, 2H), 2.93-2.88 (m, 2H), 2.50-2.49 (m, 1H), 2.15 (t, J=12 Hz, 2H), 1.05 (d, J=8 Hz, 6H) (compound 50);

$^1$H NMR (DMSO-d6, 400 MHz) δ 10.42 (s, 1H), 9.66 (s, 1H), 9.20 (s, 1H), 7.86-7.84 (m, 1H), 7.71 (s, 1H), 7.59 (s, 1H), 7.22 (d, J=8 Hz, 1H), 6.85 (s, 1H), 6.76 (s, 1H), 3.93

(s, 3H), 3.80 (s, 3H), 3.38 (br, 3H), 3.07-3.01 (m, 3H), 2.37 (s, 3H), 1.96-1.82 (m, 4H) (compound 52);

¹H NMR (DMSO-d6, 400 MHz) δ 10.55 (s, 1H), 9.66 (s, 1H), 9.22 (s, 1H), 7.78-7.76 (m, 2H), 7.72 (s, 1H), 7.24 (d, J=8 Hz, 1H), 6.85 (s, 1H), 6.76 (s, 1H), 4.28 (s, 2H), 3.93 (s, 3H), 3.80 (s, 3H), 3.49-3.42 (m, 3H), 3.09 (t, J=6 Hz, 2H) (compound 53);

¹H NMR (DMSO-d6, 400 MHz) δ 10.52 (s, 1H), 9.65 (s, 1H), 9.21 (s, 1H), 7.77 (br, 1H), 7.71 (s, 1H), 7.62 (d, J=16 Hz, 1H), 7.10 (t, J=8 Hz, 1H), 6.86 (s, 1H), 6.76 (s, 1H), 3.93 (s, 3H), 3.82 (s, 3H), 3.35-3.17 (m, 4H), 2.34-2.28 (m, 2H), 1.22 (s, 1H), 1.02 (d, J=8 Hz, 6H) (compound 56);

¹H NMR (DMSO-d6, 400 MHz) δ 10.73 (s, 1H), 9.83 (s, 1H), 9.26 (s, 1H), 8.02 (d, J=8 Hz, 2H), 7.74 (s, 1H), 7.46 (d, J=8 Hz, 2H), 6.87 (d, J=4 Hz, 1H), 6.78 (d J=4 Hz, 1H), 3.93 (s, 3H), 3.82 (s, 3H), 3.57 (br, 1H), 3.39-3.32 (m, 4H), 2.73-2.64 (m, 2H), 1.22 (s, 1H), 0.92 (d, J=8 Hz, 6H) (compound 59).

Example 61: Preparation of Compound 61 (6-(2,6-dichloro-3,5-dimethoxyphenyl)-N-(4-(4-ethylpiperazin-1-yl)phenyl)-[1,2,4]triazolo[4',3':1,6]pyrido[2,3-d]pyrimidin-2-amine)

Route A

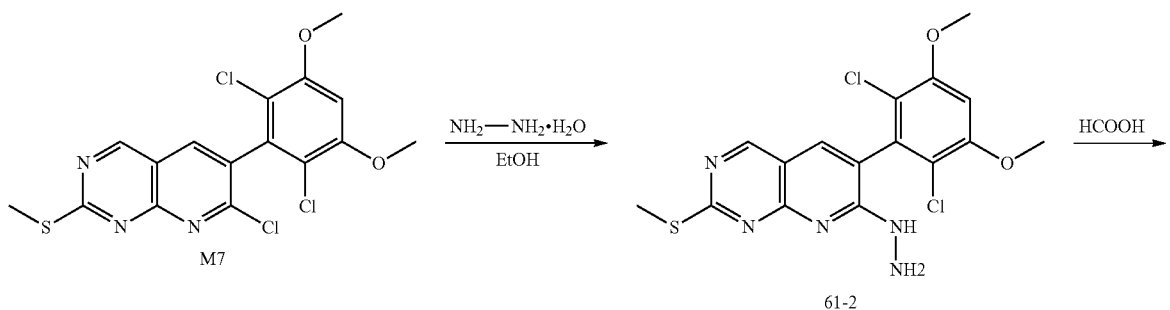

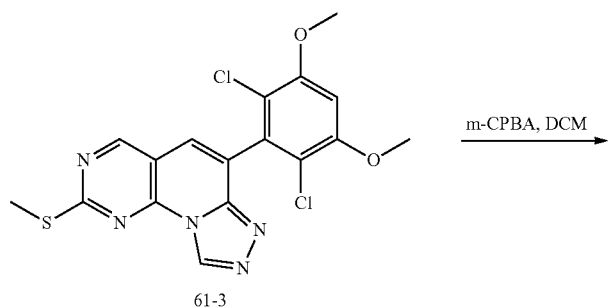

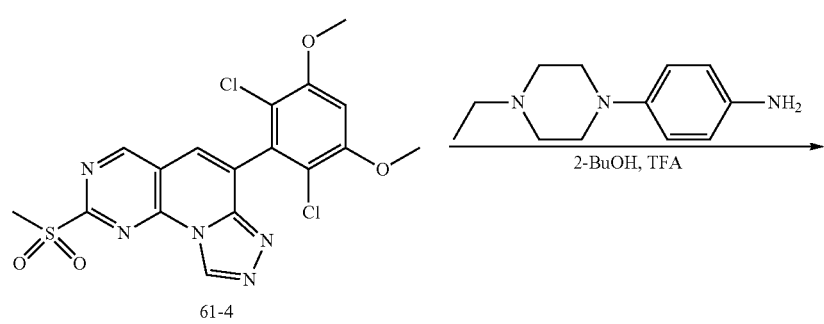

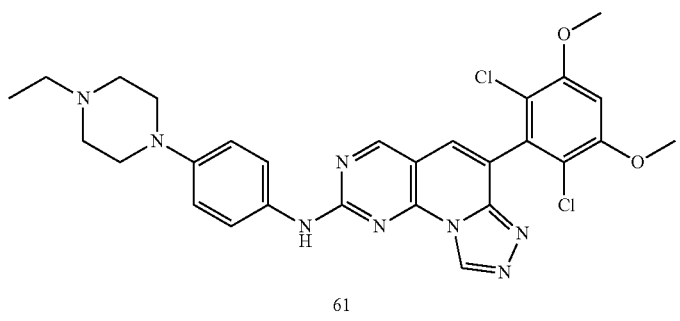 [SMILES: CCN1CCN(c2ccc(Nc3ncc4cc(-c5c(Cl)c(OC)cc(OC)c5Cl)c5nncn5c4n3)cc2)CC1]

Step 1: Preparation of Compound 61-2

Compound 61-2 was prepared by a similar procedure as described in the Step 1 of Route A of Example 1.
LC-MS [M+H⁺] 412.0.

Step 2: Preparation of Compound 61-3

Compound 61-3 was prepared by a similar procedure as described in the Step 2 of Route A of Example 1.
LC-MS [M+H⁺] 422.0.

Step 3: Preparation of Compound 61-4

Compound 61-4 was prepared by a similar procedure as described in the Step 3 of Route A of Example 1.
LC-MS [M+H⁺] 454.0.

Step 4: Preparation of Compound 61

Compound 61 was prepared by similar procedure as described in the step 5 of Example 2.
LC-MS [M+H⁺] 579.2.
¹H NMR (DMSO-d6, 400 MHz) δ 9.67 (s, 1H), 9.17 (s, 1H), 7.80 (brs, 2H), 7.66 (s, 1H), 7.10 (s, 1H), 7.06 (d, J=8 Hz, 2H), 4.00 (s, 6H), 3.23-2.76 (m, 8H), 2.76-2.59 (m, 2H), 1.18 (t, J=6 Hz, 3H).

Step 1: Preparation of Compound 61-4

Under nitrogen protection at 0° C., 697 mg of SO$_2$Cl$_2$ was added into the mixture of 500 mg of compound 1-2, 15 ml of DCM and 5 ml of NMP with stirring. The reaction was stirred for 1 hr at 0° C. and quenched with water. Then the mixture was extracted with DCM, washed with saline solution and dried over anhydrous Na$_2$SO$_4$. The mixture was concentrated under reduced pressure to get 700 mg of crude compound 61-4. It was used for the next step directly without purification.

LC-MS [M+H⁺] 454.0.

Step 2: Preparation of Compound 61

Compound 61 was prepared by similar procedure as described in the step 5 of Example 2.
LC-MS [M+H⁺] 579.2.

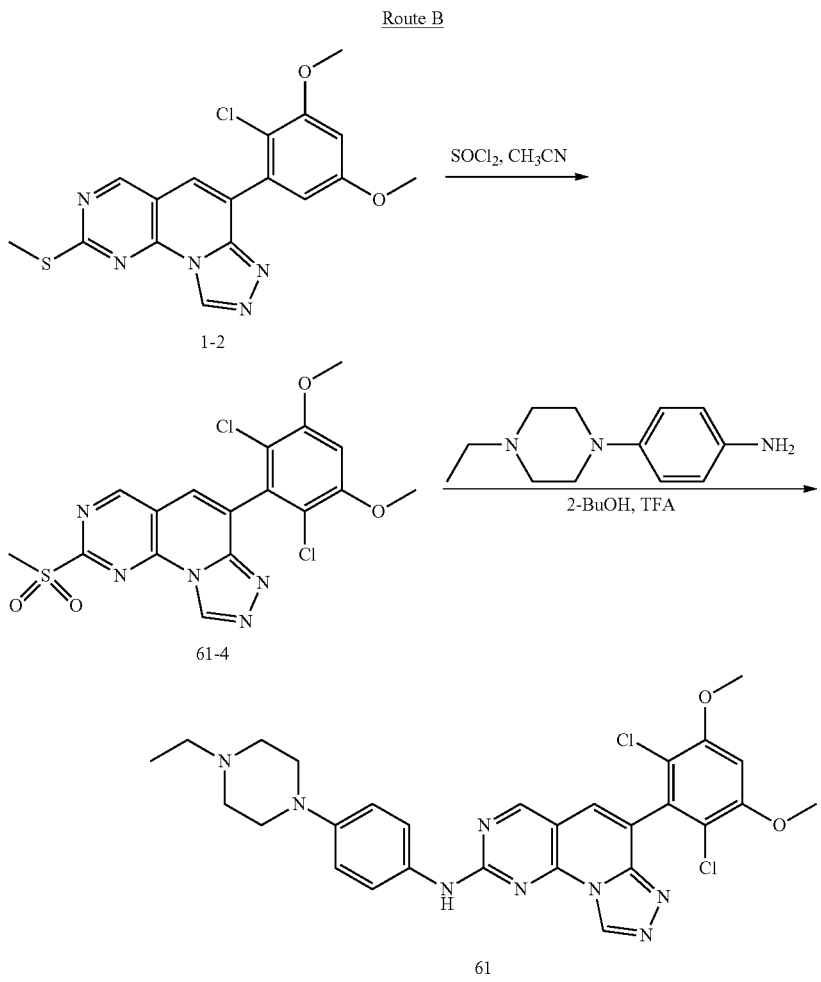

Route B

Route C
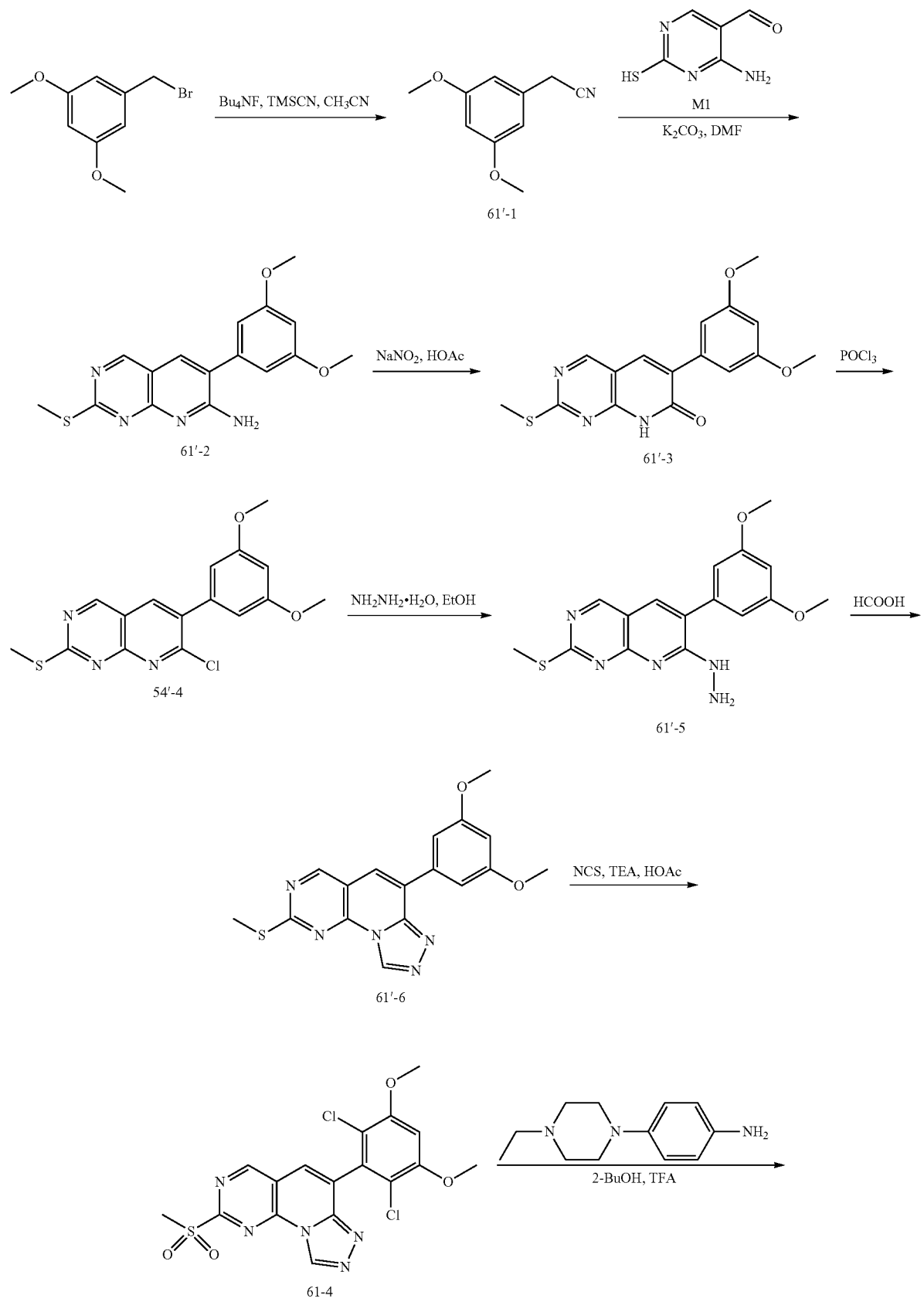

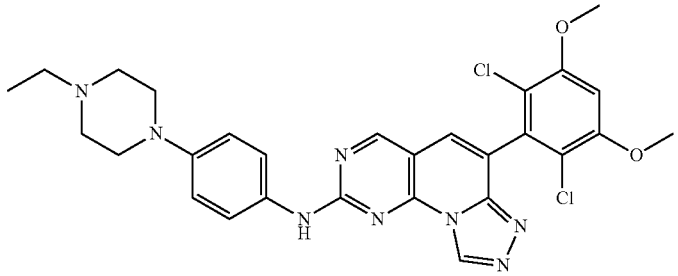

61

Step 1: Preparation of Compound 61'-1

40.0 g of 3,5-dimethoxybromobenzyl and 400 ml of acetonitrile was cooled down to 0° C. with stirring, and in which was added 34.3 g of TMSCN and 346 ml of 1M of Bu$_4$NF-THF successively. The mixture was raised to 60° C. slowly and reacted for 1 hr after the dripping is finished. The mixture was concentrated under reduced pressure after the reaction is finished, the residue was poured into 500 ml of ice water, and a large amount of solid was precipitated with stirring. The mixture was filtrated, and the solid was washed with water, dried to get 30.9 g of compound 61'-1, which was white solid. It was used in the next step directly without purification.

Step 2: Preparation of Compound 61'-2

A mixture of 26.5 g of compound 61'-1 and 300 ml of THF was cooled down to 0° C. with stirring, and in which was added 6.4 g of NaH (60% dispersed in mineral oil) in batches. The mixture was reacted for 1.5 hrs with stirring under the constant temperature. 18.1 g of compound M1 was added in batches, the mixture was raised to room temperature naturally, and reacted overnight. The reaction system was quenched by adding saturated aqueous solution of ammonium chloride and extracted with EA. The organic phase was combined, washed with water and dried. The mixture was filtrated, and concentrated under reduced pressure. The resulting solid was dried under vacuum at 50° C. overnight to get 24.7 g of compound 61'-2, which was yellow solid. It was used in the next reaction directly without purification.

LC-MS [M+H$^+$] 329.1.

Step 3: Preparation of Compound 61'-3

A mixture of 24.7 g of compound 61'-2 and 250 ml of glacial acetic acid was added into 31.2 g of sodium nitrite in batches. The mixture was raised to 70° C. slowly and reacted for 5 hrs after the dripping is finished. The mixture was cooled down to room temperature, and was poured into ice water, then a large amount of solid was precipitated. The mixture was filtrated, and the solid was rinsed to neutral with water and dried under vacuum at 50° C. overnight to get 24.6 g of compound 61'-3, which was yellow solid. It was used in the next reaction directly without purification.

LC-MS [M+H$^+$] 330.1.

Step 4: Preparation of Compound 61'-4

A mixture of 24.6 g of compound 61'-3, 250 ml of acetonitrile and 122.5 ml of POCl$_3$ was heated to reflux for 3 hrs. After the reaction is finished, the mixture was cooled down to room temperature and concentrated under reduced pressure to remove most solvent. The residue was quenched by pouring into ice water and extracted with EA. The organic phase was combined, washed with water and dried. Filtrated and concentrated under reduced pressure. The obtained solid was dried overnight under vacuum at 50° C. to get 25.0 g of compound 61'-4, which was light yellow solid. It was used in the next reaction directly without purification.

LC-MS [M+H$^+$] 348.1.

Step 5: Preparation of Compound 61'-5

Compound 61'-5 of was prepared by a similar procedure as described in the step 1 of Route A of Example 1.

LC-MS [M+H$^+$] 344.1.

Step 6: Preparation of Compound 61'-6

Compound 61'-6 was prepared by a similar procedure as described in the step 1 of Route A of Example 1.

LC-MS [M+H$^+$] 354.1.

Step 7: Preparation of Compound 61-4

A mixture of 10.0 g of compound 61-4, 8.59 g of TEA and 200 ml of glacial acetic acid was added into 17.0 g of NCS in batches. The mixture was reacted for 2 hrs at room temperature. After the reaction was finished, the mixture was diluted with EA and washed three times with water. The organic phase was washed twice with saturated sodium carbonate aqueous solution and washed twice with water and dried. Filtrated and concentrated under reduced pressure, the obtained solid was dried overnight under vacuum at 50° C. to get 12.5 g of compound 61-4, which was yellow solid. It was used in the next reaction directly without purification.

LC-MS [M+H$^+$] 454.0.

Step 8: Preparation of Compound 61

Compound 61 was prepared by a similar procedure in the step 5 of Example 2.

LC-MS [M+H$^+$] 579.2.

The compounds of table 3 were prepared in a similar procedure as described in the Example 61 via different reaction starting materials and appropriate reagents.

TABLE 3

| Examples | Chemical structure | Chemical name | LC-MS [M + H+] |
|---|---|---|---|
| 62 | 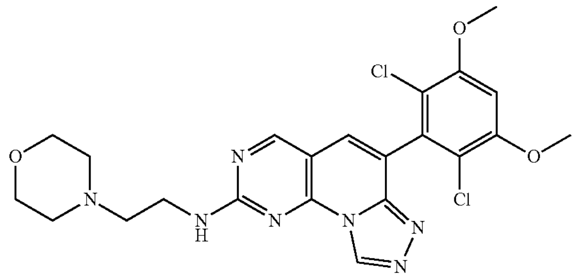 [SMILES: COc1cc(OC)c(Cl)c(-c2cc3cnc(NCCN4CCOCC4)nc3n3cnnc23)c1Cl] | 6-(2,6-dichloro-3,5-dimethoxyphenyl)-N-(2-morpholinoethyl)-[1,2,4]triazolo[4',3':1,6]pyrido[2,3-d]pyrimidin-2-amine | 504.1 |
| 63 | 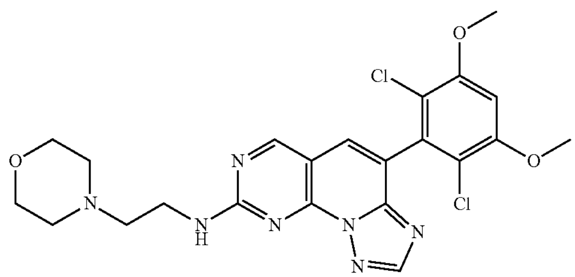 [SMILES: COc1cc(OC)c(Cl)c(-c2cc3cnc(NCCN4CCOCC4)nc3n3ncnc23)c1Cl] | 4-(2,6-dichloro-3,5-dimethoxyphenyl)-N-(2-morpholinoethyl)-[1,2,4]triazolo[1',5':1,6]pyrido[2,3-d]pyrimidin-8-amine | 504.1 |
| 64 | 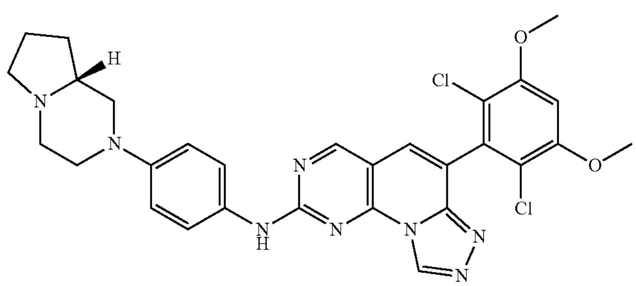 [SMILES: COc1cc(OC)c(Cl)c(-c2cc3cnc(Nc4ccc(N5CCN6CCC[C@@H]6C5)cc4)nc3n3cnnc23)c1Cl] | (R)-6-(2,6-dichloro-3,5-dimethoxyphenyl)-N-(4-(hexahydropyrrolo[1,2-a]pyrazin-2(1H)-yl)phenyl)-[1,2,4]triazolo[4',3':1,6]pyrido[2,3-d]pyrimidin-2-amine | 591.5 |
| 65 | 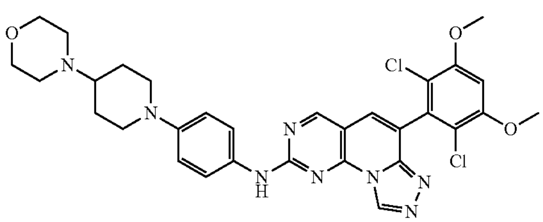 [SMILES: COc1cc(OC)c(Cl)c(-c2cc3cnc(Nc4ccc(N5CCC(N6CCOCC6)CC5)cc4)nc3n3cnnc23)c1Cl] | 6-(2,6-dichloro-3,5-dimethoxyphenyl)-N-(4-(4-morpholinopiperidin-1-yl)phenyl)-[1,2,4]triazolo[4',3':1,6]pyrido[2,3-d]pyrimidin-2-amine | 635.2 |

Nuclear magnetic date of compound 64 is as shown below:

$^1$H NMR (DMSO-d6, 400 MHz) δ 10.43 (s, 1H), 9.66 (s, 1H), 9.18 (s, 1H), 7.81 (br, 2H), 7.66 (s, 1H), 7.09 (s, 1H), 7.08-1.06 (m, 2H), 4.00 (s, 6H), 3.75-3.58 (m, 2H), 3.25-2.72 (m, 3H), 2.44-2.08 (m, 4H), 1.87-1.34 (m, 4H).

Example 66: Preparation of Compound 66 (6-(2-chloro-3,5-dimethoxyphenyl)-N²-(4-(4-ethylpiperazin-1-yl)phenyl)-[1,2,4]triazolo[4',3':1,6]pyrido[2,3-d]pyrimidin-2,9-diamine)

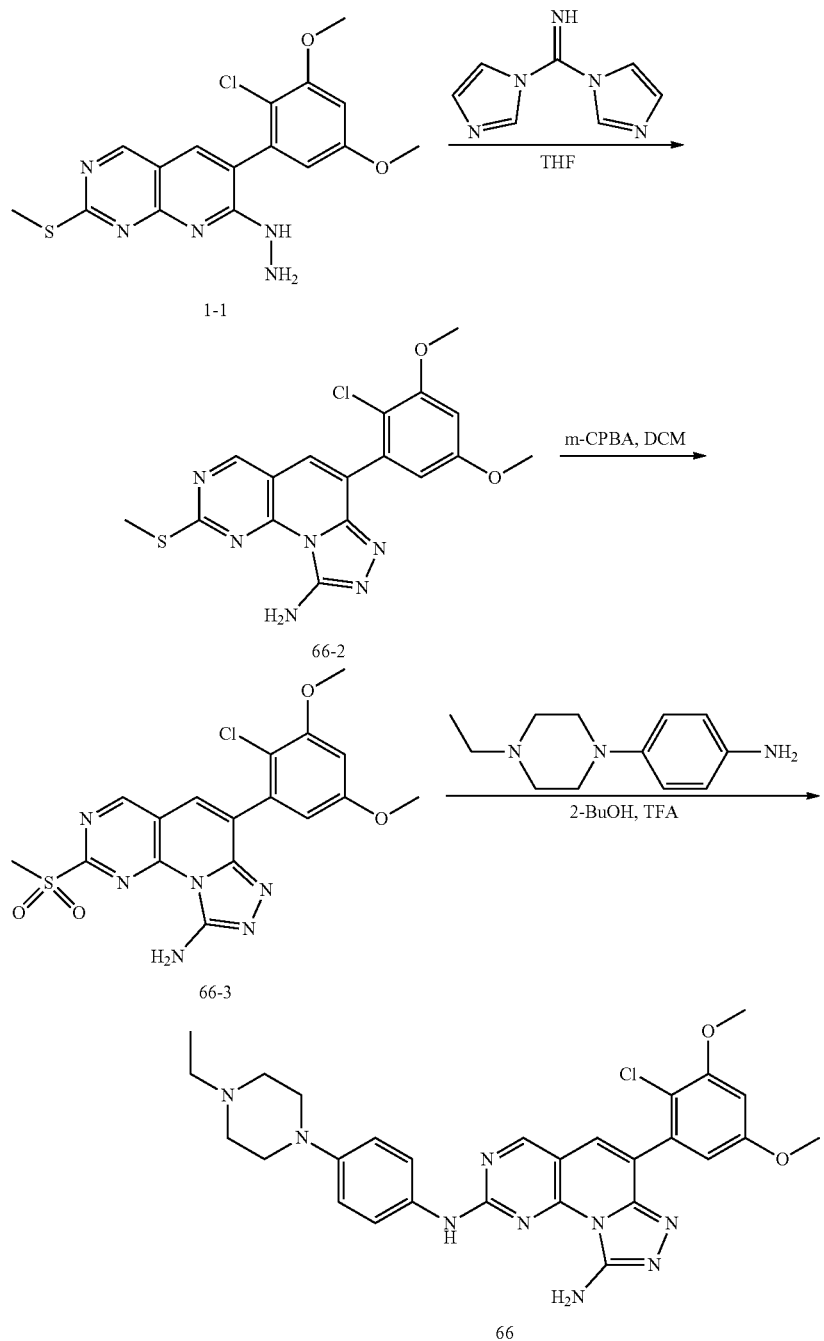

Step 1: Preparation of Compound 66-2

A mixture of 100 mg of compound 1-1, 45 mg of Di(1H-imidazolyl) imide and 10 ml of THF was heated reflux for 12 hrs. The reaction mixture was diluted with water, extracted with EA, washed with saline solution, dried over anhydrous Na₂SO₄, and concentrated under reduced pressure. The residue was purified via silica column chromatography (dichloromethane/methanol=40/1) to get 50 mg of compound 66-2, the yield was 47.0%, which was pale yellow solid.

LC-MS [M+H⁺] 403.1.

Step 2: Preparation of Compound 66-3

Compound 66-3 was synthesized by a similar procedure as described in the step 4 of Example 2.

LC-MS [M+H⁺] 435.1.

Step 3: Preparation of Compound 66
Compound 66 was synthesized by a similar procedure as described in the step 5 of Example 2.
LC-MS [M+H$^+$] 560.2.
Example 67: Preparation of Compound 67 (6-(5-chloro-2-methyl-1H-benzo[d]imidazol-6-yl)-N-(4-(4-ethylpiperazin-1-yl)phenyl)-[1,2,4]triazolo[4',3':1,6]pyrido[2,3-d]pyrimidin-2-amine)
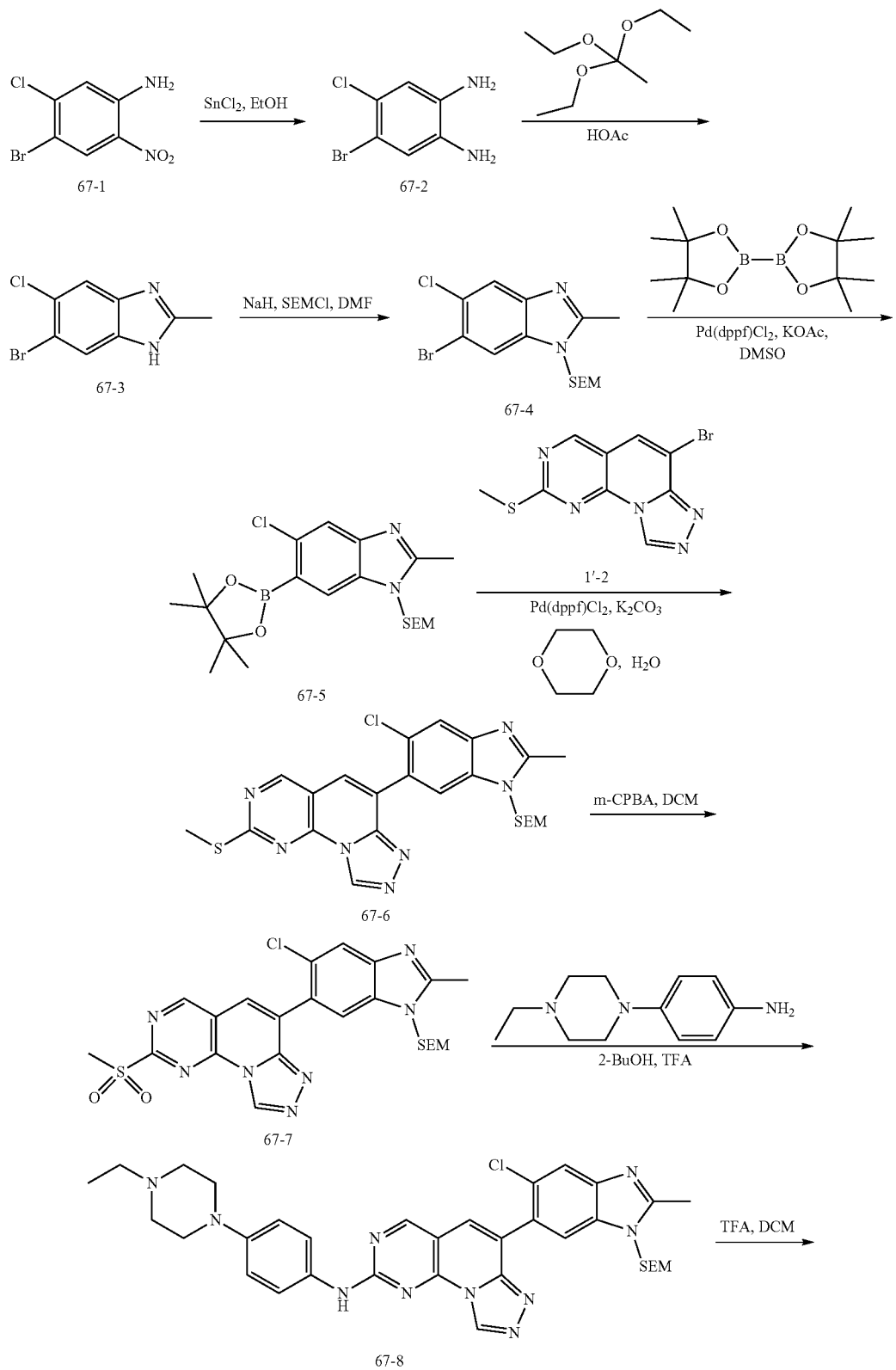

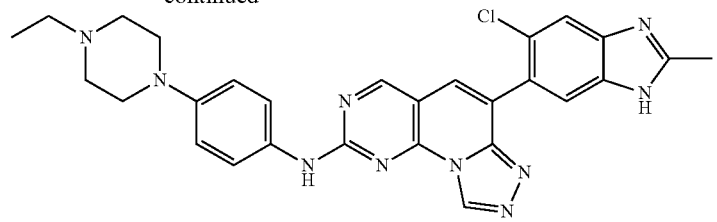

67

Step 1: Preparation of Compound 67-2

A mixture of 5.23 g of compound 67-1, 18.77 g of stannous chloride dehydrate and 125 ml of EtOH was reacted for 12 hrs at 70° C. The mixture was concentrated under reduced pressure, the residue was dissolved into water, and the pH was adjusted to 8 with saturated NaHCO$_3$. The mixture was extracted with EA, washed with saline, dried over anhydrous Na$_2$SO$_4$ and concentrated to get 4.4 g of compound 67-2, which was yellow solid.
LC-MS [M+H$^+$] 220.9.

Step 2: Preparation of Compound 67-3

A mixture of 4.4 g of compound 67-2, 50 ml of acetic acid and 4.83 g of triethyl orthoacetate was stirred at 120° C. for 1.5 hrs in a sealed container, the reaction solution was concentrated under reduced pressure to get 5.9 g of compound 67-3, which was light yellow solid. It was used in the next reaction directly without purification.
LC-MS [M+H$^+$] 244.9.

Step 3: Preparation of Compound 67-4

Under nitrogen protection at 0° C., 1.32 g of NaH (60% in mineral oil) was added into solution of 5.40 g of compound 67-3 dissolved into 100 ml of THF in batches with stirring, the reaction mixture was stirred for 1.5 hrs at 0° C. 7.33 g of 2-(trimethylsilyl) ethoxymethyl chloride was added into the reaction solution with stirring at 0° C., and the reaction mixture was reacted for 12 hrs at RT. The reaction was quenched with water, extracted with EA, washed with saline, dried over anhydrous Na$_2$SO$_4$, and concentrated under reduced pressure to get 4.52 g crude product of compound 67-4, which was grey solid.
LC-M [M+H$^+$] 375.0.

Step 4: Preparation of Compound 67-5

A mixture of 1 g of compound 67-4, 811 mg of pinacol diborate ester, 195 mg of Pd(dppf)Cl$_2$, 1.0 g of potassium acetate and 20 ml of DMSO was stirred for 3 hrs at 100° C. under the nitrogen protection. The reaction mixture was cooled down to RT and diluted with water. The mixture was filtrated and the solid was washed with hex/EA (20/1). the organic phased was combined, dried over anhydrous Na$_2$SO$_4$, and concentrated to get 1 g crude product of compound 67-5, which was light brown solid. It was used in the next reaction directly without purification.
LC-MS [M+H$^+$] 423.2.

Step 5: Preparation of Compound 67-6

A mixture of 467 mg of compound 1'-2, 1 g of compound 67-5, 115 mg of Pd(dppf)Cl$_2$, 652 mg of potassium carbonate, 20 ml of 1,4-dioxane and 2 ml of water was stirred for 12 hrs at 100° C. under nitrogen protection. The reaction mixture was concentrated under reduced pressure, the residue was purified via silica gel column (DCM/MeOH=20/1) to get 650 mg of compound 67-6, which was light brown solid, the yield was 80.5%.
LC-MS [M+H$^+$] 512.1.

Step 6: Preparation of Compound 67-7

650 mg of compound 67-6 was dissolved into 50 ml of DCM, in which was added 329 mg of M-chloroperoxybenzoic acid. The reaction mixture was stirred for 1.5 hrs at RT, then concentrated under reduced pressure to get 700 mg crude product of compound 67-7, which was light yellow solid. It was used in the next production directly without purification.
LC-MS [M+H$^+$] 544.1.

Step 7: Preparation of Compound 67-8

A mixture of 700 mg of compound 67-7, 396 mg of M2, 50 ml of 2-butanol, 10 ml of TFA was stirred for 12 hrs at 120° C. The reaction solution was concentrated under reduced pressure, the residue was dissolved into 1N hydrochloric acid. The mixture was filtered, the filtrate was extracted with EA, and the pH was adjusted to 8 with saturated NaHCO$_3$. The reaction solution was filtered, and the solid was washed with water, the obtained solid was dried under vacuum to get 400 mg crude product of compound 67-8, which was brown solid.
LC-MS [M+H$^+$] 669.3.

Step 8: Preparation of Compound 67

A mixture of 400 mg of compound 67-8, 40 ml of DCM and 10 ml of TFA was stirred for 3 hrs at RT, the reaction mixture was concentrated under reduced pressure. The residue was dissolved into water, and the pH was adjusted to 8 with saturated NaHCO$_3$. The mixture was extracted with DCM, washed with saline, dried over anhydrous Na$_2$SO$_4$, and concentrated under reduced pressure. The residue was purified via silica column chromatography (DCM/MeOH=10/1) to get 156 mg of compound 67, which was yellow solid.
LC-MS [M+H$^+$] 539.2.

The compounds of Table 4 were prepared by a similar procedure as described in the Example 67 via different reaction starting materials and appropriate reagents.

TABLE 4

| Ex. NO | Chemical structure | Chemical name | LC-MS [M + H+] |
|---|---|---|---|
| 68 | 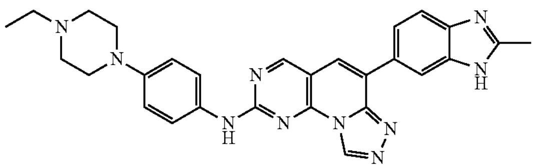 [SMILES: CCN1CCN(c2ccc(Nc3ncc4cc(-c5ccc6nc(C)[nH]c6c5)c5nncn5c4n3)cc2)CC1] | N-(4-(4-ethylpiperazin-1-yl)phenyl)-6-(2-methyl-1H-benzo[d]imidazol-6-yl)-[1,2,4]triazolo[4',3':1,6]pyrido[2,3-d]pyrimidin-2-amine | 505.3 |
| 69 | 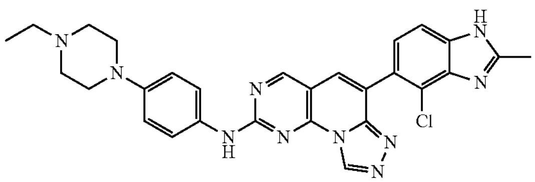 [SMILES: CCN1CCN(c2ccc(Nc3ncc4cc(-c5ccc6[nH]c(C)nc6c5Cl)c5nncn5c4n3)cc2)CC1] | 6-(4-chloro-2-methyl-1H-benzo[d]imidazol-5-yl)-N-(4-(4-ethylpiperazin-1-yl)phenyl)-[1,2,4]triazolo[4',3':1,6]pyrido[2,3-d]pyrimidin-2-amine | 539.2 |
| 70 | 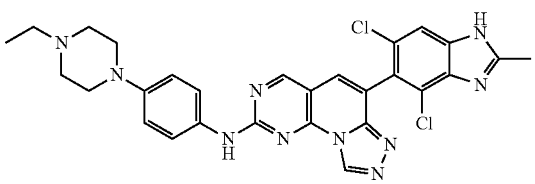 [SMILES: CCN1CCN(c2ccc(Nc3ncc4cc(-c5c(Cl)cc6[nH]c(C)nc6c5Cl)c5nncn5c4n3)cc2)CC1] | 6-(4,6-dichloro-2-methyl-1H-benzo[d]imidazol-5-yl)-N-(4-(4-ethylpiperazin-1-yl)phenyl)-[1,2,4]triazolo[4',3':1,6]pyrido[2,3-d]pyridimin-2-amine | 573.2 |
| 71 | 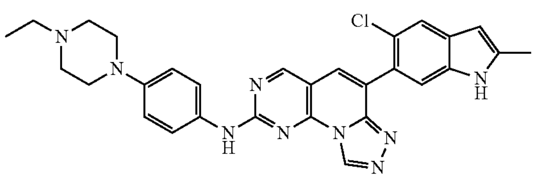 [SMILES: CCN1CCN(c2ccc(Nc3ncc4cc(-c5cc6[nH]c(C)cc6cc5Cl)c5nncn5c4n3)cc2)CC1] | 6-(5-chloro-2-methyl-1H-indol-6-yl)-N-(4-(4-ethylpiperazin-1-yl)phenyl)-[1,2,4]triazolo[4',3':1,6]pyrido[2,3-d]pyrimidin-2-amine | 539.1 |
| 72 | 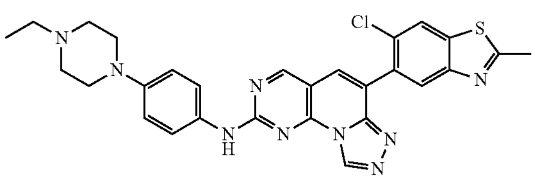 [SMILES: CCN1CCN(c2ccc(Nc3ncc4cc(-c5cc6nc(C)sc6cc5Cl)c5nncn5c4n3)cc2)CC1] | 6-(6-chloro-2-methylbenzo[d]thiazol-5-yl)-N-(4-(4-ethylpiperazin-1-yl)phenyl)-[1,2,4]triazolo[4',3':1,6]pyrido[2,3-d]pyrimidin-2-amine | 557.1 |
| 73 | 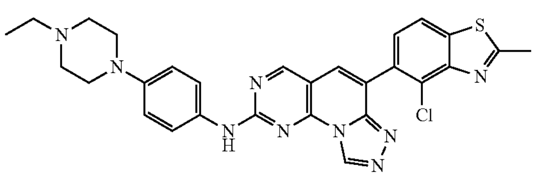 [SMILES: CCN1CCN(c2ccc(Nc3ncc4cc(-c5ccc6sc(C)nc6c5Cl)c5nncn5c4n3)cc2)CC1] | 6-(4-chloro-2-methylbenzo[d]thiazol-5-yl)-N-(4-(4-ethylpiperazini-1-yl)phenyl)-[1,2,4]triazolo[4',3':1,6]pyrido[2,3-d]pyrimidin-2-amine | 557.1 |
| 74 | 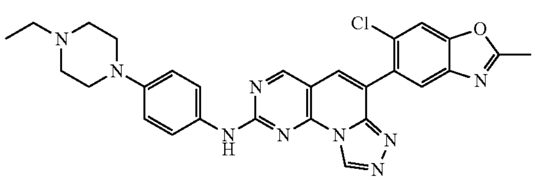 [SMILES: CCN1CCN(c2ccc(Nc3ncc4cc(-c5cc6nc(C)oc6cc5Cl)c5nncn5c4n3)cc2)CC1] | 6-(6-chloro-2-methylbenzo[d]oxazol-5-yl)-N-(4-(4-ethylpiperazin-1-yl)phenyl)-[1,2,4]triazolo[4',3':1,6]pyrido[2,3-d]pyrimidin-2-amine | 540.2 |
| 75 | 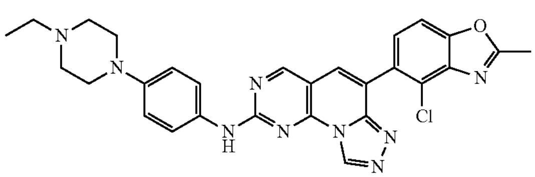 [SMILES: CCN1CCN(c2ccc(Nc3ncc4cc(-c5ccc6oc(C)nc6c5Cl)c5nncn5c4n3)cc2)CC1] | 6-(4-chloro-2-methylbenzo[d]oxazol-5-yl)-N-(4-(4-ethylpiperazin-1-yl)phenyl)-[1,2,4]triazolo[4',3':1,6]pyrido[2,3-d]pyrimidin-2-amine | 540.2 |

TABLE 4-continued

| Ex. NO | Chemical structure | Chemical name | LC-MS [M + H+] |
|---|---|---|---|
| 76 | 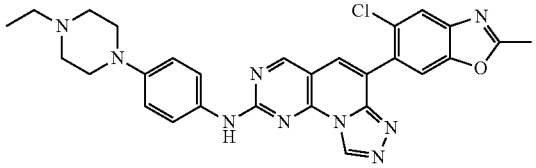 [SMILES: CCN1CCN(c2ccc(Nc3ncc4cc(-c5cc6oc(C)nc6cc5Cl)c5nncn5c4n3)cc2)CC1] | 6-(5-chloro-2-methylbenzo[d]oxazol-6-yl)-N-(4-(4-ethylpiperazin-1-yl)phenyl)-[1,2,4]triazolo[4',3':1,6]pyrido[2,3-d]pyrimidin-2-amine | 540.2 |
| 77 | 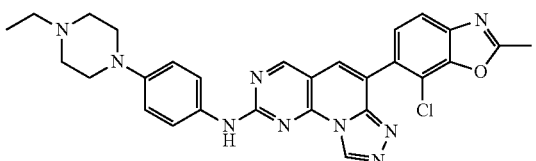 | 6-(7-chloro-2-methylbenzo[d]oxazol-6-yl)-N-(4-(4-ethylpiperazin-1-yl)phenyl)-[1,2,4]triazolo[4',3':1,6]pyrido[2,3-d]pyrimidin-2-amine | 540.2 |
| 78 | 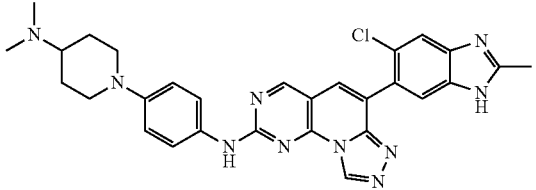 | 6-(5-chloro-2-methyl-1H-benzo[d]imidazol-6-yl)-N-(4-(4-(dimethylamino)piperazin-1-yl)phenyl)-[1,2,4]triazolo[4',3':1,6]pyrido[2,3-d]pyrimidin-2-amine | 553.1 |
| 79 | 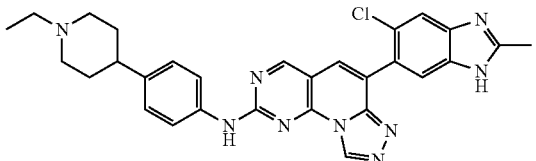 | 6-(5-chloro-2-methyl-1H-benzo[d]imidazol-6-yl)-N-(4-(1-ethylpiperidin-4-yl)phenyl)-[1,2,4]triazolo[4',3':1,6]pyrido[2,3-d]pyrimidin-2-amine | 538.1 |
| 80 | 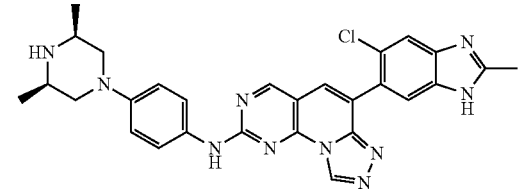 | 6-(5-chloro-2-methyl-1H-benzo[d]imidazol-6-yl)-N-(4-((3S,5R)-3,5-dimethylpiperazin-1-yl)phenyl)-[1,2,4]triazolo[4',3':1,6]pyrido[2,3-d]pyrimidin-2-amine | 539.0 |
| 81 | 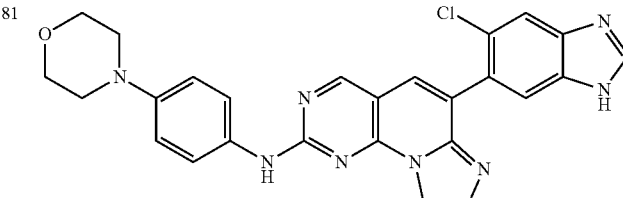 | 6-(5-chloro-2-methyl-1H-benzo[d]imidazol-6-yl)-N-(4-morpholinophenyl)-[1,2,4]triazolo[4',3':1,6]pyrido[2,3-d]pyrimidin-2-amine | 512.0 |
| 82 | 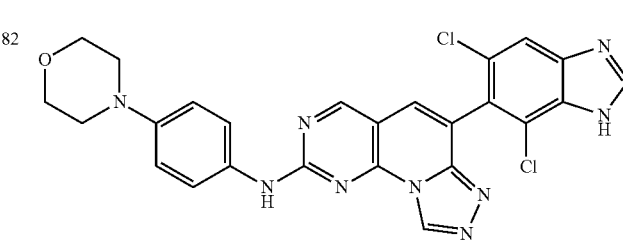 | 6-(5,7-dichloro-2-methyl-1H-benzo[d]imidazol-6-yl)-N-(4-morpholinophenyl)-[1,2,4]triazolo[4',3':1,6]pyrido[2,3-d]pyrimidin-2-amine | 546.4 |

TABLE 4-continued

| Ex. NO | Chemical structure | Chemical name | LC-MS [M + H+] |
|---|---|---|---|
| 83 | 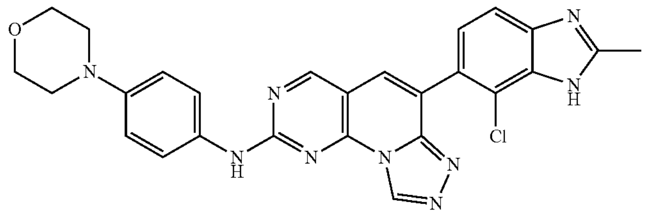 [SMILES: Cc1nc2ccc(-c3cc4cnc(Nc5ccc(N6CCOCC6)cc5)nc4n4cnnc34)c(Cl)c2[nH]1] | 6-(7-chloro-2-methyl-1H-benzo[d]imidazol-6-yl)-N-(4-morpholinophenyl)-[1,2,4]triazolo[4',3':1,6]pyrido[2,3-d]pyrimidin-2-amine | 512.0 |
| 84 | 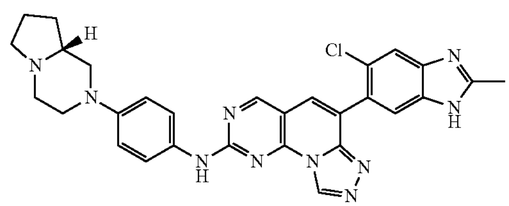 [SMILES: Cc1nc2cc(Cl)c(-c3cc4cnc(Nc5ccc(N6CCN7CCC[C@@H]7C6)cc5)nc4n4cnnc34)cc2[nH]1] | N-(4-(hexahydropyrrolo[1,2-a]pyrazin-2(1H)-yl)phenyl)-[1,2,4]triazolo[4',3':1,6]pyrido[2,3-d]pyrimidin-2-amine | 551.2 |

Nuclear magnetic date of compound 81 was as shown below:

$^1$H NMR (DMSO-d6, 400 MHz) 10.33 (s, 1H), 9.66 (s, 1H), 9.18 (s, 1H), 7.82-7.75 (m, 3H), 7.70-7.68 (m, 3H), 7.01 (d, J=8 Hz, 2H), 3.76 (t, J=4 Hz, 4H), 3.09 (t, J=4 Hz, 4H), 2.55 (s, 3H).

Example 85: Preparation of Compound 85

(6-(2-chloro-3,5-dimethoxyphenyl)-N-(4-(4-ethylpiperazin-1-yl)phenyl)-9-methyl-[1,2,4]triazolo[4',3':1,6]pyrido[2,3-d]pyrimidin-2-amine)

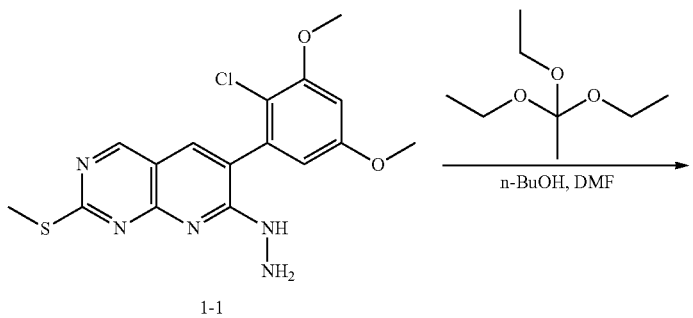

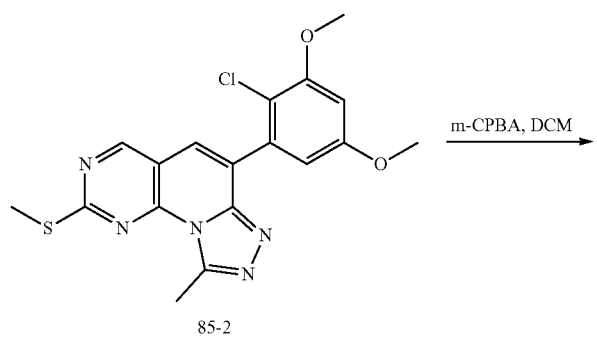

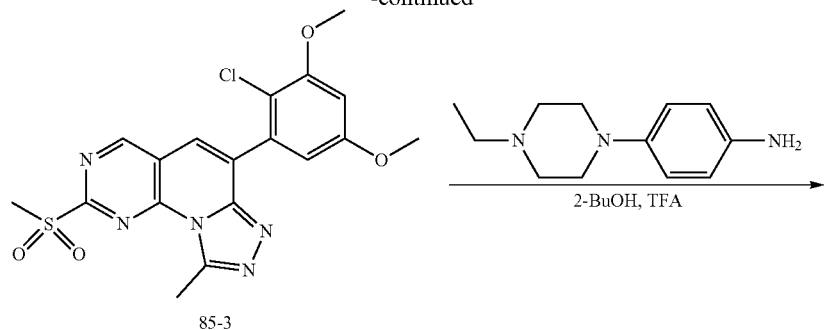

85-3

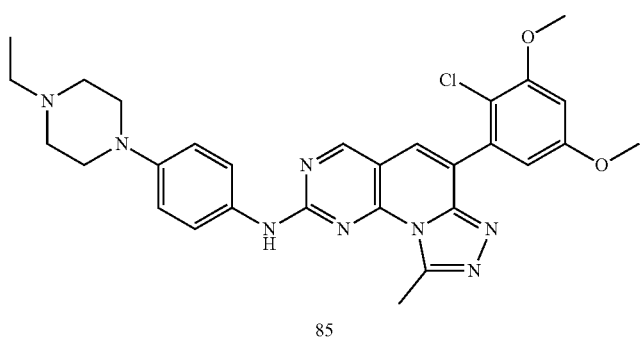

85

Step 1: Preparation of Compound 85-2

A mixture of 150 mg of compound 1-1, 5 ml of n-butyl alcohol, 5 ml of DMF and 65 mg of triethyl orthoacetate was stirred for 3 hrs at 100° C. The reaction solution was concentrated under reduced pressure, and the residue was purified via silica column chromatography (dichloromethane/MeOH=60/1) to get 72 mg of compound 85-2 as yellow solid, the yield was 45.1%.

LC-MS [M+H$^+$] 422.0.

Step 2: Preparation of Compound 85-3

Compound 85-3 was prepared by a similar procedure as described in the step 4 of Example 2.

LC-MS [M+H$^+$] 454.0.

Step 3: Preparation of Compound 85

Compound 85 was prepared by a similar procedure as described in the step 5 of Example 2.

LC-MS [M+H$^+$] 559.2.

$^1$H NMR (DMSO-d6, 400 MHz) δ 9.07 (s, 1H), 7.56 (m, 2H), 7.56 (d, J=11.8 Hz, 17H), 7.54 (s, 1H), 6.98 (d, 2H), 6.83 (s, 1H), 6.71 (s, 1H), 3.91 (s, 3H), 3.80 (s, 3H), 3.58 (s, 3H), 3.17 (m, 4H), 2.67 (m, 4H), 1.77 (q, 2H), 1.10 (t, 3H).

Example 86: Preparation of Compound 86 (N-(4-((6-(2-chloro-3,5-dimethoxyphenyl)-2-((2-morpholinoethyl)amino)-[1,2,4]triazolo[4',3':1,6]pyrido[2,3-d]pyrimidin-9-yl)methyl)phenyl)acrylamide)

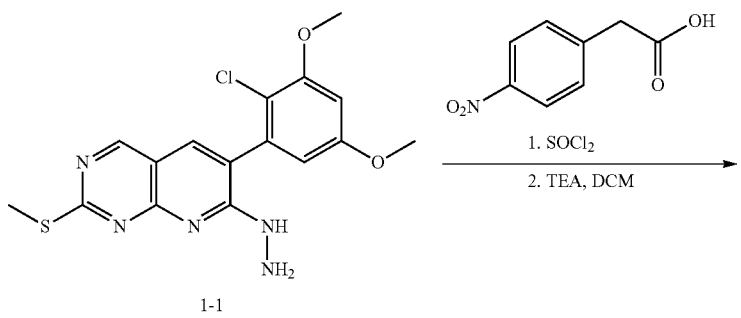

1-1

103
104
-continued
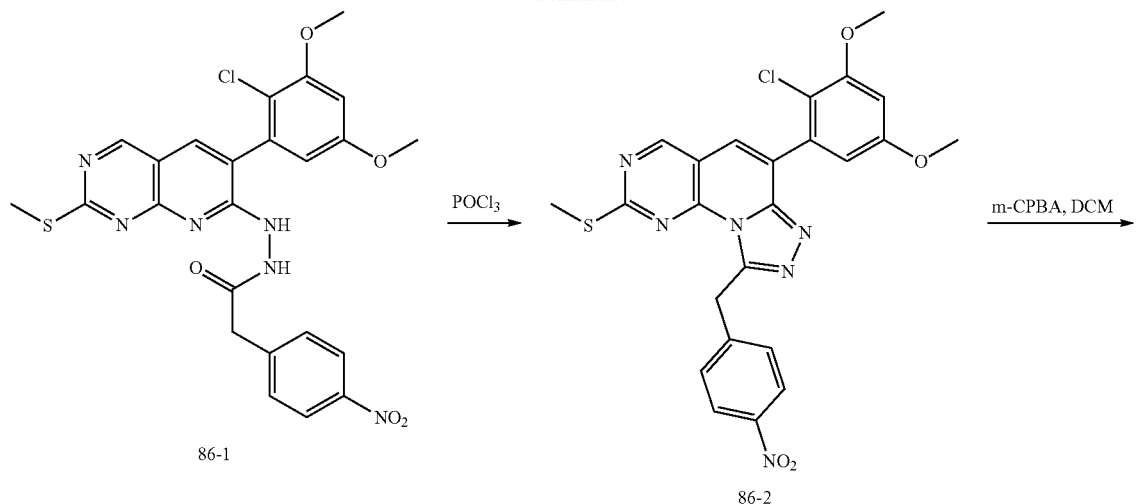
86-1 → (POCl₃) → 86-2 → (m-CPBA, DCM) →
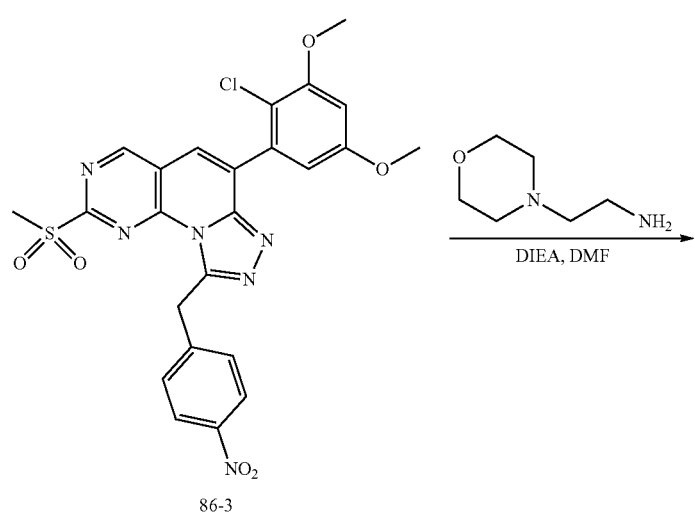
86-3
→ (morpholinoethylamine / DIEA, DMF) →
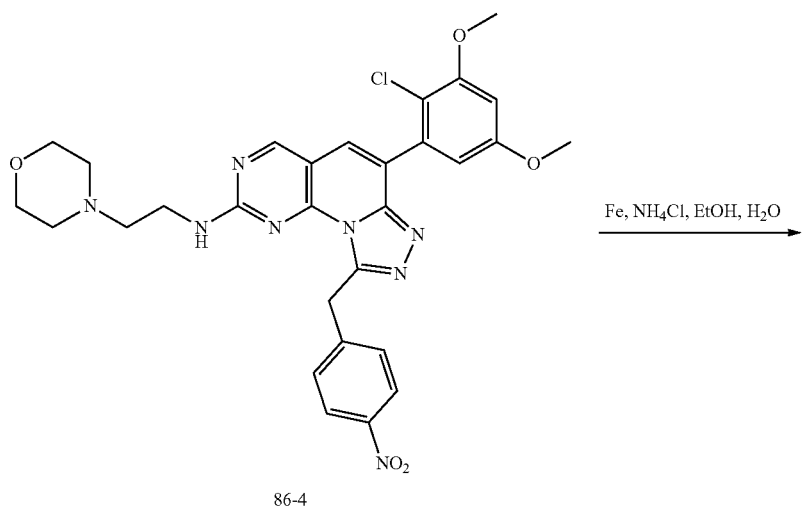
86-4
→ (Fe, NH₄Cl, EtOH, H₂O) →

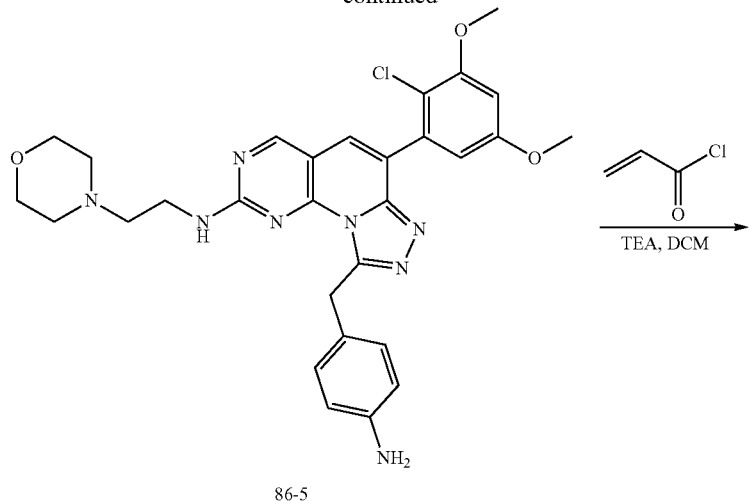

86-5

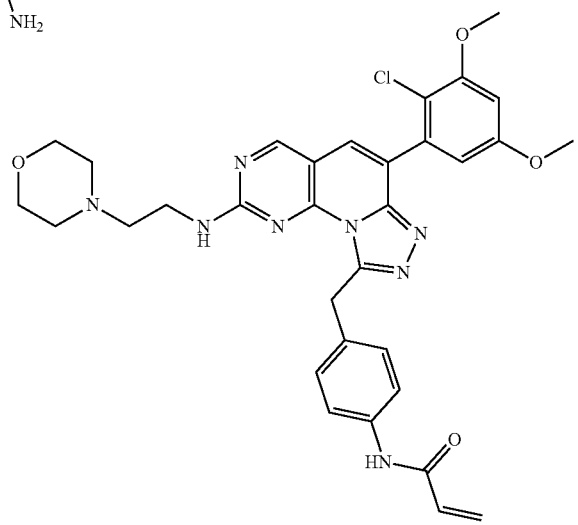

86-6

Step 1: Preparation of Compound 86-1

1.17 g of 4-nitrophenylacetic acid and 10 ml of sulfoxide chloride was heated to reflux for 30 mins. The mixture was concentrated under reduced pressure, 10 ml of dichloromethane was added to dissolve, concentrated again, and the produce was repeated twice to get colorless oil which was dissolved into 10 ml of dichloromethane. The obtained solution was added into a solution of 2.03 g of compound of 1-1, 1.63 g of TEA and 40 ml of dichloromethane at 0° C. The mixture was reacted overnight with stirring at room temperature after the dripping was finished. The reaction was quenched by adding water, and the mixture was extracted with dichloromethane. The organic phase was combined, dried over anhydrous sodium sulfate and concentrated under reduced pressure to get 3.42 g crude product of compound 86-1, which was reddish brown solid. It was used in the next reaction directly without purification.

LC-MS [M+H$^+$] 541.1.

Step 2: Preparation of Compound 86-2

A mixture of 3.42 g of compound 86-1 and 20 ml of POCl$_3$ was heated at 100° C. for 3 hrs. The mixture was cooled down to room temperature, and the reaction was quenched by adding into ice water mixture. The mixture was extracted with dichloromethane, the organic phase was combined, washed with saturated NaHCO$_3$ aqueous solution and water successively and concentrated under reduced pressure. The obtained crude product was purified via silica column chromatography (DCM/MeOH=100/1 to 50/1) to get 1.31 g of 86-2, which was yellow solid.

LC-MS [M+H$^+$] 523.1.

Step 3: Preparation of Compound 86-3

A suspension system of 1.31 g of compound 86-2 and 39 mL of dichloromethane was cooled down to 0° C., and was added into 0.76 g of m-CPBA in batches. The mixture was reacted for 30 min with stirring at room temperature, and the reacted was quenched by adding into saturated sodium thiosulfate aqueous solution. The mixture was extracted with dichloromethane, the organic phase was combined, washed with water, dried over anhydrous sodium sulfate and concentrated under reduced pressure to get 1.25 g crude product of compound 86-3, which was yellow solid. It was used in the next reaction directly without purification.

LC-MS [M+H$^+$] 555.1.

Step 4: Preparation of Compound 86-4

A mixture of 600 mg of compound 86-3, 10 mL of DMF, 432 mg of DIEA and 217 mg of N-(2-aminoethyl) morpholine was heated for 2 hrs at 80° C. The mixture was cooled down to room temperature, diluted with water, and extracted with dichloromethane. The organic phase was washed with water, dried over anhydrous sodium sulfate and concentrated under reduced pressure. The obtained crude product was purified via silica column chromatography (DCM/MeOH=20/1) to get 450 mg of compound 86-4, which was light yellow solid.

LC-MS [M+H$^+$] 605.2.

Step 5: Preparation of Compound 86-5

A mixture of 450 mg of compound 86-4, 50 ml of ethanol, 10 ml of water and 1 ml of concentrated HCl was added into 463 mg of SnCl$_2$.2H$_2$O. The obtained mixed system was heated for 2.5 hrs at 80° C. The mixed system was cooled down to room temperature without heating. The mixed system was diluted with water, and the pH was adjusted to 8~9 with saturated NaHCO$_3$ aqueous solution, and the mixed system was extracted with dichloromethane. The organic phase was combined, washed with water, dried over anhydrous sodium sulfate, and concentrated under reduced pressure to get 220 mg crude product of compound 86-5, which was light yellow solid. It was used in the next reaction directly without purification.

LC-MS [M+H$^+$] 575.2.

Step 6: Preparation of Compound 86

A mixture of 220 mg of compound 86-5, 30 ml of dichloromethane and 116 mg of TEA was cooled down to −5° C.~0° C., and in which was added 52 mg of acryloyl chloride dropwise. After the dripping was finished, the temperature was raised naturally, and the mixture was reacted for 30 mins with stirring. The mixture was quenched with water, diluted with dichloromethane, washed with saturated NaHCO$_3$ aqueous solution and water, dried over anhydrous sodium sulfate and concentrated under reduced pressure. The obtained crude product was purified via silica column chromatography (DCM/MeOH=20/1) to get 155 mg of compound 86, which was light yellow solid.

LC-MS [M+H$^+$] 629.1.

$^1$H NMR (DMSO-d6, 400 MHz) δ 10.09-10.06 (m, 1H), 8.96 (s, 1H), 8.05-7.91 (m, 1H), 7.58-7.52 (m, 3H), 7.47-7.40 (m, 1H), 7.17-7.15 (m, 1H), 6.82 (s, 1H), 6.74-6.72 (m, 1H), 6.45-6.38 (m, 1H), 6.27-6.20 (m, 1H), 5.74-5.71 (m, 1H), 5.04 (s, 2H), 3.91 (s, 3H), 3.80 (s, 3H), 3.58-3.34 (m, 8H), 2.44-2.30 (m, 4H).

The compounds of table 5 were prepared by a similar procedure as described in the Examples 85 and 86 via different reaction starting materials and appropriate reagents.

TABLE 5

| Examples | Chemical structure | Chemical name | LC-MS [M + H$^+$] |
|---|---|---|---|
| 87 | 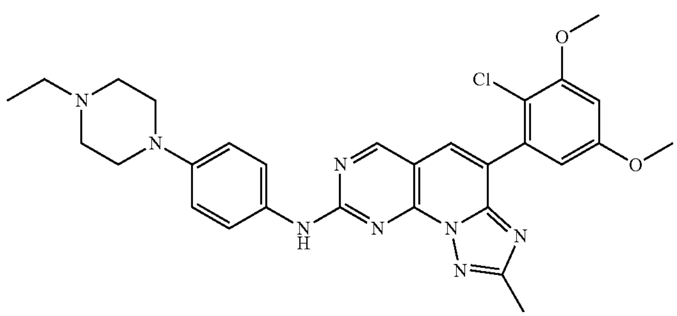 [SMILES: CCN1CCN(c2ccc(Nc3ncc4cc(-c5cc(OC)cc(OC)c5Cl)c5nc(C)nn5c4n3)cc2)CC1] | 4-(2-chloro-3,5-dimethoxyphenyl)-N-(4-(4-ethylpierazin-1-yl)phenyl)-2-methyl-[1,2,4]triazolo[1′,5′:1,6]pyrido[2,3-d]pyrimidin-8-amine | 559.2 |
| 88 | 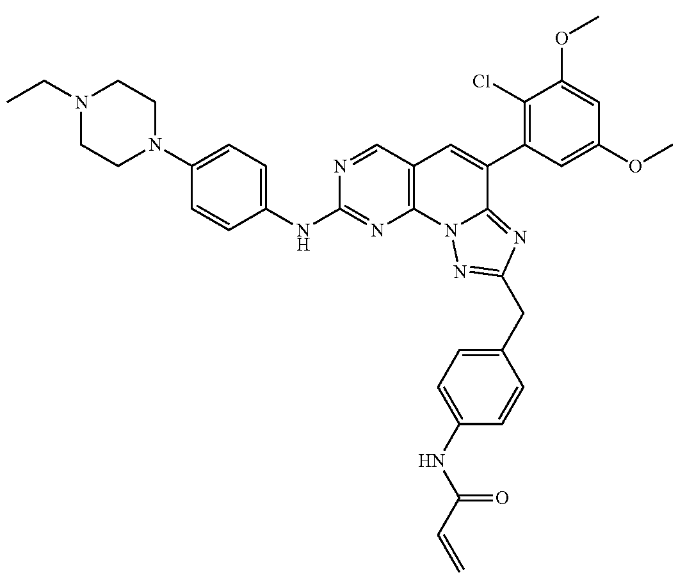 [SMILES: C=CC(=O)Nc1ccc(Cc2nc3c(-c4cc(OC)cc(OC)c4Cl)cc4cnc(Nc5ccc(N6CCN(CC)CC6)cc5)nc4n3n2)cc1] | N-(4-((4-(2-chloro-3,5-dimethoxyphenyl)-8-((4-(4-ethylpiperazin-1-yl)phenyl)amino)-[1,2,4]triazolo[1′,5′:1,6]pyrido[2,3-d]pyrimidin-2-yl)methyl)phenyl)acrylamide | 704.3 |

TABLE 5-continued

| Examples | Chemical structure | Chemical name | LC-MS [M + H+] |
|---|---|---|---|
| 89 | 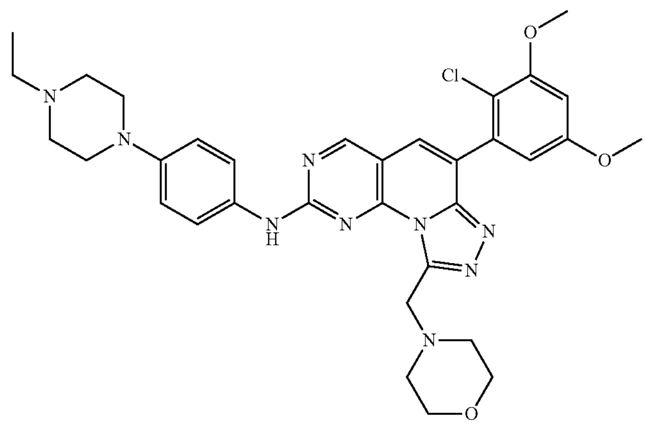 [SMILES: CCN1CCN(c2ccc(Nc3ncc4cc(-c5cc(OC)cc(OC)c5Cl)c5nnc(CN6CCOCC6)n5c4n3)cc2)CC1] | 6-(2-chloro-3,5-dimethoxyphenyl)-N-(4-(4-ethylpiperazin-1-yl)phenyl)-9-(morpholinomethyl)-[1,2,4]triazolo[4',3':1,6]pyrido[2,3-d]pyrimidin-2-amine | 644.3 |
| 90 | 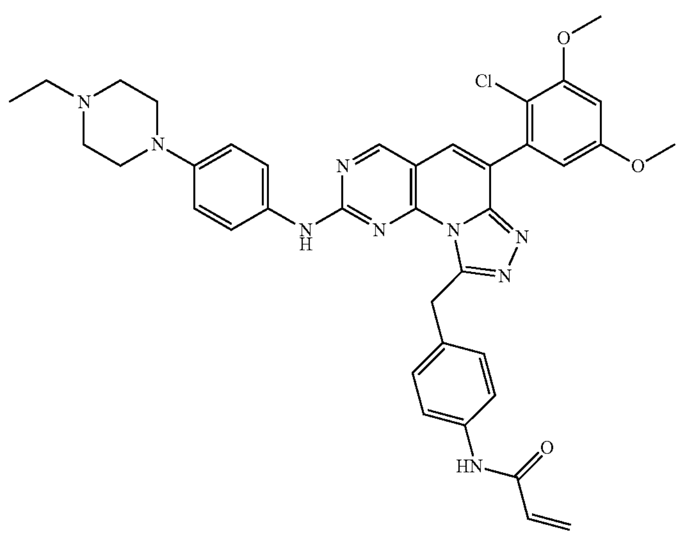 [SMILES: C=CC(=O)Nc1ccc(Cc2nnc3c(-c4cc(OC)cc(OC)c4Cl)cc4cnc(Nc5ccc(N6CCN(CC)CC6)cc5)nc4n23)cc1] | N-(4-((6-(2-chloro-3,5-dimethoxyphenyl)-2-((4-(4-ethylpiperazin-1-yl)phenyl)amino)-[1,2,4]triazolo[4',3':1,6]pyrido[2,3-d]pyrimidin-9-yl)methyl)phenyl)acrylamide | 704.3 |
| 91 | 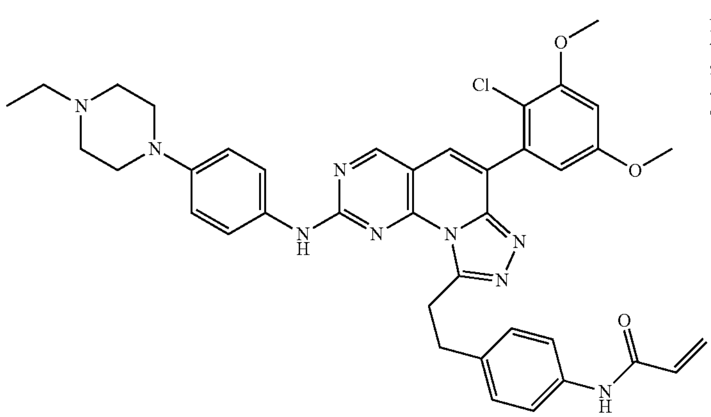 [SMILES: C=CC(=O)Nc1ccc(CCc2nnc3c(-c4cc(OC)cc(OC)c4Cl)cc4cnc(Nc5ccc(N6CCN(CC)CC6)cc5)nc4n23)cc1] | N-(4-(2-(6-(2-chloro-3,5-dimethoxyphenyl)-2-((4-(4-ethylpiperazin-1-yl)phenyl)amino)-[1,2,4]triazolo[4',3':1,6]pyrido[2,3-d]pyrimidin-9-yl)ethyl)phenyl)acrylamide | 718.3 |

TABLE 5-continued

| Examples | Chemical structure | Chemical name | LC-MS [M + H+] |
|---|---|---|---|
| 92 | 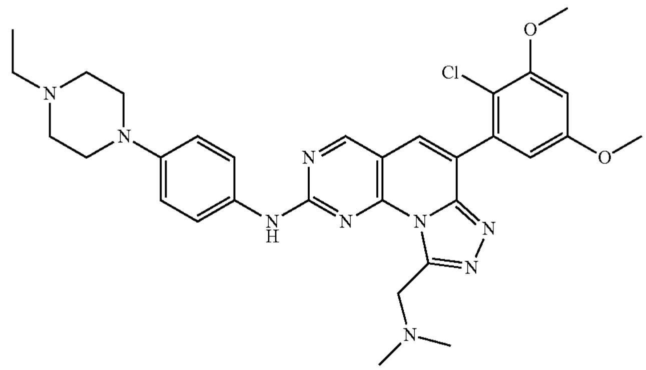 [SMILES: CCN1CCN(c2ccc(Nc3ncc4cc(-c5cc(OC)cc(OC)c5Cl)c5nnc(CN(C)C)n5c4n3)cc2)CC1] | 6-(2-chloro-3,5-dimethoxyphenyl)-9-((dimethylamino)methyl)-N-(4-(4-ethylpiperazin-1-yl)phenyl)-[1,2,4]triazolo[4',3':1,6]pyrido[2,3-d]pyrimidin-2-amine | 602.3 |
| 93 | 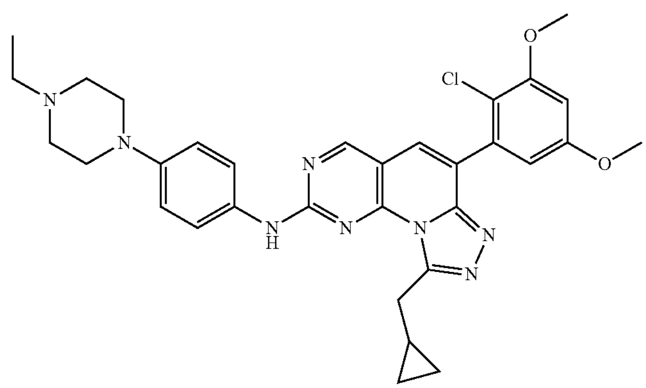 [SMILES: CCN1CCN(c2ccc(Nc3ncc4cc(-c5cc(OC)cc(OC)c5Cl)c5nnc(CC6CC6)n5c4n3)cc2)CC1] | 6-(2-chloro-3,5-dimethoxyphenyl)-9-(cyclopropylmethyl)-N-(4-(4-ethylpiperazin-1-yl)phenyl)-[1,2,4]triazolo[4',3':1,6]pyrido[2,3-d]pyrimidin-2-amine | 599.3 |
| 94 | 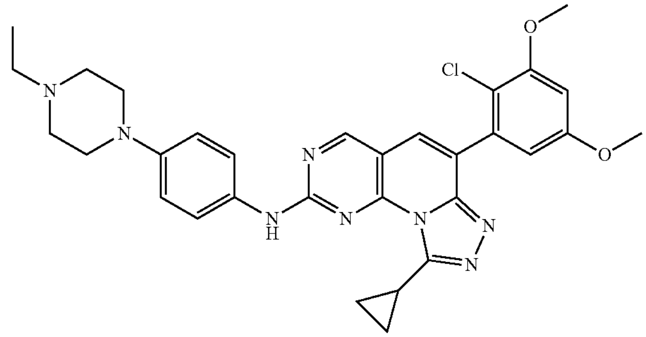 [SMILES: CCN1CCN(c2ccc(Nc3ncc4cc(-c5cc(OC)cc(OC)c5Cl)c5nnc(C6CC6)n5c4n3)cc2)CC1] | 6-(2-chloro-3,5-dimethoxyphenyl)-9-cyclopropyl-N-(4-(4-ethylpiperazin-1-yl)phenyl)-[1,2,4]triazolo[4',3':1,6]pyrido[2,3-d]pyrimidin-2-amine | 585.2 |

TABLE 5-continued

| Examples | Chemical structure | Chemical name | LC-MS [M + H+] |
|---|---|---|---|
| 95 | 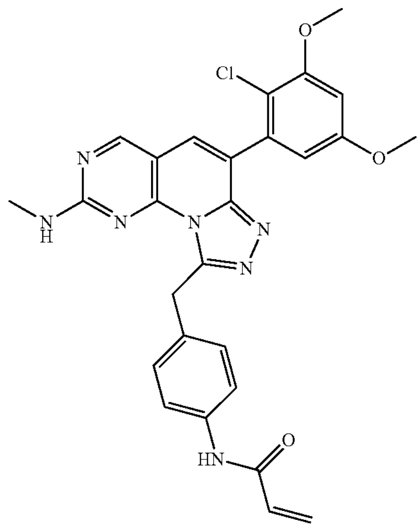 | N-(4-((6-(2-chloro-3,5-dimethoxyphenyl)-2-(methylamino)-[1,2,4]triazolo[4',3':1,6]pyrido[2,3-d]pyrimidin-9-yl)methyl)phenyl)acrylamide | 530.0 |
| 96 | 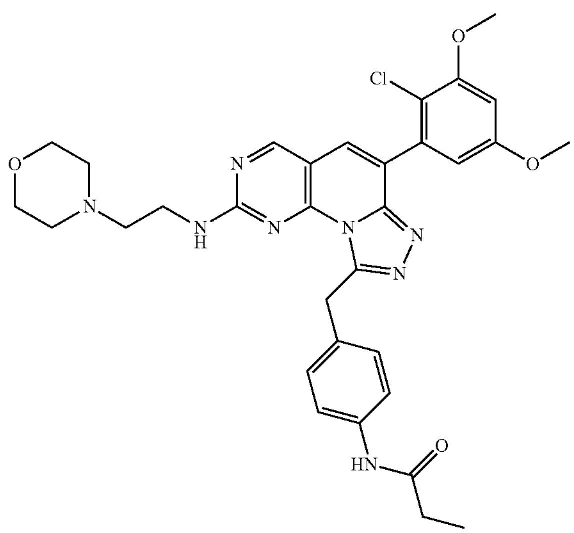 [SMILES: CCC(=O)Nc1ccc(Cc2nnc3c(-c4cc(OC)cc(OC)c4Cl)cc4cnc(NCCN5CCOCC5)nc4n23)cc1] | N-(4-((6-(2-chloro-3,5-dimethoxyphenyl)-2-((2-morpholinoethyl)amino)-[1,2,4]triazolo[4',3':1,6]pyrido[2,3-d]pyrimidin-9-yl)methyl)phenyl)propionamide | 631.1 |
| 97 | 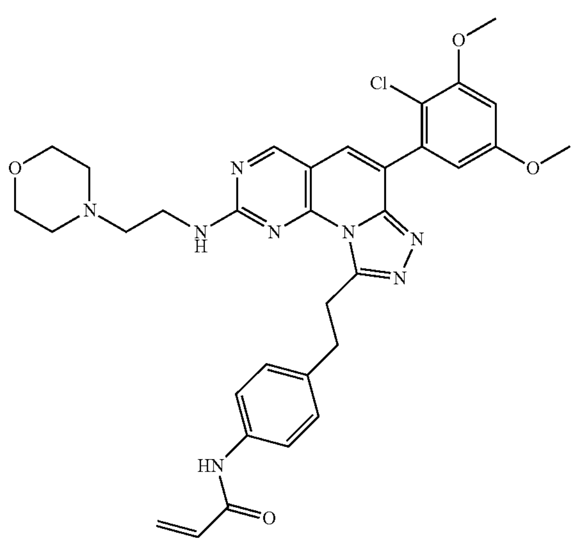 [SMILES: C=CC(=O)Nc1ccc(CCc2nnc3c(-c4cc(OC)cc(OC)c4Cl)cc4cnc(NCCN5CCOCC5)nc4n23)cc1] | N-(4-((6-(2-chloro-3,5-dimethoxyphenyl)-2-((2-morpholinoethyl)amino)-[1,2,4]triazolo[4',3':1,6]pyrido[2,3-d]pyrimidin-9-yl)ethyl)phenyl)acrylamide | 643.2 |

Nuclear magnetic date of compounds 96 and 97 were as shown below:
¹H NMR (DMSO-d6, 400 MHz) δ 9.96 (s, 1H), 8.96 (s, 1H), 8.07-7.96 (m, 1H), 7.54-7.51 (m, 3H), 7.35-7.33 (m, 1H), 7.10 (d, J=8 Hz, 1H), 6.82 (s, 1H), 6.73 (s, 1H), 5.01-4.91 (m, 2H), 3.90-3.79 (s, 3H), 3.79 (s, 3H), 3.57-3.49 (m, 4H), 3.34-3.32 (m, 2H), 2.51-2.49 (m, 2H), 2.43-2.39 (m, 2H), 2.31-2.30 (m, 4H), 1.04 (t, J=6 Hz, 3H). (Compound 96)
¹H NMR (DMSO-d6, 400 MHz) δ 10.08 (s, 1H), 8.96 (s, 1H), 8.16-8.07 (m, 1H), 7.60-7.58 (m, 2H), 7.50-7.48 (m, 1H), 7.23-7.21 (m, 2H), 7.07 (s, 1H), 6.49-6.40 (m, 1H), 6.27-6.22 (m, 1H), 5.74-5.72 (m, 1H), 3.99 (s, 3H), 3.90 (s, 3H), 3.56-3.43 (m, 6H), 3.33-3.18 (m, 4H), 2.47-2.27 (m, 4H). (Compound 97)
Example 98: Preparation of Compound 98 (6-(2-chloro-3,5-dimethoxyphenyl)-2-((4-(4-ethylpiperazin-1-yl)phenyl)amino)-[1,2,4]triazolo[4',3':1,6]pyrido[2,3-d]pyridimin-9(8H)-one)
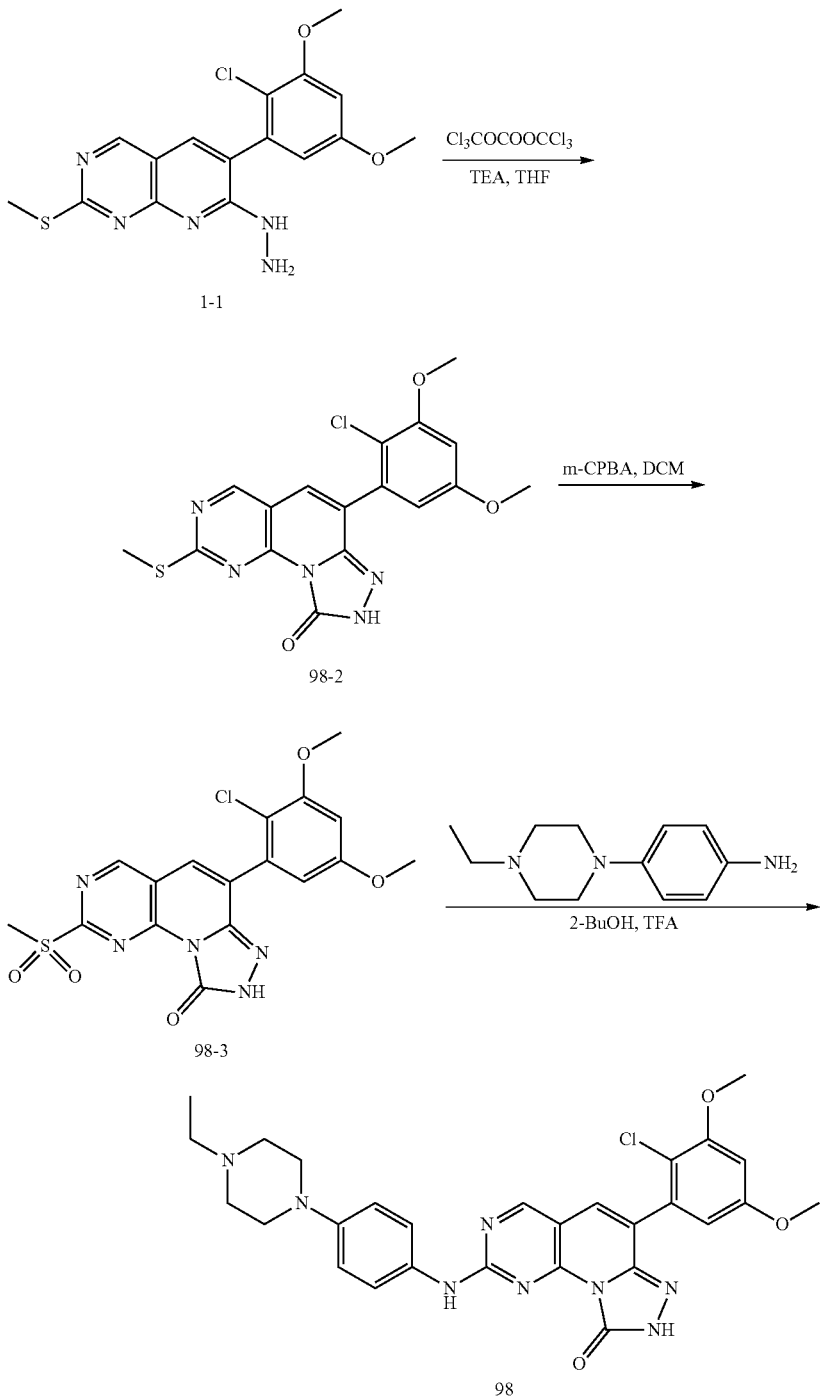

Step 1: Preparation of Compound 98-2

A mixture of 100 mg of compound 1-1, 80 mg of triphosgene, 5 ml of THF and 0.11 ml of TEA was stirred for 1 hr at 60° C. The reaction solution was concentrated under vacuum, The residue was purified via silica column chromatography (hexane/ethyl acetate=1/1) to get 93 mg of compound 98-2 as light yellow solid. The yield is 87.0%.
LC-MS [M+H⁺] 404.1.

Step 2: Preparation of Compound 98-3

The method is the same as step 4 of Example 2.
LC-MS [M+H⁺] 436.0.

Step 3: Preparation of Compound 98

Compound 98 was synthesized by a similar procedure as described in the step 5 of Example 2.
LC-MS [M+H⁺] 561.2.

Example 99: Preparation of Compound 99 (4-(4-((6-(2-chloro-3,5-dimethoxyphenyl)-[1,2,4]triazolo[4',3':1,6]pyrido[2,3-d]pyrimidin-2-yl)amino)phenyl)-1-ethylpiperazine1-oxide)

mixture was warmed up naturally stirred for 30 mins, and the reaction was complete. The mixture was quenched with water and was extracted with dichloromethane. The organic was washed with saturated NaHCO₃ aqueous solution and water, dried over anhydrous sodium sulfate and concentrated under reduced pressure. The crude product was purified via silica column chromatography (DCM/MeOH=20/1~5/1) to get 410 mg of compound 99 as yellow solid.
LC-MS [M+H⁺] 561.2.

Example 100: Preparation of Compound 100 ((8aR)-2-(4-((6-(2-chloro-3,5-dimethoxyphenyl)-[1,2,4]triazolo[4',3':1,6]pyrido[2,3-d]pyrimidin-2-yl)amino)phenyl) octahydro-5H-pyrrolo[1,2-a]pyrazine 5-oxide)

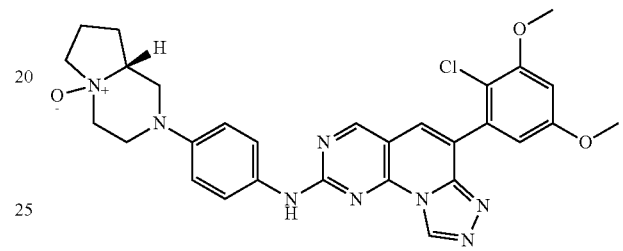

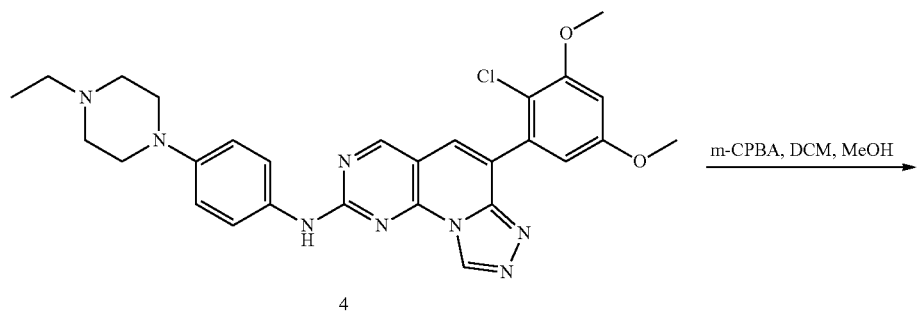

4

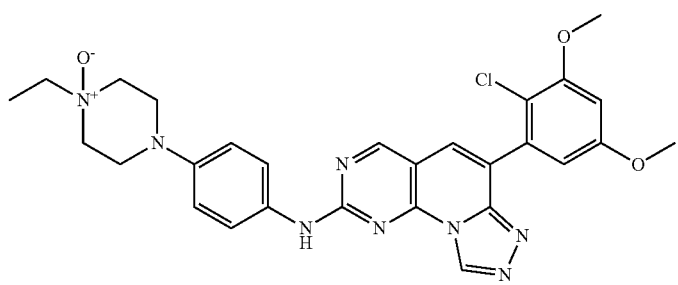

99

1.0 g of compound 4 was dissolved into 30 ml of dichloromethane and 3 ml of methanol, and cooled down to 0° C. 0.47 g of m-CPBA was dissolved into 2 ml of ethyl acetate, and was added dropwise to the above solution. The Compound 100 was synthesized by a similar procedure as described in the Example 99 via different start materials and appropriate reagent.
LC-MS [M+H⁺] 573.2.

Example 101: Preparation of Compound 101 (3-(4-(4-((6-(2-chloro-3,5-dimethoxyphenyl)-[1,2,4]triazolo[4',3':1,6]pyrido[2,3-d]pyrimidin-2-yl)amino)phenyl)piperazin-1-yl)cyclobutan-1-ol)

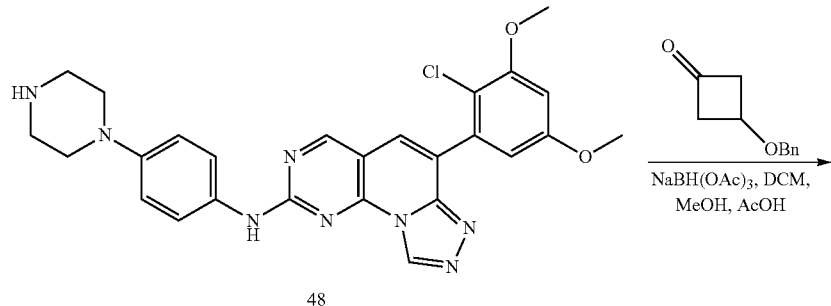
48

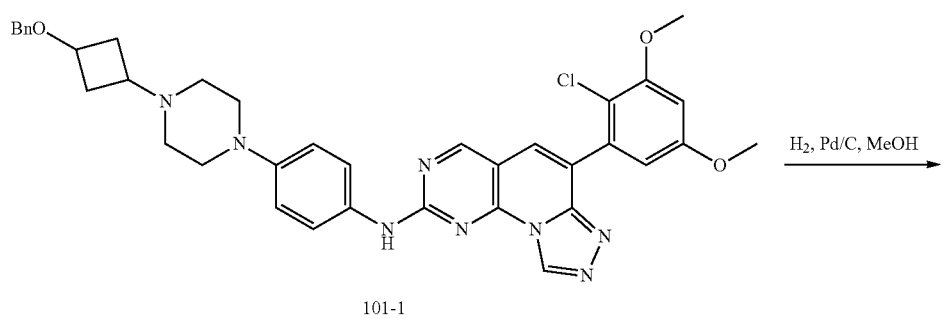
101-1

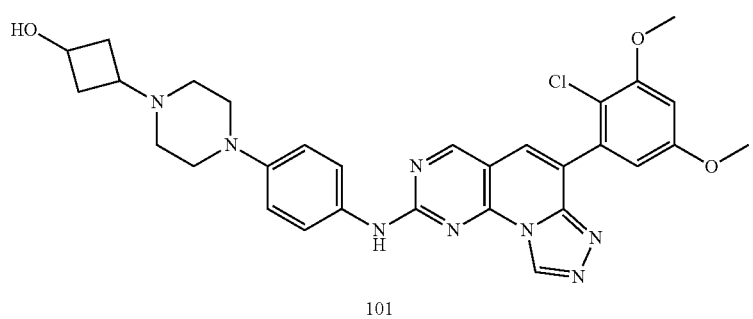
101

Step 1: Preparation of Compound 101-1

A mixture of 500 mg of compound 48, 20 ml of dichloromethane, 2 ml of methanol, 0.5 ml acetic acid was added 1.02 g of sodium triacetoxyborohydride. The mixture was stirred for 3 hrs at room temperature. When the reaction being complete, the mixture was diluted with dichloromethane, washed with saturated NaHCO$_3$ aqueous solution and water, dried over anhydrous sodium sulfate and spin dry. The crude product was purified via silica column chromatography (DCM/MeOH=20/1) to get 550 mg of compound 101-1 as yellow solid.

LC-MS [M+H$^+$] 677.3.

Step 2: Preparation of Compound 101-2

A mixture of 550 mg of compound 101-1, 30 ml of glacial acetic acid and Pd/C (100 mg) was reacted overnight under hydrogen. The reaction mixture was filtrated and concentrated under vacuum. The solid was diluted with DCM/MeOH=10/1, washed with saturated NaHCO$_3$ aqueous solution and water, dried over anhydrous sodium sulfate and spin dry. The crude product was purified via silica column chromatography (DCM/MeOH=10/1) to get 120 mg of compound 101 as yellow solid.

LC-MS [M+H$^+$] 587.2.

Example 102: Preparation of Compound 102 (6-(2-chloro-3,5-dimethoxyphenyl)-N-(4-(1-ethylpiperidin-4-yl)phenyl)-[1,2,4]triazolo[4',3':1,6]pyrido[2,3-d]pyridimin-2-amine)

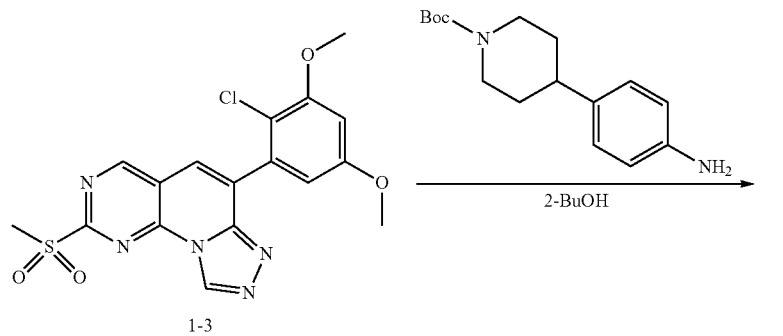

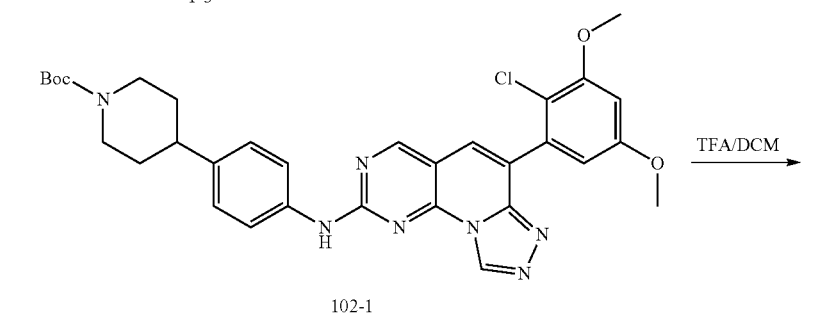

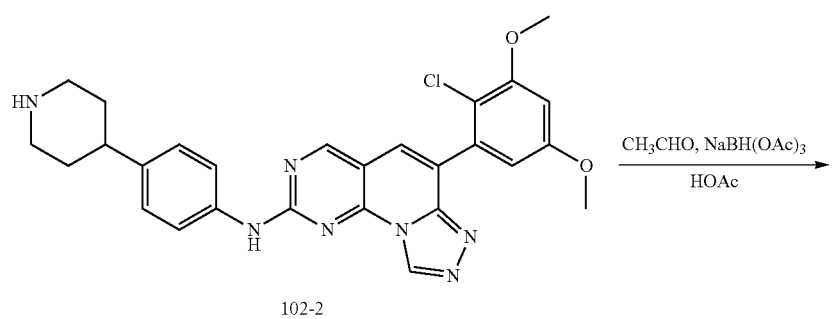

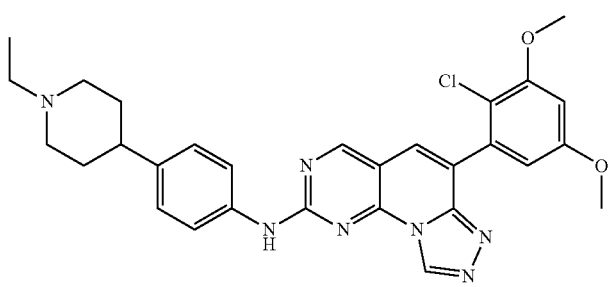

Step 1: Preparation of Compound 102-1

A mixture of 2.57 g of compound 1-3, 1.82 g of 4-(4-aminophenyl) piperidine-1-carboxylate and 20 ml of sec-butyl alcohol was refluxed for 22 hrs. The mixture was cooled down and filtered. The solid was dried to get 2.73 g of compound 102-1 as yellow solid.

LC-MS [M+H⁺] 616.2.

Step 2: Preparation of Compound 102-2

Below 10° C., 10 ml of TFA was added into a solution of 2.73 g of compound 102-1 dissolved into 100 ml of dichloromethane. The mixture was reacted for 2 hrs at room temperature and concentrated under vacuum. The solid was dissolved into dichloromethane, and the pH was adjusted to 7-8 with saturated NaHCO₃ aqueous solution, then the liquid was separated. The organic phase was washed with water, dried over anhydrous sodium sulfate and concentrated under reduced pressure. The solid was dried to get 2.46 g of compound 102-2 as yellow solid. It was used directly in the next reaction without purification.

LC-MS [M+H⁺] 516.2.

Step 3: Preparation of Compound 102

A mixture of 2.46 g of compound 102-2, 6.30 g of paraldehyde and 100 ml of acetic acid was refluxed for 1 h, and was cooled down to 25° C., to which was added 15.15 g of sodium triacetoxycyanoborohydride. The mixture was reacted for 3 hrs and was quenched with ice water. The pH value of the reaction system was adjusted to 7 with 20% NaOH. The reaction system was filtrated, the solid was dissolved with 100 ml of DCM/MeOH=10/1, washed with water, dried over anhydrous sodium sulfate and concentrated under reduced pressure. The crude product was purified via silica column chromatography (DCM/MeOH=50/1-20/1) to get 566 mg of compound 102 as yellow solid.

LC-MS [M+H⁺] 544.2.

$^1$H NMR (DMSO-d6, 400 MHz) δ 10.47 (s, 1H), 9.71 (s, 1H), 9.18 (s, 1H), 7.85 (d, J=8 Hz, 2H), 7.70 (s, 1H), 7.28 (d, J=8 Hz, 2H), 6.86 (d, J=4 Hz, 1H), 6.77 (d J=4 Hz, 1H), 3.93 (s, 3H), 3.81 (s, 3H), 3.14-3.12 (m, 2H), 2.58-2.53 (m, 3H), 2.27-2.22 (m, 2H), 1.84-1.70 (m, 4H), 1.09 (t, J=8 Hz, 3H).

Example 103: Preparation of Compound 103 (6-(2-chloro-3,5-dimethoxyphenyl)-N-(4-(4-(2,2,2-trifluorophenyl)piperazin-1-yl)phenyl)-[1,2,4]triazolo[4',3': 1,6]pyrido[2,3-d]pyrimidin-2-amine)

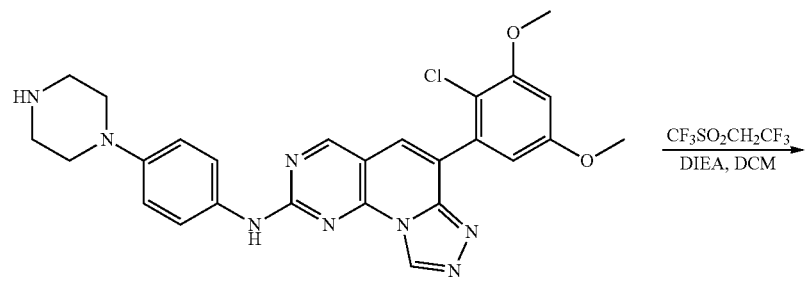

48

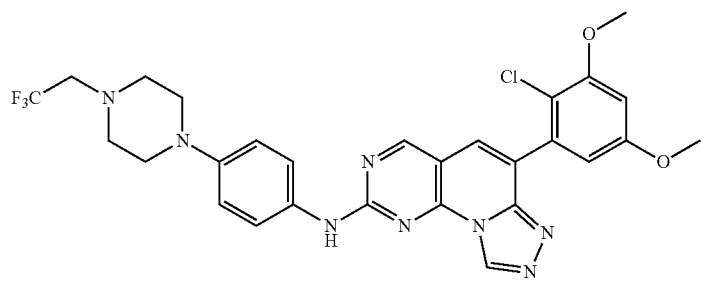

103

A mixture of 50 mg of compound 48, 10 ml of dichloromethane and 14 mg of DIEA was dropped 25 mg of trifluoroethyl trifluoromethanesulfonate. The reaction system was refluxed for 3.5 hrs and concentrated under reduced pressure. The crude product was purified via silica column chromatography (DCM/MeOH=20/1) to get 18 mg of compound 103 as yellow solid.

LC-MS [M+H⁺] 599.2.

Example 104 Preparation of Compound 104 (6-(2-chloro-3,5-dimethoxyphenyl)-N-(4-(4-cyclopentyp-iperazin-1-yl)phenyl)-[1,2,4]triazolo[4',3':1,6]pyrido[2,3-d]pyridimin-2-amine)

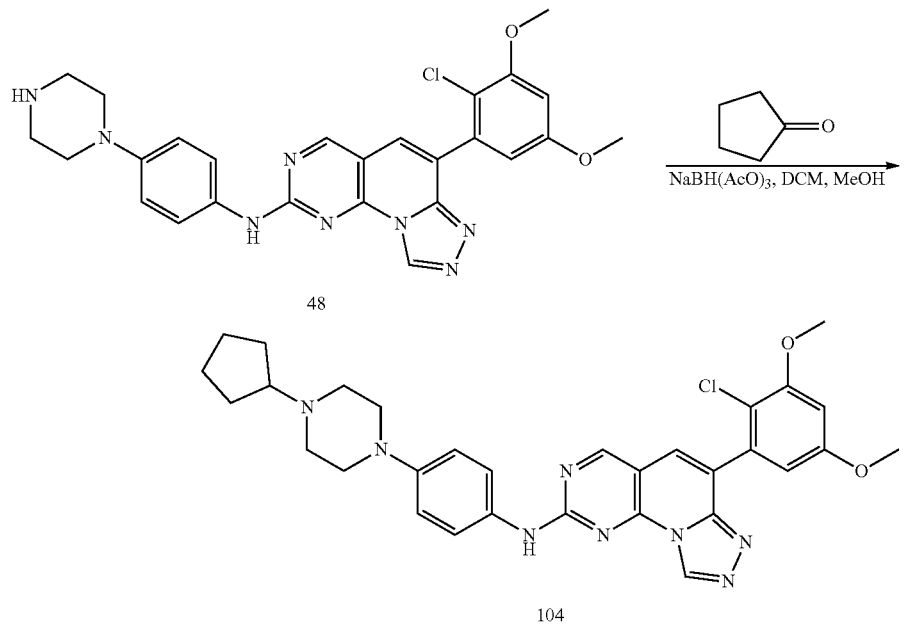

A mixture of 100 mg of compound 48, 20 ml of dichloromethane, 2 ml of methanol and 1 ml of cyclopentanone was added 122 mg of sodium triacetoxyborohydride in batches. The mixture was reacted overnight with stirring at room temperature. The reaction was quenched with water and was extracted with dichloromethane. The organic phase was combined, washed with water, dried over anhydrous sodium sulfate and concentrated under reduced pressure. The crude product was purified via silica column chromatography (DCM/MeOH=10/1) to get 70 mg of compound 104 as yellow solid.

LC-MS [M+H$^+$] 585.2.

Example 105: Preparation of Compound 105 (6-(2-chloro-3,5-dimethoxyphenyl)-N-(4-(4-cyclobutylpiperazin-1-yl)phenyl)-[1,2,4]triazolo[4',3':1,6]pyrido[2,3-d]pyrimidin-2-amine)

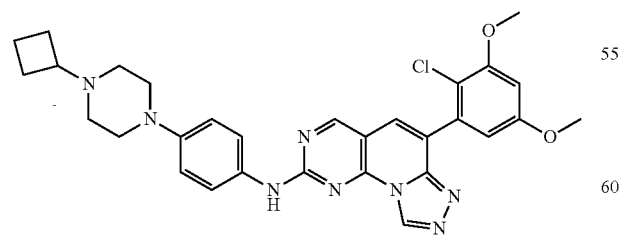

Compound 105 was synthesized in a similar method to example 104 via different start materials and appropriate reagent.

LC-MS [M+H$^+$] 571.2.

Example 106: Preparation of Compound 106 (6-(2-chloro-3,5-dimethoxyphenyl)-N-(4-(4-acetylpiperazine-1-yl)phenyl)-[1,2,4]triazolo[4',3':1,6]pyrido[2,3-d]pyrimidin-2-amine)

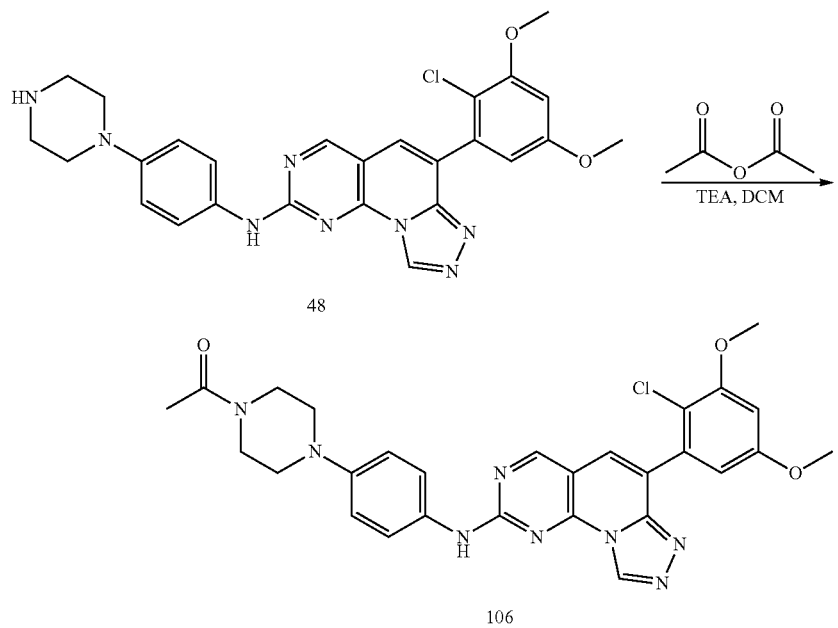

A mixture of 100 mg of compound 48, 0.08 ml of TEA and 20 ml of dichloromethane was cooled down to 0° C. 24 mg of acetic anhydride was dropwised into the mixture and warmed up to room temperature naturally. The mixture was reacted for 30 mins with stirring and the reaction was complete. The reaction was quenched with methanol and concentrated under reduced pressure. The crude product was purified via silica column chromatography (DCM/MeOH=12/1) to get 45 mg of compound 106 as yellow solid.

LC-MS [M+H$^+$] 559.2.

Example 107: Preparation of Compound 107 (4-(4-((6-(2-chloro-3,5-dimethoxyphenyl)-[1,2,4]triazolo[4',3':1,6]pyrido[2,3-d]pyrimidin-2-yl)amino)phenyl)-N,N-dimethylpiperazine-1-carboxamide)

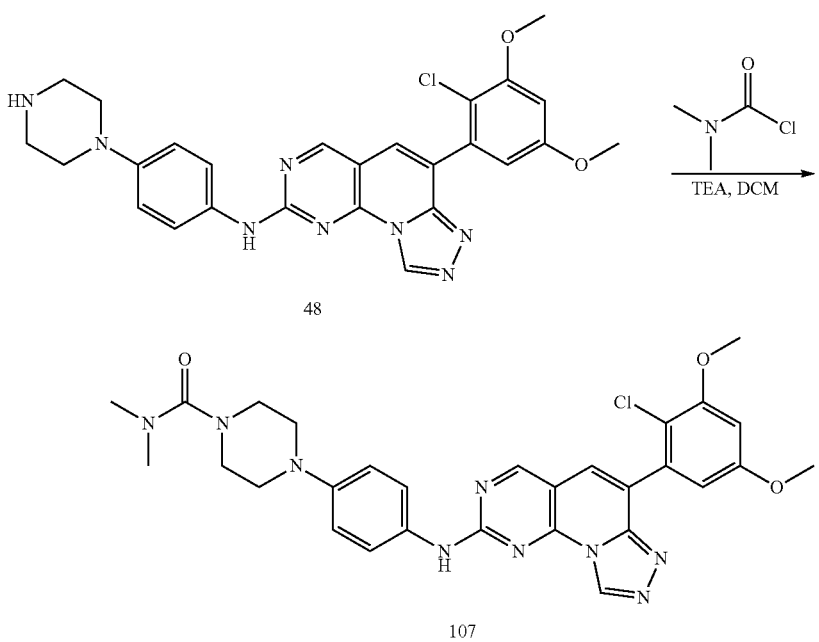

A mixture of 500 mg of compound 48, 30 ml of dichloromethane and 294 mg of TEA was cooled down to 0° C. and 156 mg of dimethylcarbamoyl chloride was dropwise into the mixture. The mixture was warmed up to room temperature naturally and reacted for 1 hr with stirring. The reaction was quenched with water and was extracted with dichloromethane. The organic phase was combined, washed with water, dried over anhydrous sodium sulfate and concentrated under reduced pressure. The crude product was purified via silica column chromatography (DCM/MeOH=20/1) to get 325 mg of compound 107 as yellow solid.

LC-MS [M+H$^+$] 588.2.

Example 108: Preparation of Compound 108 (6-(4-((6-(2-chloro-3,5-dimethoxyphenyl)-[1,2,4]triazolo[4',3':1,6]pyrido[2,3-d]pyrimidin-2-yl)amino)phenyl)-N,N-dimethyl-2,6-diazaspiro[3.3]heptane-2-carboxamide)

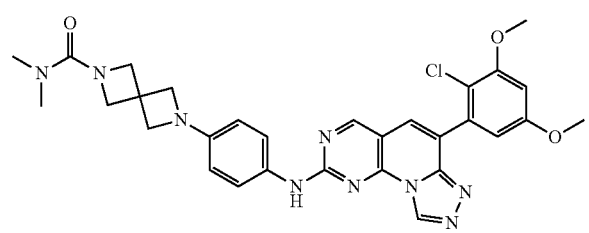

108

Compound 108 was synthesized in a similar method to example 48 and example 107 via different start materials and appropriate reagent.

LC-MS [M+H$^+$] 600.2.

Example 109: Preparation of Compound 109 ((S)-3-((4-((6-(2-chloro-3,5-dimethoxyphenyl)-[1,2,4]triazolo[4',3':1,6]pyrido[2,3-d]pyrimidin-2-yl)amino)phenyl)amino)-N,N-dimethylpyrrolidine-1-carboxamide

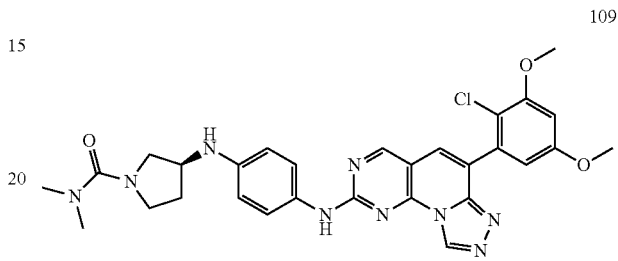

109

Compound 109 was synthesized in a similar method to example 48 and example 107 via different start materials and appropriate reagent.

LC-MS [M+H$^+$] 588.1.

$^1$H NMR (DMSO-d6, 400 MHz) δ 10.18 (s, 1H), 9.60 (s, 1H), 9.11 (s, 1H), 7.65-7.62 (m, 3H), 6.85 (s, 1H), 6.75 (s, 1H), 6.68-6.66 (m, 2H), 5.72 (d, J=8 Hz, 1H), 3.92 (s, 3H), 3.79 (s, 3H), 3.65-3.61 (m, 2H), 3.15-3.11 (m, 2H), 2.73 (s, 6H), 2.12-2.07 (m, 1H), 1.80-1.77 (m, 1H).

Example 110: Preparation of Compound 110 (6-(2-chloro-3,5-dimethoxyphenyl)-N-(6-(4-methylpiperazin-1-yl)pyridin-3-yl)-[1,2,4]triazolo[4',3':1,6]pyrido[2,3-d]pyrimidin-2-amine)

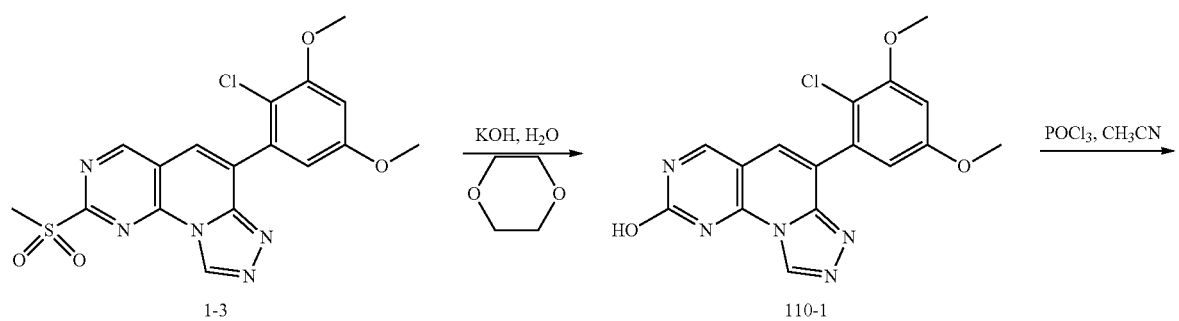

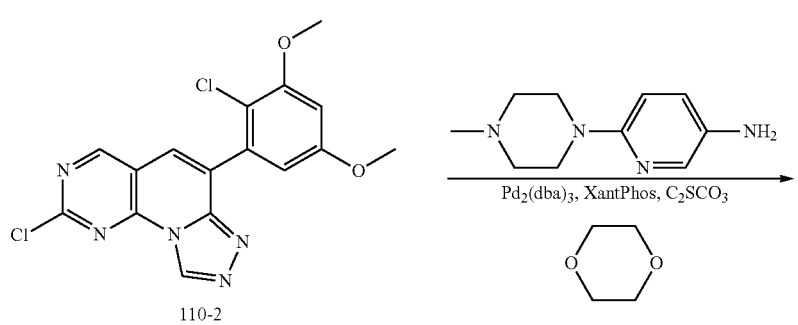

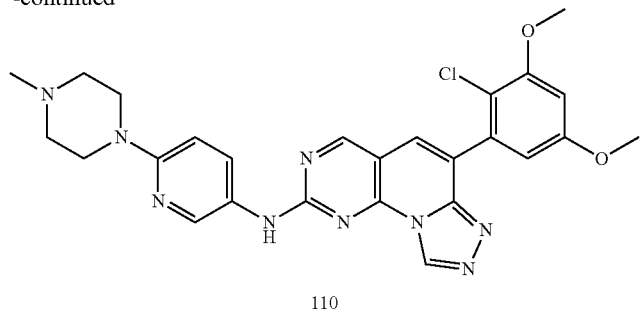

110

Step 1: Preparation of Compound 110-1

A mixture of 10.01 g of compound 1-3, 100 ml of water, 25 ml of dioxane and 6.68 g of potassium hydroxide was stirred at 80° C. and was reacted overnight. When the reaction was complete, the mixture was cooled to room temperature, the pH value was adjusted to 3 using concentrated hydrochloric acid and a large amount of solid was separated. The solid was obtained by filtration, washed with water and dried over anhydrous sodium sulfate to get 7.27 g of compound 110-1 as light yellow solid.

LC-MS [M+H$^+$] 358.1.

Step 2: Preparation of Compound 110-2

A mixture of 7.27 g of compound 110-1, 120 ml of acetonitrile and 35 ml of phosphorus oxychloride was heated to reflux and reacted overnight. When the reaction was complete, the mixture was cooled down to room temperature. The reaction was quenched by adding ice water, followed by filtration, the solid was washed three times with water and dried overnight under vacuum at 50° C. to get 6.73 g of compound 110-2 as light yellow solid.

LC-MS [M+H$^+$] 376.0.

Step 3: Preparation of Compound 110

A mixture of 240 mg of compound 110-2, 130 mg of 5-amino-2-(4-methyl-1-piperazine)pyridine, 14 mg of Pd(OAc)$_2$, 7 mg of XantPhos, 626 mg of cesium carbonate and 15 ml of dioxane was reacted for 4 h at 100° C. under the atmosphere of nitrogen. When the reaction was complete, the mixture was cooled down to room temperature and concentrated under reduced pressure. The residue was dissolved using dichloromethane, washed with water and dried over anhydrous sodium sulfate. The mixture was filtrated and the filtrate was concentrated. The crude product was purified via silica column chromatography (DCM/MeOH=5/1) to get 120 mg of compound 110 as yellow solid.

LC-MS [M+H$^+$] 532.2.

Example 111: Preparation of Compound 111 (6-(2-chloro-3,5-dimethoxyphenyl)-N-(6-((4-ethylpiperazin-1-yl)methyl)pyridin-3-yl)-[1,2,4]triazolo[4',3':1,6]pyrido[2,3-d]pyridimin-2-amine)

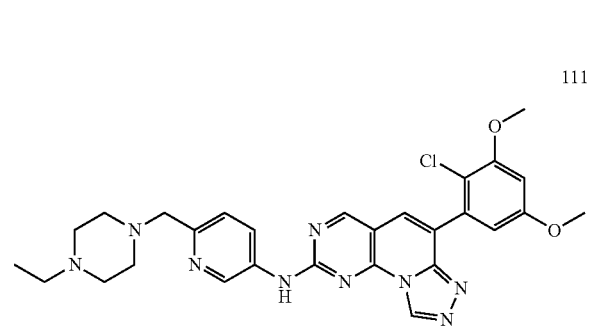 [SMILES: CCN1CCN(Cc2ccc(Nc3ncc4cc(-c5cc(OC)cc(OC)c5Cl)c5nncn5c4n3)cn2)CC1]

111

Compound 111 was synthesized by a similar procedure as described in the Example 110 via different start materials and appropriate reagent.

LC-MS [M+H$^+$] 560.2.

Example 112: Preparation of Compound 112 (N-(4-((4-(2-chloro-3,5-dimethoxyphenyl)-8-((2-morpholinoethyl)amino)-[1,2,4]triazolo[1',5':1,6]pyrido[2,3-d]pyridimin-2-yl)methyl)phenyl)acrylamide)

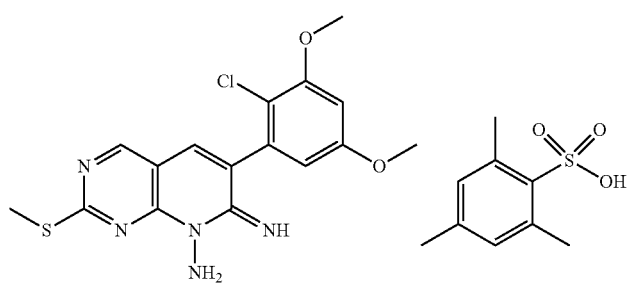

2'-1

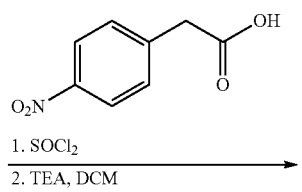

1. SOCl$_2$
2. TEA, DCM

133 134
-continued
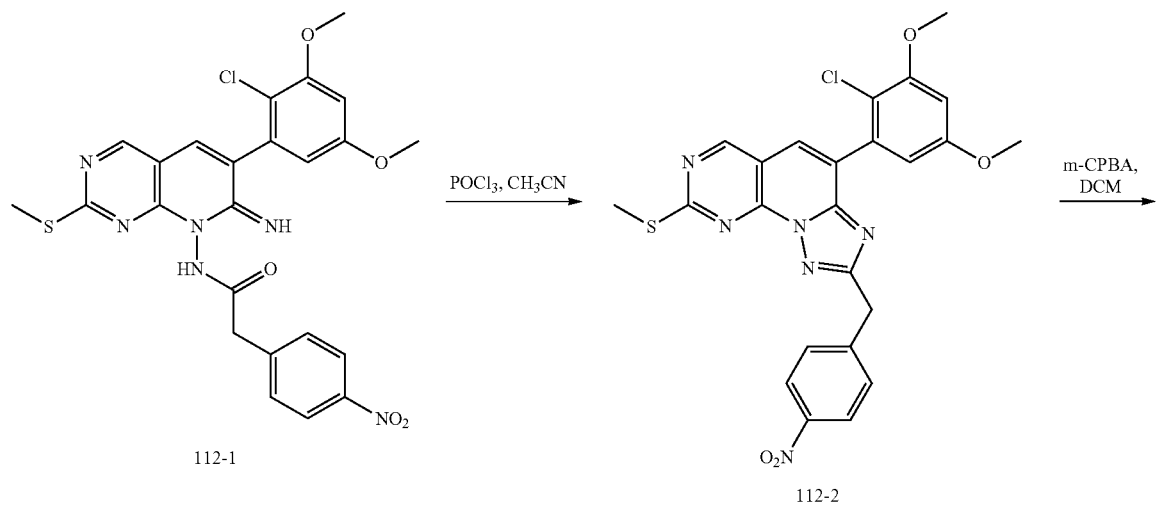
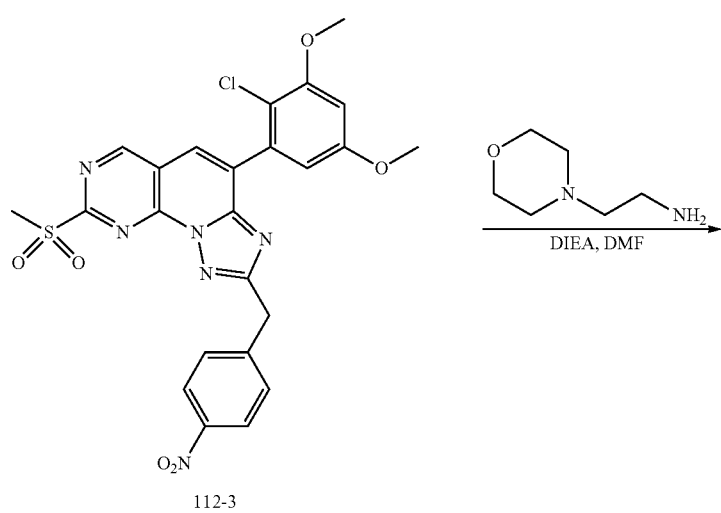
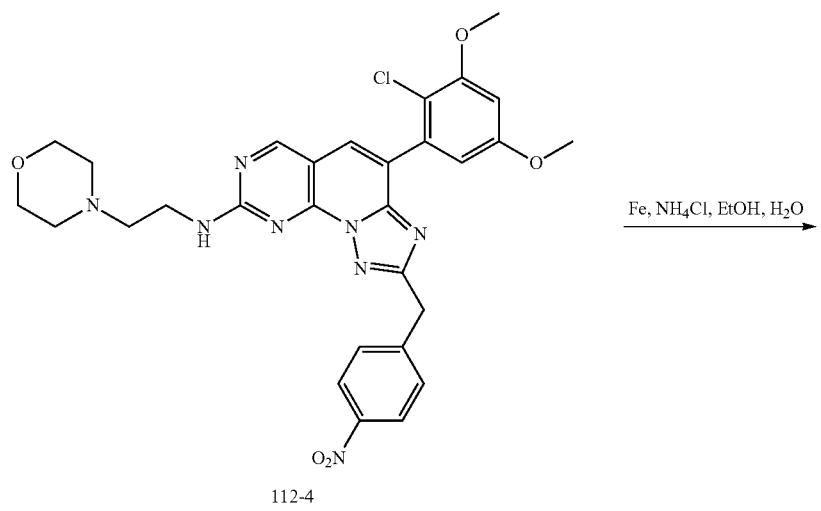

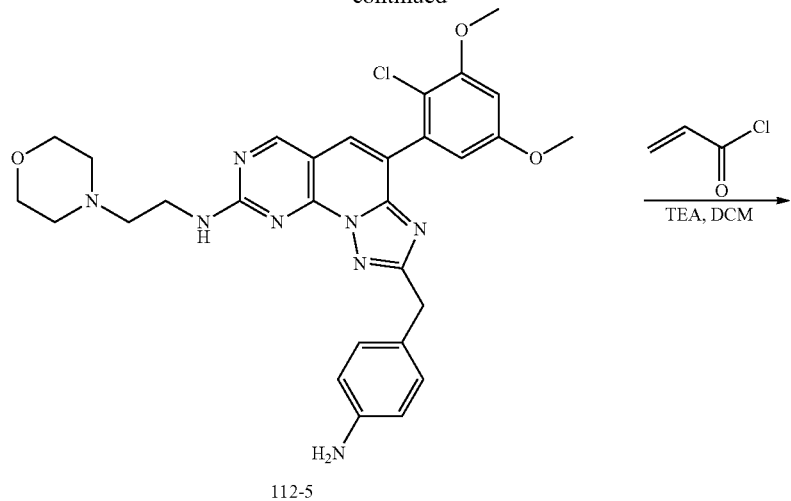

Step 1: Preparation of Compound 112-1

A mixture of 575 mg of 4-nitrophenylacetic acid and 10 ml of sulfoxide chloride was heated to reflux for 1 h, removed the sulfoxide chloride by concentrated under reduced pressure, dissolved by adding 10 ml of dichloromethane and concentrated under reduced pressure. Repeated these action twice and concentrated under reduced pressure for 15 mins. The obtained oily matter was dissolved into 3 ml of dichloromethane, then the mixture was added dropwise into a mixed solution of 800 mg of compound 2'-1, 20 ml of dichloromethane and 643 mg of TEA. When finished, the mixture was warmed up to room temperature naturally and reacted overnight with stirring. When the reaction was complete, the reaction was quenched by adding water, the mixture was extracted with dichloromethane. Organic phase was combined, washed with water, dried over anhydrous sodium sulfate, filtrated and concentrated under reduced pressure to get 1.15 g of crude product 112-1 as a reddish brown solid. It was used to the next reaction directly without purification.

LC-MS [M+H$^+$] 541.1.

Step 2: Preparation of Compound 112-2

A mixture of 1.15 g of compound 112-1, 20 ml of acetonitrile and 2 ml of phosphorus oxychloride was heated to reflux for 2 hrs, and removed most solvents by concentrated under reduced pressure. The residue was dissolved into dichloromethane, washed twice with saturated sodium bicarbonate aqueous solution and water respectively, dried over anhydrous sodium sulfate, filtrated and concentrated under reduced pressure. The obtained crude product was purified via silica column chromatography (Hex/EA=5/1) to get 380 mg of compound 112-2 as light brown solid.

LC-MS [M+H$^+$] 523.1.

Step 3: Preparation of Compound 112-3

380 mg of compound 112-2 was dissolved into 10 ml of dichloromethane, the mixture was cooled down to 0° C., and to which was added 221 mg of m-CPBA in batches, the mixture was warmed up naturally and reacted for 1 hr with stirring. The reaction was quenched by adding saturated sodium bicarbonate aqueous solution, extracted with dichloromethane, washed with water, dried over anhydrous sodium sulfate, filtrated and concentrated under reduced pressure to get 400 mg of crude product of 112-3 as yellow solid. It was used in the next reaction directly without purification.

LC-MS [M+H⁺] 555.1.

Step 4: Preparation of Compound 112-4

A mixture of 400 mg of compound 112-3, 10 ml of DMF, 273 mg of DIEA and 138 mg of N-(2-aminoethyl)morpholine was reacted for 3.5 hrs at 80° C. When the reaction was complete, the mixture was cooled down to room temperature, diluted with water and extracted with dichloromethane. The organic phase was combined, washed with water, dried over anhydrous sodium sulfate, filtrated and spinned dry. The obtained crude product was purified via silica column chromatography (DCM/MeOH=20/1) to get 150 mg of compound 112-4 as reddish brown solid.

LC-MS [M+H⁺] 605.2.

Step 5: Preparation of Compound 112-5

A mixture of 150 mg of compound 112-4, 20 ml of ethanol, 4 ml of water and 154 mg of SnCl$_2$.2H$_2$O was reacted for 2.5 hrs at 80° C. When the reaction was complete, the mixture was cooled down to room temperature, filtrated. The filtrate was diluted with water, extracted with dichloromethane. The organic phase was combined, washed with water, dried over anhydrous sodium sulfate, filtrated and concentrated under reduced pressure. The obtained crude product was purified via silica column chromatography (DCM/MeOH=20/1) to get 20 mg of compound 112-5 as light yellow solid.

LC-MS [M+H⁺] 575.2.

Step 6: Preparation of Compound 112

A mixture of 20 mg of compound 112-5, 10 ml of dichloromethane and 11 mg of TEA was cooled down to 0° C., to which was added dropwise 5 mg of acryloyl chloride. The mixture was warmed up to room temperature naturally and reacted for 1 hr with stirring. The reaction was quenched with water and extracted with dichloromethane. The organic phase was combined, washed with water, dried over anhydrous sodium sulfate, filtrated and concentrated under reduced pressure. The obtained crude product was purified via silica column chromatography (DCM/MeOH=20/1) to get 15 mg of compound 112 as white solid with yield of 68.6%.

LC-MS [M+H⁺] 629.2.

Example 113: Preparation of Compound 113 (1-(4-((6-(2-chloro-3,5-dimethoxyphenyl)-2-(methylamino)-[1,2,4]triazolo[4',3':1,6]pyrido[2,3-d]pyrimidin-9-yl)propyl)piperazin-1-yl) prop-2-en-1-one)

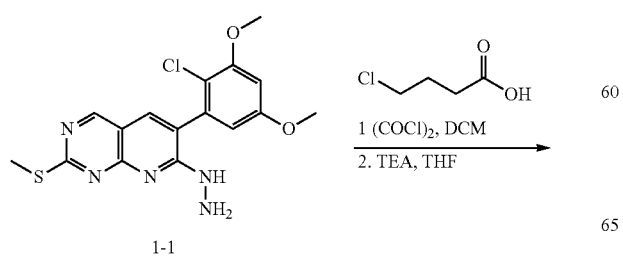

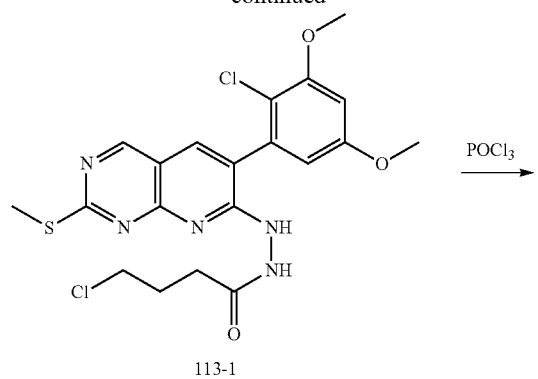

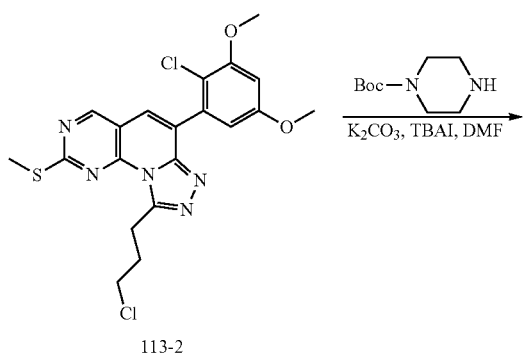

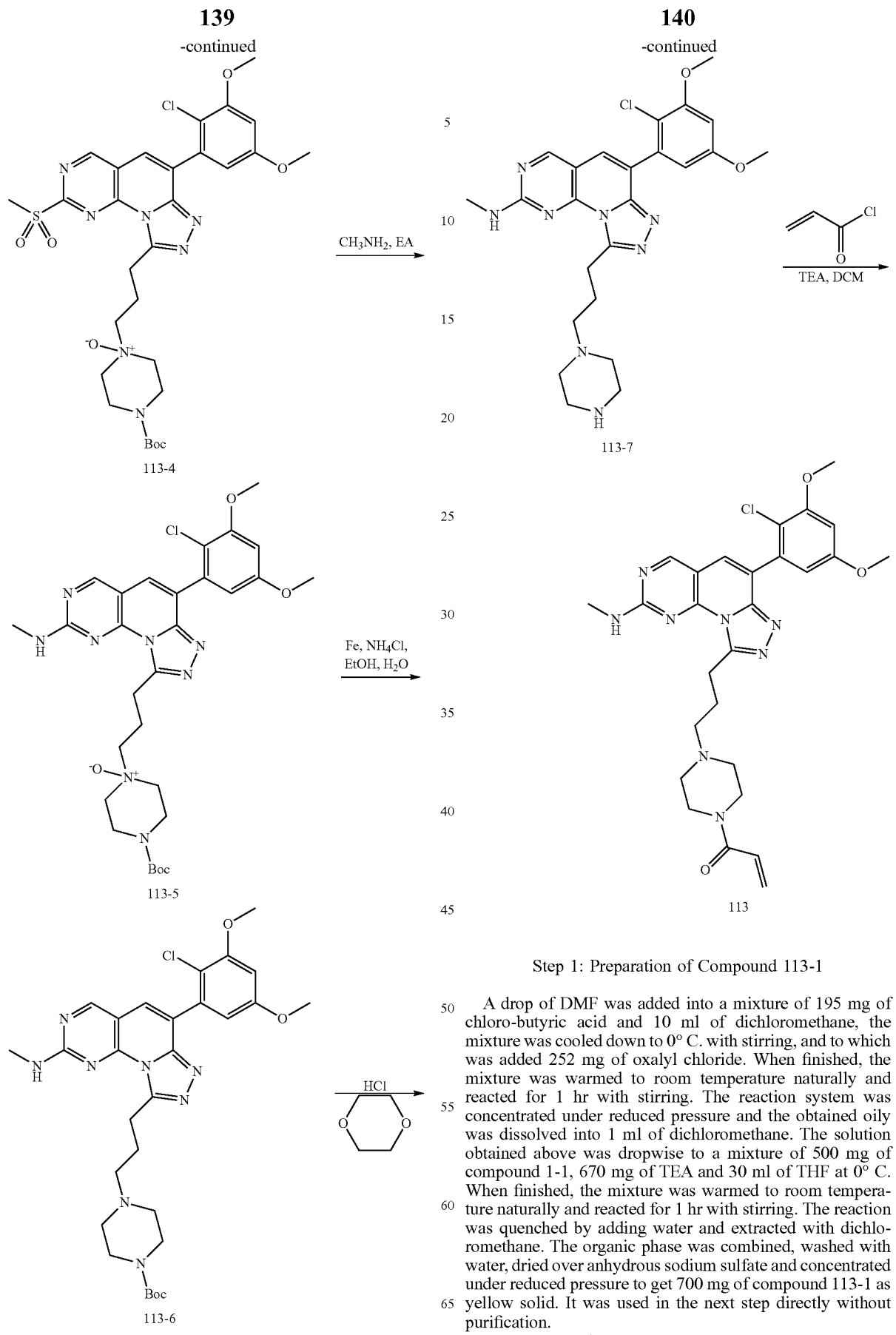

Step 1: Preparation of Compound 113-1

A drop of DMF was added into a mixture of 195 mg of chloro-butyric acid and 10 ml of dichloromethane, the mixture was cooled down to 0° C. with stirring, and to which was added 252 mg of oxalyl chloride. When finished, the mixture was warmed to room temperature naturally and reacted for 1 hr with stirring. The reaction system was concentrated under reduced pressure and the obtained oily was dissolved into 1 ml of dichloromethane. The solution obtained above was dropwise to a mixture of 500 mg of compound 1-1, 670 mg of TEA and 30 ml of THF at 0° C. When finished, the mixture was warmed to room temperature naturally and reacted for 1 hr with stirring. The reaction was quenched by adding water and extracted with dichloromethane. The organic phase was combined, washed with water, dried over anhydrous sodium sulfate and concentrated under reduced pressure to get 700 mg of compound 113-1 as yellow solid. It was used in the next step directly without purification.

LC-MS [M+H$^+$] 482.1.

Step 2: Preparation of Compound 113-2

A mixture of 700 mg of compound 113-1 and 10 ml of POCl₃ was reacted for 2 hrs at 100° C. When the reaction was complete, the mixture was cooled to room temperature and poured into ice water to quench. A large amount of solid was precipitated from the mixture with stirring, filtrated, then the solid was washed with water and dried to get 540 mg of compound 113-2 as white solid. It was used in the next step directly without purification.

LC-MS [M+H$^+$] 464.1.

Step 3: Preparation of Compound 113-3

A mixture of 540 mg of compound 113-2, 482 mg of potassium carbonate, 433 mg of 1-Boc-piperazine, 43 mg of tetrabutylammonium iodide and 30 ml of DMF was reacted overnight at 80° C. The mixture was diluted with water, extracted with dichloromethane, dried over anhydrous sodium sulfate, filtrated and concentrated under reduced pressure. The obtained crude product was purified via silica column chromatography (DCM/MeOH=20/1) to get 470 mg of compound 113-3 as reddish brown solid.

LC-MS [M+H$^+$] 614.2.

Step 4: Preparation of Compound 113-4

A mixture of 470 mg of compound 113-3 and 10 ml of dichloromethane was cooled to 0° C. and to which was added 461 mg of m-CPBA in batches. The mixture was warmed to room temperature naturally and reacted for 1 hr. The reaction was quenched by adding water and extracted with dichloromethane. The organic phase was combined, washed with water, dried over anhydrous sodium sulfate, filtrated and concentrated under reduced pressure to get 650 mg of compound 113-4 as yellow solid. It was used in the next step directly without purification.

LC-MS [M+H$^+$] 662.2.

Step 5: Preparation of Compound 113-5

A mixture of 650 mg of compound 113-4, 2.5 ml of methylamine tetrahydrofuran solution (2.0M) and 10 ml of ethyl acetate was reacted overnight at room temperature. When the reaction was complete, the mixture was diluted with dichloromethane, washed with water, dried over anhydrous sodium sulfate, filtrated and concentrated under reduced pressure to get 340 mg of compound 113-5 as brown solid. It was used in the next step directly without purification.

LC-MS [M+H$^+$] 613.3.

Step 6: Preparation of Compound 113-6

A mixture of 340 mg of compound 113-5, 297 mg of NH₄Cl, 155 mg of iron powder, 10 ml of anhydrous ethanol and 3 ml of water was reacted for 1 hr at 80° C. The mixture was cooled down to room temperature, filtrated and the filtrate was concentrated under reduced pressure. The obtained residue was dissolved into dichloromethane, washed with water, dried over anhydrous sodium sulfate, filtrated and concentrated under reduced pressure. The crude product was purified via silica column chromatography (DCM/MeOH=25/1) to get 50 mg of compound 113-6 as light yellow solid.

LC-MS [M+H$^+$] 597.3.

Step 7: Preparation of Compound 113-7

50 mg of compound 113-6 was dissolved into 3 ml of 1,4-dioxane, and to which was added 3 ml of 4M HCl 1,4-dioxane solution with stirring. The mixture was reacted for 30 mins at room temperature with stirring, concentrated under reduced pressure and dried under vacuum to get 51 mg of compound 113-7 as light yellow solid. It was used in the next step directly without purification.

LC-MS [M+H$^+$] 497.2.

Step 8: Preparation of Compound 113

A mixture of 51 mg of compound 113-7, 52 mg of TEA and 10 ml of dichloromethane was cooled down to 0° C., to which was added 9 mg of acryloyl chloride in 0.5 ml of dichloromethane solution with stirring. When finished, the mixture was reacted for 1 hr at 0° C. The reaction was quenched by adding water, extracted with dichloromethane, washed with saturated sodium bicarbonate aqueous solution, dried over anhydrous sodium sulfate, filtrated and concentrated under reduced pressure. The crude product was purified via silica column chromatography (DCM/MeOH=20/1) to get 38 mg of compound 113 as light yellow solid.

LC-MS [M+H$^+$] 551.2.

Example 114: Preparation of Compound 114 (1-(4-((6-(2-chloro-3,5-dimethoxyphenyl)-2-(methylamino)-[1,2,4]triazolo[4',3':1,6]pyrido[2,3-d]pyrimidin-9-yl)ethyl)piperazin-1-yl)prop-2-en-1-one)

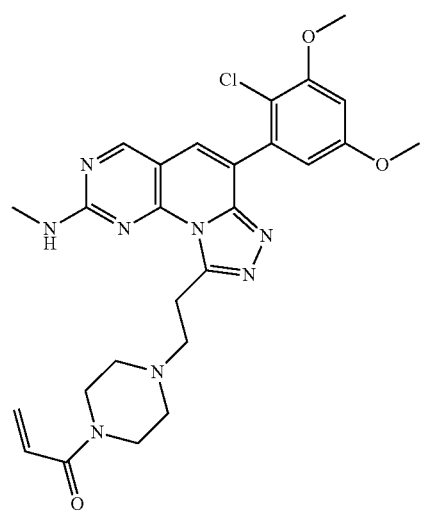

The compound 114 was prepared by a similar procedure as described in the Example 113 via different reaction starting materials and appropriate reagent.

LC-MS [M+H$^+$] 537.2.

Example 115: Preparation of Compound 115 (1-(4-(3-(4-(2-chloro-3,5-dimethoxyphenyl)-8-(methyl-amino)-[1,2,4]triazolo[1',5': 1,6]pyrido[2,3-d]pyrimidin-2-yl)propyl)piperazin-1-yl) prop-2-en-1-one)
Route A
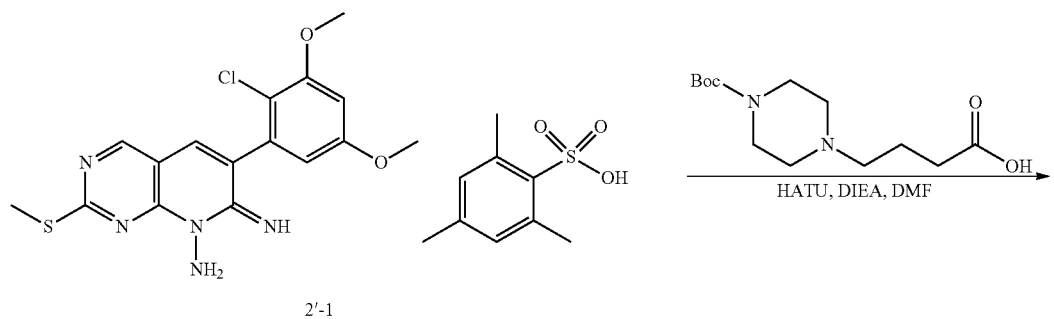
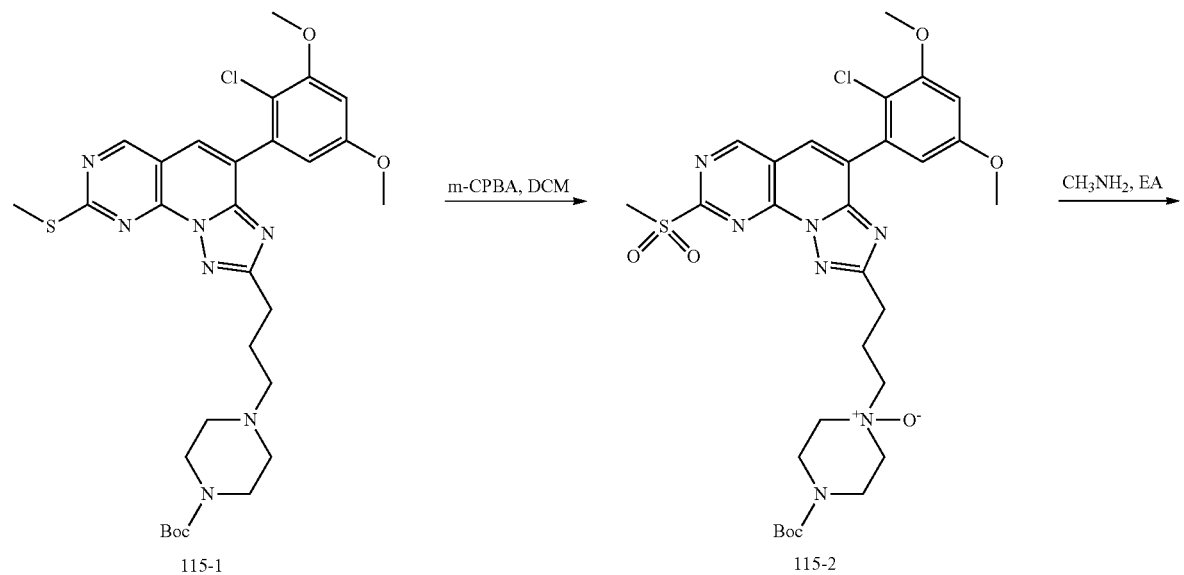
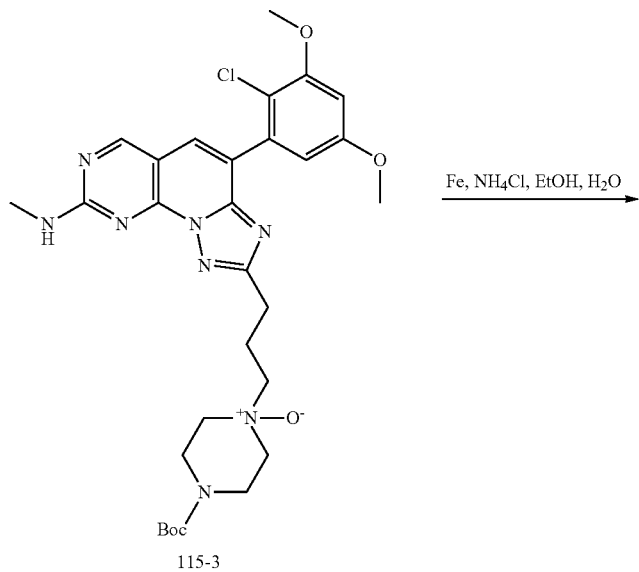

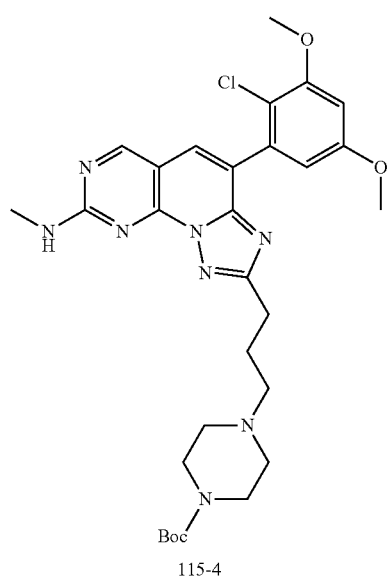

115-4

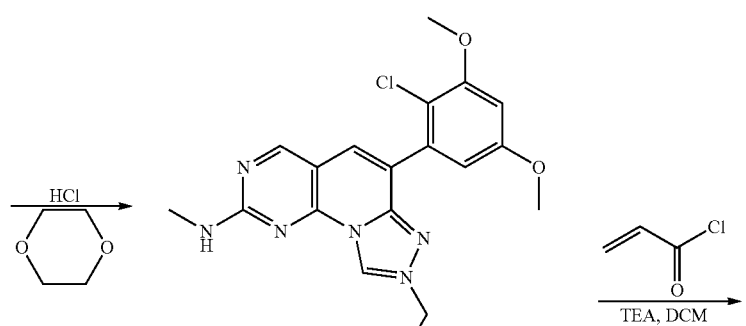

115-5

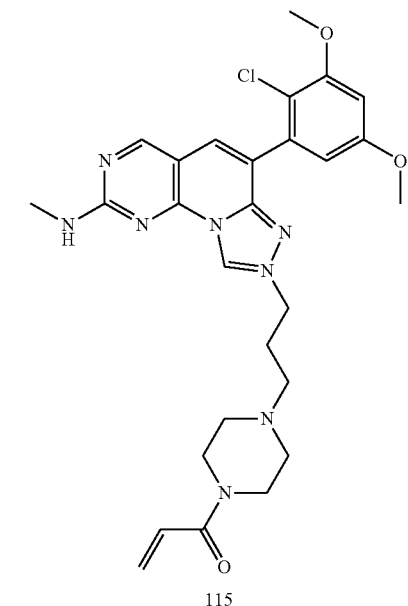

115

Step 1: Preparation of Compound 115-1

5.0 g of compound 2'-1, 2.24 g of DIEA, 4.7 g of 4-(4-Boc-piperazine-1-yl)-butyric acid, 6.58 g of HATU and 60 ml of DMF was reacted for 30 min at room temperature with stirring, then the mixture was warmed to 100° C. and reacted for 2 hrs. The mixture was cooled down to room temperature, quenched by adding water and extracted with dichloromethane. The organic phase was combined washed with water, dried over anhydrous sodium sulfate, filtrated and concentrated under reduced pressure. The crude product was purified via silica column chromatography (DCM/MeOH=0%~5%) to get 3.4 g of compound 115-1 as reddish brown oily.

LC-MS [M+H$^+$] 614.2.

Step 2: Preparation of Compound 115-2

Using compound 115-1 as a raw material, compound 115-2 was synthesized by a similar procedure as described in the step 4 of Example 112.

LC-MS [M+H$^+$] 662.2.

Step 3: Preparation of Compound 115-3

Using compound 115-2 as a raw material, compound 115-3 was synthesized by a similar procedure as described in the step 5 of Example 112.

LC-MS [M+H$^+$] 613.3.

Step 4: Preparation of Compound 115-4

Using compound 115-3 as a raw material, compound 115-4 was synthesized by a similar procedure as described in the step 6 of Example 112.

LC-MS [M+H$^+$] 597.3.

Step 5: Preparation of Compound 115-5
Using compound 115-4 as a raw material, compound 115-5 was synthesized by a similar procedure as described in the step 7 of Example 112.
LC-MS [M+H$^+$] 497.2.
Step 6: Preparation of Compound 115
Using compound 115-5 as a raw material, compound 115 was synthesized by a similar procedure as described in the step 7 of Example 115.
LC-MS [M+H$^+$] 551.2.
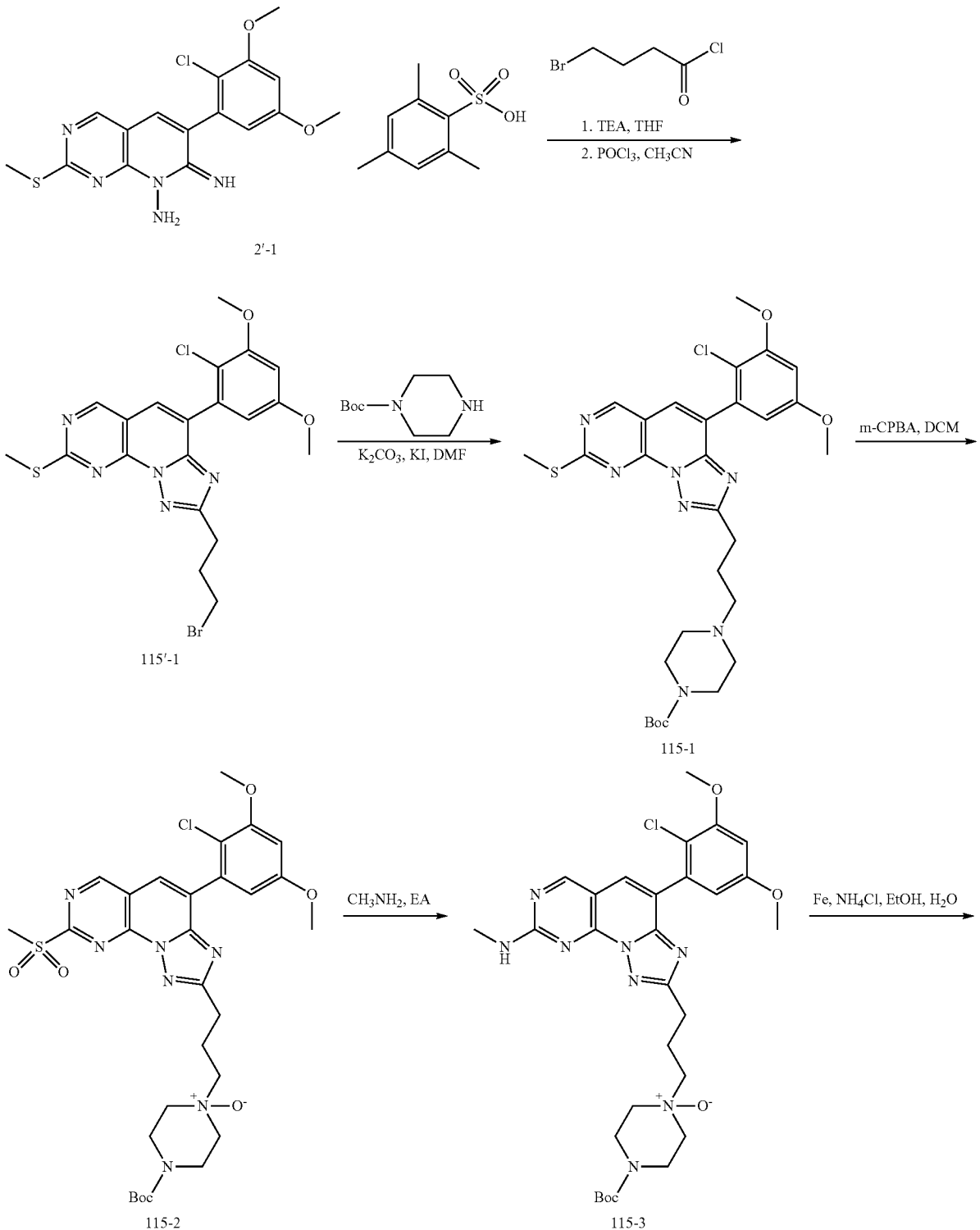

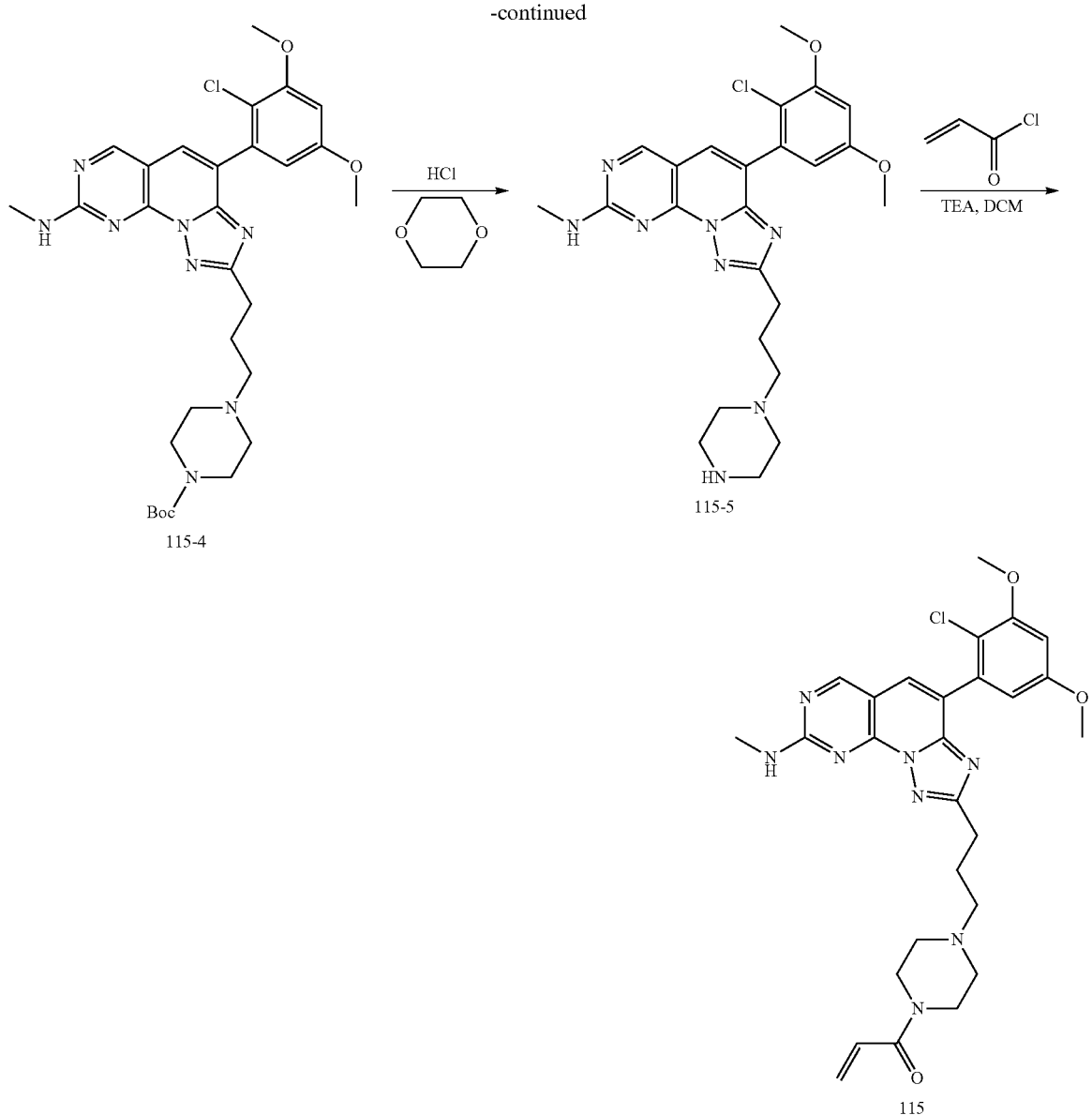

Step 1: Preparation of Compound 115'-1

A mixture of 14.0 g of compound 2'-1, 8.6 g of TEA and 150 ml of THF was cooled down to 0° C. with stirring, to which was added 6.7 g of 4-bromo butyryl chloride, when finished, the mixture was warmed to room temperature naturally. When the reaction was complete, the reaction was quenched by adding water and the mixture was extracted with dichloromethane. The organic phase was combined, washed with water, dried over anhydrous sodium sulfate, filtrated and concentrated under reduced pressure. The obtained crude product was dissolved into 240 ml of acetonitrile, added 11 ml of POCl$_3$ and reacted overnight at 80° C. When the reaction was complete, the mixture was cooled down to room temperature, the reaction system was quenched by adding ice water and extracted with dichloromethane. The organic phase was combined, washed twice with water, saturated sodium bicarbonate aqueous solution and saturated salt water respectively, dried over anhydrous sodium sulfate, filtrated and concentrated under reduced pressure. The obtained crude product was purified via silica column chromatography (DCM/EA=10/1) to get 5.3 g of compound 115'-1 as light yellow solid.

LC-MS [M+H$^+$] 508.0.

Step 2: Preparation of Compound 115-1

A mixture of 100 mg of compound 115'-1, 41 mg of 1-Bocpiperazine, 83 mg of potassium carbonate, 4 mg of potassium and 5 ml of DMF was reacted overnight at 80° C. When the reaction was complete, the mixture was cooled down to room temperature, diluted with water and extracted with ethyl acetate. The organic phase was combined, washed with water, dried over anhydrous sodium sulfate, filtrated and concentrated under reduced pressure. The obtained solid was purified via silica column chromatography (DCM/MeOH=20/1) to get 85 mg of compound 115-1 as light yellow solid.

LC-MS [M+H$^+$] 614.2.

Step 3: Preparation of Compound 115-2

Using compound 115-1 as a raw material, compound 115-2 was synthesized by a similar procedure as described in the step 2 of Route A of Example 115.
LC-MS [M+H$^+$] 662.2.

Step 4: Preparation of Compound 115-3

Using compound 115-2 as a raw material, compound 115-3 was synthesized in a similar procedure to step 3 of Route A of Example 115.
LC-MS [M+H$^+$] 613.3.

Step 5: Preparation of Compound 115-4

Using compound 115-3 as a raw material, compound 115-4 was synthesized in a similar procedure to step 4 of route A of Example 115.
LC-MS [M+H$^+$] 597.3.

Step 6: Preparation of Compound 115-5

Using compound 115-4 as a raw material, compound 115-5 was synthesized in a similar procedure to step 5 of route A of Example 115.
LC-MS [M+H$^+$] 497.2.

Step 7: Preparation of Compound 115

Using compound 115-5 as a raw material, compound 115 was synthesized in a similar procedure to step 6 of route A of Example 115.
LC-MS [M+H$^+$] 551.2.

The compounds of table 6 were prepared by a similar procedure as described in the Example 115 via different reaction starting materials and corresponding reagent.

TABLE 6

| Examples | Chemical structure | Chemical name | LC-MS [M + H$^+$] |
| --- | --- | --- | --- |
| 116 | 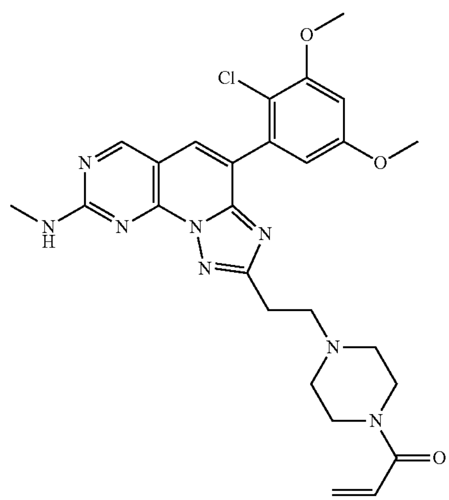 [SMILES: C=CC(=O)N1CCN(CCc2nc3c(-c4cc(OC)cc(OC)c4Cl)cc4cnc(NC)nc4n3n2)CC1] | 1-(4-(2-(4-(2-chloro-3,5-dimethoxy-phenyl)-8-(methylamino)-[1,2,4]triazolo[1',5':1,6]pyrido[2,3-d]pyrimidin-2-yl)ethyl)piperazin-1-yl)prop-2-en-1-one | 537.0 |
| 117 | 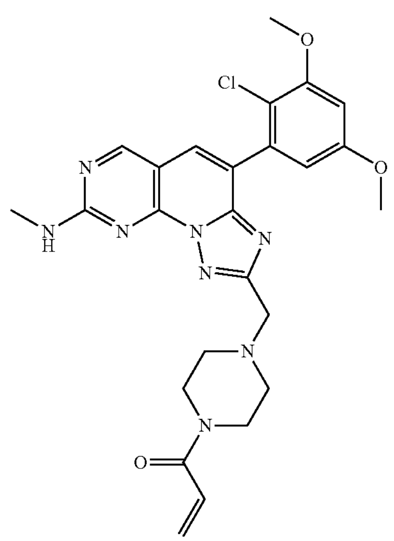 | 1-(4-((4-(2-chloro-3,5-dimethoxy-phenyl)-8-(methylamino)-[1,2,4]triazolo[1',5':1,6]pyrido[2,3-d]pyrimidin-2-yl)methyl)piperazin-1-yl)prop-2-en-1-one | 523.0 |

TABLE 6-continued

| Examples | Chemical structure | Chemical name | LC-MS [M + H$^+$] |
|---|---|---|---|
| 118 | 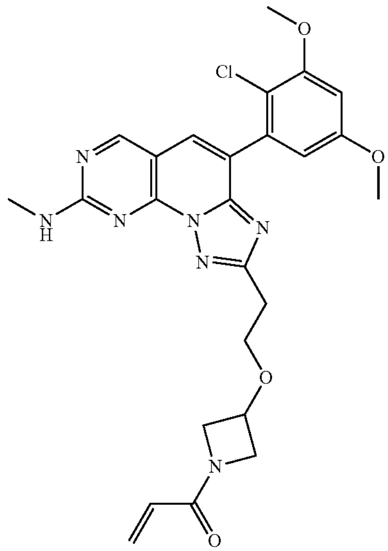 | 1-(3-(2-(4-(2-chloro-3,5-dimethoxy-phenyl)-8-(methylamino)-[1,2,4]triazolo[1',5':1,6]pyrido[2,3-d]pyrimidin-2-yl)ethoxy)azetidin-1-yl)prop-2-en-1-one | 524.0 |
| 119 | 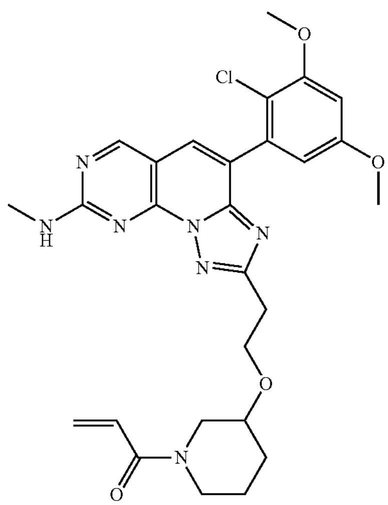 | 1-(3-(2-(4-(2-chloro-3,5-dimethoxy-phenyl)-8-(methylamino)-[1,2,4]triazolo[1',5':1,6]pyrido[2,3-d]pyrimidin-2-yl)ethoxy)piperidin-1-yl)prop-2-en-1-one | 552.0 |

Example 120: Preparation of Compound 120 (N-(4-(2-(4-(2,6-dichloro-3,5-dimethoxyphenyl)-8-(methylamino)-[1,2,4]triazolo[1',5':1,6]pyrido[2,3-d]pyrimidin-2-yl)ethyl)phenyl)acrylamide)

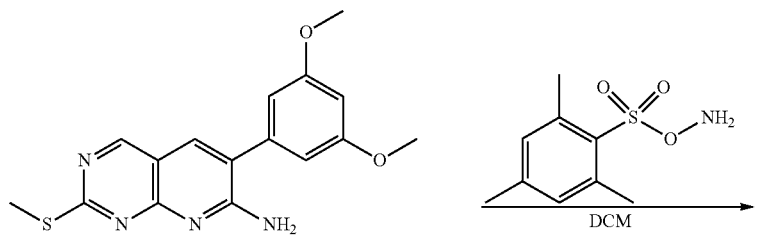

56'-2

155                                   156
-continued
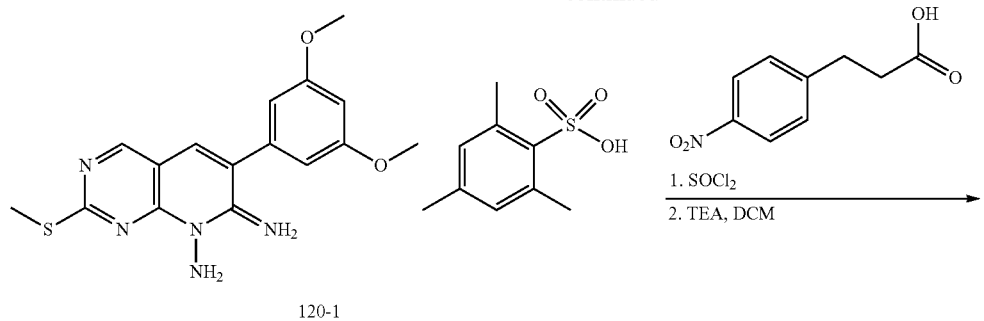
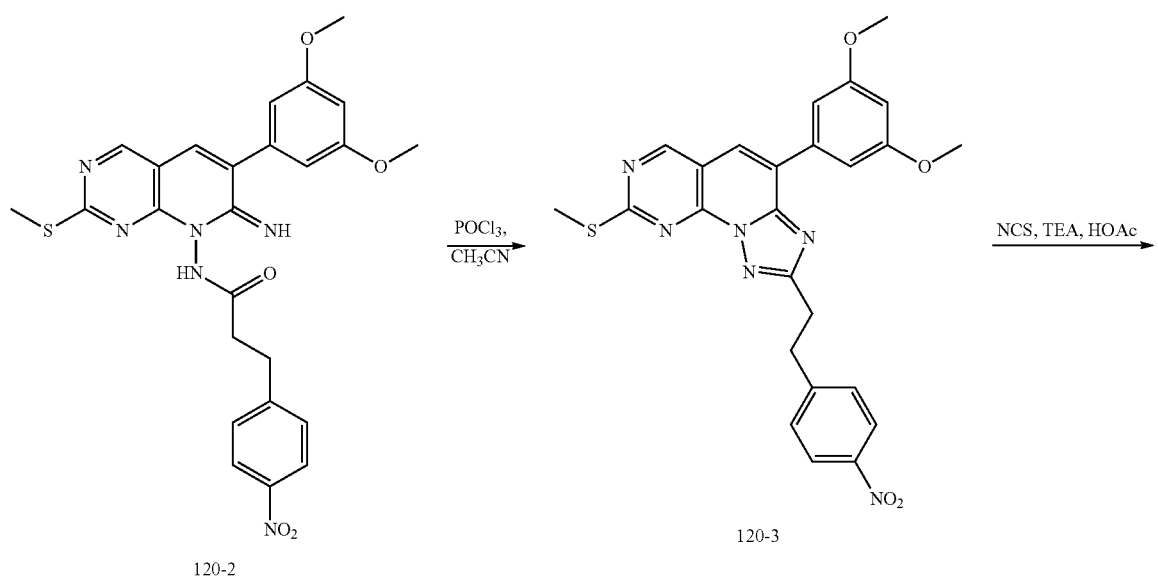
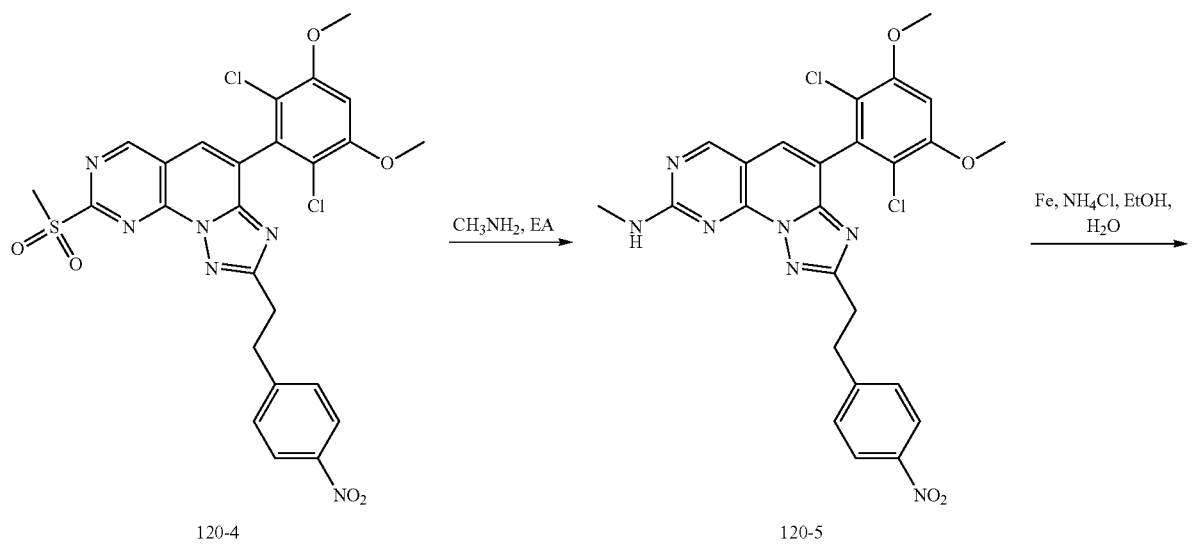

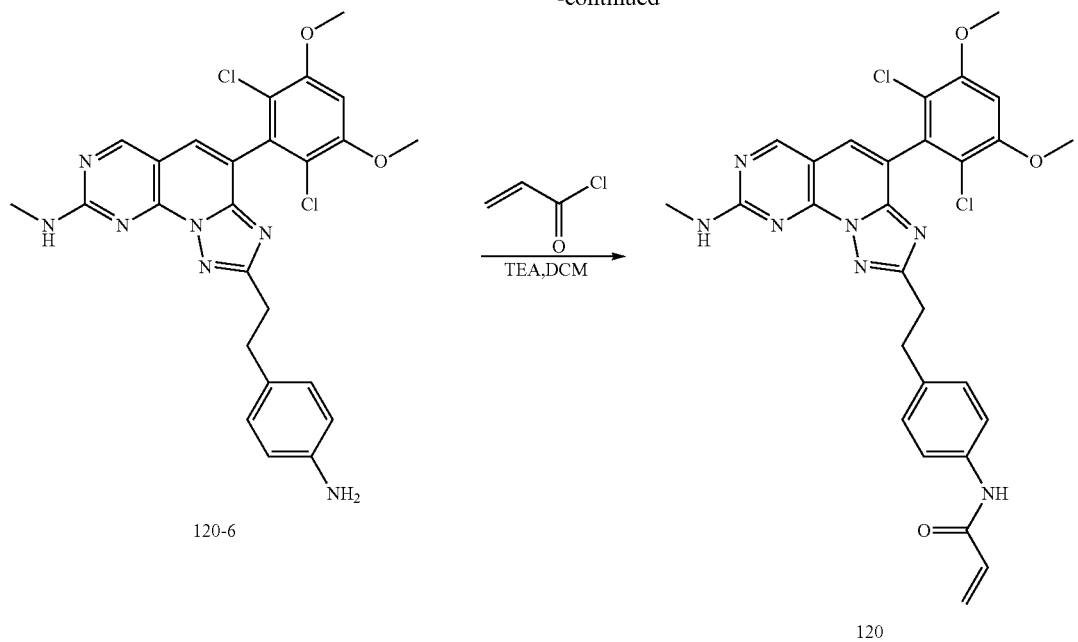

Step 1: Preparation of Compound 120-1

31.2 g of 2-[(aminooxy)sulfonyl]-1,3,5-trimethylbenzene was dispersed in 900 ml of dichloromethane and cooled down to 0° C. 23.8 g of compound 2-1 was added in batches with stirring. The mixture was warmed to room temperature naturally and reacted overnight. After the reaction was completed, the mixture was filtrated, the solid was rinsed twice with small amount of DCM and was dried, then to get 34.9 g of compound 120-1, which was light yellow solid.

LC-MS [M+H$^+$] 344.1.

Step 2: Preparation of Compound 120-2

A mixture of 162 mg of 4-nitrophenylpropionic acid and 5 ml of sulfoxide chloride was refluxed for 1 hr. The mixture was concentrated under reduced pressure to remove sulfoxide chloride, then 10 ml of dichloromethane was added, the mixture was concentrated under reduced pressure and the operation was repeated twice. The mixture was concentrated under reduced pressure in vacuum for 15 mins. The obtained oily was dissolved into 2 ml of dichloromethane and was dropwise into a mixture of 300 mg of compound 120-1, 15 ml of dichloromethane and 0.38 ml of TEA at 0° C. When finished, the mixture was warmed to room temperature naturally and reacted overnight with stirring. When the reaction was complete, the reaction was quenched by adding water and extracted with dichloromethane. The organic phase was combined, washed with water, dried over anhydrous sodium sulfate, filtrated and concentrated under reduced pressure to get 300 mg of compound 120-2 as reddish brown solid. It was used in the next step directly without purification.

LC-MS [M+H$^+$] 521.2.

Step 3: Preparation of Compound 120-3

A mixture of 300 mg of compound 120-2, 1 ml of phosphorus oxychloride and 10 ml of acetonitrile was refluxed for 1 hr at 80° C., the reaction was suspended and the mixture was cooled down to room temperature. The reaction was quenched with ice water, extracted with dichloromethane, washed with saturated brine, dried over anhydrous Na$_2$SO$_4$ and concentrated under reduced pressure. The residue was purified via silica column chromatography (dichloromethane/methanol=25/1) to get 277 mg of compound 120-3 as light yellow solid.

LC-MS [M+H$^+$] 503.1.

Step 4: Preparation of Compound 120-4

368 mg of NCS was added into a mixture of 277 mg of compound 120-3, 0.23 ml of TEA and 4 ml acetic acid in batches, the mixture was stirred for 1 hr at room temperature. When completed, the mixture was diluted with ethyl acetate, washed twice with water, saturated sodium bicarbonate aqueous solution and saturated brine respectively, dried over anhydrous sodium sulfate, filtrated and concentrated under reduced pressure to get 332 mg of compound 120-4 as yellow solid. It was used directly in the next reaction without purification.

LC-MS [M+H$^+$] 603.0.

Step 5: Preparation of Compound 120-5

A mixture of 332 mg of compound 120-4, 2.75 ml of methylamine tetrahydrofuran solution and 10 ml of ethyl acetate was stirred for 1 hr at room temperature. The reaction was quenched with water, extracted with ethyl acetate, washed with water, dried over anhydrous sodium sulfate and concentrated under reduced pressure. The residue was purified via silica column chromatography (dichloromethane/methanol=25/1) to get 305 mg of compound 120-4 as yellow solid.

LC-MS [M+H⁺] 554.1.

Step 6: Preparation of Compound 120-6

A mixture of 305 mg of compound 120-4, 50 mg of Pd/C and 40 ml of methanol was reacted for 1 hr with stirring at room temperature under hydrogen atmosphere. The mixture was filtrated, and the filtrate was concentrated under reduced pressure to get 99 mg of compound 120-5 as light yellow solid. It was used directly in the next reaction without purification.

LC-MS [M+H⁺] 524.1.

Step 7: Preparation of Compound 120

26 mg of acryloyl chloride was dropwise to a mixture of 99 mg of compound 120-5, 0.08 ml of triethylamine and 10 ml of dichloromethane with stirring at 0° C., when finished, the mixture was reacted for 1 hr at 0° C. The reaction was quenched with saturated sodium bicarbonate aqueous solution and extracted with dichloromethane. The organic phase was combined, washed with water, dried with anhydrous sodium sulfate and concentrated under reduced pressure. The residue was purified via silica column chromatography (dichloromethane/methanol=25/1) to get 25 mg of compound 120 as light yellow solid.

LC-MS [M+H⁺] 578.1.

Example 121: Preparation of Compound 121 (N-(3-(2-(4-(2,6-dichloro-3,5-dimethoxyphenyl)-8-(methylamino)-[1,2,4]triazolo[1',5':1,6]pyrido[2,3-d]pyrimidin-2-yl)ethyl)phenyl)acrylamide)

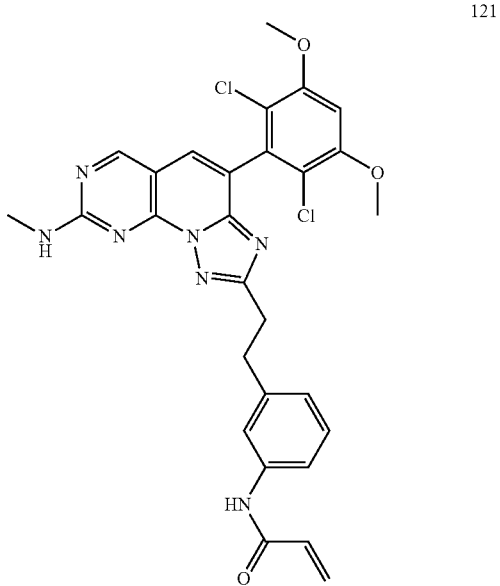

121

Compound 121 was prepared in a similar procedure to example 120 via different reaction starting material and the appropriate reagent.

LC-MS [M+H⁺] 578.1.

Example 122: Preparation of Compound 122 (1-(4-(2-(4-(2,6-dichloro-3,5-dimethoxyphenyl)-8-(methylamino)-[1,2,4]triazolo[1',5':1,6]pyrido[2,3-d]pyrimidin-2-yl)propyl)piperazin-1-yl) prop-2-en-1-one)

Route A

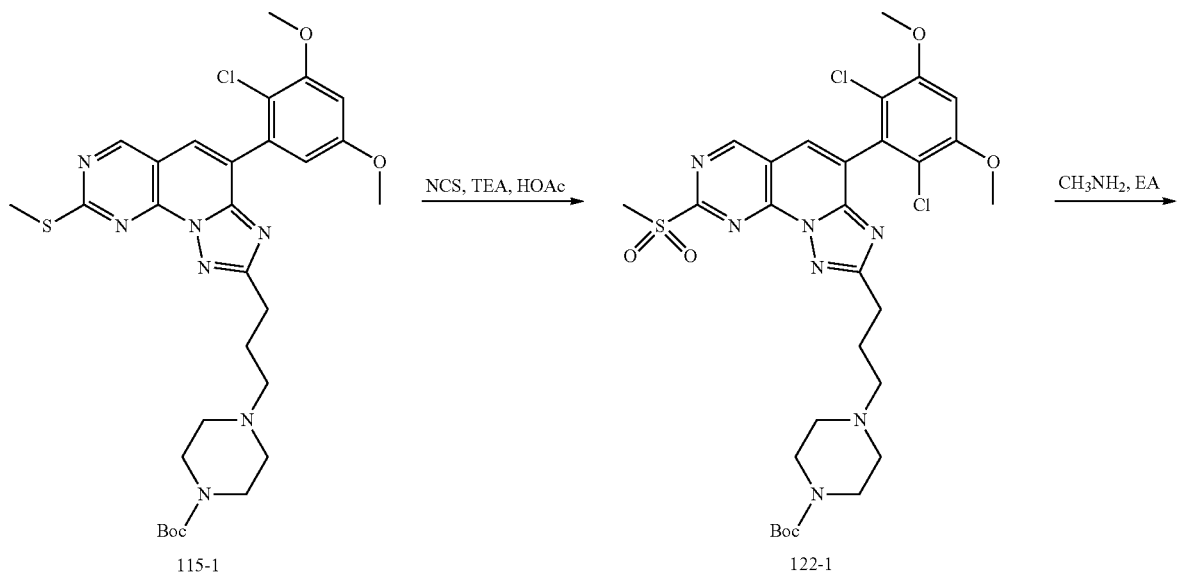

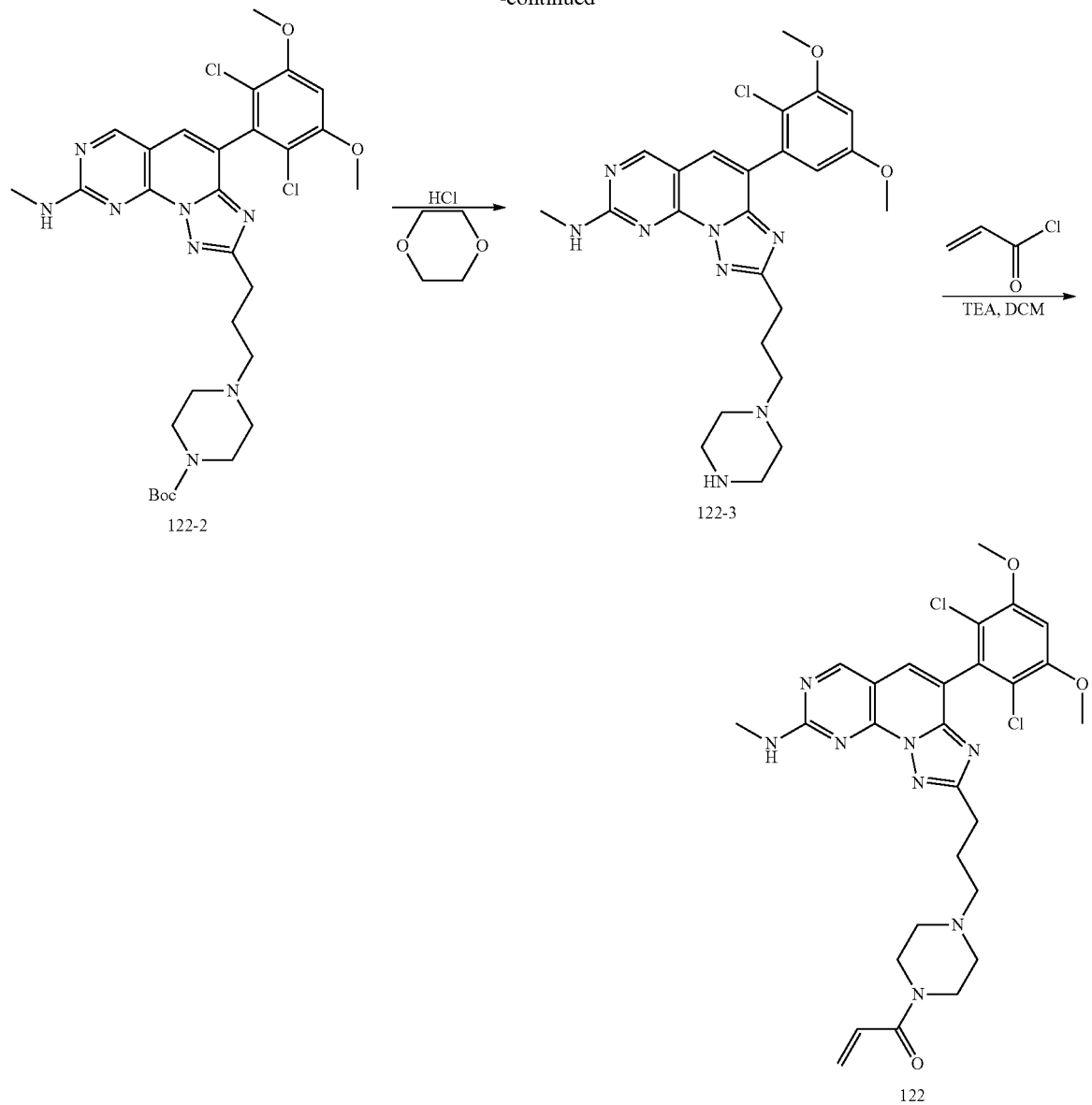

Step 1: Preparation of Compound 122-1

A mixture of 176 mg of compound 122-1, 67 mg of TEA, 134 mg of NCS and 10 ml of glacial acetic acid was reacted for 1 hr with stirring at room temperature. The mixture was diluted with ethyl acetate, washed twice with water, saturated sodium carbonate aqueous solution and saturated brine respectively, dried over anhydrous sodium sulfate, filtrated and concentrated under reduced pressure to get 180 mg of compound 122-1 as light yellow solid. It was used directly in the next reaction without purification.

LC-MS [M+H$^+$] 680.2.

Step 2: Preparation of Compound 122-2

A mixture of 180 mg of compound 122-1, 1.3 ml of methylamine tetrahydrofuran solution and 10 ml of ethyl acetate was reacted for 1 hr with stirring at room temperature. The mixture was diluted with ethyl acetate, washed with water, dried over anhydrous sodium sulfate, filtrated and concentrated under reduced pressure. The crude product was purified via silica column chromatography (DCM/MeOH=0% 5%) to get 140 mg of compound 122-2 as light yellow solid.

LC-MS [M+H$^+$] 631.2.

Step 3: Preparation of Compound 122-3

Using compound 122-2 as a raw material, compound 122-3 was synthesized in a similar procedure to step 5 of route A of example 122.

LC-MS [M+H$^+$] 497.2.

Step 4: Preparation of Compound 122

Using 122-3 as a raw material, compound 122 was synthesized in a similar procedure to step 6 of route A of Example 122.

LC-MS [M+H$^+$] 585.2.

Route B
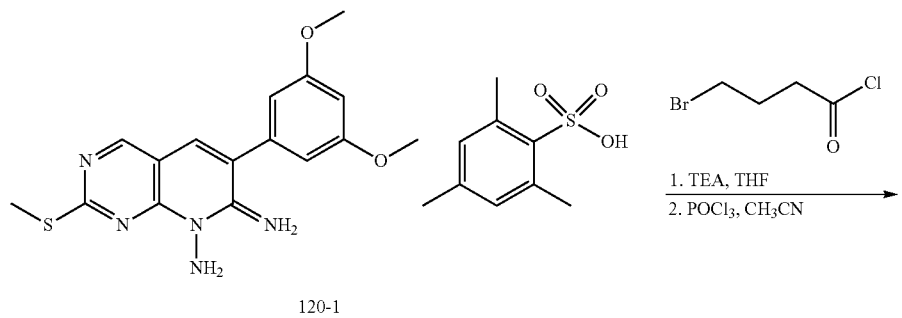
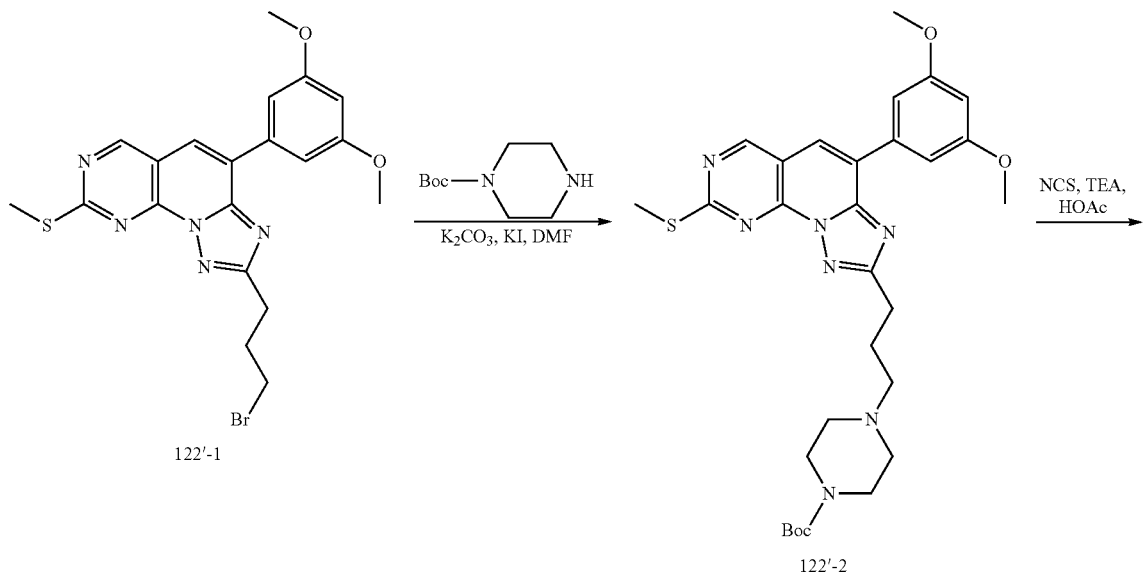
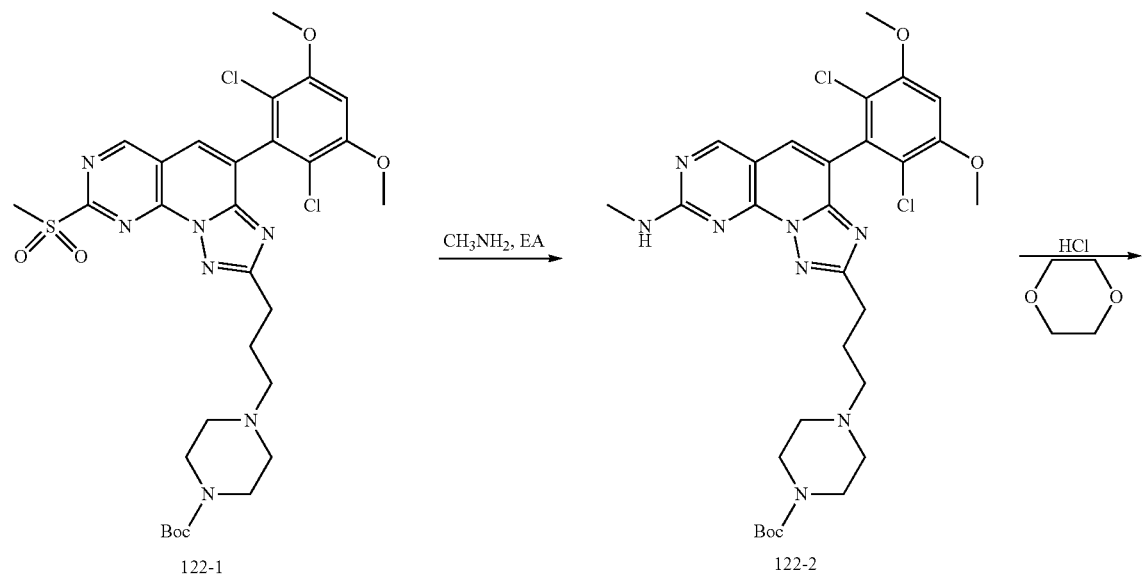

-continued

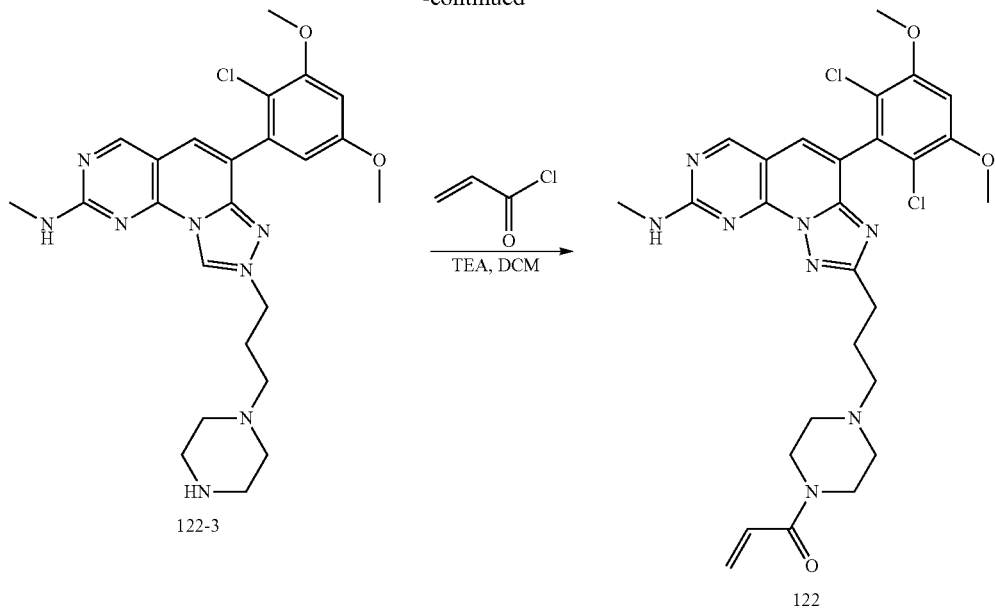

Step 1: Preparation of Compound 122'-1

A mixture of 59.8 g of compound 120-1, 35.4 g of TEA and 500 ml of THF was cooled down to 0° C. with stirring. 51.0 g of 4-bromobutyryl chloride was dropwise into the mixture, when finished, the mixture was warmed up to room temperature and the mixture was reacted overnight with stirring. The reaction was quenched with water and was extracted with dichloromethane. The organic phase was combined, washed with saturated sodium bicarbonate and water, dried over anhydrous sodium sulfate, filtrated and concentrated under reduced pressure. The residue was dissolved into a mixture of 500 ml of acetonitrile and 50 ml of $POCl_3$ and reacted for 3 hrs at 80° C. The mixture was cooled down to room temperature, quenched with ice water and extracted with dichloromethane. The organic phase was combined, washed twice with water, saturated sodium bicarbonate aqueous solution and saturated brine respectively, dried over anhydrous sodium sulfate, filtrated and concentrated under reduced pressure. The crude product was purified via silica column chromatography (Hex/EA=1/1) to get 15.7 g of compound 121'-1 as light yellow solid.

LC-MS $[M+H^+]$ 474.1.

Step 2: Preparation of Compound 122'-2

A mixture of 8.2 g of compound 122'-1, 4.8 g of 1-Bocpiperazine, 7.2 g of potassium carbonate, 0.29 g of potassium iodide and 50 ml of DMF was stirred at 80° C. and reacted for 3 hrs. The mixture was cooled down to room temperature, diluted with water and extracted with ethyl acetate. The organic phase was combined, washed three times with saturated brine, dried over anhydrous sodium sulfate and concentrated under reduced pressure. The crude product was purified via silica column chromatography (DCM/MeOH=20/1) to get 7.8 g of compound 122'-2 as light yellow solid.

LC-MS $[M+H^+]$ 580.3.

Step 3: Preparation of Compound 122-1

The temperature of a mixture of 7.8 g of compound 122'-2, 4.1 g of TEA and 80 ml of glacial acetic acid was controlled below 5° C. and 8.1 g NCS was added into the mixture in batches. The mixture was stirred at room temperature and reacted for 2 hrs. The mixture was quenched with water and extracted with ethyl acetate. The organic phase was combined, washed twice with water, saturated sodium carbonate aqueous solution and saturated brine respectively, dried over anhydrous sodium sulfate, filtrated and concentrated under reduced pressure to get 9.92 g of compound 122-1 as yellow solid.

LC-MS $[M+H^+]$ 680.2.

Steps 4, 5, and 6 are the same as steps 2, 3 and 4 of route A of example 122, respectively.

The compounds of table 7 were prepared in a similar procedure to example 122 via different reaction starting materials and corresponding reagent.

TABLE 7

| Examples | Chemical structure | Chemical name | LC-MS [M + H+] |
|---|---|---|---|
| 123 | 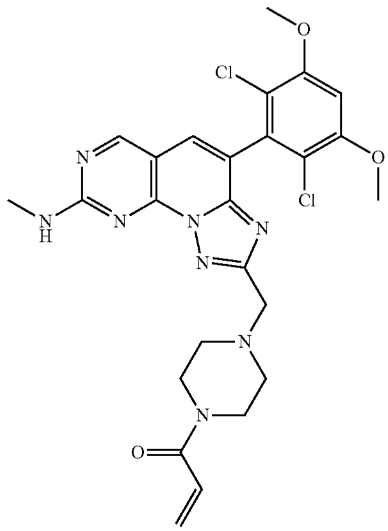 | 1-(4-(2-(4-(2,6-dichloro-3,5-dimethoxyphenyl)-8-(methylamino)-[1,2,4]triazolo[1',5':1,6]pyrido[2,3-d]pyrimidin-2-yl)methyl)piperazin-1-yl)prop-2-en-1-one | 557.4 |
| 124 | 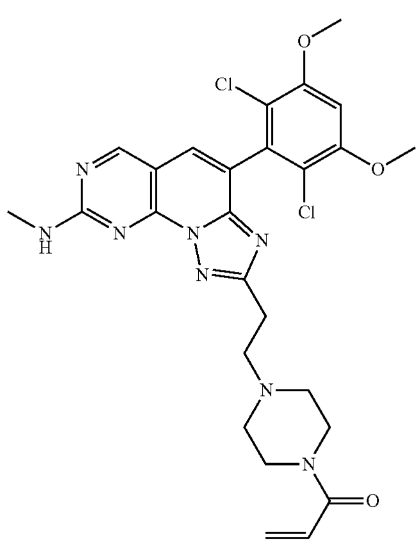 | 1-(4-(2-(4-(2,6-dichloro-3,5-dimethoxyphenyl)-8-(methylamino)-[1,2,4]triazolo[1',5':1,6]pyrido[2,3-d]pyrimidin-2-yl)ethyl)piperazin-1-yl)prop-2-en-1-one | 571.5 |

TABLE 7-continued
| Examples | Chemical structure | Chemical name | LC-MS [M + H+] |
|---|---|---|---|
| 125 | 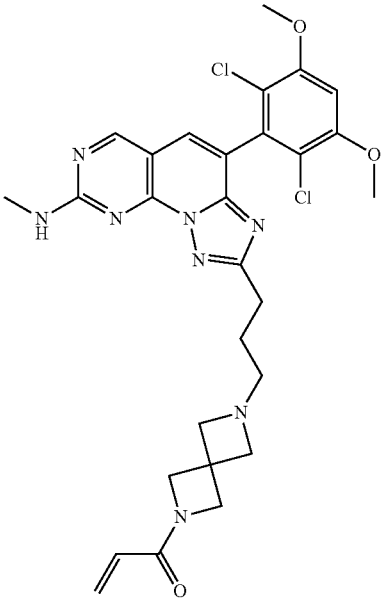 | 1-(6-(3-(4-(2,6-dichloro-3,5-dimethoxyphenyl)-8-(methylamino)-[1,2,4]triazolo[1',5':1,6]pyrido[2,3-d]pyrimidin-2-yl)propyl)-2,6-diazaspiro[3.3]heptan-2-yl)prop-2-en-1-one | 597.5 |
| 126 | 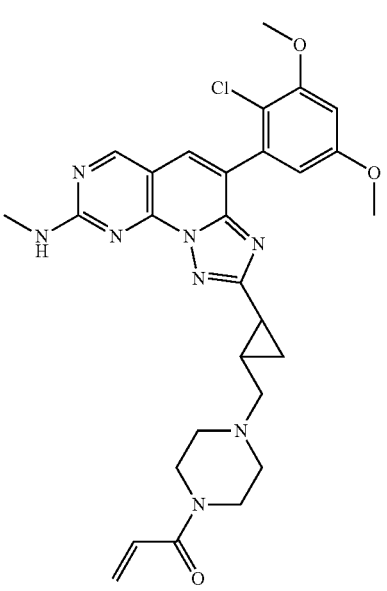 | 1-(4-((2-(4-(2-chloro-3,5-dimethoxyphenyl)-8-(methylamino)-[1,2,4]triazolo[1',5':1,6]pyrido[2,3-d]pyrimidin-2-yl)cyclopropyl)methyl)piperazin-1-yl)prop-2-en-1-one | 563.1 |

TABLE 7-continued

| Examples | Chemical structure | Chemical name | LC-MS [M + H⁺] |
|---|---|---|---|
| 127 | 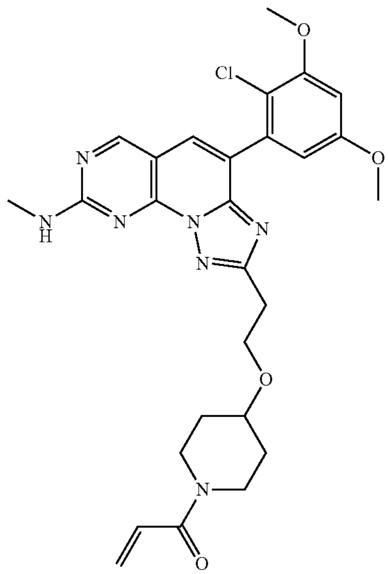 | 1-(4-(2-(4-(2-chloro-3,5-dimethoxyphenyl)-8-(methylamino)-[1,2,4]triazolo[1',5':1,6]pyrido[2,3-d]pyrimidin-2-yl)ethoxy)piperidin-1-yl)prop-2-en-1-one | 552.0 |
| 128 | 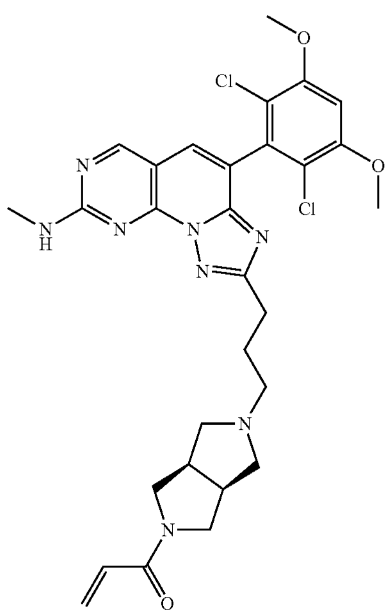 | 1-((3aR,6aS)-5-(2-(4-(2,6-dichloro-3,5-dimethoxyphenyl)-8-(methylamino)-[1,2,4]triazolo[1',5':1,6]pyrido[2,3-d]pyrimidin-2-yl)propyl)hexahydropyrrolo[3,4-c]pyrrol-2(1H)-yl)prop-2-en-1-one | 611.5 |

TABLE 7-continued
| Examples | Chemical structure | Chemical name | LC-MS [M + H+] |
|---|---|---|---|
| 129 | 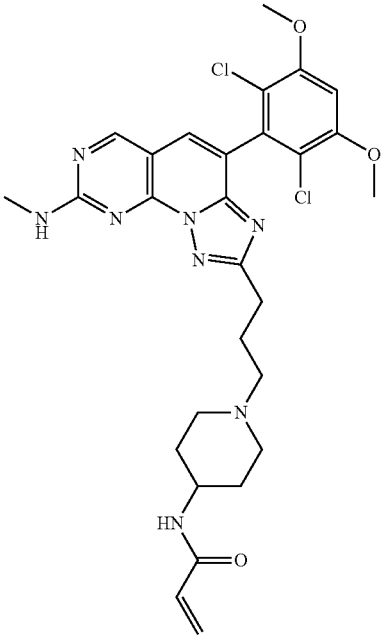 | N-(1-(2-(4-(2,6-dichloro-3,5-dimethoxyphenyl)-8-(methylamino)-[1,2,4]triazolo[1',5':1,6]pyrido[2,3-d]pyrimidin-2-yl)propyl)piperidin-4-yl)acrylamide | 599.5 |
| 130 | 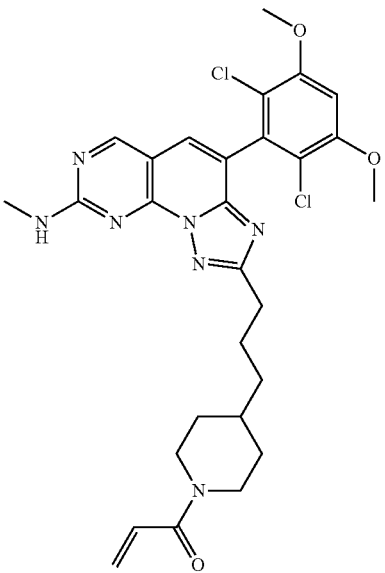 | 1-(4-(3-(4-(2,6-dichloro-3,5-dimethoxyphenyl)-8-(methylamino)-[1,2,4]triazolo[1',5':1,6]pyrido[2,3-d]pyrimidin-2-yl)propyl)piperidin-1-yl)prop-2-en-1-one | 584.5 |

TABLE 7-continued
| Examples | Chemical structure | Chemical name | LC-MS [M + H+] |
|---|---|---|---|
| 131 | 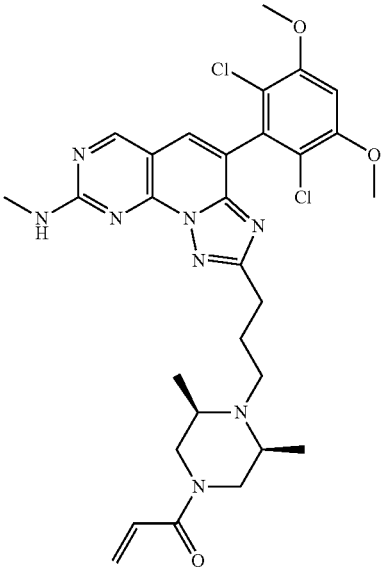 | 1-((3S,5R)-4-(3-(4-(2,6-dichloro-3,5-dimethoxyphenyl)-8-(methylamino)-[1,2,4]triazolo[1',5':1,6]pyrido[2,3-d]pyrimidin-2-yl)propyl)azetidine-1-yl)prop-2-en-1-one | 613.5 |
| 132 | 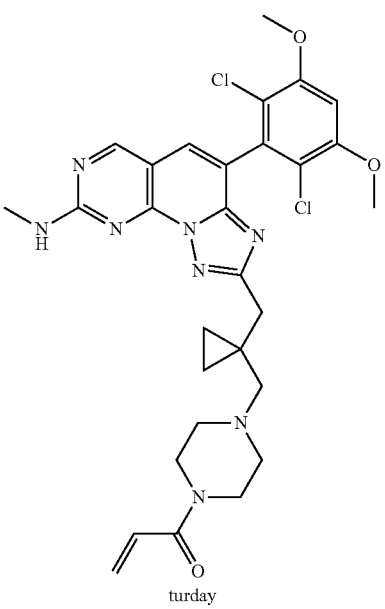 | 1-(4-((1-((4-(2,6-dichloro-3,5-dimethoxyphenyl)-8-(methylamino)-[1,2,4]triazolo[1',5':1,6]pyrido[2,3-d]pyrimidin-2-yl)methyl)cyclopropyl)methyl)piperazin-1-yl)prop-2-en-1-one | 611.5 |

TABLE 7-continued
| Examples | Chemical structure | Chemical name | LC-MS [M + H⁺] |
|---|---|---|---|
| 133 | 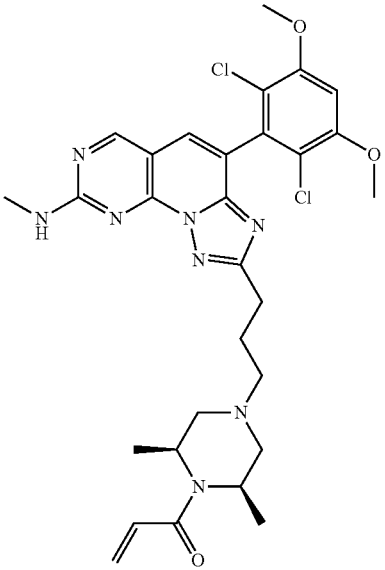 | 1-((2R,6S)-4-(3-(4-(2,6-dichloro-3,5-dimethoxyphenyl)-8-(methylamino)-[1,2,4]triazolo[1',5':1,6]pyrido[2,3-d]pyrimidin-2-yl)propyl)-2,6-dimethylpiperazin-1-yl)prop-2-en-1-one | 613.5 |
| 134 | 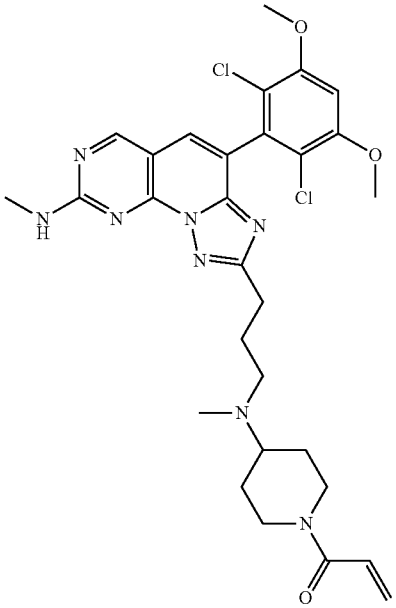 [SMILES: C=CC(=O)N1CCC(N(C)CCCc2nc3c(-c4c(Cl)c(OC)cc(OC)c4Cl)cc4cnc(NC)nc4n3n2)CC1] | 1-(4-((3-(4-(2,6-dicholo-3,5-dimethoxyphenyl)-8-(methylamino)-[1,2,4]triazolo[1',5':1,6]pyrido[2,3-d]pyrimidin-2-yl)propyl)(methyl)amino)piperidin-1-yl)prop-2-en-1-one | 613.5 |

TABLE 7-continued
| Examples | Chemical structure | Chemical name | LC-MS [M + H+] |
|---|---|---|---|
| 135 | 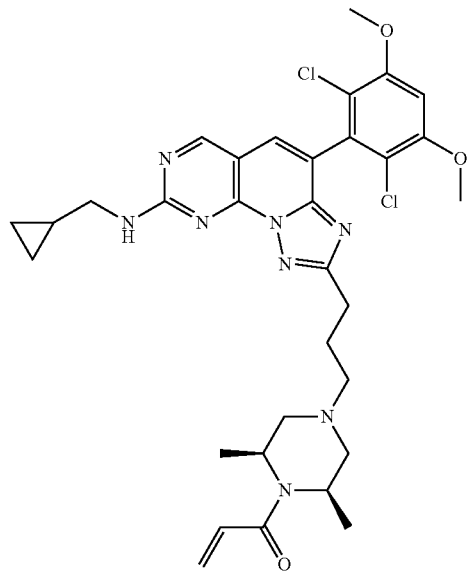 [SMILES: C=CC(=O)N1[C@H](C)CN(CCCc2nc3c(-c4c(Cl)c(OC)cc(OC)c4Cl)cc4cnc(NCC5CC5)nc4n3n2)C[C@@H]1C] | 1-((2R,6S)-4-(3-(8-((cyclopropyl-methyl)amino)-4-(2,6-dichloro-3,5-dimethoxyphenyl)-[1,2,4]triazolo[1',5':1,6]pyrido[2,3-d]pyrimidin-2-yl)propyl)-2,6-dimethylpiperazin-1-yl)prop-2-en-1-one | 653.6 |
| 136 | 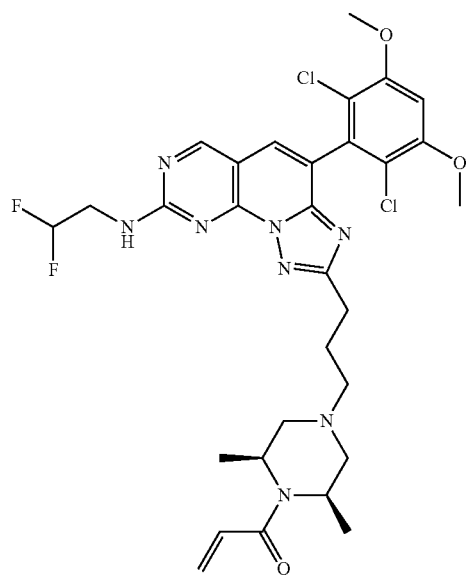 [SMILES: C=CC(=O)N1[C@H](C)CN(CCCc2nc3c(-c4c(Cl)c(OC)cc(OC)c4Cl)cc4cnc(NCC(F)F)nc4n3n2)C[C@@H]1C] | 1-((2R,6S)-4-(3-(4-(2,6-dichloro-3,5-dimethoxyphenyl)-8-((2,2-difluoroethyl)amino)-[1,2,4]triazolo[1',5':1,6]pyrido[2,3-d]pyrimidin-2-yl)propyl)-2,6-dimethylpiperazin-1-yl)prop-2-en-1-one | 663.6 |

TABLE 7-continued

| Examples | Chemical structure | Chemical name | LC-MS [M + H+] |
|---|---|---|---|
| 137 | 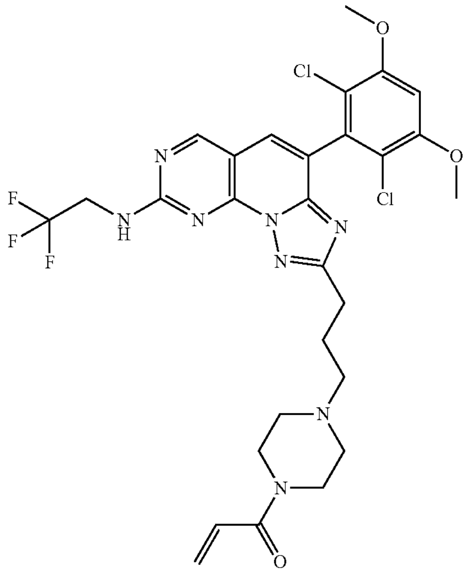 [SMILES: C=CC(=O)N1CCN(CCCc2nc3c(-c4c(Cl)c(OC)cc(OC)c4Cl)cc4cnc(NCC(F)(F)F)nc4n3n2)CC1] | 1-(4-(3-(4-(2,6-dichloro-3,5-dimethoxyphenyl)-8-((2,2,2-trifluoroethyl)amino)-[1,2,4]triazolo[1',5':1,6]pyrido[2,3-d]pyrimidin-2-yl)propyl)piperazin-1-yl)prop-2-en-1-one | 653.5 |
| 138 | 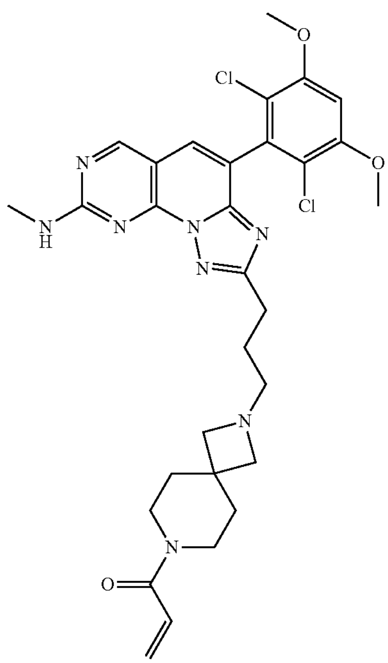 | 1-(2-(3-(4-(2,6-dichloro-3,5-dimethoxyphenyl)-8-(methylamino)-[1,2,4]triazolo[1',5':1,6]pyrido[2,3-d]pyrimidin-2-yl)propyl)-2,7-diazaspiro[3.5]nonan-7-yl)prop-2-en-1-one | 625.6 |

TABLE 7-continued

| Examples | Chemical structure | Chemical name | LC-MS [M + H⁺] |
|---|---|---|---|
| 139 | 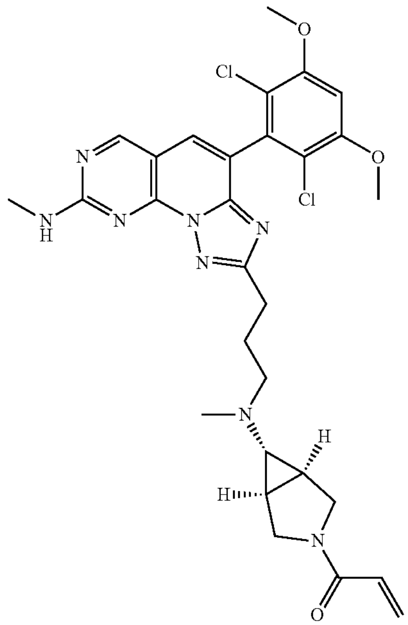 [SMILES: C=CC(=O)N1C[C@@H]2[C@H](C1)[C@H]2N(C)CCCc1nc2c(-c3c(Cl)c(OC)cc(OC)c3Cl)cc3cnc(NC)nc3n2n1] | 1-((1R,5S,6s)-6-((3-(4-(2,6-dichloro-3,5-dimethoxyphenyl)-8-(methylamino)-[1,2,4]triazolo[1',5':1,6]pyrido[2,3-d]pyrimidin-2-yl)propyl)(methyl)amino)-3-azabicyclo[3.1.0]hexan-3-yl)prop-2-en-1-one | 611.5 |
| 140 | 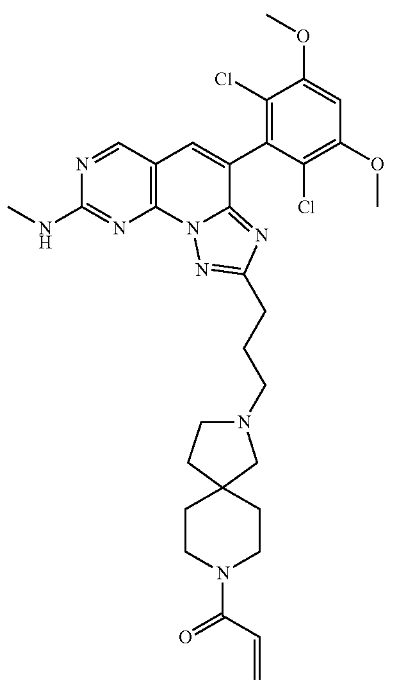 | 1-(2-(3-(4-(2,6-dichloro-3,5-dimethoxyphenyl)-8-(methylamino)-[1,2,4]triazolo[1',5':1,6]pyrido[2,3-d]pyrimidin-2-yl)propyl)-2,8-diazaspiro[4.5]decan-8-yl)prop-2-en-1-one | 639.6 |

TABLE 7-continued

| Examples | Chemical structure | Chemical name | LC-MS [M + H+] |
|---|---|---|---|
| 141 | 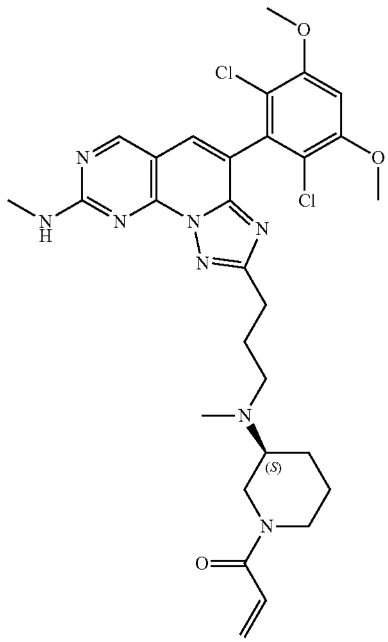 | (S)-1-(3-((3-(4-(2,6-dichloro-3,5-dimethoxyphenyl)-8-(methylamino)-[1,2,4]triazolo[1',5':1,6]pyrido[2,3-d]pyrimidin-2-yl)propyl)(methyl)amino)piperidin-1-yl)prop-2-en-1-one | 613.5 |
| 142 | 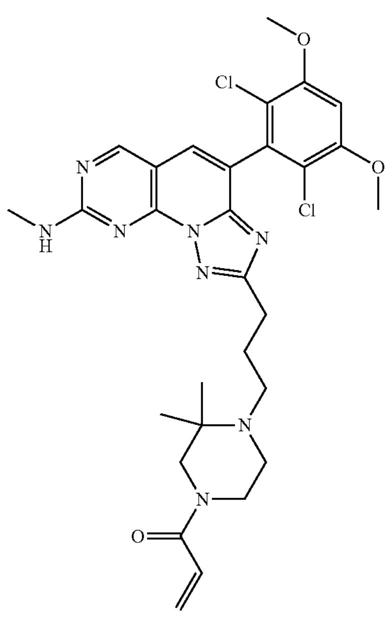 | 1-(4-(3-(4-(2,6-dichloro-3,5-dimethoxyphenyl)-8-(methylamino)-[1,2,4]triazolo[1',5':1,6]pyrido[2,3-d]pyrimidin-2-yl)propyl)-3,3-dimethylpiperazin-1-yl)prop-2-en-1-one | 613.5 |

TABLE 7-continued

| Examples | Chemical structure | Chemical name | LC-MS [M + H⁺] |
|---|---|---|---|
| 143 | 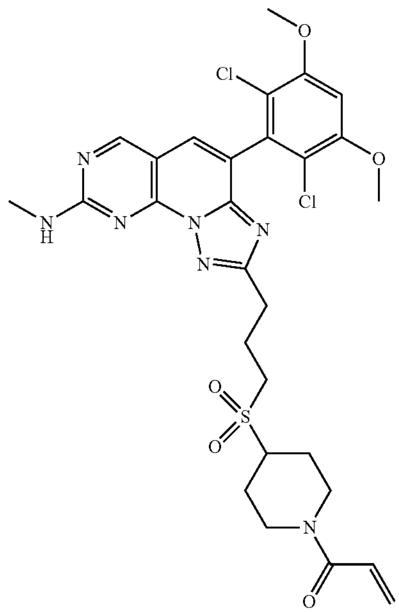 [SMILES: C=CC(=O)N1CCC(S(=O)(=O)CCCc2nc3c(-c4c(Cl)c(OC)cc(OC)c4Cl)cc4cnc(NC)nc4n3n2)CC1] | 1-(4-((3-(4-(2,6-dichloro-3,5-dimethoxyphenyl)-8-(methylamino)-[1,2,4]triazolo[1',5':1,6]pyrido[2,3-d]pyrimidin-2-yl)propyl)sulfonyl)piperidin-1-yl)prop-2-en-1-one | 648.6 |
| 144 | 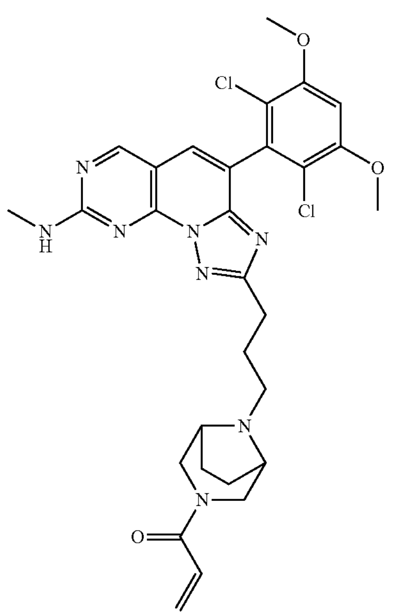 | 1-(8-(3-(4-(2,6-dichloro-3,5-dimethoxyphenyl)-8-(methylamino)-[1,2,4]triazolo[1',5':1,6]pyrido[2,3-d]pyrimidin-2-yl)propyl)-3,8-diazabicyclo[3.2.1]octan-3-yl)prop-2-en-1-one | 611.5 |

TABLE 7-continued
| Examples | Chemical structure | Chemical name | LC-MS [M + H+] |
|---|---|---|---|
| 145 | 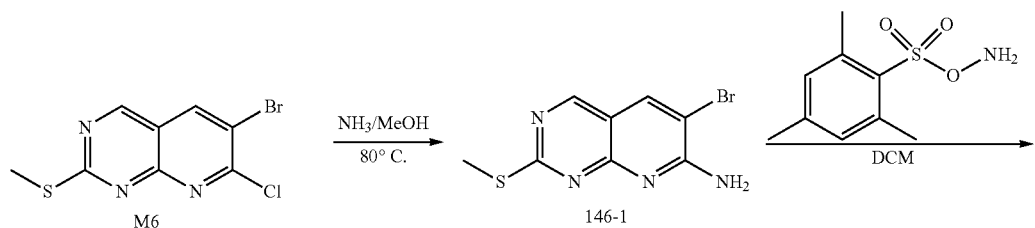 | 1-(5-(3-(4-(2,6-dichloro-3,5-dimethoxyphenyl)-8-(methylamino)-[1,2,4]triazolo[1',5':1,6]pyrido[2,3-d]pyrimidin-2-yl)propyl)-2,5-diazabicyclo[2.2.1]heptan-2-yl)prop-2-en-1-one | 597.5 |
Example 146: Preparation of Compound 146 (1-(4-(3-(4-(5-chloro-2-methyl-1H-benzo[d]imidazol-6-yl)-8-(methylamino)-[1,2,4]triazolo[1',5':1,6]pyrido[2,3-d]pyrimidin-2-yl)propyl)piperazin-1-yl)prop-2-en-1-one)
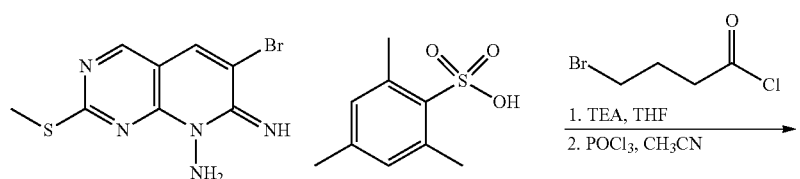

-continued
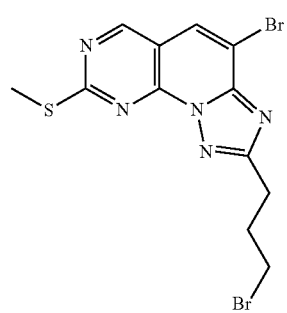
146-3
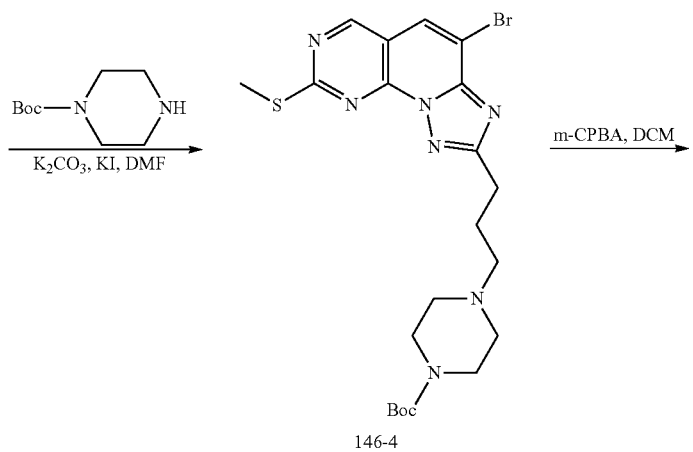
146-4
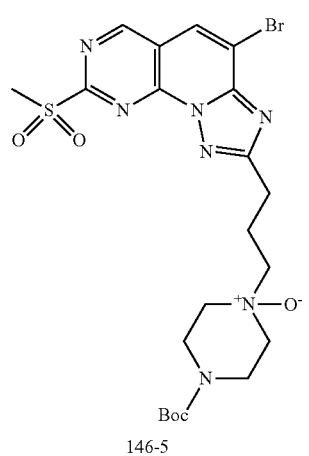
146-5
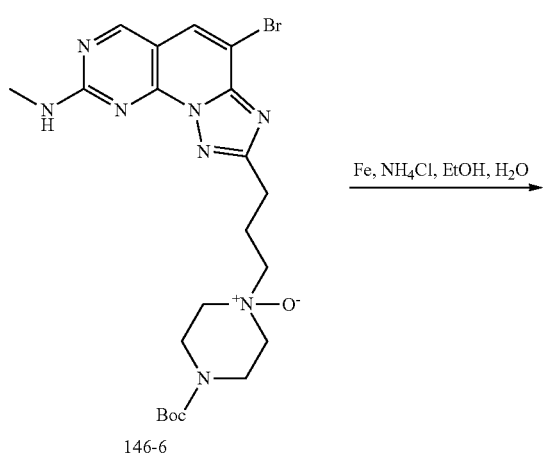
146-6
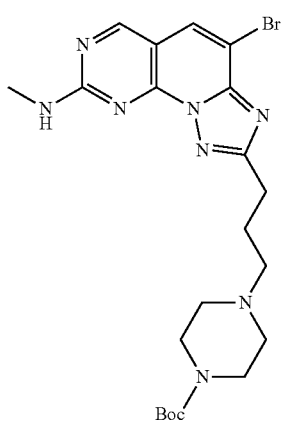
146-7
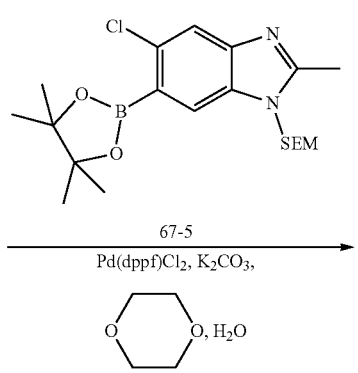
67-5

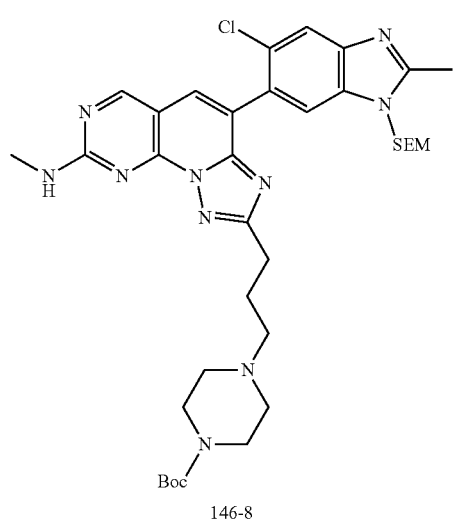

146-8

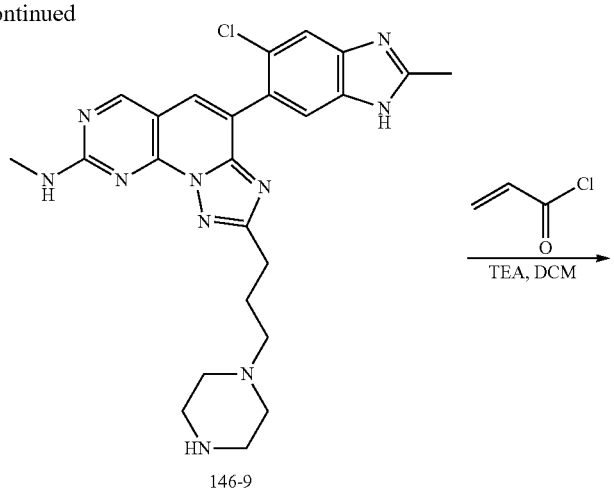

146-9

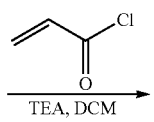

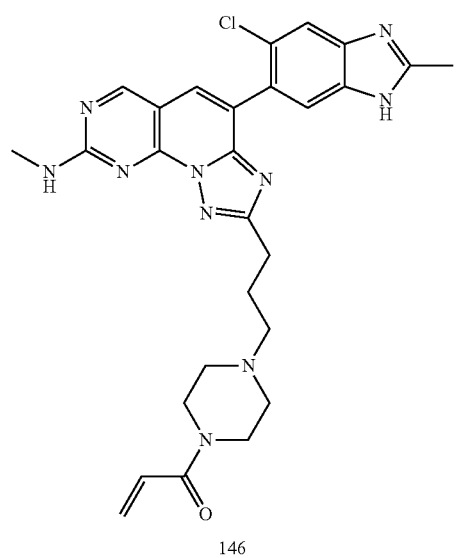

146

Step b1: Preparation of Compound 146-1

A mixture of 500 mg of compound M6 and 5 ml of ammonia methanol solution (7M) was reacted for 24 hrs at 80° C. The reaction was concentrated under reduced pressure. The residue was diluted with 50 ml of dichloromethane, washed three times with water, and dried over anhydrous sodium sulfate. The solution was filtrated and concentrated under reduced pressure. The crude product was purified by column chromatography (Hex/EA=1/1) to get 440 mg of compound 146-1, which is light yellow solid.

LC-MS [M+H$^+$] 270.1.

Step 2: Preparation of Compound 146-2

Using compound 146-1 as a raw material, compound 146-2 was synthesized by the same procedure as described in the step 1 of route B of Example 2.

LC-MS [M+H$^+$] 286.0.

Step 3: Preparation of Compound 146-3

Using compound 146-2 as a raw material, compound 146-3 was synthesized by the same procedure as described in the step 1 of route B of Example 115.

LC-MS [M+H$^+$] 417.9.

Step 4: Preparation of Compound 146-4

Using compound 146-3 as a raw material, compound 146-4 was synthesized by the same procedure as described in the step 2 of route B of Example 115.

LC-MS [M+H$^+$] 522.1.

Step 5: Preparation of Compound 146-5

Using compound 146-4 as a raw material, compound 146-5 was synthesized by the same procedure as described in the step 3 of route B of Example 115.

LC-MS [M+H$^+$] 570.1.

Step 6: Preparation of Compound 146-6

Using compound 146-5 as a raw material, compound 146-6 was synthesized by the same procedure as described in the step 4 of route B of Example 115.

LC-MS [M+H$^+$] 521.2.

Step 7: Preparation of Compound 146-7

Using compound 146-6 as a raw material, compound 146-7 was synthesized by the same procedure as described in the step 5 of route B of Example 115.
LC-MS [M+H$^+$] 505.2.

Step 8: Preparation of Compound 146-8

Using compound 146-7 and compound 67-5 as raw materials, compound 146-8 was synthesized by the same procedure as described in the step 5 of Example 67.
LC-MS [M+H$^+$] 721.3.

Step 9: Preparation of Compound 146-9

A mixture of 50 mg of compound 146-8, 5 ml of trifluoroacetate and 5 ml of dichloromethane was reacted for 2 hrs at room temperature. The solution was concentrated under reduced pressure to remove the solvent. The obtained residue was diluted with 50 ml of dichloromethane, washed with saturated aqueous sodium hydrogen carbonated and water, and dried over anhydrous sodium sulfate. The solution was filtered and spun dry to give 35 mg of compound 146-9, which was brown solid. It was used directly in the next reaction without purification.
LC-MS [M+H$^+$] 491.2.

Step 10: Preparation of Compound 146

A mixture of 35 mg of compound 146-9, 22 mg of TEA and 10 ml of dichloromethane was cooled down to 0° C., to which was added 13 mg of acryloyl chloride, and reacted for 30 mins at 0° C. The reaction was quenched with water and extracted with dichloromethane. The organic phase was combined, washed with saturated sodium bicarbonate and water, and dried over anhydrous sodium sulfate. The solution was filtered and concentrated under reduced pressure. The crude product was purified by column chromatography (DCM/MeOH=15/1) to get 18 mg of compound 146, which was white solid.
LC-MS [M+H$^+$] 545.2.

Example 147: Preparation of Compound 147 (2-(4-(3-(4-(2,6-dichloro-3,5-dimethoxyphenyl)-8-(methylamino)-[1,2,4]triazolo[1',5':1,6]pyrido[2,3-d] pyridimin-2-yl)propyl)piperazine-1-carbonyl)-4-methylpent-2-enenitrile)

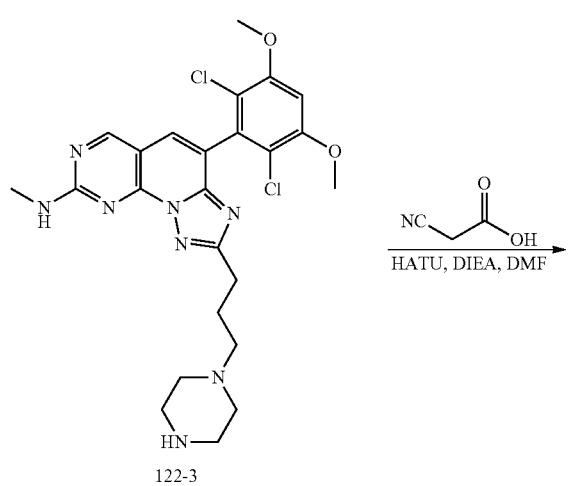

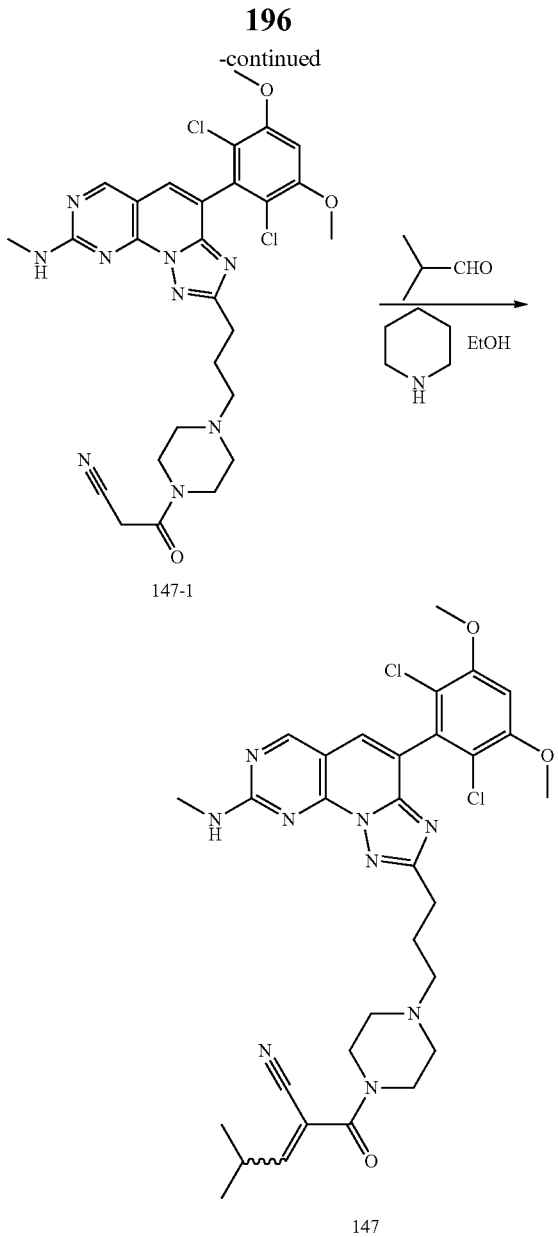

Step 1: Preparation of Compound 147-1

A mixture of 388 mg of compound 147-3, 10 ml of DMF, 472 mg of DIEA, 94 mg of cyanoacetic acid and 833 mg of HATU was reacted overnight with stirring at room temperature. The reaction was quenched with water and extracted with ethyl acetate. The organic phase was combined, washed with water and dried over anhydrous sodium sulfate. The solution was filtered and concentrated under reduced pressure.

The obtained crude product was purified by column chromatography (DCM/MeOH=15/1) to get 64 mg of compound 147-1, which is light yellow solid.
LC-MS [M+H$^+$] 598.2.

Step 2: Preparation of Compound 147-2

64 mg of compound 147-1, 20 mg of piperidine and 6 ml of absolute ethanol, to which was added 42 mg of isobutyraldehyde, the mixture was reacted overnight with stirring at room temperature. The solution was concentrated under reduced pressure, the residue was purified by column chromatography (DCM/MeOH=15/1) to give 14 mg of compound 147, which was light yellow solid.

LC-MS [M+H$^+$] 652.2.

Example 148: Preparation of Compound 148 (2-(4-(3-(4-(2,6-dichloro-3,5-dimethoxyphenyl)-8-(methylamino)-[1,2,4]triazolo[1',5':1,6]pyrido[2,3-d]pyrimidin-2-yl)propyl)piperazine-1-carbonyl)-4,4-dimethylpent-2-enenitrile)

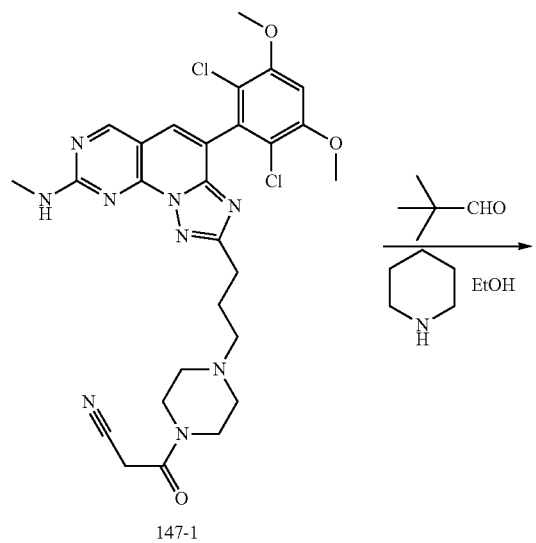

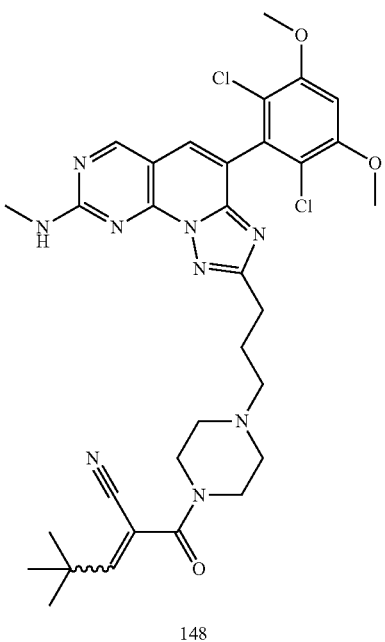

29 mg of compound 147-1, 8 mg of piperidine and 5 ml of absolute ethanol, to which was added 21 mg of pentaldehyde. The mixture was refluxed, reacted overnight with stirring, and concentrated under reduced pressure. The obtained residue was purified by column chromatography (DCM/MeOH=15/1) to get 10 mg of compound 148, which was light yellow solid.

LC-MS [M+H$^+$] 666.2.

Pharmacological Test

Example A: Kinase Assay

Method 1: The inhibitory activity of some compounds of the present disclosure against FGFR1, FGFR2, FGFR3, FGFR4, KDR was tested by mobility shift assay (concentration of ATP is Km value).

Test method:
Reagent: basic kinase buffer: 50 mM HEPES (pH 7.5); 0.0015% Brij-35
Stop buffer: 100 mM HEPES (pH 7.5); 0.015% Brij-35; 0.2% Coating Reagent #3; 50 mM EDTA
Preparing of compounds: dilute test compounds to specific concentration using 100% DMSO
Reaction process:
1) preparing of 2.5× enzyme solution
adding kinase to 1× basic kinase buffer
2) preparing of 2.5× peptide solution
adding FAM-labeled peptide and ATP to 1× basic kinase buffer
3) preparing of analysis board
transferring 10 μL of test compound to 384-well plate, adding 904, of 1× basic kinase buffer
4) adding 104, of 2.5× enzyme solution to each well of the assay plate and incubating for 10 min at room temperature
5) adding 104, of 2.5× enzyme solution to each well of the assay plate and incubating for specific time at 28° C. 6) stop the reaction by adding 254, of stop solution to each well
7) reading data with Caliper and calculating IC50 value.

The IC$_{50}$ value of the embodiment is shown in table 5, wherein, A means IC$_{50}$<1 nM; B means IC$_{50}$ is 1-10 nM; C means IC$_{50}$>10 nM; D means IC$_{50}$>100 nM.

TABLE 5

IC$_{50}$(nM) value of compounds

| Compound Number | FGFR1 | FGFR2 | FGFR3 | FGFR4 | KDR |
|---|---|---|---|---|---|
| Compound 2 | B | / | / | / | / |
| Compound 4 | 0.74 | / | / | 27 | 5.3 |
| Compound 10 | B | / | / | / | / |
| Compound 11 | A | / | / | / | / |
| Compound 12 | B | / | / | / | / |
| Compound 13 | A | / | / | / | / |
| Compound 14 | A | / | / | / | / |
| Compound 15 | A | / | / | / | / |
| Compound 16 | C | / | / | / | / |
| Compound 17 | C | / | / | / | / |
| Compound 18 | B | / | / | / | / |
| Compound 19 | B | / | / | / | / |
| Compound 20 | B | / | / | / | / |
| Compound 21 | A | / | / | / | / |
| Compound 23 | A | / | / | / | / |
| Compound 24 | 0.5 | 1.8 | 0.8 | 26.0 | 2.2 |
| Compound 25 | A | / | / | / | / |
| Compound 26 | A | / | / | / | / |
| Compound 28 | 1.0 | / | / | 104.0 | 7.1 |
| Compound 29 | 0.8 | 1.7 | 1.2 | 21.0 | 2.9 |
| Compound 31 | B | / | / | / | / |
| Compound 32 | A | / | / | / | / |
| Compound 39 | B | / | / | / | / |
| Compound 42 | 0.7 | 1.3 | 1.6 | 20 | 2.6 |
| Compound 43 | A | / | / | / | / |
| Compound 44 | B | / | / | / | / |

TABLE 5-continued

IC$_{50}$(nM) value of compounds

| Compound Number | FGFR1 | FGFR2 | FGFR3 | FGFR4 | KDR |
|---|---|---|---|---|---|
| Compound 45 | 0.8 | / | / | 21.0 | 2.8 |
| Compound 46 | 1.2 | / | / | 56.0 | 4.5 |
| Compound 48 | B | / | / | | |
| Compound 50 | 1.0 | / | / | 35.0 | 2.4 |
| Compound 51 | 0.4 | / | / | 42.0 | 2.4 |
| Compound 52 | A | / | / | / | / |
| Compound 53 | 0.6 | / | / | 14.0 | 1.5 |
| Compound 56 | 0.8 | / | / | 51.0 | 2.6 |
| Compound 58 | B | / | / | / | / |
| Compound 59 | 0.7 | / | / | 98.0 | 6.2 |
| Compound 61 | A | / | / | / | / |
| Compound 64 | 0.8 | 2.7 | 0.6 | 14.0 | 6.2 |
| Compound 65 | 0.7 | / | / | 6.7 | 4.3 |
| Compound 67 | 0.86 | / | / | 90 | 9 |
| Compound 71 | A | / | / | B | |
| Compound 78 | 1.9 | / | / | 600.0 | 29.0 |
| Compound 79 | 1.5 | / | / | 559.0 | 13.0 |
| Compound 81 | 2.0 | / | / | 191.0 | 15.0 |
| Compound 84 | A | / | / | / | / |
| Compound 86 | C | / | / | / | / |
| Compound 93 | B | / | / | / | / |
| Compound 96 | D | / | / | / | / |
| Compound 97 | B | / | / | / | / |
| Compound 99 | C | / | / | / | / |
| Compound 100 | A | / | / | / | / |
| Compound 101 | B | / | / | / | / |
| Compound 102 | 1.8 | / | / | 60.0 | 4.1 |
| Compound 102-2 | 1.0 | / | / | 26.0 | 2.5 |
| Compound 103 | B | / | / | / | / |
| Compound 104 | A | / | / | / | / |
| Compound 105 | B | / | / | / | / |
| Compound 106 | A | / | / | / | / |
| Compound 107 | A | / | / | / | / |
| Compound 108 | C | / | / | / | / |
| Compound 109 | B | / | / | / | / |
| Compound 110 | B | / | / | / | / |
| Compound 111 | 2.2 | / | / | 288.0 | 18.0 |
| Compound 112 | D | / | / | / | / |
| Compound 113 | C | / | / | / | / |
| Compound 114 | D | / | / | / | / |
| Compound 115 | 1.3 | / | / | 6.8 | 786.0 |
| Compound 120 | B | / | / | / | / |
| Compound 121 | B | / | / | / | / |
| Compound 122 | B | / | / | / | / |
| Compound 123 | 11.0 | / | / | 730.0 | |
| Compound 125 | B | / | / | / | / |
| Compound 128 | B | / | / | / | / |
| Compound 130 | B | / | / | / | / |
| Compound 133 | B | / | / | / | / |
| Compound 134 | B | / | / | / | / |
| Compound 135 | B | / | / | / | / |
| Compound 136 | B | / | / | / | / |
| Compound 142 | B | / | / | / | / |

Method 2: the inhibitory activity of compound 4 of the present disclosure against FGFR1, FGFR2, FGFR3, FGFR4 was tested by isotope-labeled $^{33}$P-ATP change method (concentration of ATP is Km value).

Test method:

Reagent: basic kinase buffer: 20 mM Hepes (pH 7.5), 10 mM MgCl$_2$, 1 mM EGTA, 0.02% Brij35, 0.02 mg/mL BSA, 0.1 mM Na$_3$VO$_4$, 2 mM DTT, 1% DMSO Adding the corresponding coenzyme factor to each kinase reaction Preparing of compounds: diluted the test compounds to specific concentration using 100% DMSO, and the dilution process is completed by epMotion 5070

Reaction process: 1) formulating the substrate in freshly configured reaction buffer 2) adding the required coenzyme factor to the above substrate solution 3) adding kinase to the substrate solution and mixing gently 4) adding the compounds dissolved in 100% DMSO to the above kinase reaction mixture, mixed well and incubating for 20 min at room temperature 5) adding $^{33}$P-ATP (specific activity 10 µCi/µL) to the reaction mixture to initiate the reaction and incubating for 2 h at room temperature 6) detection of kinase activity by filter-binding The experiment data is shown in table 6:

TABLE 6

| Kinase species | IC$_{50}$(nM) value of compounds | | |
|---|---|---|---|
| | BGJ398 | JNJ42756493 | Compound 4 |
| FGFR1 | 0.79 | 2.51 | 0.71 |
| FGFR2 | 0.33 | 0.56 | 0.16 |
| FGFR3 | 1.65 | 2.76 | 1.34 |
| FGFR4 | 34.62 | 0.69 | 5.06 |

Compound 4 could inhibit the kinase activity of FGFR1, 2 and 3 wild-type, the activity is roughly equivalent to the similar drugs BGJ398 and JNJ42756493, and compound 4 has a slightly lower inhibitory activity against FGFR4.

Example B: Cell Proliferation Assay

Method 1: the growth inhibitory effect of some compounds of the present disclosure on human tumor cell NCI-H1581 cultured in vitro was observed using CellTiter 96® AQ$_{ueous}$ One Solution cell proliferation assay kit method.

Test method: 180 µl of the cell suspension was added to a 96-well plate and placed in a CO$_2$ incubator overnight. Test compounds were dissolved in DMSO and subjected to a 3-fold gradient dilution for a total of 10 concentrations. 20 µl of the medium containing the test compound or DMSO was transferred to the corresponding cell wells respectively and was incubated for 144 hrs in 5% CO$_2$ at 37° C. 40 µl of CellTiter 96® AQueous One Solution cell proliferation assay kit was added to detection board and was incubated for 2 hrs in 5% CO$_2$ at 37° C. The IC$_{50}$ value was calculated by recording the light absorption value (OD490) at 490 nm using VICTOR TM X5 instrument.

Method 2: the growth inhibitory effect of some compounds of the present disclosure on human tumor cell NCI-H1581 and SNU-16 cultured in vitro was observed using CellTiter Glo assay method.

Test method: adding the appropriate volume of whole medium and the cells was suspended. 180 µl of the cell suspension was added to a 96-well plate and placed in a CO$_2$ incubator overnight. Test compounds were dissolved in DMSO and subjected to a 3-fold gradient dilution for a total of 10 concentrations. Test compounds or DMSO reference materials was transferred to the corresponding wells containing 100 µl of medium respectively and was incubated for 96 hrs in 5% CO$_2$ at 37° C. 100 µl of CellTiter-Glo reagent was added to the assay plate and incubated for 10 min at room temperature to stabilize the luminescence signal. The IC$_{50}$ value was calculated by recording the RLU (relative luminescence unit) using VICTOR TM X5 instrument.

The experiment data is shown in table 7 and table 8, wherein, A means IC$_{50}$<1 nM; B means IC$_{50}$=1-10 nM; C means IC$_{50}$>10-100 nM; D means IC$_{50}$>100 nM.

TABLE 7

| Compound Number | IC$_{50}$(nM) value of compounds on NCI-H1581 cells |
|---|---|
| JNJ42756493 | 0.5 |
| BGJ398 | 3.4 |
| Compound 2 | A |
| Compound 4 | 0.4 |
| Compound 10 | B |
| Compound 11 | A |
| Compound 12 | B |
| Compound 13 | B |
| Compound 14 | A |
| Compound 15 | A |
| Compound 16 | C |
| Compound 17 | C |
| Compound 18 | B |
| Compound 19 | B |
| Compound 20 | A |
| Compound 21 | B |
| Compound 22 | B |
| Compound 23 | A |
| Compound 24 | 1.2 |
| Compound 25 | B |
| Compound 26 | A |
| Compound 28 | 2.9 |
| Compound 29 | 2.0 |
| Compound 31 | C |
| Compound 32 | B |
| Compound 33 | B |
| Compound 34 | B |
| Compound 37 | B |
| Compound 38 | B |
| Compound 39 | C |
| Compound 40 | D |
| Compound 42 | 3.2 |
| Compound 43 | B |
| Compound 44 | B |
| Compound 45 | 0.9 |
| Compound 46 | 2.4 |
| Compound 48 | B |
| Compound 49 | A |
| Compound 50 | 0.2 |
| Compound 51 | 1.4 |
| Compound 52 | A |
| Compound 53 | 0.7 |
| Compound 55 | B |
| Compound 56 | 1.2 |
| Compound 58 | C |
| Compound 59 | 1.8 |
| Compound 60 | A |
| Compound 61 | A |
| Compound 64 | 0.5 |
| Compound 65 | 0.6 |
| Compound 67 | B |
| Compound 71 | A |
| Compound 78 | 5.3 |
| Compound 79 | 11.5 |
| Compound 81 | 9.3 |
| Compound 83 | D |
| Compound 84 | B |
| Compound 86 | B |
| Compound 96 | D |
| Compound 97 | C |
| Compound 99 | B |
| Compound 100 | C |
| Compound 101 | B |
| Compound 102 | 0.7 |
| Compound 102-2 | 0.9 |
| Compound 103 | B |
| Compound 104 | B |
| Compound 105 | B |
| Compound 106 | B |
| Compound 107 | B |
| Compound 108 | C |
| Compound 109 | B |
| Compound 110 | B |
| Compound 111 | 8.2 |
| Compound 112 | C |
| Compound 113 | C |
| Compound 114 | D |
| Compound 115 | 0.5 |
| Compound 116 | C |
| Compound 117 | C |
| Compound 120 | B |
| Compound 122 | A |
| Compound 123 | 5.8 |
| Compound 124 | B |
| Compound 125 | B |
| Compound 128 | B |
| Compound 129 | B |
| Compound 131 | C |
| Compound 133 | A |
| Compound 134 | A |
| Compound 135 | B |
| Compound 136 | B |
| Compound 137 | B |
| Compound 142 | B |
| Compound 147 | C |
| Compound 148 | D |

TABLE 8

| Compound Number | IC$_{50}$(nM) value of compounds on SNU-16 cells |
|---|---|
| JNJ42756493 | A |
| Compound 24 | A |
| Compound 29 | A |
| Compound 42 | A |
| Compound 43 | A |
| Compound 50 | A |
| Compound 64 | A |
| Compound 84 | B |
| Compound 110 | A |
| Compound 120 | A |
| Compound 128 | A |
| Compound 130 | A |
| Compound 138 | B |
| Compound 142 | A |
| Compound 147 | C |

The growth inhibitory effect of compound 4 on human tumor cell NCI-H1581 (human non-small cell lung cancer cells), RT-112 (human bladder cancer cell), OPM-2 (human myeloma cell), NCI-H716 (human colorectal cancer cell), MFE-296 (human endometrial cancer cells), JHH-7 (human hepatoma cell), DMS 114 (human lung cancer cell), SNU-16 (human gastric cancer cell), MDA-MB-453 (human breast cancer cell) and RT4 (human bladder cancer cell) cultured in vitro was observed using CellTiter Glo assay method.

Test method: 100 μl of the cell suspension was added to a 96-well plate and placed in a CO$_2$ incubator overnight. Test compounds were dissolved in DMSO and subjected to a 3-fold gradient dilution for a total of 10 concentrations. The test compound or DMSO was transferred to the corresponding cell wells respectively and was incubated for 96 hrs in 5% CO$_2$ at 37° C. 100 μl of CellTiter-Glo reagent was added to the assay plate and incubated for 10 min at room temperature to stabilize the luminescence signal. The IC$_{50}$ value was calculated by recording the RLU (relative luminescence unit) using Enspire. The experiment data is shown in table 9.

TABLE 9

| Cell types | IC$_{50}$ (nM) | | |
|---|---|---|---|
| | JNJ42756493 | BGJ398 | Compound 4 |
| RT-112 | 0.8 | 4.4 | 1.0 |
| OPM-2 | 2.5 | 18.0 | 4.0 |
| NCI-H716 | 0.6 | 4.6 | 0.5 |
| MFE-296 | 16.7 | 51.4 | 2.7 |
| JHH-7 | 3.8 | 54.1 | 6.6 |
| DMS 114 | 14.8 | 33.6 | 7.4 |
| SNU-16 | 1.2 | 9.5 | 1.1 |
| MDA-MB-453 | 11.0 | 543.6 | 61.3 |
| NCI-H1581 | 1.5 | 18.2 | 1.2 |
| RT4 | 2.4 | 16.9 | 1.9 |

Compound 4 inhibited the growth of human tumor cells in vitro in a dose-dependent manner and was extremely sensitive to cell lines (NCI-H1581, RT-112, OPM-2, NCI-H716, MFE-296, JHH-7, DMS 114 and SNU-16) with abnormal changes in FGFR signaling pathway, with IC$_{50}$ value of 0.5-2.7 nM.

Example C: Xenograft Tumor Models

Reagent: DMSO, polyethylene glycol-15-hydroxystearate (Solutol), saline.

Animals: for inoculation of NCI-H1581 cell line: BALB/C-nude strains nude mice: SPF animals, weighing 18~22 g, female, provided by Vitrallihua Experimental Animal Technology Co., Ltd. Fed with SPF feed, free to drink distilled water.

For inoculation of SNU-16 cell line: BALB/C-nude strains nude mice: SPF animals, weighing 18~22 g, female, provided by Shanghai Xipuer-Beikai Experimental Animal Technology Co., Ltd. Fed with SPF feed, free to drink distilled water.

Human cancer cell line: NCI-H1581 human non-small cell lung cancer cell line, provided by Shanghai Ruizhi Chemical Research Co., Ltd.; SNU-16 human gastric cancer cell line, provided by ATCC.

Figure 2:
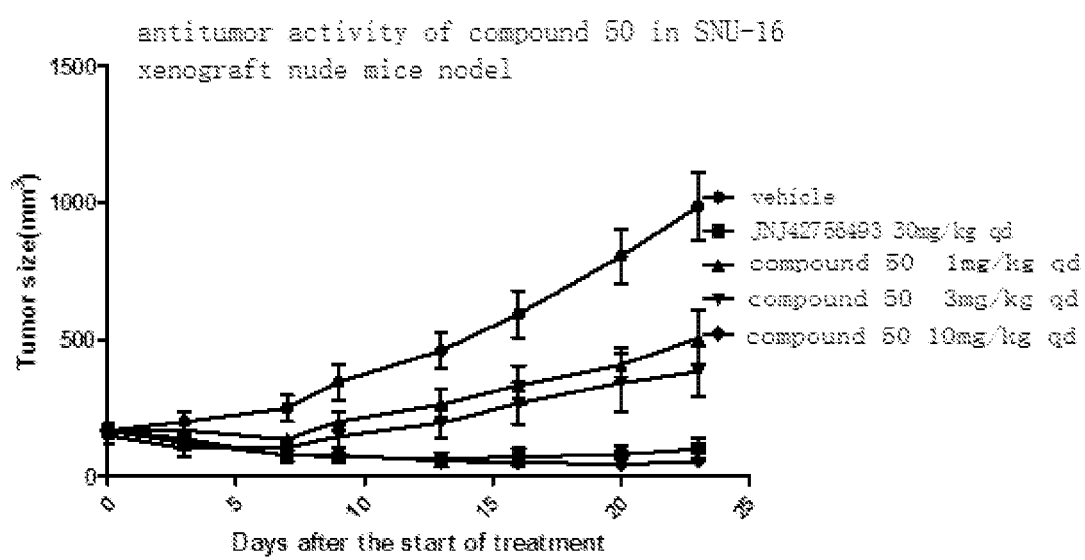
FIG. 2: Inhibition curve of compound 50 in human SNU-16 cell line xenograft nude mice; abscissa represents the number of days after inoculation of NCI-H1581 cells, and ordinate represents tumor volume.
Figure 3:
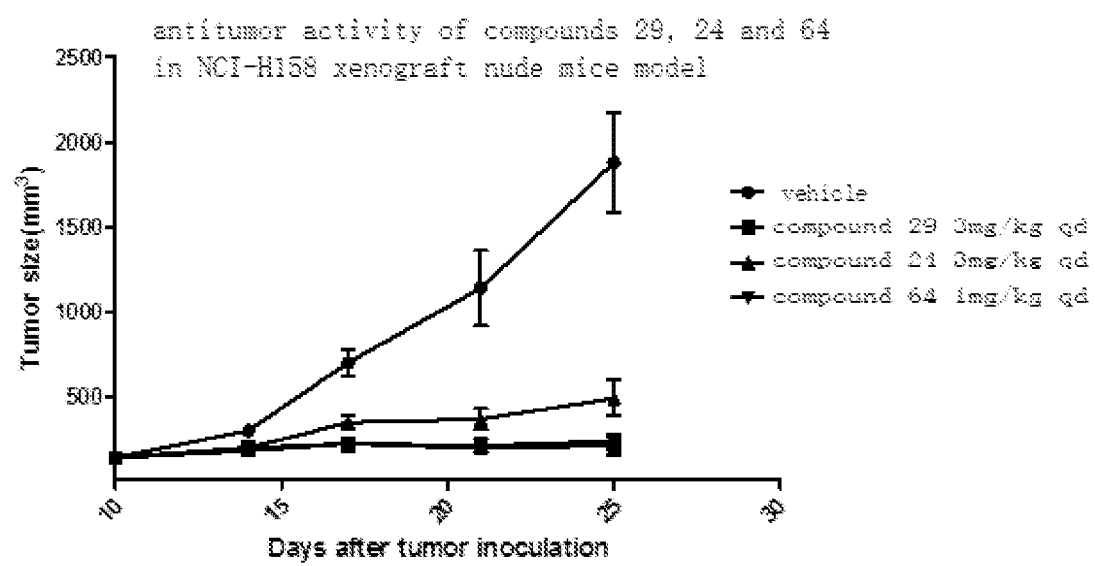
FIG. 3: Inhibition curve of compound 24, compound 29 and compound 64 in human NCI-H1581 cell line xenograft nude mice; abscissa represents the number of days after inoculation of NCI-H1581 cells, and ordinate represents tumor volume.

Method of tumor transplantation assay: The NCI-H1581 cell line was inoculated subcutaneously into the right axilla of nude mice in an ultra-clean bench under sterile operation with an amount of 1×10$^7$/100 µL/cell, the SNU-16 cell line was inoculated subcutaneously into the right axilla of nude mice with an amount of 0.5×10$^7$/100 µL/cell. After 10 days, the tumors were grown and touched (about 100-200 mm$^3$). The animals were randomly divided into groups of 6 animals and each was weighted. The positive drug group was intragastrically administered once a day. The experimental group was intragastrically administered once or twice daily, and the administration time period was the same as that of the positive drug control group. Nude mice were housed in a room temperature of 20-22° C., relative humidity of 40-60%, and the shielding system was supplemented by the environment of a clean laminar flow cabinet. The subcutaneous tumor volume was measured with a caliper every 3-4 days after the experiment, and the tumor growth curve was drawn to calculate the tumor inhibition rate. The test results were statistically analyzed using GraphPad Prism 5 software, and the experimental data are shown in FIGS. 1 to 3.

The invention claimed is:

1. A compound of Formula I or a pharmaceutically acceptable salt thereof:

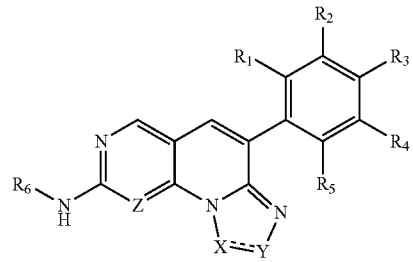

Formula (I)

wherein,
  $=\!=$ represents a double bond,
  X and Y are each independently selected from N and CR$_{10}$, and at least one of X and Y is N; or
  X is C$=$O, Y is NH, and $=\!=$ represents a single bond;
  Z is N;
  R$_1$, R$_2$, R$_3$, R$_4$ and R$_5$ are each independently selected from H, halogen, C$_{1-8}$ alkoxy, substituted C$_{1-8}$ alkoxy, C$_{1-8}$ alkyl, substituted C$_{1-8}$ alkyl, C$_{2-8}$ alkenyl, substituted C$_{2-8}$ alkenyl, C$_{2-8}$ alkynyl, substituted C$_{2-8}$ alkynyl, C$_{3-8}$ cycloalkyl, substituted C$_{3-8}$ cycloalkyl, C$_{6-10}$ aryl, substituted C$_{6-10}$ aryl, C$_{5-10}$ heteroaryl, substituted C$_{5-10}$ heteroaryl, C$_{3-10}$ heterocyclyl and substituted C$_{3-10}$ heterocyclyl; or
  R$_3$ and R$_4$ together with the carbon atom to which they are attached may form a 5-8 membered substituted or unsubstituted heterocyclic or heteroaryl ring, wherein the heterocyclic or heteroaryl ring comprises 1, 2 or 3 hetero atoms independently selected from N, O or S;
  R$_6$ is C$_{1-8}$ alkyl, substituted C$_{1-8}$ alkyl, C$_{2-8}$ alkenyl, substituted C$_{2-8}$ alkenyl, C$_{2-8}$ alkynyl, substituted C$_{2-8}$ alkynyl, C$_{6-10}$ aryl, substituted C$_{6-10}$ aryl, C$_{3-8}$ cycloalkyl, substituted C$_{3-8}$ cycloalkyl, C$_{3-10}$ heterocyclyl, substituted C$_{3-10}$ heterocyclyl, C$_{5-10}$ heteroaryl or substituted C$_{5-10}$ heteroaryl;
  R$_6$ may be optionally substituted by R$_7$;
  R$_7$ is hydroxyl, halogen, C$_{1-8}$ alkyl, substituted C$_{1-8}$ alkyl, C$_{2-8}$ alkenyl, substituted C$_{2-8}$ alkenyl, C$_{2-8}$ alkynyl, substituted C$_{2-8}$ alkynyl, C$_{1-8}$ alkoxy, substituted C$_{1-8}$ alkoxy, C$_{6-10}$ aryl, substituted C$_{6-10}$ aryl, C$_{3-8}$ cycloalkyl, substituted C$_{3-8}$ cycloalkyl, C$_{3-10}$ heterocyclyl, substituted C$_{3-10}$ heterocyclyl, C$_{5-10}$ heteroaryl, substituted C$_{5-10}$ heteroaryl, heterocyclylalkyl, substituted heterocyclylalkyl, heterocyclic carbonyl, substituted heterocyclic carbonyl, —NR$_{11}$R$_{12}$, —NR$_{11}$—C$_{1-8}$alkylene-NR$_{11}$R$_{12}$ or R$_7$ is substituted or unsubstituted C$_{5-8}$ heterocyclic ring which fused to R$_6$;
  R$_{10}$ is H, halogen, amino, C$_{1-6}$ alkyl, substituted C$_{1-6}$ alkyl, C$_{2-8}$ alkenyl, substituted C$_{2-8}$ alkenyl, C$_{2-8}$ alkynyl, substituted C$_{2-8}$ alkynyl, C$_{3-8}$ cycloalkyl, substituted C$_{3-8}$ cycloalkyl, C$_{6-10}$ aryl, substituted C$_{6-10}$ aryl, C$_{5-10}$ heteroaryl, substituted C$_{5-10}$ heteroaryl, C$_{3-10}$ heterocyclyl or substituted C$_{3-10}$ heterocyclyl;
  R$_{10}$ may be optionally substituted by R$_8$;
  R$_8$ is hydroxyl, halogen, C$_{1-8}$ alkyl, substituted C$_{1-8}$ alkyl, C$_{2-8}$ alkenyl, substituted C$_{2-8}$ alkenyl, C$_{2-8}$ alkynyl, substituted C$_{2-8}$ alkynyl, C$_{3-10}$ heterocycloalkoxy, substituted C$_{3-10}$ heterocycloalkoxy, C$_{6-10}$ aryl, substituted C$_{6-10}$ aryl, C$_{3-8}$ cycloalkyl, substituted C$_{3-8}$ cycloalkyl, C$_{3-10}$ heterocyclyl, substituted $C_{3-10}$ heterocyclyl, —S(O$_2$)C$_{3-10}$ heterocyclyl, substituted —S(O$_2$)C$_{3-10}$ heterocyclyl, C$_{5-10}$ heteroaryl, substituted C$_{5-10}$ heteroaryl or —NR$_{11}$R$_{12}$;

$R_{11}$ and $R_{12}$ are each independently H, C$_{1-8}$ alkyl, substituted C$_{1-8}$ alkyl, C$_{2-8}$ alkenyl, substituted C$_{2-8}$ alkenyl, C$_{2-8}$ alkynyl, substituted C$_{2-8}$ alkynyl, C$_{3-8}$ cycloalkyl, substituted C$_{3-8}$ cycloalkyl, C$_{6-10}$ aryl, substituted C$_{6-10}$ aryl, C$_{5-10}$ heteroaryl, substituted C$_{5-10}$ heteroaryl, C$_{3-10}$ heterocyclyl or substituted C$_{3-10}$ heterocyclyl.

2. The compound of claim 1, wherein X is N or CR$_{10}$, R$_{10}$ is H, amino, C$_{1-6}$ alkyl, substituted C$_{1-6}$ alkyl, C$_{3-6}$ cycloalkyl or substituted C$_{3-6}$ cycloalkyl.

3. The compound of claim 1, wherein X is CR$_{10}$, R$_{10}$ is H.

4. The compound of claim 1, wherein X is CR$_{10}$, R$_{10}$ is C$_{1-6}$ alkyl, C$_{1-6}$ alkyl substituted with C$_{5-10}$ heterocyclyl, C$_{1-6}$ alkyl substituted with C$_{6-10}$ aryl, C$_{1-6}$ alkyl substituted with C$_{3-6}$ cycloalkyl, C$_{1-6}$ alkyl or C$_{3-6}$ cycloalkyl substituted with amino, wherein the C$_{5-10}$ heterocyclyl, C$_{6-10}$ aryl, C$_{3-6}$ cycloalkyl or amino can be optionally substituted.

5. The compound of claim 1, wherein X is CR$_{10}$, R$_{10}$ is C$_{1-6}$ alkyl or C$_{3-6}$ cycloalkyl, R$_{10}$ can be substituted with R$_8$, R$_8$ is (R$_{11}$) ethylene-C(O)—N-phenyl, ethyl-C(O)—N-phenyl, morpholinyl, —NR$_{11}$R$_{12}$, cyclopropane, ethylene-C(O)-piperazinyl, ethylene-C(O)-azetidinoxy, ethylene-C(O)-piperidinyloxy, ethylene-C(O)-aza C$_{6-10}$ spirocyclic, ethylene-C(O)-aza C$_{6-10}$ bicyclic, ethylene-C(O)—N-piperidinyl, ethylene-C(O)-piperidinyl, ethylene-C(O)-C$_{1-8}$ alkyl piperazinyl, —N(R$_{11}$) ethylene-C(O)-piperidinyl, —N(R$_{11}$) ethylene-C(O)-aza C$_{6-10}$ bicyclic, ethylene-C(O)-piperidinyl-S(O$_2$)- or isopentenyl-C(O)-piperazinyl substituted with cyano.

6. The compound of claim 1, wherein Y is N or CR$_{10}$, R$_{10}$ is H, amino, C$_{1-6}$ alkyl, substituted C$_{1-6}$ alkyl, C$_{3-6}$ cycloalkyl or substituted C$_{3-6}$ cycloalkyl.

7. The compound of claim 1, wherein Y is N.

8. The compound of claim 1, wherein Y is CR$_{10}$, R$_{10}$ is C$_{1-6}$ alkyl, C$_{1-6}$ alkyl substituted with C$_{5-10}$ heterocyclyl, C$_{1-6}$ alkyl substituted with C$_{6-10}$ aryl, C$_{1-6}$ alkyl substituted with C$_{3-6}$ cycloalkyl, C$_{1-6}$ alkyl substituted with amino or C$_{3-6}$ cycloalkyl, wherein C$_{5-10}$ heterocyclyl, C$_{6-10}$ aryl, C$_{3-6}$ cycloalkyl or amino can be optionally substituted.

9. The compound of claim 1, wherein Y is CR$_{10}$, R$_{10}$ is C$_{1-6}$ alkyl or C$_{3-6}$ cycloalkyl, R$_{10}$ can be substituted with R$_8$, R$_8$ is (R$_{11}$)ethylene-C(O)-N-phenyl, ethyl-C(O)-N-phenyl, morpholinyl, cyclopropane, ethylene-C(O)-piperazinyl, ethylene-C(O)-azetidinoxy, ethylene-C(O)-piperidinyloxy, ethylene-C(O)-aza C$_{6-10}$ spirocyclic, ethylene-C(O)-aza C$_{6-10}$ bicyclyl, ethylene-C(O)-N-piperidinyl, ethylene-C(O)-piperidinyl, ethylene-C(O)-C$_{1-8}$ alkyl piperazinyl, —N(R$_{11}$) ethylene-C(O)-piperidinyl, —N(R$_{11}$)ethylene-C(O)-azaC$_{6-10}$ bicyclyl, ethylene-C(O)-piperidinyl-S(O$_2$)- or isopentenyl-C(O)-piperazinyl substituted with cyano.

10. The compound of claim 1, wherein R$_1$, R$_3$ and R$_5$ are each independently H, F or Cl.

11. The compound of claim 1, wherein R$_1$ and R$_5$ are selected from the group below:
(i) both R$_1$ and R$_5$ are H;
(ii) both R$_1$ and R$_5$ are Cl;
(iii) R$_1$ is H, R$_5$ is Cl;
(iv) R$_1$ is Cl, R$_5$ is H;
(v) both R$_1$ and R$_5$ are F;
(vi) R$_1$ is H, R$_5$ is F; or
(vii) R$_1$ is F, R$_5$ is H.

12. The compound of claim 1, wherein R$_1$ is Cl, both R$_3$ and R$_5$ are H.

13. The compound of claim 1, wherein R$_3$ is H.

14. The compound of claim 1, wherein R$_2$ and R$_4$ are each independently selected from H and C$_{1-3}$ alkoxy.

15. The compound of claim 1, wherein both R$_2$ and R$_4$ are CH$_3$O—.

16. The compound of claim 1, wherein R$_3$ and R$_4$ together with the carbon atom to which they are attached form a substituted 5-membered heterocyclic ring comprising 1-2 hetero atoms independently selected from N, O or S, and the 5-membered heterocyclic ring is substituted with C$_{1-3}$ alkyl.

17. The compound of claim 16, wherein R$_3$ and R$_4$ together with the carbon atom to which they are attached form a substituted 5-membered heterocyclic ring comprising one or two nitrogen atoms; or one nitrogen atom and one sulfur atom; or one nitrogen and one oxygen atom, and the 5-membered heterocyclic is substituted with methyl.

18. The compound of claim 16, wherein R$_3$ and R$_4$ together with the carbon atom to which they are attached form a heterocyclic ring which is

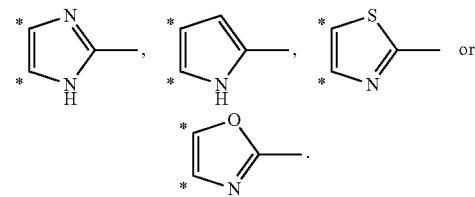

19. The compound of claim 1, wherein R$_6$ is C$_{1-6}$ alkyl, substituted C$_{1-6}$ alkyl, C$_{6-10}$ aryl, substituted C$_{6-10}$ aryl, C$_{3-6}$ cycloalkyl, substituted C$_{3-6}$ cycloalkyl, C$_{5-10}$ heterocyclyl, substituted C$_{5-10}$ heterocyclyl, C$_{6-10}$ heteroaryl or substituted C$_{6-10}$ heteroaryl.

20. The compound of claim 1, wherein R$_6$ is C$_{1-4}$ alkyl, cyclopentyl, phenyl, phenyl substituted with F, phenyl substituted with methoxy, phenyl substituted with Cl, phenyl substituted with methyl, pyridyl, tetrahydropyranyl, R$_6$ substituted with R$_7$, wherein R$_7$ is hydroxyl, F, Cl, piperazinyl substituted with ethyl, morpholinyl, piperazinyl substituted with isopropyl, piperazinyl substituted with oxetane, piperazinyl substituted with methyl, piperazinyl-CH$_2$- substituted with ethyl, piperazinyl substituted with ethyl and oxyl, piperazinyl substituted with trimethyl, trimethylethylenediamine, piperazinyl substituted with methyl piperidinyl, aza-C$_{6-10}$ bicyclyl substituted with methyl, aza-C$_{6-10}$ bicyclyl, —N(methyl)-C$_{1-6}$ methylene-morpholinyl, C$_{4-10}$ aza cycloalkyl substituted with C$_{2-6}$ alkoxy, piperidinyl substituted with morpholinyl, piperazinyl substituted with hydroxyethyl, C$_{2-6}$ alkoxy substituted with morpholinyl, piperidinyl substituted with ethyl, piperidinyl substituted with methyl, dimethylaminopiperidinyl, C$_{6-10}$ aza bicyclyl substituted with oxyl, nitroxoxa C$_{6-10}$ bicyclyl, morpholinyl-CH$_2$—, methyl piperazinyl-CH$_2$—, piperidinyl substituted with C$_{3-10}$ cycloalkyl, methylamino-piperidinyl, piperazinyl substituted with dimethyl, piperidinyl, piperazinyl-CH$_2$—, piperazinyl-C(O)- substituted with dimethyl, piperazinyl substituted with hydroxycyclobutane, trifluoromethyl-CH$_2$-piperazinyl, piperazinyl substituted with C$_{3-10}$ cycloalkyl, methyl-C(O)-piperazinyl, (dimethyl)-N—C(O)-piperazinyl, (dimethyl)-N—C(O)-aza C$_{6-10}$ spirocyclic, (dimethyl)-N—C(O)-tetrahydropyrrole-NH—, R$_7$ is a nitrogen-containing 6-membered heterocyclic ring which fused to R$_6$, wherein the nitrogen-containing 6-membered heterocyclic ring is unsubstituted or substituted with ethyl.

21. The compound of claim 1, wherein $R_6$ is methyl,
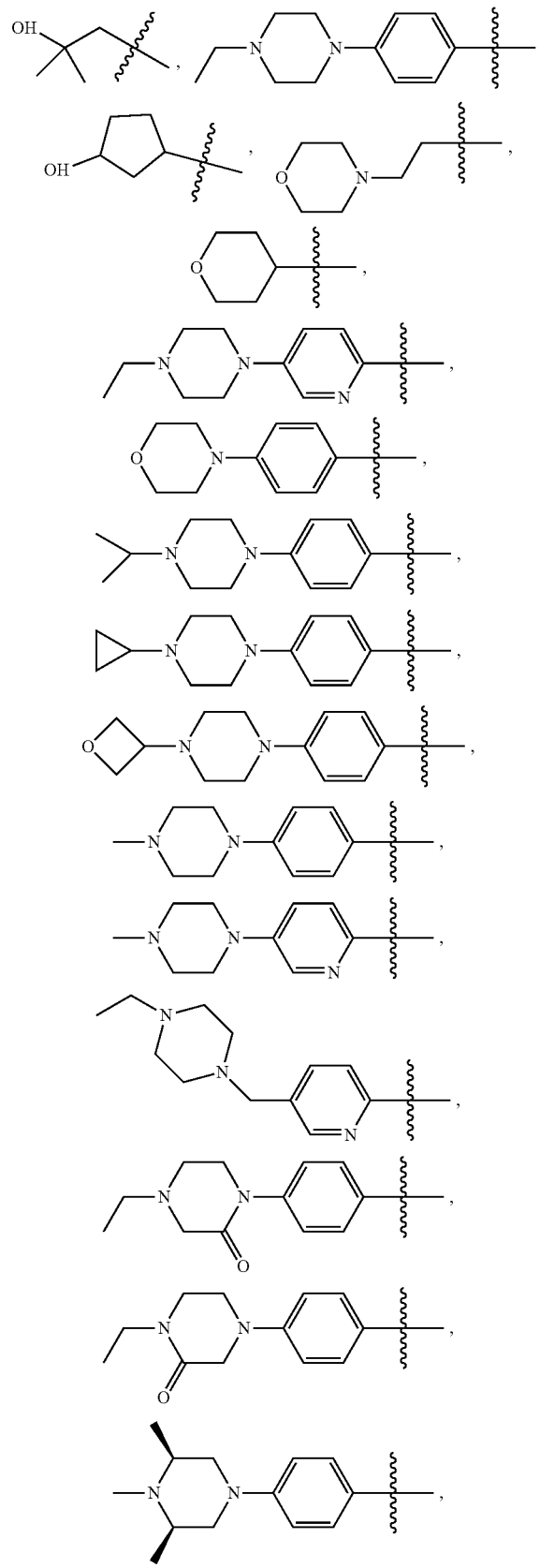
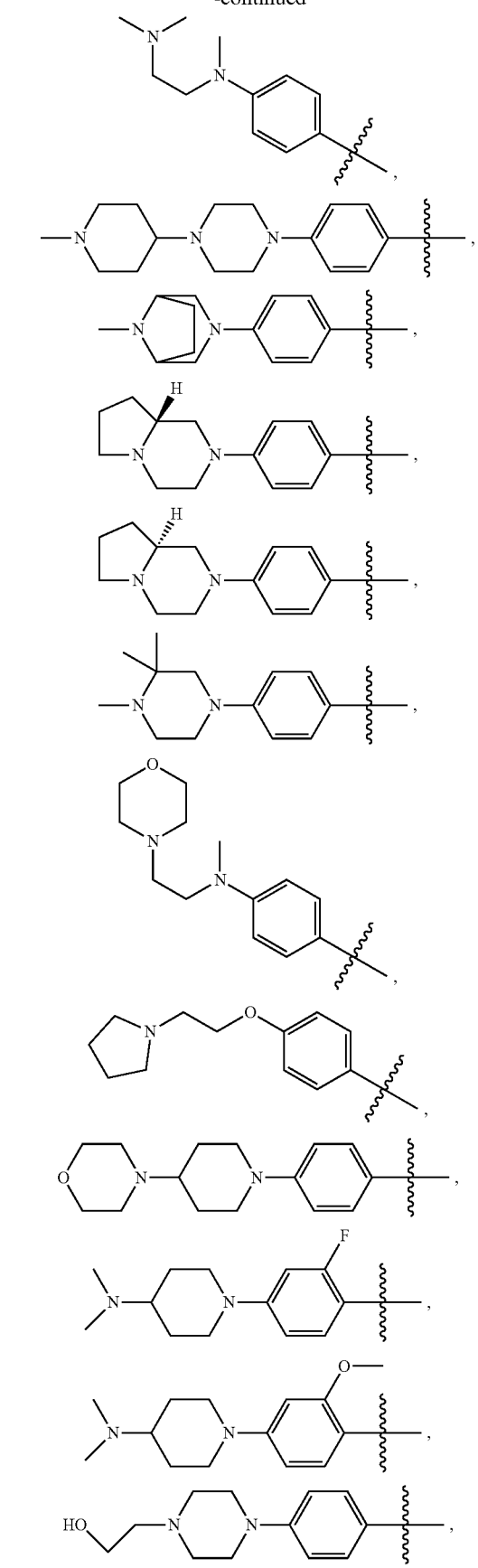

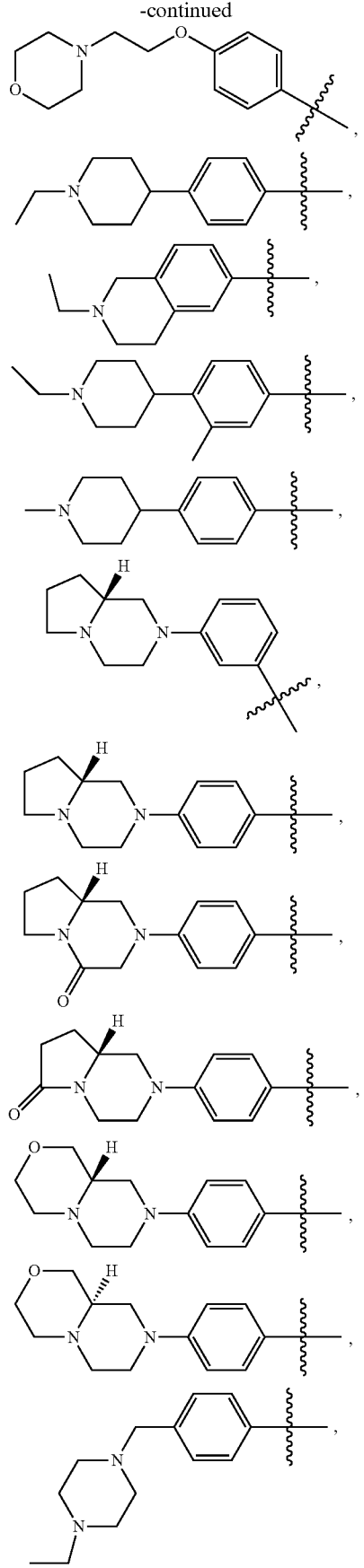
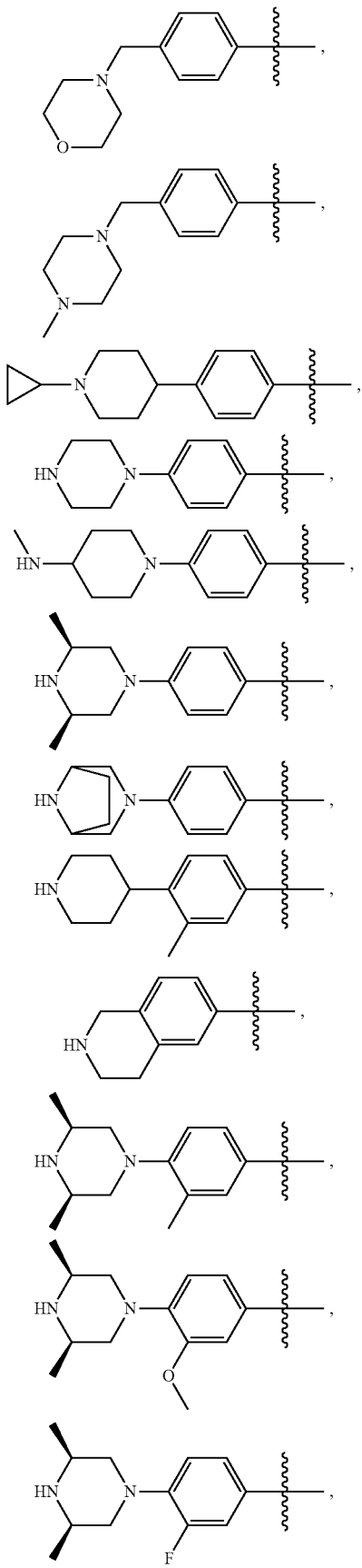

211
-continued
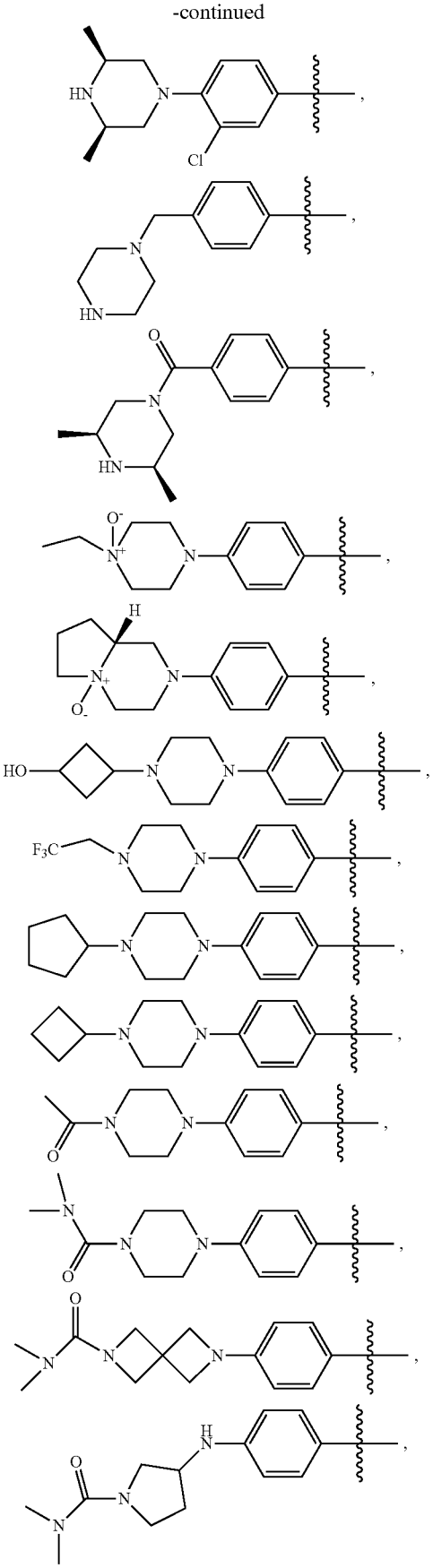
212
-continued
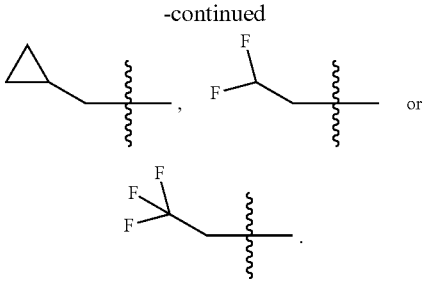
22. The compound of claim 1, wherein $R_{11}$ and $R_{12}$ are each independently selected from H, $C_{1-6}$ alkyl, substituted $C_{1-6}$ alkyl, $C_{3-6}$ cycloalkyl and substituted $C_{3-6}$ cycloalkyl.
23. The compound of claim 1, wherein $R_{11}$ and $R_{12}$ are each independently selected from H, methyl and ethyl.
24. The compound of claim 1, wherein $R_{10}$ is H, —$CH_3$, amino,
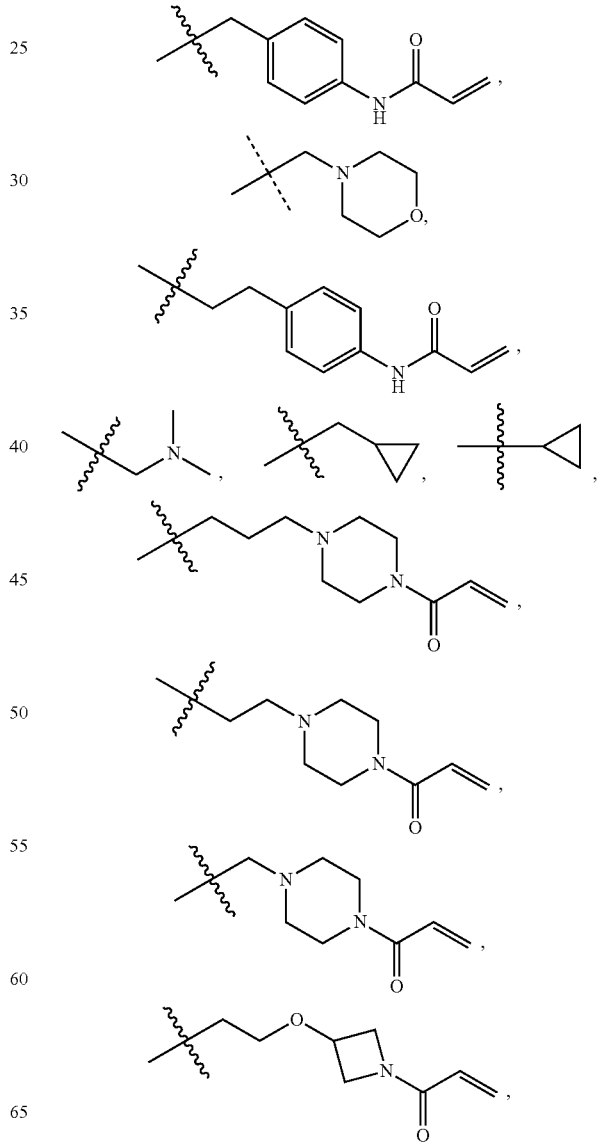

213
-continued
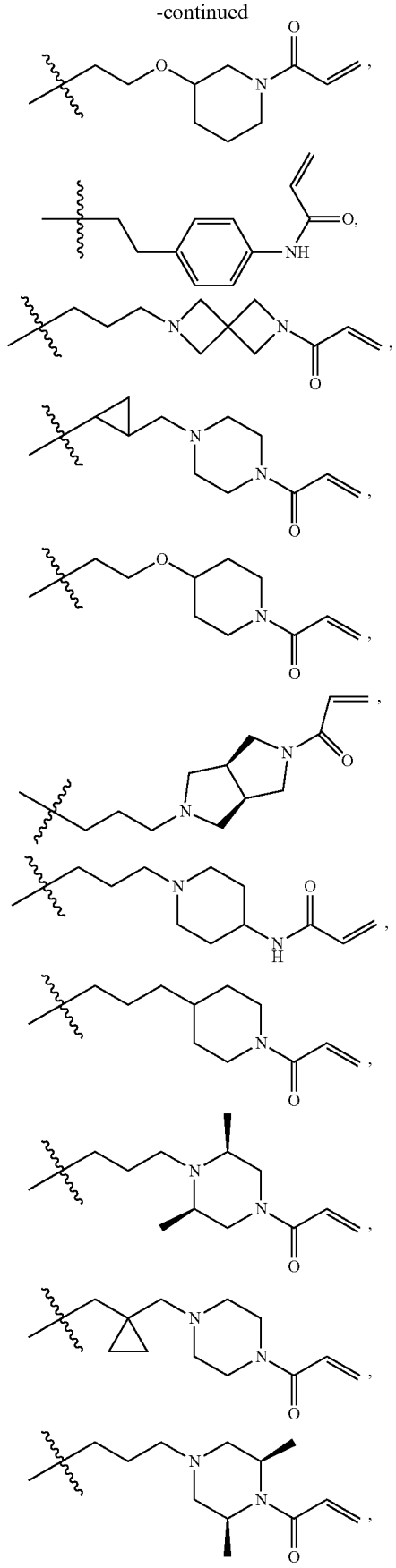
214
-continued
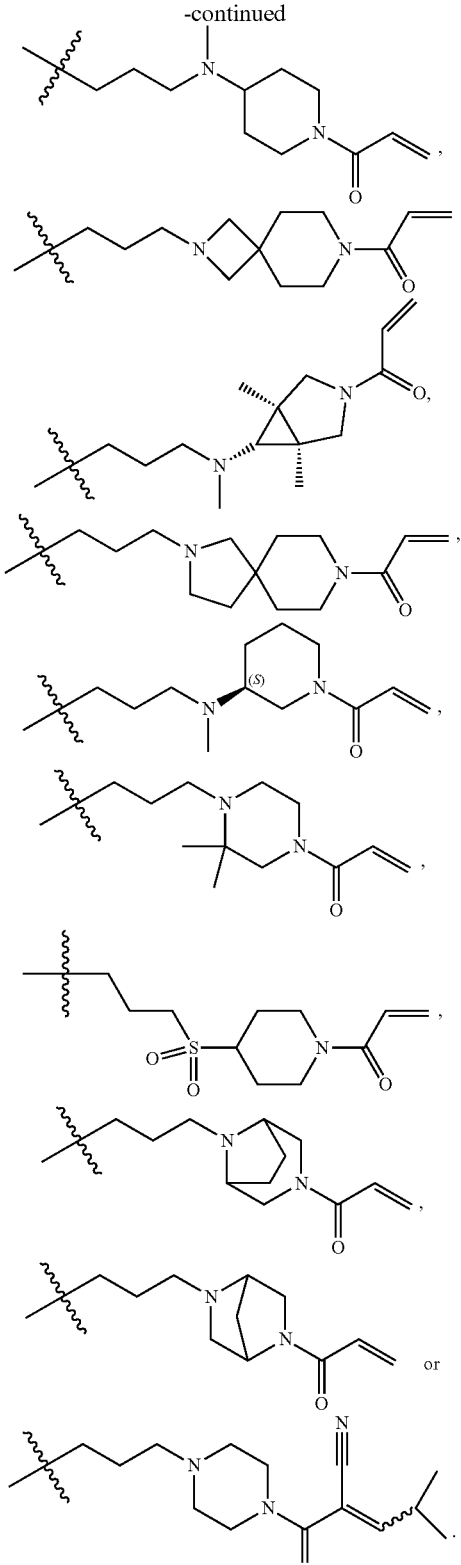
25. The compound of claim 1, wherein $R_{10}$ is H or —$CH_3$.
26. The compound of claim 1, wherein the compound is:
(1) 1-((6-(2-chloro-3,5-dimethoxyphenyl)-[1,2,4]triazolo[4',3':1,6]pyrido[2,3-d] pyrimidin-2-yl)amino)-2-methylpropan-2-ol;

(2) 4-(2-chloro-3,5-dimethoxyphenyl)-N-(4-(4-ethylpiperazin-1-yl)phenyl)-[1,2,4]triazolo[1',5':1,6]pyrido[2,3-d]pyrimidin-8-amine;

(3) 3-((6-(2-chloro-3,5-dimethoxyphenyl)-[1,2,4]triazolo[4',3':1,6]pyrido[2,3-d] pyrimidin-2-yl)amino)cyclopentan-1-ol;

(4) 6-(2-chloro-3,5-dimethoxyphenyl)-N-(4-(4-ethylpiperazin-1-yl)phenyl)-[1,2,4]triazolo[4',3':1,6]pyrido[2,3-d]pyrimidin-2-amine;

(5) 6-(2-chloro-3,5-dimethoxyphenyl)-N-(2-morpholinoethyl)-[1,2,4]triazolo[4',3':1,6]pyrido[2,3-d]pyrimidin-2-amine;

(6) 1-((4-(2-chloro-3,5-dimethoxyphenyl)-[1,2,4]triazolo[1',5':1,6]pyrido[2,3-d] pyrimidin-8-yl)amino)-2-methylpropan-2-ol;

(7) 6-(2-chloro-3,5-dimethoxyphenyl)-N-(tetrahydro-2H-pyran-4-yl)-[1,2,4]triazolo[4',3':1,6]pyrido[2,3-d]pyrimidin-2-amine;

(8) 6-(2-chloro-3,5-dimethoxyphenyl)-N-(5-(4-ethylpiperazin-1-yl)pyridin-2-yl)-[1,2,4]triazolo[4',3':1,6]pyrido[2,3-d]pyrimidin-2-amine;

(9) 6-(3,5-dimethoxyphenyl)-N-(4-(4-ethylpiperazin-1-yl)phenyl)-[1,2,4]triazolo[4',3':1,6]pyrido[2,3-d]pyrimidin-2-amine;

(10) 6-(2-chloro-3,5-dimethoxyphenyl)-N-(4-morpholinophenyl)-[1,2,4]triazolo[4',3':1,6]pyrido[2,3-d]pyrimidin-2-amine;

(11) 6-(2-chloro-3,5-dimethoxyphenyl)-N-(4-(4-isopropylpiperazin-1-yl)phenyl)-[1,2,4]triazolo[4',3':1,6]pyrido[2,3-d]pyrimidin-2-amine;

(12) 6-(2-chloro-3,5-dimethoxyphenyl)-N-(4-(4-cyclopropylpiperazin-1-yl) phenyl)-[1,2,4]triazolo[4',3':1,6]pyrido[2,3-d]pyrimidin-2-amine;

(13) 6-(2-chloro-3,5-dimethoxyphenyl)-N-(4-(4-(oxetan-3-yl)piperazin-1-yl) phenyl)-[1,2,4]triazolo[4',3':1,6]pyrido[2,3-d]pyrimidin-2-amine;

(14) 6-(2-chloro-3,5-dimethoxyphenyl)-N-(4-(4-(dimethylamino)piperidin-1-yl) phenyl)-[1,2,4]triazolo[4',3':1,6]pyrido[2,3-d]pyrimidin-2-amine;

(15) 6-(2-chloro-3,5-dimethoxyphenyl)-N-(4-(4-methylpiperazin-1-yl)phenyl)-[1,2,4]triazolo[4',3':1,6]pyrido[2,3-d]pyrimidin-2-amine;

(16) 6-(2-chloro-3,5-dimethoxyphenyl)-N-(5-(4-methylpiperazin-1-yl)pyridin-2-yl)-[1,2,4]triazolo[4',3':1,6]pyrido[2,3-d]pyrimidin-2-amine;

(17) 6-(2-chloro-3,5-dimethoxyphenyl)-N-(5-((4-ethylpiperazin-1-yl)methyl) pyridin-2-yl)-[1,2,4]triazolo[4',3':1,6]pyrido[2,3-d]pyrimidin-2-amine;

(18) 6-(2-chloro-3,5-dimethoxyphenyl)-N-(4-(4-ethyl-2-oxopiperazin-1-yl)phenyl)-[1,2,4]triazolo[4',3':1,6]pyrido[2,3-d]pyrimidin-2-amine;

(19) 6-(2-chloro-3,5-dimethoxyphenyl)-N-(4-(4-ethyl-3-oxopiperazin-1-yl)phenyl)-[1,2,4]triazolo[4',3':1,6]pyrido[2,3-d]pyrimidin-2-amine;

(20) 6-(2-chloro-3,5-dimethoxyphenyl)-N-(4-((3S,5R)-3,4,5-trimethylpiperazin-1-yl)phenyl)-[1,2,4]triazolo[4',3':1,6]pyrido[2,3-d]pyrimidin-2-amine;

(21) 6-(2-chloro-3,5-dimethoxyphenyl)-N-(4-(N-(2-dimethylaminoethyl-N-methylamino)phenyl)-[1,2,4]triazolo[4',3':1,6]pyrido[2,3-d]pyridimin-2-amine;

(22) 6-(2-chloro-3,5-dimethoxyphenyl)-N-(4-(4-(1-methylpiperidin-4-yl) piperazin-1-yl)phenyl)-[1,2,4]triazolo[4',3':1,6]pyrido[2,3-d]pyrimidin-2-amine;

(23) 6-(2-chloro-3,5-dimethoxyphenyl)-N-(4-(8-methyl-3,8-diazabicyclo[3.2.1] octan-3-yl)phenyl)-[1,2,4]triazolo[4',3':1,6]pyrido[2,3-d]pyrimidin-2-amine;

(24) (R)-6-(2-chloro-3,5-dimethoxyphenyl)-N-(4-(hexahydropyrrolo[1,2-a] pyrazin-2(1H)-yl)phenyl)-[1,2,4]triazolo[4',3':1,6]pyrido[2,3-d]pyrimidin-2-amine;

(25) (S)-6-(2-chloro-3,5-dimethoxyphenyl)-N-(4-(hexahydropyrrolo[1,2-a] pyrazin-2(1H)-yl)phenyl)-[1,2,4]triazolo[4',3':1,6]pyrido[2,3-d]pyrimidin-2-amine;

(26) 6-(2-chloro-3,5-dimethoxyphenyl)-N-(4-(3,3,4-trimethylpiperazin-1-yl) phenyl)-[1,2,4]triazolo[4',3':1,6]pyrido[2,3-d]pyrimidin-2-amine;

(27) $N^1$-(6-(2-chloro-3,5-dimethoxyphenyl)-[1,2,4]triazolo[4',3':1,6]pyrido[2,3-d] pyrimidin-2-yl)-$N^4$-methyl-$N^4$-(2-morpholinoethyl)benzene-1,4-diamine;

(28) 6-(2-chloro-3,5-dimethoxyphenyl)-N-(4-(2-(pyrrolidin-1-yl)ethoxy)phenyl)-[1,2,4]triazolo[4',3':1,6]pyrido[2,3-d]pyrimidin-2-amine;

(29) 6-(2-chloro-3,5-dimethoxyphenyl)-N-(4-(4-morpholinopiperidin-1-yl) phenyl)-[1,2,4]triazolo[4',3':1,6]pyrido[2,3-d]pyrimidin-2-amine;

(30) 6-(2-chloro-3,5-dimethoxyphenyl)-N-(4-(4-(dimethylamino)piperidin-1-yl)-2-fluorophenyl)-[1,2,4]triazolo[4',3':1,6]pyrido[2,3-d]pyrimidin-2-amine;

(31) 6-(2-chloro-3,5-dimethoxyphenyl)-N-(4-(4-(dimethylamino)piperidin-1-yl)-2-methoxyphenyl)-[1,2,4]triazolo[4',3':1,6]pyrido[2,3-d]pyrimidin-2-amine;

(32) 2-(4-(4-((6-(2-chloro-3,5-dimethoxyphenyl)-[1,2,4]triazolo[4',3':1,6]pyrido[2,3-d]pyrimidin-2-yl)amino) phenyl)piperazin-1-yl)ethan-1-ol;

(33) 6-(2-chloro-3,5-dimethoxyphenyl)-N-(4-(2-morpholinoethoxy)phenyl)-[1,2,4]triazolo[4',3':1,6]pyrido[2,3-d]pyrimidin-2-amine;

(34) 6-(2-chloro-3,5-dimethoxyphenyl)-N-(4-(1-ethylpiperidin-4-yl)phenyl)-[1,2,4]triazolo[4',3':1,6]pyrido[2,3-d]pyrimidin-2-amine;

(35) 6-(2-chloro-3,5-dimethoxyphenyl)-N-(2-ethyl-1,2,3,4-tetrahydroisoquinolin-6-yl)-[1,2,4]triazolo[4',3':1,6]pyrido[2,3-d]pyrimidin-2-amine;

(36) 6-(2-chloro-3,5-dimethoxyphenyl)-N-(4-(1-ethylpiperidin-4-yl)-3-methylphenyl)-[1,2,4]triazolo[4',3':1,6]pyrido[2,3-d]pyrimidin-2-amine;

(37) 6-(2-chloro-3,5-dimethoxyphenyl)-N-(4-(1-methylpiperidin-4-yl)phenyl)-[1,2,4]triazolo[4',3':1,6]pyrido[2,3-d]pyrimidin-2-amine;

(38) (R)-6-(2-chloro-3,5-dimethoxyphenyl)-N-(3-(hexahydropyrrolo[1,2-a] pyrazin-2(1H)-yl)phenyl)-[1,2,4]triazolo[4',3':1,6]pyrido[2,3-d]pyrimidin-2-amine;

(39) (R)-6-(3,5-dimethoxyphenyl)-N-(4-(hexahydropyrrolo[1,2-a]pyrazin-2(1H)-yl)phenyl)-[1,2,4]triazolo[4',3':1,6]pyrido[2,3-d]pyrimidin-2-amine;

(40) (R)-2-(4-((6-(2-chloro-3,5-dimethoxyphenyl)-[1,2,4]triazolo[4',3':1,6]pyrido[2,3-d]pyrimidin-2-yl)amino) phenyl)hexahydropyrrolo[1,2-a]pyrazin-4(1H)-one;

(41) (R)-2-(4-((6-(2-chloro-3,5-dimethoxyphenyl)-[1,2,4]triazolo[4',3':1,6]pyrido[2,3-d]pyrimidin-2-yl)amino) phenyl)hexahydropyrrolo[1,2-a]pyrazin-6(2H)-one;

(42) (S)-6-(2-chloro-3,5-dimethoxyphenyl)-N-(4-(hexahydropyrazino[2,1-c][1,4] oxazin-8(1H)-yl)phenyl)-[1,2,4]triazolo[4',3':1,6]pyrido[2,3-d]pyrimidin-2-amine;

(43) (R)-6-(2-chloro-3,5-dimethoxyphenyl)-N-(4-(hexahydropyrazino[2,1-c][1,4] oxazin-8(1H)-yl)phenyl)-[1,2,4]triazolo[4',3':1,6]pyrido[2,3-d]pyrimidin-2-amine;

(44) 6-(2-chloro-3,5-dimethoxyphenyl)-N-(4-((4-ethylpiperazin-1-yl)methyl) phenyl)-[1,2,4]triazolo[4',3':1,6]pyrido[2,3-d]pyrimidin-2-amine;

(45) 6-(2-chloro-3,5-dimethoxyphenyl)-N-(4-(morpholinomethyl)phenyl)-[1,2,4]triazolo[4',3':1,6]pyrido[2,3-d]pyrimidin-2-amine;

(46) 6-(2-chloro-3,5-dimethoxyphenyl)-N-(4-((4-methylpiperazin-1-yl)methyl) phenyl)-[1,2,4]triazolo[4',3':1,6]pyrido[2,3-d]pyrimidin-2-amine;

(47) 6-(2-chloro-3,5-dimethoxyphenyl)-N-(4-(1-cyclopropylpiperidin-4-yl) phenyl)-[1,2,4]triazolo[4',3':1,6]pyrido[2,3-d]pyrimidin-2-amine;

(48) 6-(2-chloro-3,5-dimethoxyphenyl)-N-(4-(piperazin-1-yl)phenyl)-[1,2,4]triazolo[4',3':1,6]pyrido[2,3-d]pyrimidin-2-amine;

(49) 6-(2-chloro-3,5-dimethoxyphenyl)-N-(4-(4-(methylamino)piperidin-1-yl) phenyl)-[1,2,4]triazolo[4',3':1,6]pyrido[2,3-d]pyrimidin-2-amine;

(50) 6-(2-chloro-3,5-dimethoxyphenyl)-N-(4-((3S,5R)-3,5-dimethylpiperazin-1-yl)phenyl)-[1,2,4]triazolo[4',3':1,6]pyrido[2,3-d]pyrimidin-2-amine;

(51) N-(4-(3,8-diazabicyclo[3.2.1]octan-3-yl)phenyl)-6-(2-chloro-3,5-dimethoxyphenyl)-[1,2,4]triazolo[4',3':1,6]pyrido[2,3-d]pyrimidin-2-amine;

(52) 6-(2-chloro-3,5-dimethoxyphenyl)-N-(3-methyl-4-(piperidin-4-yl)phenyl)-[1,2,4]triazolo[4',3':1,6]pyrido[2,3-d]pyrimidin-2-amine;

(53) 6-(2-chloro-3,5-dimethoxyphenyl)-N-(1,2,3,4-tetrahydroisoquinolin-6-yl)-[1,2,4]triazolo[4',3':1,6]pyrido[2,3-d]pyrimidin-2-amine;

(54) 6-(2-chloro-3,5-dimethoxyphenyl)-N-(4-((3S,5R)-3,5-dimethylpiperazin-1-yl)-3-methylphenyl)-[1,2,4]triazolo[4',3':1,6]pyrido[2,3-d]pyrimidin-2-amine;

(55) 6-(2-chloro-3,5-dimethoxyphenyl)-N-(4-((3S,5R)-3,5-dimethylpiperazin-1-yl)-3-methoxyphenyl)-[1,2,4]triazolo[4',3':1,6]pyrido[2,3-d]pyrimidin-2-amine;

(56) 6-(2-chloro-3,5-dimethoxyphenyl)-N-(4-((3S,5R)-3,5-dimethylpiperazin-1-yl)-3-fluorophenyl)-[1,2,4]triazolo[4',3':1,6]pyrido[2,3-d]pyrimidin-2-amine;

(57) 6-(2-chloro-3,5-dimethoxyphenyl)-N-(3-chloro-4-((3S,5R)-3,5-dimethyl piperazin-1-yl)phenyl)-[1,2,4]triazolo[4',3':1,6]pyrido[2,3-d]pyrimidin-2-amine;

(58) 6-(2-chloro-3,5-dimethoxyphenyl)-N-(4-(piperazin-1-ylmethyl)phenyl)-[1,2,4]triazolo[4',3':1,6]pyrido[2,3-d]pyrimidin-2-amine;

(59) (4-((6-(2-chloro-3,5-dimethoxyphenyl)-[1,2,4]triazolo[4',3':1,6]pyrido[2,3-d]pyrimidin-2-yl)amino)phenyl)((3S,5R)-3,5-dimethylpiperazin-1-yl)methanone;

(60) (4-((6-(2,6-dichloro-3,5-dimethoxyphenyl)-[1,2,4]triazolo[4',3':1,6]pyrido[2,3-d]pyrimidin-2-yl)amino)phenyl)((3S,5R)-3,5-dimethylpiperazin-1-yl) methanone;

(61) 6-(2,6-dichloro-3,5-dimethoxyphenyl)-N-(4-(4-ethylpiperazin-1-yl)phenyl)-[1,2,4]triazolo[4',3':1,6]pyrido[2,3-d]pyrimidin-2-amine;

(62) 6-(2,6-dichloro-3,5-dimethoxyphenyl)-N-(2-morpholinoethyl)-[1,2,4]triazolo[4',3':1,6]pyrido[2,3-d]pyrimidin-2-amine;

(63) 4-(2,6-dichloro-3,5-dimethoxyphenyl)-N-(2-morpholinoethyl)-[1,2,4]triazolo[1',5':1,6]pyrido[2,3-d]pyrimidin-8-amine;

(64) (R)-6-(2,6-dichloro-3,5-dimethoxyphenyl)-N-(4-(hexahydropyrrolo[1,2-a] pyrazin-2(1H)-yl)phenyl)-[1,2,4]triazolo[4',3':1,6]pyrido[2,3-d]pyrimidin-2-amine;

(65) 6-(2,6-dichloro-3,5-dimethoxyphenyl)-N-(4-(4-morpholinopiperidin-1-yl) phenyl)-[1,2,4]triazolo[4',3':1,6]pyrido[2,3-d]pyrimidin-2-amine;

(66) 6-(2-chloro-3,5-dimethoxyphenyl)-$N^2$-(4-(4-ethylpiperazin-1-yl)phenyl)-[1,2,4]triazolo[4',3':1,6]pyrido[2,3-d]pyrimidine-2,9-diamine;

(67) 6-(5-chloro-2-methyl-1H-benzo[d]imidazol-6-yl)-N-(4-(4-ethylpiperazin-1-yl)phenyl)-[1,2,4]triazolo[4',3':1,6]pyrido[2,3-d]pyrimidin-2-amine;

(68) N-(4-(4-ethylpiperazin-1-yl)phenyl)-6-(2-methyl-1H-benzo[d]imidazol-6-yl)-[1,2,4]triazolo[4',3':1,6]pyrido[2,3-d]pyrimidin-2-amine;

(69) 6-(4-chloro-2-methyl-1H-benzo[d]imidazol-5-yl)-N-(4-(4-ethylpiperazin-1-yl)phenyl)-[1,2,4]triazolo[4',3':1,6]pyrido[2,3-d]pyrimidin-2-amine;

(70) 6-(4,6-dichloro-2-methyl-1H-benzo[d]imidazol-5-yl)-N-(4-(4-ethyl piperazin-1-yl)phenyl)-[1,2,4]triazolo[4',3':1,6]pyrido[2,3-d]pyrimidin-2-amine;

(71) 6-(5-chloro-2-methyl-1H-indol-6-yl)-N-(4-(4-ethylpiperazin-1-yl)phenyl)-[1,2,4]triazolo[4',3':1,6]pyrido[2,3-d]pyrimidin-2-amine;

(72) 6-(6-chloro-2-methylbenzo[d]thiazol-5-yl)-N-(4-(4-ethylpiperazin-1-yl) phenyl)-[1,2,4]triazolo[4',3':1,6]pyrido[2,3-d]pyrimidin-2-amine;

(73) 6-(4-chloro-2-methylbenzo[d]thiazol-5-yl)-N-(4-(4-ethylpiperazin-1-yl) phenyl)-[1,2,4]triazolo[4',3':1,6]pyrido[2,3-d]pyrimidin-2-amine;

(74) 6-(6-chloro-2-methylbenzo[d]oxazol-5-yl)-N-(4-(4-ethylpiperazin-1-yl) phenyl)-[1,2,4]triazolo[4',3':1,6]pyrido[2,3-d]pyrimidin-2-amine;

(75) 6-(4-chloro-2-methylbenzo[d]oxazol-5-yl)-N-(4-(4-ethylpiperazin-1-yl) phenyl)-[1,2,4]triazolo[4',3':1,6]pyrido[2,3-d]pyrimidin-2-amine;

(76) 6-(5-chloro-2-methylbenzo[d]oxazol-6-yl)-N-(4-(4-ethylpiperazin-1-yl) phenyl)-[1,2,4]triazolo[4',3':1,6]pyrido[2,3-d]pyrimidin-2-amine;

(77) 6-(7-chloro-2-methylbenzo[d]oxazol-6-yl)-N-(4-(4-ethylpiperazin-1-yl) phenyl)-[1,2,4]triazolo[4',3':1,6]pyrido[2,3-d]pyrimidin-2-amine;

(78) 6-(5-chloro-2-methyl-1H-benzo[d]imidazol-6-yl)-N-(4-(4-(dimethylamino) piperidin-1-yl)phenyl)-[1,2,4]triazolo[4',3':1,6]pyrido[2,3-d]pyrimidin-2-amine;

(79) 6-(5-chloro-2-methyl-1H-benzo[d]imidazol-6-yl)-N-(4-(1-ethylpiperidin-4-yl)phenyl)-[1,2,4]triazolo[4',3':1,6]pyrido[2,3-d]pyrimidin-2-amine;

(80) 6-(5-chloro-2-methyl-1H-benzo[d]imidazol-6-yl)-N-(4-((3S,5R)-3,5-dimethylpiperazin-1-yl)phenyl)-[1,2,4]triazolo[4',3':1,6]pyrido[2,3-d]pyrimidin-2-amine;

(81) 6-(5-chloro-2-methyl-1H-benzo[d]imidazol-6-yl)-N-(4-morpholinophenyl)-[1,2,4]triazolo[4',3':1,6]pyrido[2,3-d]pyrimidin-2-amine;

(82) 6-(5,7-dichloro-2-methyl-1H-benzo[d]imidazol-6-yl)-N-(4-morpholino phenyl)-[1,2,4]triazolo[4',3':1,6]pyrido[2,3-d]pyrimidin-2-amine;

(83) 6-(7-chloro-2-methyl-1H-benzo[d]imidazol-6-yl)-N-(4-morpholinophenyl)-[1,2,4]triazolo[4',3':1,6]pyrido[2,3-d]pyrimidin-2-amine;

(84) N-(4-(hexahydropyrrolo[1,2-a]pyrazin-2(1H)-yl) phenyl)-[1,2,4]triazolo[4',3':1,6]pyrido[2,3-d]pyrimidin-2-amine;

(85) 6-(2-chloro-3,5-dimethoxyphenyl)-N-(4-(4-ethylpiperazin-1-yl)phenyl)-9-methyl-[1,2,4]triazolo[4',3':1,6]pyrido[2,3-d]pyrimidin-2-amine;

(86) N-(4-((6-(2-chloro-3,5-dimethoxyphenyl)-2-((2-morpholinoethyl)amino)-[1,2,4]triazolo[4',3':1,6]pyrido[2,3-d]pyrimidin-9-yl)methyl)phenyl)acrylamide;

(87) 4-(2-chloro-3,5-dimethoxyphenyl)-N-(4-(4-ethylpiperazin-1-yl)phenyl)-2-methyl-[1,2,4]triazolo[1',5':1,6]pyrido[2,3-d]pyrimidin-8-amine;

(88) N-(4-((4-(2-chloro-3,5-dimethoxyphenyl)-8-((4-(4-ethylpiperazin-1-yl) phenyl)amino)-[1,2,4]triazolo[1',5':1,6]pyrido[2,3-d]pyrimidin-2-yl)methyl)phenyl) acrylamide;

(89) 6-(2-chloro-3,5-dimethoxyphenyl)-N-(4-(4-ethylpiperazin-1-yl)phenyl)-9-(morpholinomethyl)-[1,2,4]triazolo[4',3':1,6]pyrido[2,3-d]pyrimidin-2-amine;

(90) N-(4-((6-(2-chloro-3,5-dimethoxyphenyl)-2-((4-(4-ethylpiperazin-1-yl) phenyl)amino)-[1,2,4]triazolo[4',3':1,6]pyrido[2,3-d]pyrimidin-9-yl)methyl)phenyl) acrylamide;

(91) N-(4-(2-(6-(2-chloro-3,5-dimethoxyphenyl)-2-((4-(4-ethylpiperazin-1-yl) phenyl)amino)-[1,2,4]triazolo[4',3':1,6]pyrido[2,3-d]pyrimidin-9-yl)ethyl)phenyl) acrylamide;

(92) 6-(2-chloro-3,5-dimethoxyphenyl)-9-((dimethylamino)methyl)-N-(4-(4-ethylpiperazin-1-yl)phenyl)-[1,2,4]triazolo[4',3':1,6]pyrido[2,3-d]pyrimidin-2-amine;

(93) 6-(2-chloro-3,5-dimethoxyphenyl)-9-(cyclopropylmethyl)-N-(4-(4-ethyl piperazin-1-yl)phenyl)-[1,2,4]triazolo[4',3':1,6]pyrido[2,3-d]pyrimidin-2-amine;

(94) 6-(2-chloro-3,5-dimethoxyphenyl)-9-cyclopropyl-N-(4-(4-ethylpiperazin-1-yl)phenyl)-[1,2,4]triazolo[4',3':1,6]pyrido[2,3-d]pyrimidin-2-amine;

(95) N-(4-((6-(2-chloro-3,5-dimethoxyphenyl)-2-(methylamino)-[1,2,4]triazolo[4',3':1,6]pyrido[2,3-d]pyrimidin-9-yl)methyl)phenyl)acrylamide;

(96) N-(4-((6-(2-chloro-3,5-dimethoxyphenyl)-2-((2-morpholinoethyl)amino)-[1,2,4]triazolo[4',3':1,6]pyrido[2,3-d]pyrimidin-9-yl)methyl)phenyl)propionamide;

(97) N-(4-(2-(6-(2-chloro-3,5-dimethoxyphenyl)-2-((2-morpholinoethyl)amino)-[1,2,4]triazolo[4',3':1,6]pyrido[2,3-d]pyrimidin-9-yl)ethyl)phenyl)acrylamide;

(98) 6-(2-chloro-3,5-dimethoxyphenyl)-2-((4-(4-ethylpiperazin-1-yl)phenyl) amino)-[1,2,4]triazolo[4',3':1,6]pyrido[2,3-d]pyrimidin-9(8H)-one;

(99) 4-(4-((6-(2-chloro-3,5-dimethoxyphenyl)-[1,2,4]triazolo[4',3':1,6]pyrido[2,3-d]pyrimidin-2-yl)amino)phenyl)-1-ethylpiperazine 1-oxide;

(100) (8aR)-2-(4-((6-(2-chloro-3,5-dimethoxyphenyl)-[1,2,4]triazolo[4',3':1,6] pyrido[2,3-d]pyrimidin-2-yl)amino)phenyl)octahydro-5H-pyrrolo[1,2-a]pyrazine 5-oxide;

(101) 3-(4-(4-((6-(2-chloro-3,5-dimethoxyphenyl)-[1,2,4]triazolo[4',3':1,6] pyrido[2,3-d]pyrimidin-2-yl)amino)phenyl)piperazin-1-yl)cyclobutan-1-ol;

(102) 6-(2-chloro-3,5-dimethoxyphenyl)-N-(4-(1-ethylpiperidin-4-yl)phenyl)-[1,2,4]triazolo[4',3':1,6]pyrido[2,3-d]pyrimidin-2-amine;

(103) 6-(2-chloro-3,5-dimethoxyphenyl)-N-(4-(4-(2,2,2-trifluoroethyl)piperazin-1-yl)phenyl)-[1,2,4]triazolo[4',3':1,6]pyrido[2,3-d]pyrimidin-2-amine;

(104) 6-(2-chloro-3,5-dimethoxyphenyl)-N-(4-(4-cyclopentylpiperazin-1-yl) phenyl)-[1,2,4]triazolo[4',3':1,6]pyrido[2,3-d]pyrimidin-2-amine;

(105) 6-(2-chloro-3,5-dimethoxyphenyl)-N-(4-(4-cyclobutylpiperazin-1-yl) phenyl)-[1,2,4]triazolo[4',3':1,6]pyrido[2,3-d]pyrimidin-2-amine;

(106) (6-(2-chloro-3,5-dimethoxyphenyl)-N-(4-(4-acetylpiperazine-1- yl) phenyl)-[1,2,4]triazolo[4',3':1,6]pyrido[2,3-d]pyrimidin-2-amine);

(107) 4-(4-((6-(2-chloro-3,5-dimethoxyphenyl)-[1,2,4]triazolo[4',3':1,6]pyrido[2,3-d]pyrimidin-2-yl)amino)phenyl)-N,N-dimethylpiperazine-1-carboxamide;

(108) 6-(4-((6-(2-chloro-3,5-dimethoxyphenyl)-[1,2,4]triazolo[4',3':1,6]pyrido[2,3-d]pyrimidin-2-yl)amino)phenyl)-N,N-dimethyl-2,6-diazaspiro[3.3]heptane-2-carboxamide;

(109) (S)-3-((4-((6-(2-chloro-3,5-dimethoxyphenyl)-[1,2,4]triazolo[4',3':1,6] pyrido[2,3-d]pyrimidin-2-yl)amino)phenyl)amino)-N,N-dimethylpyrrolidine-1-carboxamide;

(110) 6-(2-chloro-3,5-dimethoxyphenyl)-N-(6-(4-methylpiperazin-1-yl)pyridin-3-yl)-[1,2,4]triazolo[4',3':1,6]pyrido[2,3-d]pyrimidin-2-amine;

(111) 6-(2-chloro-3,5-dimethoxyphenyl)-N-(6-((4-ethylpiperazin-1-yl)methyl) pyridin-3-yl)-[1,2,4]triazolo[4',3':1,6]pyrido[2,3-d]pyrimidin-2-amine;

(112) N-(4-((4-(2-chloro-3,5-dimethoxyphenyl)-8-((2-morpholinoethyl)amino)-[1,2,4]triazolo[1',5':1,6]pyrido[2,3-d]pyrimidin-2-yl)methyl)phenyl)acrylamide;

(113) (1-(4-((6-(2-chloro-3,5-dimethoxyphenyl)-2-(methylamino)-[1,2,4]triazolo[4',3':1,6]pyrido[2,3-d]pyrimidin-9-yl)propyl)piperazin-1-yl)prop-2-en-1-one);

(114) 1-(4-(2-(6-(2-chloro-3,5-dimethoxyphenyl)-2-(methylamino)-[1,2,4]triazolo[4',3':1,6]pyrido[2,3-d]pyrimidin-9-yl)ethyl)piperazin-1-yl)prop-2-en-1-one;

(115) 1-(4-(3-(4-(2-chloro-3,5-dimethoxyphenyl)-8-(methylamino)-[1,2,4]triazolo[1',5':1,6]pyrido[2,3-d]pyrimidin-2-yl)propyl)piperazin-1-yl)prop-2-en-1-one;

(116) 1-(4-(2-(4-(2-chloro-3,5-dimethoxyphenyl)-8-(methylamino)-[1,2,4]triazolo[1',5':1,6]pyrido[2,3-d]pyrimidin-2-yl)ethyl)piperazin-1-yl)prop-2-en-1-one;

(117) 1-(4-((4-(2-chloro-3,5-dimethoxyphenyl)-8-(methylamino)-[1,2,4]triazolo[1',5':1,6]pyrido[2,3-d]pyrimidin-2-yl)methyl)piperazin-1-yl)prop-2-en-1-one;

(118) 1-(3-(2-(4-(2-chloro-3,5-dimethoxyphenyl)-8-(methylamino)-[1,2,4]triazolo[1',5':1,6]pyrido[2,3-d]pyrimidin-2-yl)ethoxy)azetidin-1-yl)prop-2-en-1-one;

(119) 1-(3-(2-(4-(2-chloro-3,5-dimethoxyphenyl)-8-(methylamino)-[1,2,4]triazolo[1',5':1,6]pyrido[2,3-d]pyrimidin-2-yl)ethoxy)piperidin-1-yl)prop-2-en-1-one;

(120) N-(4-(2-(4-(2,6-dichloro-3,5-dimethoxyphenyl)-8-(methylamino)-[1,2,4]triazolo[1',5':1,6]pyrido[2,3-d]pyrimidin-2-yl)ethyl)phenyl)acrylamide;

(121) N-(3-(2-(4-(2,6-dichloro-3,5-dimethoxyphenyl)-8-(methylamino)-[1,2,4]triazolo[1',5':1,6]pyrido[2,3-d]pyrimidin-2-yl)ethyl)phenyl)acrylamide;

(122) 1-(4-(3-(4-(2,6-dichloro-3,5-dimethoxyphenyl)-8-(methylamino)-[1,2,4]triazolo[1',5':1,6]pyrido[2,3-d]pyrimidin-2-yl)propyl)piperazin-1-yl)prop-2-en-1-one;

(123) 1-(4-(2-(4-(2,6-dichloro-3,5-dimethoxyphenyl)-8-(methylamino)-[1,2,4]triazolo[1',5':1,6]pyrido[2,3-d]pyrimidin-2-yl)methyl)piperazin-1-yl)prop-2-en-1-one;

(124) 1-(4-(2-(4-(2,6-dichloro-3,5-dimethoxyphenyl)-8-(methylamino)-[1,2,4]triazolo[1',5':1,6]pyrido[2,3-d]pyrimidin-2-yl)ethyl)piperazin-1-yl)prop-2-en-1-one;

(125) 1-(6-(3-(4-(2,6-dichloro-3,5-dimethoxyphenyl)-8-(methylamino)-[1,2,4]triazolo[1',5':1,6]pyrido[2,3-d]pyrimidin-2-yl)propyl)-2,6-diazaspiro[3.3]heptan-2-yl)prop-2-en-1-one;

(126) 1-(4-((2-(4-(2-chloro-3,5-dimethoxyphenyl)-8-(methylamino)-[1,2,4]triazolo[1',5':1,6]pyrido[2,3-d]pyrimidin-2-yl)cyclopropyl)methyl)piperazin-1-yl)prop-2-en-1-one;

(127) 1-(4-(2-(4-(2-chloro-3,5-dimethoxyphenyl)-8-(methylamino)-[1,2,4]triazolo[1',5':1,6]pyrido[2,3-d]pyrimidin-2-yl)ethoxy)piperidin-1-yl)prop-2-en-1-one;

(128) 14(3aR,6aS)-5-(3-(4-(2,6-dichloro-3,5-dimethoxyphenyl)-8-(methylamino)-[1,2,4]triazolo[1',5':1,6]pyrido[2,3-d]pyrimidin-2-yl)propyl) hexahydropyrrolo[3,4-c]pyrrol-2(1H)-yl)prop-2-en-1-one;

(129) N-(1-(2-(4-(2,6-dichloro-3,5-dimethoxyphenyl)-8-(methylamino)-[1,2,4]triazolo[1',5':1,6]pyrido[2,3-d]pyrimidin-2-yl)propyl)piperidin-4-yl)acrylamide;

(130) 1-(4-(3-(4-(2,6-dichloro-3,5-dimethoxyphenyl)-8-(methylamino)-[1,2,4]triazolo[1',5':1,6]pyrido[2,3-d]pyrimidin-2-yl)propyl)piperidin-1-yl)prop-2-en-1-one;

(131) 1-((3S,5R)-4-(3-(4-(2,6-dichloro-3,5-dimethoxyphenyl)-8-(methylamino)-[1,2,4]triazolo[1',5':1,6]pyrido[2,3-d]pyrimidin-2-yl)propyl)-3,5-dimethylpiperazin-1-yl)prop-2-en-1-one;

(132) 1-(4-((1-((4-(2,6-dichloro-3,5-dimethoxyphenyl)-8-(methylamino)-[1,2,4]triazolo[1',5':1,6]pyrido[2,3-d]pyrimidin-2-yl)methyl)cyclopropyl) methyl)piperazin-1-yl)prop-2-en-1-one;

(133) 1-((2R,6S)-4-(3-(4-(2,6-dichloro-3,5-dimethoxyphenyl)-8-(methylamino)-[1,2,4]triazolo[1',5':1,6]pyrido[2,3-d]pyrimidin-2-yl)propyl)-2,6-dimethylpiperazin-1-yl)prop-2-en-1-one;

(134) 1-(4-((3-(4-(2,6-dichloro-3,5-dimethoxyphenyl)-8-(methylamino)-[1,2,4]triazolo[1',5':1,6]pyrido[2,3-d]pyrimidin-2-yl)propyl)(methyl)amino)piperidin-1-yl)prop-2-en-1-one;

(135) 1-((2R,6S)-4-(3-(8-((cyclopropylmethyl)amino)-4-(2,6-dichloro-3,5-dimethoxyphenyl)-[1,2,4]triazolo[1',5':1,6]pyrido[2,3-d]pyrimidin-2-yl)propyl)-2,6-dimethylpiperazin-1-yl)prop-2-en-1-one;

(136) 1-((2R,6S)-4-(3-(4-(2,6-dichloro-3,5-dimethoxyphenyl)-8-((2,2-difluoroethyl)amino)-[1,2,4]triazolo[1',5':1,6]pyrido[2,3-d]pyrimidin-2-yl)propyl)-2,6-dimethylpiperazin-1-yl)prop-2-en-1-one;

(137) 1-(4-(3-(4-(2,6-dichloro-3,5-dimethoxyphenyl)-8-((2,2,2-trifluoroethyl) amino)-[1,2,4]triazolo[1',5': 1,6]pyrido[2,3-d]pyrimidin-2-yl)propyl)piperazin-1-yl)prop-2-en-1-one;

(138) 1-(2-(3-(4-(2,6-dichloro-3,5-dimethoxyphenyl)-8-(methylamino)-[1,2,4]triazolo[1',5':1,6]pyrido[2,3-d]pyrimidin-2-yl)propyl)-2,7-diazaspiro[3.5]nonan-7-yl)prop-2-en-1-one;

(139) 1-((1R,5S,6S)-6-((3-(4-(2,6-dichloro-3,5-dimethoxyphenyl)-8-(methylamino)-[1,2,4]triazolo[1',5':1,6]pyrido[2,3-d]pyrimidin-2-yl)propyl) (methyl)amino)-3-azabicyclo[3.1.0]hexan-3-yl)prop-2-en-1-one;

(140) 1-(2-(3-(4-(2,6-dichloro-3,5-dimethoxyphenyl)-8-(methylamino)-[1,2,4]triazolo[1',5':1,6]pyrido[2,3-d]pyrimidin-2-yl)propyl)-2,8-diazaspiro[4.5]decan-8-yl)prop-2-en-1-one;

(141) (S)-1-(3-((3-(4-(2,6-dichloro-3,5-dimethoxyphenyl)-8-(methylamino)-[1,2,4]triazolo[1',5':1,6]pyrido[2,3-d]pyrimidin-2-yl)propyl)(methyl)amino)piperidin-1-yl)prop-2-en-1-one;

(142) 1-(4-(3-(4-(2,6-dichloro-3,5-dimethoxyphenyl)-8-(methylamino)-[1,2,4]triazolo[1',5':1,6]pyrido[2,3-d]pyrimidin-2-yl)propyl)-3,3-dimethylpiperazin-1-yl)prop-2-en-1-one;

(143) 1-(4-((3-(4-(2,6-dichloro-3,5-dimethoxyphenyl)-8-(methylamino)-[1,2,4]triazolo[1',5': 1,6]pyrido[2,3-d]pyrimidin-2-yl)propyl)sulfonyl)piperidin-1-yl)prop-2-en-1-one;

(144) 1-(8-(3-(4-(2,6-dichloro-3,5-dimethoxyphenyl)-8-(methylamino)-[1,2,4]triazolo[1',5': 1,6]pyrido[2,3-d]pyrimidin-2-yl)propyl)-3,8-diazabicyclo[3.2.1]octan-3-yl)prop-2-en-1-one;

(145) 1-(5-(3-(4-(2,6-dichloro-3,5-dimethoxyphenyl)-8-(methylamino)-[1,2,4]triazolo[1',5':1,6]pyrido[2,3-d]pyrimidin-2-yl)propyl)-2,5-diazabicyclo[2.2.1]heptan-2-yl)prop-2-en-1-one;

(146) 1-(4-(3-(4-(5-chloro-2-methyl-1H-benzo[d]imidazol-6-yl)-8-(methylamino)-[1,2,4]triazolo[1',5':1,6]pyrido[2,3-d]pyrimidin-2-yl)propyl)piperazin-1-yl)prop-2-en-1-one;

(147) 2-(4-(3-(4-(2,6-dichloro-3,5-dimethoxyphenyl)-8-(methylamino)-[1,2,4]triazolo[1',5':1,6]pyrido[2,3-d]pyrimidin-2-yl)propyl)piperazine-1-carbonyl)-4-methylpent-2-enenitrile; or (148) 2-(4-(3-(4-(2,6-dichloro-3,5-dimethoxyphenyl)-8-(methylamino)-[1,2,4]triazolo[1',5':1,6]pyrido[2,3-d]pyrimidin-2-yl)propyl)piperazine-1-carbonyl)-4,4-dimethylpent-2-enenitrile.

27. A pharmaceutical composition comprising a compound of claim 1 and a pharmaceutically acceptable excipient.

28. The pharmaceutical composition according to claim 27, wherein the said compound in a weight ratio to the excipient within the range from about 0.0001:1-10.

29. A method for treating a condition mediated by FGFR, comprising administering to the subject a therapeutically effective amount of the compound of claim 1, wherein the condition mediated by FGFR is cancer.

30. The method of claim 29, wherein said FGFR comprising FGFR1, FGFR2, FGFR3 or FGFR4.

31. The method of claim 29, wherein the cancer is breast cancer, multiple myeloma, bladder cancer, endometrial cancer, gastric cancer, cervical cancer, rhabdomyosarcoma, non-small cell lung cancer, small cell lung cancer, pleomorphic lung cancer, ovarian cancer, esophageal cancer, melanoma, colorectak cancer, hepatocellular carcinoma, head and neck cancer, hepatobiliary cell carcinoma, myelodysplastic syndrome, malignant glioma, prostate cancer, thyroid cancer, Schwann cell tumor, lung squamous cell carcinoma, mossy keratosis, Synovial sarcoma, skin cancer, pancreatic cancer, testicular cancer or liposarcoma.

32. A method for treating cancer, comprising administering to a subject a therapeutically effective amount of the compound of claim 1, wherein the cancer is breast cancer, multiple myeloma, bladder cancer, endometrial cancer, gastric cancer, cervical cancer, rhabdomyosarcoma, non-small cell lung cancer, small cell lung cancer, pleomorphic lung cancer, ovarian cancer, esophageal cancer, melanoma, colorectal cancer, hepatocellular carcinoma, head and neck cancer, hepatobiliary cell carcinoma, myelodysplastic syndrome, malignant glioma, prostate cancer, thyroid cancer, Schwann cell tumor, lung squamous cell carcinoma, mossy keratosis, Synovial sarcoma, skin cancer, pancreatic cancer, testicular cancer or liposarcoma.

33. The method of claim 29, wherein the subject is human.

* * * * *